US012616759B2

(12) United States Patent
Chiosis et al.

(10) Patent No.: US 12,616,759 B2
(45) **Date of Patent: *May 5, 2026**

(54) USES OF LABELED HSP90 INHIBITORS

(71) Applicant: Sloan-Kettering Institute for Cancer Research, New York, NY (US)

(72) Inventors: Gabriela Chiosis, New York, NY (US); Nagavarakishore Pillarsetty, Jackson Heights, NY (US); Jason S. Lewis, New York, NY (US); Steven M. Larson, New York, NY (US); Tony Taldone, Forest Hills, NY (US); Mary L. Alpaugh, Teaneck, NJ (US); Erica M. Gomes-DaGama, New Rochelle, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 261 days.

This patent is subject to a terminal disclaimer.

(21) Appl. No.: 18/104,037

(22) Filed: Jan. 31, 2023

(65) Prior Publication Data

US 2024/0058482 A1 Feb. 22, 2024

Related U.S. Application Data

(63) Continuation of application No. 16/934,881, filed on Jul. 21, 2020, now Pat. No. 11,607,465, which is a continuation of application No. 14/131,420, filed as application No. PCT/US2012/045861 on Jul. 6, 2012, now abandoned.

(60) Provisional application No. 61/506,010, filed on Jul. 8, 2011.

(51) Int. Cl.

| | |
|---|---|
| ***A61K 51/04*** | (2006.01) |
| ***A61K 31/52*** | (2006.01) |
| ***G01N 33/50*** | (2006.01) |
| ***G01N 33/574*** | (2006.01) |

(52) U.S. Cl.

CPC .......... *A61K 51/0459* (2013.01); *A61K 31/52* (2013.01); *G01N 33/5011* (2013.01); *G01N 33/5017* (2013.01); *G01N 33/574* (2013.01); *G01N 33/57407* (2013.01); *G01N 33/57426* (2013.01); *G01N 33/5044* (2013.01); *G01N 2500/04* (2013.01); *G01N 2800/52* (2013.01)

(58) Field of Classification Search

CPC .... A61K 51/00; A61K 51/04; A61K 51/0459; A61K 31/00; A61K 31/52; G01N 33/5011; G01N 33/5017; G01N 33/574; G01N 33/57407; G01N 33/57426; G01N 33/5044; G01N 33/6896; G01N 2500/04; G01N 2800/52; A61P 35/00; A61P 35/02; A61P 43/00

See application file for complete search history.

(56) References Cited

U.S. PATENT DOCUMENTS

| | | | | |
|---|---|---|---|---|
| 7,834,181 | B2 | 11/2010 | Chiosis et al. | |
| 8,703,942 | B2 | 4/2014 | Chiosis et al. | |
| 8,710,035 | B2 | 4/2014 | Pan et al. | |
| 9,149,485 | B2 | 10/2015 | Pan et al. | |
| 9,328,114 | B2 | 5/2016 | Chiosis et al. | |
| 9,346,808 | B2 | 5/2016 | Sun et al. | |
| 9,403,828 | B2 | 8/2016 | Chiosis | |
| 9,555,137 | B2 * | 1/2017 | Chiosis | A61K 51/0459 |
| 10,000,494 | B2 | 6/2018 | Chiosis | |
| 10,071,130 | B2 | 9/2018 | Conzen | |
| 10,172,863 | B2 | 1/2019 | Chiosis et al. | |
| 11,607,465 | B2 * | 3/2023 | Chiosis | G01N 33/6896 |
| 2005/0074457 | A1 | 4/2005 | Kamal et al. | |
| 2005/0161059 | A1 | 7/2005 | Franklin et al. | |
| 2006/0073151 | A1 | 4/2006 | Jay et al. | |
| 2007/0178537 | A1 | 8/2007 | Chiosis et al. | |
| 2007/0213328 | A1 | 9/2007 | Drysdale et al. | |
| 2008/0090887 | A1 | 4/2008 | Ying et al. | |
| 2009/0298857 | A1 | 12/2009 | Chiosis et al. | |
| 2010/0129829 | A1 | 5/2010 | Sausville et al. | |
| 2011/0104054 | A1 | 5/2011 | Chiosis et al. | |
| 2011/0118298 | A1 * | 5/2011 | Fritz | A61P 35/02 435/7.1 |
| 2011/0312980 | A1 | 12/2011 | Chiosis | |
| 2012/0208806 | A1 | 8/2012 | Chiosis et al. | |
| 2012/0252818 | A1 | 10/2012 | Chiosis et al. | |
| 2014/0045867 | A1 | 2/2014 | Taldone et al. | |
| 2014/0088121 | A1 | 3/2014 | Sun et al. | |
| 2014/0227183 | A1 | 8/2014 | Chiosis et al. | |
| 2014/0294725 | A1 | 10/2014 | Chiosis et al. | |
| 2014/0315929 | A1 | 10/2014 | Chiosis | |

(Continued)

FOREIGN PATENT DOCUMENTS

| | | | |
|---|---|---|---|
| AU | 2012282903 | A1 | 2/2014 |
| AU | 2012282905 | A1 | 2/2014 |

(Continued)

OTHER PUBLICATIONS

Taldone et al., Bioorganic & Medicinal Chemistry Letters, (online Jul. 14, 2011), vol. 21, pp. 5347-5352. (Year: 2011).*

(Continued)

*Primary Examiner* — D. L. Jones

(74) *Attorney, Agent, or Firm* — Foley & Lardner LLP

(57) ABSTRACT

This invention concerns various methods of using labeled HSP90 inhibitors to improve treatment of cancer patients with HSP90 inhibitors, including ex vivo and in vivo methods for determining whether a tumor will likely respond to therapy with an HSP90 inhibitor.

3 Claims, 50 Drawing Sheets

Figures 1A, 1B, 1C, 1D, 1E:
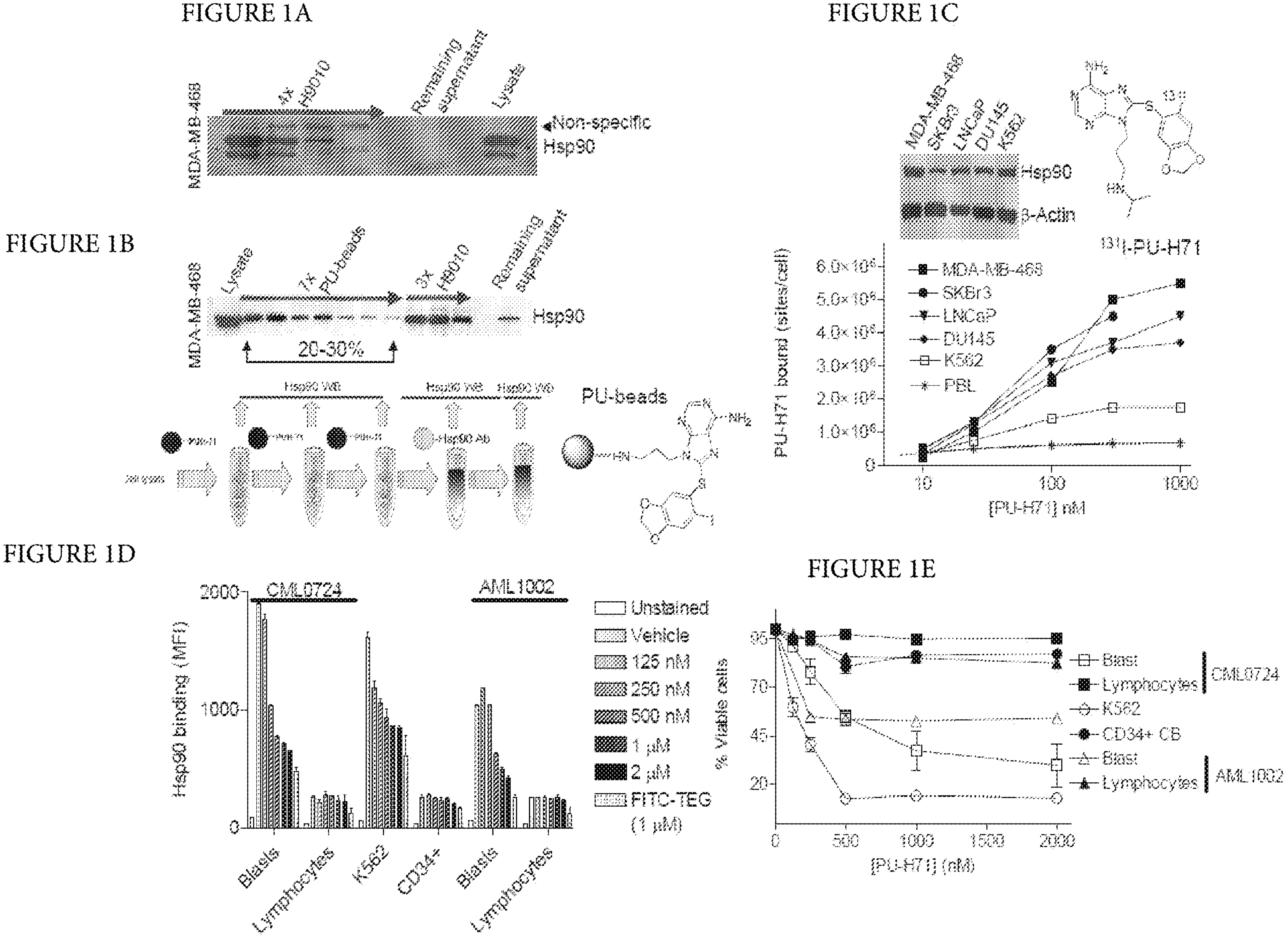

Specification includes a Sequence Listing.

(56) References Cited

U.S. PATENT DOCUMENTS

| | | | |
|---|---|---|---|
| 2014/0378452 | A1 | 12/2014 | Chiosis et al. |
| 2016/0015837 | A1 | 1/2016 | Dunphy et al. |

FOREIGN PATENT DOCUMENTS

| | | | |
|---|---|---|---|
| AU | 2017204369 | A1 | 7/2017 |
| CA | 2841173 | A1 | 6/2013 |
| CN | 1509763 | A | 7/2004 |
| CN | 1860132 | A | 11/2006 |
| CN | 1922304 | A | 2/2007 |
| CN | 101506351 | A | 8/2009 |
| CN | 101627121 | A | 1/2010 |
| CN | 101678081 | A | 3/2010 |
| CN | 101854955 | A | 10/2010 |
| CN | 101888777 | A | 11/2010 |
| EP | 1 457 499 | A1 | 9/2004 |
| EP | 2 729 806 | A1 | 5/2014 |
| EP | 3 208 615 | A2 | 8/2017 |
| JP | 2005-520795 | A | 7/2005 |
| JP | 2009-542716 | A | 12/2009 |
| JP | 2011-500601 | A | 1/2011 |
| JP | 2014-527620 | A | 10/2014 |
| WO | WO-03/050295 | A2 | 6/2003 |
| WO | WO-2006/084030 | A2 | 8/2006 |
| WO | WO-2008/005937 | A2 | 1/2008 |
| WO | WO-2008/070472 | A2 | 6/2008 |
| WO | WO-2009/036092 | A2 | 3/2009 |
| WO | WO-2009/049184 | A2 | 4/2009 |
| WO | WO-2009/126310 | A2 | 10/2009 |
| WO | WO-2010/020618 | A1 | 2/2010 |
| WO | WO-2011/044394 | A1 | 4/2011 |
| WO | WO-2011/060328 | A1 | 5/2011 |
| WO | WO-2012/138894 | A1 | 10/2012 |
| WO | WO-2012/138896 | A1 | 10/2012 |
| WO | WO-2012/149493 | A2 | 11/2012 |
| WO | WO-2013/009655 | A2 | 1/2013 |
| WO | WO-2013/009657 | A1 | 1/2013 |
| WO | WO-2014/144715 | A1 | 9/2014 |
| WO | WO-2016/044629 | A1 | 3/2016 |

OTHER PUBLICATIONS

An et al., “The Heat Shock Protein 90 Antagonist Geldanamycin Alters Chaperone Association with p210bcr-abl and v-src Proteins before Their Degradation by the Proteasome”, Cell Growth & Differentiation, vol. 11, Jul. 2000, pp. 355-360.

Andersen et al., “Pathway-Based Identification of Biomarkers for Targeted Therapeutics: Personalized Oncology with PBK Pathway Inhibitors”, Science Translational Medicine, vol. 2, No. 43, 43ra55, Aug. 4, 2010, pp. 1-15.

Apsel et al., “Targeted polypharmacology: Discovery of dual inhibitors of tyrosine and phosphoinositide kinases”, Nature Chem. Biol., vol. 4, No. 11, Oct. 12, 2008, pp. 691-699.

Ashman et al., “Phosphoproteomics and cancer research”, Clin. Transl. Oncol., vol. 11, Apr. 7, 2009, pp. 356-362.

Bedford et al., “Protein Arginine Methylation in Mammals: Who, What, and Why”, Molecular Cell, vol. 33, Jan. 16, 2009, pp. 1-13.

Beliakoff et al., “Hsp90: an emerging target for breast cancer therapy”, Anti-Cancer Drugs, vol. 15, No. 7, May 18, 2004, pp. 651-662.

Bhojani et al., “Targeted Imaging and Therapy of Brain Cancer using Theranostic Nanoparticles”, Mol. Pharm., vol. 7, No. 6, Dec. 6, 2010, pp. 1921-1929.

Brehme et al., “Charting the molecular network of the drug target Bcr-Abl”, Proc. Natl. Acad. Sci., vol. 106, No. 18, May 5, 2009, pp. 7414-7419.

Breinig et al., “Targeting Heat Shock Protein 90 with Non-Quinone Inhibitors: A Novel Chemotherapeutic Approach in Human Hepatocellular Carcinoma”, Hepatology, vol. 50, No. 5, Jul. 31, 2009, pp. 102-112.

Briones, “Targeted therapy of BCL6-dependent diffuse large B-cell lymphomas by heat-shock protein 90 inhibition”, Expert Review of Hematology, vol. 3, No. 2, 2010 (published online Jan. 10, 2014), pp. 157-159.

Burke et al., “BCR-ABL: a multi-faceted promoter of DNA mutation in chronic myelogeneous leukemia”, Leukemia, vol. 24, May 6, 2010, pp. 1105-1112.

Caldas-Lopes et al., “Antitumor Efficacy of the Purine-Scaffold Hsp90 Inhibitor PU-H71 in Diffuse Large-B Cell Lymphoma”, Blood, The American Society of Hematology, vol. 112, No. 11, Nov. 1, 2008, pp. 1-4.

Caldas-Lopes et al., “Hsp90 inhibitor PU-H71, a multimodal inhibitor of malignancy, induces complete responses in triple-negative breast cancer models”, PNAS, vol. 106, No. 20, May 19, 2009, pp. 8368-8373.

Caldas-Lopes et al., “The Hsp90 inhibitor PU-H71 is a potent suppressor of metastasis in triple-negative breast cancer models”, Proceedings of the Annual Meeting of the American Association for Cancer Research, 2010, vol. 51, Abstract 5766, [online] <URL: http://cancerres.aacrjournals.org/content/70/8_Supplement/5766> (retrieved on Jul. 18, 2018).

Calderwood, “Heat shock proteins in breast cancer progression—a suitable case for treatment?” Int. J. Hyperthermia, vol. 26, No. 7, 2010, pp. 681-685.

Carayol et al., “Critical roles for mTORC2- and rapamycin-insensitive mTORC1-complexes in growth and survival of BCR-ABL-expressing leukemic cells”, Proc. Natl. Acad. Sci., vol. 107, No. 28, Jul. 13, 2010, pp. 12469-12474.

Cerchietti et al., “A purine scaffold heat shock protein 90 (Hsp90) inhibitor destabilizes BCL6 and has specific anti-tumor activity in BCL6 dependent lymphomas in vitro and in vivo”, Proceeding of the Annual Meeting of the American Association of Cancer Research, vol. 50, Apr. 18-22, 2009, pp. 1-2.

Cerchietti et al., “A purine scaffold Hsp90 inhibitor destabilizes BCL-6 and has specific antitumor activity in BCL-6-dependent B cell lymphomas”, Nature Medicine, vol. 15, No. 12, Dec. 22, 2009, pp. 1369-1376.

Chandarlapaty et al., “SNX2112, a Synthetic Heat Shock Protein 90 Inhibitor, Has Potent Antitumor Activity against HER Kinase-Dependent Cancers”, Clinical Cancer Research, vol. 14, No. 1, Jan. 1, 2008, pp. 240-248.

Chiosis et al., “Tumor Selectivity of Hsp90 Inhibitors: The Explanation Remains Elusive”, ACS Chemical Biology, vol. 1., No. 5, Jun. 16, 2006, pp. 279-284.

Chopra, “[N-11C-methyl]-[4-[(4-Methyl-1-piperazinyl)methyl)-N-[4-methyl-3-[[4-(3-pyridyl)-2-pyrimidinyl]amino]phenyl]benzamide”, Molecular Imaging & Contrast Agent Database (MICAD), Bethesda, MD, National Center for Biotechnology Information (US), 2004-2013, May 30, 2007, pp. 1-3.

Chou et al., “Quantitative Analysis of Dose-Effect Relationships: The Combined Effects of Multiple Drugs or Enzyme Inhibitors”, Adv. Enzyme Regul., vol. 22, 1984, pp. 27-55.

Chou, “Theoretical Basis, Experimental Design, and Computerized Simulation of Synergism and Antagonism in Drug Combination Studies”, Pharmacological Reviews, vol. 58, No. 3, Sep. 2006, pp. 621-681.

Citri et al., “The Achilles Heel of ErbB-2/HER2: Regulation by the Hsp90 Chaperone Machine and Potential for Pharmacological Intervention”, Cell Cycle, vol. 3, No. 2, Feb. 2004, pp. 51-60.

Covey et al., “Modulated multiparametric phosphoflow cytometry in hematological malignancies: technology and clinical applications”, Best Practice & Research Clinical Haematology, vol. 23, No. 3, Sep. 2010, pp. 319-331.

Da Rocha Dias et al., “Activated B-RAF Is an Hsp90 Client Protein That Is Targeted by the Anticancer Drug 17-Allylamino-17-Demethoxygeldanamycin”, Cancer Res., vol. 65, No. 23, Dec. 1, 2005, pp. 10686-10691.

De Groot et al., “STAT5 Activation by BCR-Abl Contributes to Transformation of K562 Leukemia Cells”, Blood, vol. 94, No. 3, Aug. 1, 1999, pp. 1108-1112.

(56) References Cited

OTHER PUBLICATIONS

Deininger et al., "Specific Targeted Therapy of Chronic Myelogenous Leukemia with Imatinib", Pharmacological Reviews, vol. 55, No. 3, Jul. 17, 2003, pp. 401-423 (2003).
Dezwaan et al., "HSP90: The Rosetta stone for cellular protein dynamics?", Cell Cycle, vol. 7, No. 8, Apr. 15, 2008, pp. 1006-1012.
Dickey et al., "The high-affinity HSP90-CHIP complex recognizes and selectively degrades phosphorylated tau client proteins", The Journal of Clinical Investigation, vol. 117, No. 3, Mar. 2007, pp. 648-658.
Dierov et al., "BCR/ABL translocates to the nucleus and disrupts an ATR-dependent intra-S phase checkpoint", Cancer Cell, vol. 5, Mar. 2004, pp. 275-285.
Eccles et al., "NVP-AUY922: A Novel Heat Shock Protein 90 Inhibitor Active against Xenograft Tumor Growth, Angiogenesis, and Metastasis", Cancer Research, vol. 68, No. 8, Apr. 15, 2008, pp. 2850-2860.
Erdjument-Bromage et al., "Examination of micro-tip reversed-phase liquid chromatographic extraction of peptide pools for mass spectrometric analysis", Journal of Chromatography A, vol. 826, No. 2, Nov. 27, 1998, pp. 167-181.
Extended European Search Report for EPO Appl. Ser. No. 12811358.6 dated Mar. 4, 2015 (6 pages).
Extended European Search Report for EPO Appl. Ser. No. 17156149.1 dated Oct. 4, 2017 (20 pages).
Extended European Search Report for EPO Appl. Ser. No. 19202091.5 dated Aug. 14, 2020 (12 pages).
Fabian et al., "A small molecule-kinase interaction map for clinical kinase inhibitors", Nature Biotechnology, vol. 23, No. 3, Feb. 13, 2005, pp. 329-336.
Gambhir, "Molecular Imaging of Cancer with Positron Emission Tomography", Sep. 2002, Nature Reviews: Cancer, vol. 2, pp. 683-693.
Ginos et al., "[13N)Cisplatin PET to Assess Pharmacokinetics of Intra-Arterial Versus Intravenous Chemotherapy for Malignant Brain Tumors", The Journal of Nuclear Medicine, vol. 28, No. 12, Dec. 1987, pp. 1844-1852.
Grbovic et al., "V600E B-Raf requires the Hsp90 chaperone for stability and is degraded in response to Hsp90 inhibitors", Proc. Natl. Acad. Sci., vol. 103, No. 1, Jan. 3, 2006, pp. 57-62.
Gyurkocza et al., "Antileukemic Activity of Shepherdin and Molecular Diversity of Hsp90 Inhibitors", Journal of the National Cancer Institute, vol. 98, No. 15, Aug. 2, 2006, pp. 1068-1077.
Hacker et al., "Regulation and Function of IKK and IKK-Related Kinases", Science's STKE, vol. 357, re13, Oct. 17, 2006, pp. 1-20.
Hanash et al., "The grand challenge to decipher the cancer proteome", Nature Reviews—Cancer, vol. 10, Sep. 2010, pp. 652-660.
He et al., "Identification of Potent Water Soluble Purine-Scaffold Inhibitors of the Heat Shock Protein 90", J. Med. Chem., vol. 49, No. 1, Dec. 8, 2005, pp. 381-390.
Hendriks et al., "Involvement of SLP-65 and Btk in tumor suppression and malignant transformation of pre-B cells", Seminars in Immunology, vol. 18, No. 1, Feb. 2006, pp. 67-76.
Higgins et al., "The Evolution of Imaging in Cancer: Current State and Future Challenges", Semin. Oncol., vol. 38, No. 1, Feb. 2011, pp. 3-15.
Holland et al., "Measuring the Pharmacodynamic Effects of a Novel Hsp90 Inhibitor on HER2/neu Expression in Mice Using 89ZR-DFO-Trastuzumab", PLoS ONE, vol. 5, No. 1, e8859, Jan. 25, 2010, pp. 1-11.
Horn et al., "Design and evaluation of genome-wide libraries for RNA interference screens", Genome Biology, vol. 11, No. R61, Jun. 15, 2010, pp. 1-12.
Howes et al., "A fluorescence polarization assay for inhibitors of Hsp90", Analytical Biochemistry, vol. 350, Jan. 23, 2006, pp. 202-213.
Immormino et al., "Structural and Quantum Chemical Studies of 8-Aryl-sulfanyl Adenine Class Hsp90 Inhibitors", Journal of Medicinal Chemistry, vol. 49, No. 16, Jul. 8, 2006, pp. 4953-4960.
International Search Report and Written Opinion for PCT Appl. Ser. No. PCT/US2012/045861 dated Jan. 28, 2013 (21 pages).
International Search Report and Written Opinion for PCT Appl. Ser. No. PCT/US2012/045864 dated Oct. 19, 2012 (11 pages).
Jaganathan et al., "Enhanced Sensitivity of Pancreatic Cancer Cells to Concurrent Inhibition of Aberrant Signal Transducer and Activator of Transcription 3 and Epidermal Growth Factor Receptor or Src", The Journal of Pharmacology and Experimental Therapeutics, vol. 333, No. 2, Jan. 25, 2010, pp. 373-381.
Janin, "ATPase inhibitors of heat-shock protein 90, second season", Drug Discovery Today, vol. 15, Nos. 9/10, Mar. 15, 2010, pp. 342-353.
Jennings et al., "Recent Advances in Flow Cytometry: Application to the Diagnosis of Hematologic Malignancy", Blood, vol. 90, No. 8, Oct. 15, 1997, pp. 2863-2892.
Kamal et al., "A high-affinity conformation of Hsp90 confers tumour selectivity on Hsp90 inhibitors", Nature, vol. 425, Sep. 25, 2003, pp. 407-410.
Kang et al., "Regulation of tumor cell mitochondrial homeostasis by an organelle-specific hsp90 chaperone network", Cell, vol. 13, Oct. 19, 2007, pp. 257-270.
Katzav, "Flesh and blood: The story of Vav1, a gene that signals in hematopoietic cells but can be transforming in human malignancies", Cancer Letters, vol. 255, No. 2, Oct. 8, 2007, pp. 241-254.
Klejman et al., "The Src family kinase Hck couples BCR/ABL to STAT5 activation in myeloid leukemia cells", The EMBO Journal, vol. 21, No. 21, Nov. 1, 2002, pp. 5766-5774.
Kolch et al., "Functional proteomics to dissect tyrosine kinase signalling pathways in cancer", Nature Reviews—Cancer, vol. 10, Aug. 19, 2010, pp. 618-629.
Le et al., "FAK silencing inhibits leukemogenesis in BCR/ABL-transformed hematopoietic cells", American Journal of Hematology, vol. 84, Feb. 19, 2009, pp. 273-278.
Leopoldo et al., "Developments in fluorescent probes for receptor research", Drug Discovery Today, vol. 14, Nos. 13/14, Jul. 2009, pp. 706-712.
Leung, "[18F]-N-(2-Chloro-6-methylphenyl)-2-(6-(4-(2-fluoroethyl)piperazin-1-yl)-2-methylpyrimidin-4-ylamino) thiazole-5-carboxamide", Molecular Imaging & Contrast Agent Database (MICAD), Bethesda (MD), National Center for Biotechnology Information (US), 2004-2010, Aug. 30, 2008, pp. 1-3.
Ley et al., "DNA sequencing of a cytogenetically normal acute myeloid leukemia genome", Nature, vol. 456, No. 7218, Nov. 6, 2008, pp. 66-72.
Li et al., "Physiological Modulation of Intestinal Motility by Enteric Dopaminergic Neurons and the D2 Receptor: Analysis of Dopamine Receptor Expression, Location, Development, and Function in Wild-Type and Knock-Out Mice", The Journal of Neuroscience, vol. 26, No. 10, Mar. 8, 2006, pp. 2798-2807.
Lim et al., "Structure, function and regulation of STAT proteins", Molecular BioSystems, vol. 2, Sep. 26, 2006, pp. 536-550.
Liu et al., "Use of radiolabelled choline as a pharmacodynamic marker for the signal transduction inhibitor geldananycin", British Journal of Cancer, vol. 87, No. 7, Sep. 23, 2002, pp. 783-789.
Llauger-Bufi et al., "Synthesis of Novel Fluorescent Probes for the Molecular Chaperone Hsp90", Bioorganic & Medicinal Chemistry Letters, vol. 13, No. 22, Nov. 17, 2003, pp. 3975-3978.
Lundh et al., "Biodistribution of Free 211At and 125I—in Nude Mice Bearing Tumors Derived from Anaplastic Thyroid Carcinoma Cell Lines", Cancer Biotherapy Radiopharmaceuticals, vol. 21, No. 6, Dec. 2006, pp. 591-600.
Luo et al., "Heat shock protein 90 in neurodegenerative diseases", Molecular Neurodegeneration, vol. 5, No. 24, Jun. 3, 2010, pp. 1-8.
Mahajan et al., "Transcription Factor STAT5A Is a Substrate of Bruton's Tyrosine Kinase in B Cells", The Journal of Biological Chemistry, vol. 276, No. 33, Jun. 18, 2001, pp. 31216-31228.
Maloney et al., "Gene and Protein Expression Profiling of Human Ovarian Cancer Cells Treated with the Heat Shock Protein 90 Inhibitor 17-allylamino-17-Demethoxygeldanamycin", Cancer Research, vol. 67, No. 7, Apr. 1, 2007, pp. 3239-3253.
Mankoff, "Molecular imaging to select cancer therapy and evaluate treatment response", The Quarterly Journal of Nuclear Medicine and Molecular Imaging, vol. 53, No. 2, Apr. 2009, pp. 181-192.

(56) References Cited

OTHER PUBLICATIONS

Marik et al., "Emerging Role of ImmunoPET in Receptor Targeted Cancer Therapy", Current Drug Delivery, vol. 8, Jan. 2011, pp. 70-78.
Marubayashi et al., "HSP90 is a therapeutic target in JAK2-dependent myeloproliferative neoplasms in mice and humans", The Journal of Clinical Investigation, vol. 120, No. 10, Oct. 2010, pp. 3578-3593.
McClellan et al., "Diverse Cellular Functions of the Hsp90 Molecular Chaperone Uncovered Using Systems Approaches", Cell, vol. 131, Oct. 5, 2007, pp. 121-135.
McCubrey et al., "Targeting survival cascades induced by activation of Ras/Raf/MEK/ERK, PI3K/PTEN/Akt/mTOR and Jak/STAT pathways for effective leukemia therapy", Leukemia, vol. 22, Mar. 13, 2008, pp. 708-722.
Mihailovic et al., "Protein Kinase D2 Mediates Activation of Nuclear Factor kappaB by Ber-Abl in Ber-Abl+ Human Myeloid Leukemia Cells", Cancer Research, vol. 64, Dec. 15, 2004, pp. 8939-8944.
Modi et al., "Combination of Trastuzumab and Tanespimycin (17-AAG, KOS-953) Is Safe and Active in Trastuzumab-Refractory HER-2-Overexpressing Breast Cancer: A Phase I Dose-Escalation Study", Journal of Clinical Oncology, vol. 25, No. 34, Dec. 1, 2007, pp. 5410-5417.
Moffat et al., "A lentiviral RNAi library for human and mouse genes applied to an arrayed viral high-content screen," Cell, vol. 124, Mar. 24, 2006, pp. 1283-1298.
Moulick et al., "Synthesis of a red-shifted fluorescence polarization probe for Hsp90", Bioorganic & Medicinal Chemistry Letters, vol. 16, No. 17, Jun. 22, 2006, pp. 4515-4518.
Munday et al., "Quantitative Proteomic Analysis of A549 Cells Infected with Human Respiratory Syncytial Virus", Molecular & Cellular Proteomics, vol. 9, No. 11, Jul. 20, 2010, pp. 2438-2459.
Murphy et al., "HER2-Positive Breast Cancer: Beyond Trastuzumab", Oncology (Williston Park), vol. 24, No. 5, Apr. 30, 2010, pp. 410-415.
Nagengast et al., "89Zr-Bevacizumab PET of Early Antiangiogenic Tumor Response to Treatment with HSP90 Inhibitor NVP-AUY922", The Journal of Nuclear Medicine, vol. 51, No. 5, Apr. 15, 2010, pp. 761-767.
Naka et al., "TGF-beta-FOXO signaling maintains leukaemia-initiating cells in chronic myeloid leukaemia", Nature, vol. 463, Feb. 4, 2010, pp. 676-678.
Nobukuni et al., "hvps34, an ancient player, enters a growing game: mTOR Complex1/S6K1 signaling" Current Opinion in Cell Biology, vol. 19, Feb. 23, 2007, pp. 135-141.
Nomura et al., "Activity-based protein profiling for biochemical pathway discovery in cancer", Nat. Rev. Cancer, vol. 10, No. 9, Sep. 2010, pp. 630-638.
Oda et al., "Calpain is a signal transducer and activator of transcription (STAT) 3 and STATS protease", Blood, vol. 99, No. 5, Mar. 1, 2002, pp. 1850-1852.
Papac et al., "Comparative in vitro and in vivo metabolism of MPC-3100, an oral HSP90 inhibitor, in rat, dog, monkey and human", 102nd AACR annual meeting, Cancer Research, vol. 71, Abstract No. 3233, Apr. 15, 2011, pp. 1-2.
Parsons et al., "An Integrated Genomic Analysis of Human Glioblastoma Multiforme", Science, vol. 321, No. 5897, Sep. 26, 2008, pp. 1807-1812.
Partial European Search Report for EPO Appl. Ser. No. 17156149.1 dated Jul. 5, 2017 (16 pages).
Pashtan et al., "Targeting Hsp90 prevents escape of breast cancer cells from tyrosine kinase inhibition", Cell Cycle, vol. 7, No. 18, Sep. 15, 2008, pp. 2936-2941.
Patel et al., "Advances in the discovery and development of heat-shock protein 90 inhibitors for cancer treatment", Expert Opin. Drug Discov., vol. 6, No. 5, May 2011, pp. 559-587.
Paukku et al., "STATs as critical mediators of signal transduction and transcription: lessons learned from STATS", Cytokine & Growth Factor Reviews, vol. 15, 2004, pp. 435-455.
Pentlow et al., "Quantitative Imaging of Iodine-124 with PET", The Journal of Nuclear Medicine, vol. 37, Sep. 1996, pp. 1557-1562.
Peters et al., "Multipararneter Flow Cytometry in the Diagnosis and Management of Acute Leukemia", Arch. Pathol. Lab. Med., vol. 135, Jan. 2011, pp. 44-54.
Pick et al., "High HSP90 Expression Is Associated with Decreased Survival in Breast Cancer", The Journal of Cancer Research, vol. 67, No. 7, Apr. 1, 2007, pp. 2932-2937.
Plescia et al., "Rational design of shepherdin, a novel anticancer agent", Cancer Cell, vol. 7, No. 5, May 16, 2005, pp. 457-468.
Powers et al., "Dual Targeting of HSC70 and HSP72 Inhibits HSP90 Function and Induces Tumor-Specific Apoptosis", Cancer Cell, vol. 14, Sep. 9, 2008, pp. 250-262.
Pratt et al., "The Hsp90 chaperone machinery regulates signaling by modulating ligand binding clefts", Journal of Biological Chemistry, vol. 283, No. 34, Aug. 22, 2008, pp. 22885-22889.
Ren, "Mechanisms of BCR-ABL in the pathogenesis of chronic myelogenous leukaemia", Nature Reviews—Cancer, vol. 5, Feb. 18, 2005, pp. 172-183.
Rix et al., "Target profiling of small molecules by chemical proteomics", Nature Chemical Biology, vol. 5, No. 9, Sep. 18, 2009, pp. 616-624.
Rodina et al., "Selective compounds define Hsp90 as a major inhibitor of apoptosis in small-cell lung cancer", Nature Chemical Biology, vol. 3, No. 8, Jul. 1, 2007, pp. 498-507.
Rodina et al., "The epichaperome is an integrated chaperome network that facilitates tumour survival", Nature, vol. 538, No. 7625, Oct. 20, 2016, pp. 397-401.
Roney et al., "124I-PUH71 PET Detects Upregulated HSP90 Breast Cancer Xenografts," Journal of Nuclear Medicine, vol. 52, No. 4, Apr. 2011, pp. 662-663 (16 total pages).
Rosso et al., "A New Model for Prediction of Drug Distribution in Tumor and Normal Tissues: Pharmacokinetics of Temozolomide in Glioma Patients", Cancer Research, vol. 69, No. 1, Jan. 1, 2009, pp. 120-127.
Saleem et al., "Plasma pharmacokinetic evaluation of cytotoxic agents radiolabelled with positron emitting radioisotopes", Cancer Chemother. Pharmacol., vol. 61, Jul. 18, 2007, pp. 865-873.
Salgia et al., "Increased tyrosine phosphorylation of focal adhesion proteins in myeloid cell lines expressing p210BCR/ABL", Oncogene, vol. 11, No. 6, Sep. 21, 1995, pp. 1149-1155.
Sawyers, "The Role of MYC in Transformation by BCR-ABL", Leukemia and Lymphoma, vol. 11, Suppl. 1, 1993, pp. 45-46.
Si et al., "Activated Ca2+/Calmodulin-Dependent Protein Kinase IIgamma Is a Critical Regulator of Myeloid Leukemia Cell Proliferation", Cancer Research, vol. 68, No. 10, May 15, 2008, pp. 3733-3742.
Stravopodis et al., "Drug-Mediated Targeted Disruption of Multiple Protein Activities Through Functional Inhibition of the Hsp90 Chaperone Complex", Current Medicinal Chemistry, vol. 14, Oct. 12, 2007, pp. 3122-3138.
Taldone et al., "A facile and efficient synthesis of d6-labeled PU-H71, a purine-scaffold Hsp90 inhibitor", Journal of Labelled Compounds and Radiopharmaceuticals, vol. 53, Dec. 3, 2009, pp. 47-49.
Taldone et al., "Design, Synthesis and Evaluation of Small Molecule Hsp90 Probes", Bioorg. Med. Chem. 2011, vol. 19, No. 8, Apr. 15, 2011, pp. 2603-2614.
Taldone et al., "Purine-Scaffold Hsp90 Inhibitors", Current Topics in Medicinal Chemistry, vol. 9, Sep. 7, 2009, pp. 1436-1446.
Taldone et al., "Radiosynthesis of the iodine-124 labeled Hsp90 inhibitor PU-H71", J. Labelled Comp. Radiopharm., vol. 53, No. 3, Mar. 2016, pp. 129-132.
Taldone et al., "Synthesis of purine-scaffold fluorescent probes for heat shock protein 90 with use in flow cytometry and fluorescence microscopy", Bioorganic & Medicinal Chemistry Letters, vol. 21, Jul. 14, 2011, pp. 5347-5352.
Taldone et al., "Targeting Hsp90: small molecule inhibitors and their clinical development", Curr. Opin. Pharmacol., vol. 8, No. 4, Aug. 2008, pp. 370-374.
Taliani et al., "New Fluorescent 2-Phenylindolglyoxylamide Derivatives as Probes Targeting the Peripheral-Type Benzodiazepine Receptor: Design, Synthesis, and Biological Evaluation", Journal of Medicinal Chemistry, vol. 50, No. 2, Dec. 22, 2006, pp. 404-407.

(56) References Cited

OTHER PUBLICATIONS

Tan et al., "Biomarker-Driven Early Clinical Trials in Oncology: A Paradigm Shift in Drug Development", The Cancer Journal, vol. 15, No. 5, Sep./Oct. 2009, pp. 406-420.
Trepel et al., "Targeting the dynamic HSP90 complex in cancer", Nature Reviews—Cancer, vol. 10, Aug. 2010, pp. 537-549.
Trinkle-Mulcahy et al., "Identifying specific protein interaction partners using quantitative mass spectrometry and bead proteomes", The Journal of Cell Biology, vol. 183, Oct. 20, 2008, pp. 223-239.
Tsaytler et al., "Novel Hsp90 partners discovered using complementary proteomic approaches", Cell Stress and Chaperones, vol. 14, Apr. 26, 2009, pp. 629-638.
Tsutsumi et al., "A small molecule cell-impermeant Hsp90 antagonist inhibits tumor cell motility and invasion", Oncogene, vol. 27, Oct. 29. 2007, pp. 2478-2487.
Usmani et al., "The anti-myeloma activity of a novel purine scaffold HSP90 inhibitor PU-H71 is via inhibition of both HSP90A and HSP90B1", Journal of Hematology & Oncology, vol. 3, No. 40, Oct. 26, 2010, pp. 1-8.
Vial et al., "Immunophenotyping of Acute Leukemia: Utility of CD45 for Blast Cell Identification", Methods in Cell Biology, vol. 64, Part B, 2001, pp. 343-358.
Vilenchik et al., "Targeting Wide-Range Oncogenic Transformation via PU24FCI, a Specific Inhibitor of Tumor Hsp90", Chemistry & Biology, vol. 11, Jun. 25, 2004, pp. 787-797.
Visioni et al., "Positron Emission Tomography (PET) for benign and malignant disease", Surg. Clin. North Am., vol. 91, No. 1, Feb. 1, 2011, pp. 249-266.
Whitesell et al., "HSP90 and the Chaperoning of Cancer", Nature Reviews—Cancer, vol. 5, Sep. 20, 2005, pp. 761-772.
Winkler et al., "Isolation and mass spectrometry of transcription factor complexes", Methods, vol. 26, Mar. 2002, pp. 260-269.
Workman et al., "Drugging the Cancer Chaperone HSP90: Combinatorial Therapeutic Exploitation of Oncogene Addiction and Tumor Stress", Ann. N.Y. Acad. Sci., vol. 1113, May 18, 2007, pp. 202-216.
Workman et al., "Minimally Invasive Pharmacokinetic and Pharmacodynamic Technologies in Hypothesis-Testing Clinical Trials of Innovative Therapies", Journal of the National Cancer Institute, vol. 98, No. 9, May 3, 2006, pp. 580-598.
Xu et al., "Protein tyrosine phosphatases in the JAK/STAT pathway", Front. Biosci., vol. 13, May 1, 2008, pp. 4925-4932.
Yang et al., "Targeted molecular imaging in oncology", Annals of Nuclear Medicine, vol. 20, No. 1, Jan. 2006, pp. 1-11.
Zhang et al., "Identification of new biomarkers for clinical trials of HSP90 inhibitors", Molecular Cancer Therapeutics, vol. 5, No. 5, May 26, 2006, pp. 1256-1264.
Zhao et al., "Methylation of RUNX1 by PRMT1 abrogates SIN3A binding and potentiates its transcriptional activity", Genes & Development, vol. 22, No. 5, Mar. 1, 2008, pp. 640-653.
Zuckier et al., "Kinetics of Perrhenate Uptake and Comparative Biodistribution of Perrhenate, Pertechnetate, and Iodide by Nal Symporter-Expressing Tissues In Vivo", The Journal of Nuclear Medicine, vol. 45, No. 3, Mar. 2004, pp. 500-507.
Zuehlke et al., "Hsp90 and co-chaperones twist the functions of diverse client proteins", Biopolymers, vol. 93, No. 3, Mar. 2010, pp. 211-217.

* cited by examiner

FIGURE 4D
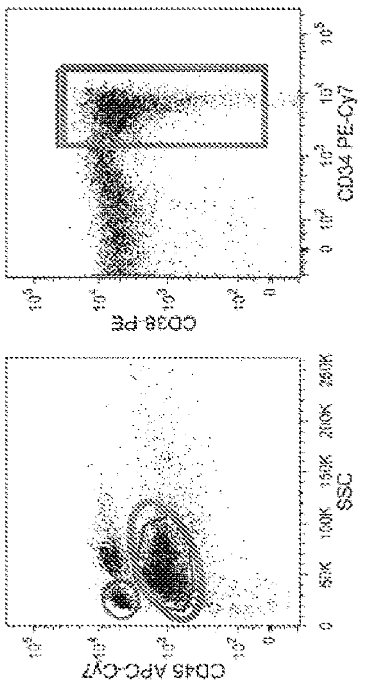
FIGURE 4E
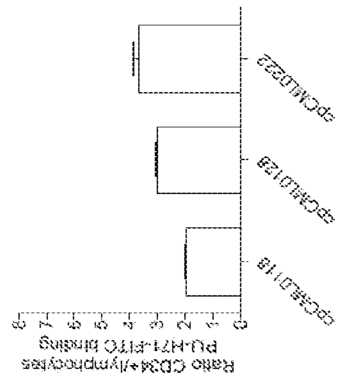
FIGURE 4F
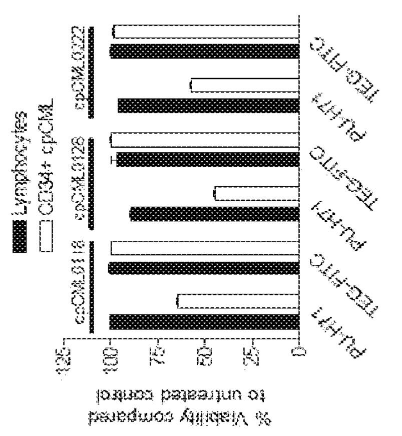
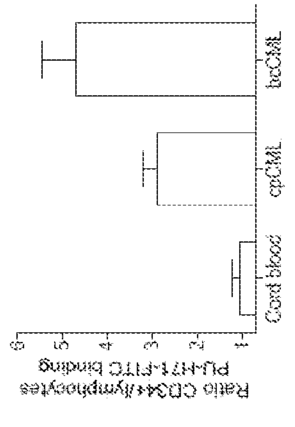
FIGURE 4G
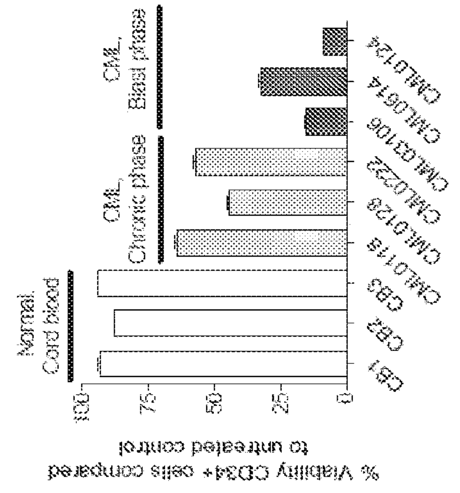
FIGURE 4H

| Sample | Phenotype | % blasts |
|---|---|---|
| #614 | Myeloid blast crisis | 91 |
| #124 | Myeloid blast crisis | 91 |
| #957 | Myeloid blast crisis | 90 |
| #203 | Myeloid blast crisis | 81 |
| #157 | Lymphoid blast crisis | 97 |
| #259 | Myeloid blast crisis | 18 |

GM

1

2 PU-H71

SNX-2112

NVP-AUY922

17-DMAG

17-AAG

PU-DZ13

PU-HZ151

Texas Red

NBD

FITC

3

4 PU-H71-FITC1

5 PU-H71-TR

6

7

8 PU-H71-NBD1

9 PU-H71-FITC2

2 PU-H71

10 PU-H71-NBD2

11

12

13

14 PU-H71-FITC3

15 PU-H71-NBD3

| | DMSO | FITC9 | PU-FITC | Ratio PUFITC (EpCAM+/ CD45+CD14- |
|---|---|---|---|---|
| CD45+CD14- | 3.15 | 13.5 | 105 | 84.32 |
| EpCAM+ | 78.4 | 209 | 7924 | |

PU-H71

$[^{124}I]$-PU-H71

FIGURE 31A
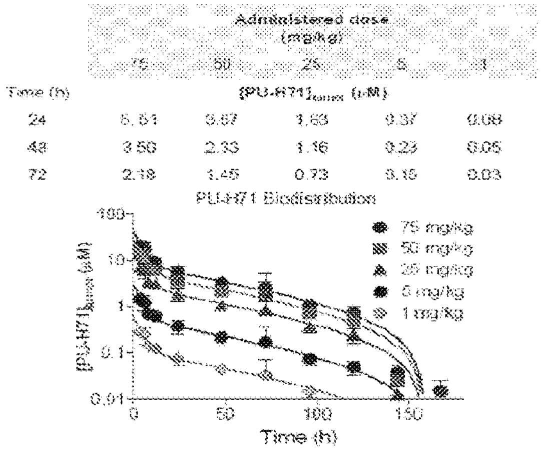
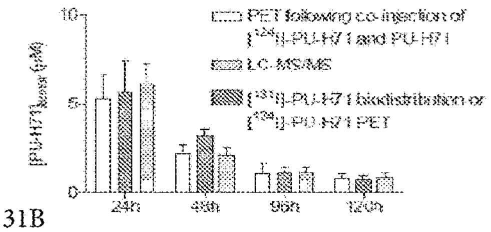
FIGURE 31B
FIGURE 31C
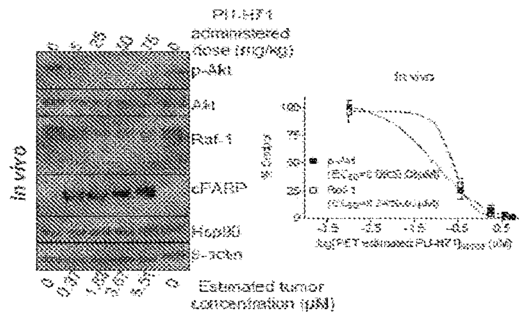
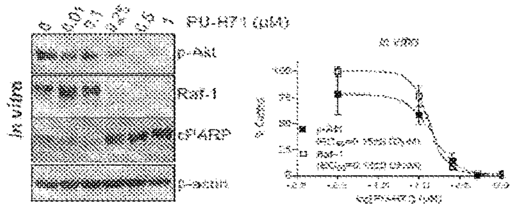
FIGURE 31D
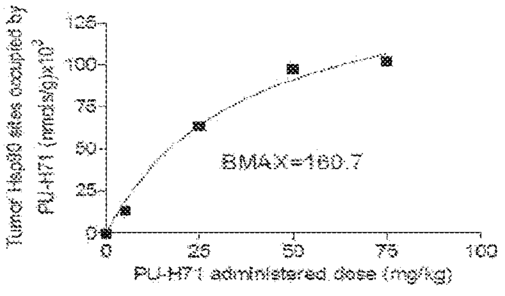
FIGURE 31E
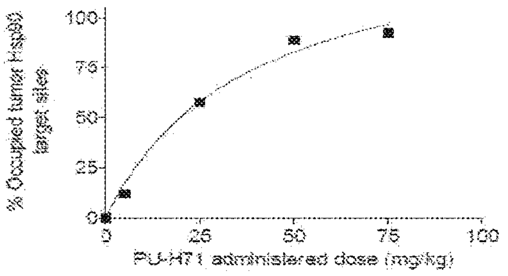
FIGURE 31F FIGURE 32A
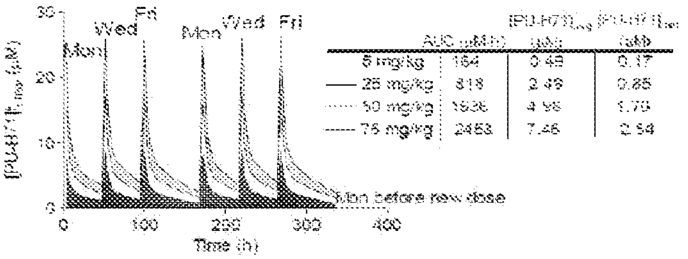
FIGURE 32B
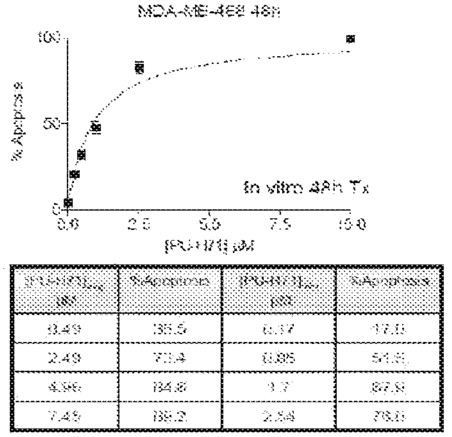
FIGURE 32C
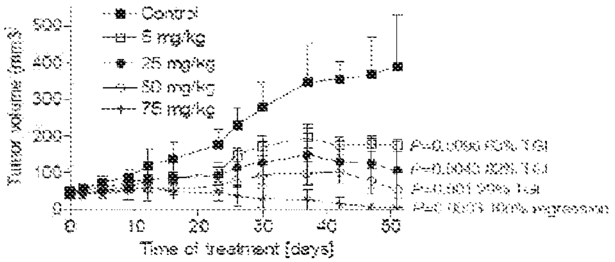
FIGURE 32D
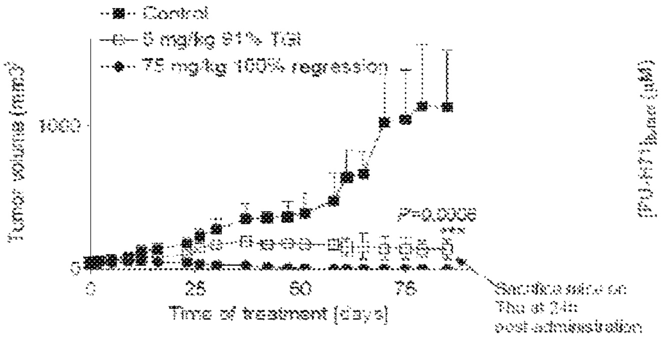
FIGURE 32E
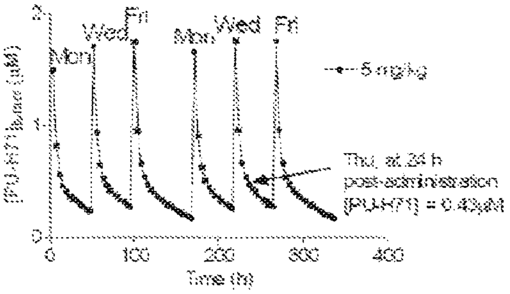
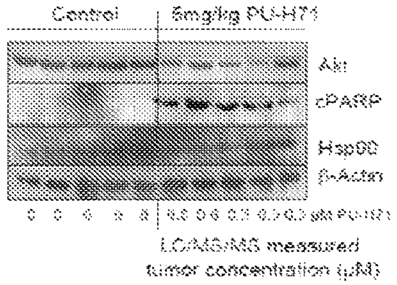
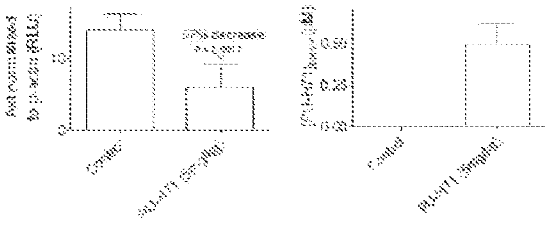
FIGURE 32F
FIGURE 32G

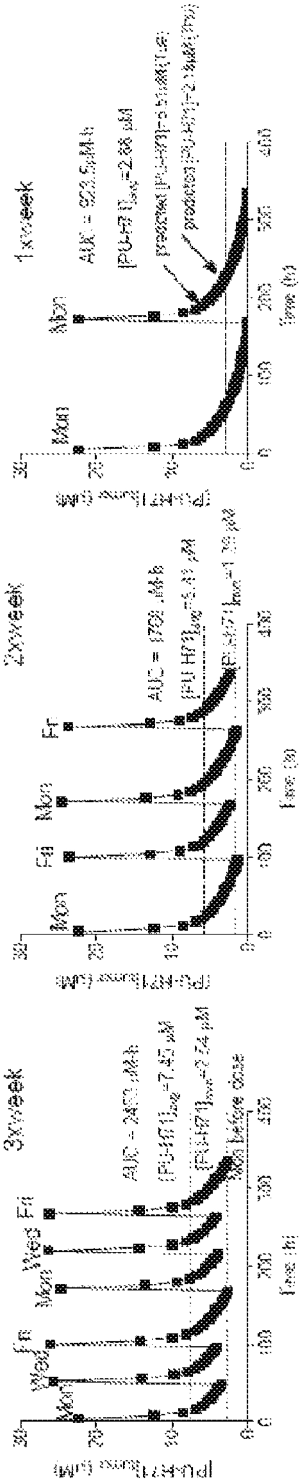
FIGURE 33A
In vitro 48h Tx
| $[PU\text{-}H71]_{avg}$ µM | %Apoptosis | $[PU\text{-}H71]_{min}$ µM | %Apoptosis |
|---|---|---|---|
| 2.68 | 78.2 | 0 | 0 |
| 5.41 | 85.7 | 1.29 | 59.0 |
| 7.45 | 89.2 | 2.54 | 76.0 |
FIGURE 33B
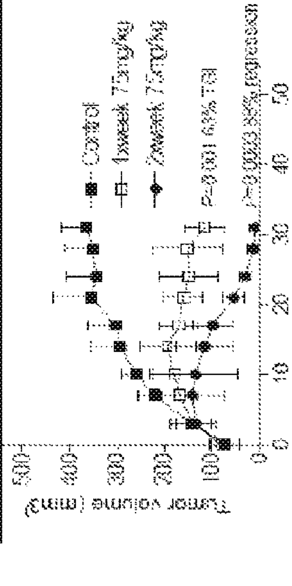
FIGURE 33C
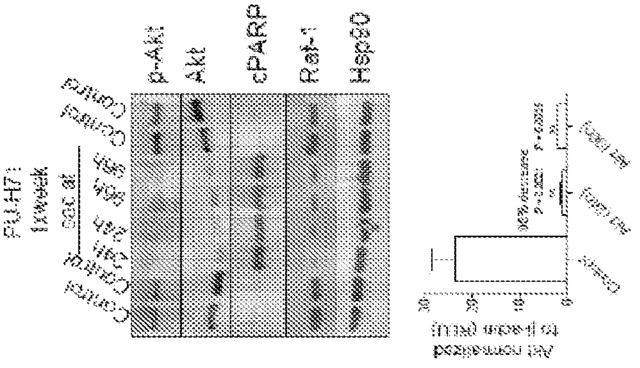
FIGURE 33D
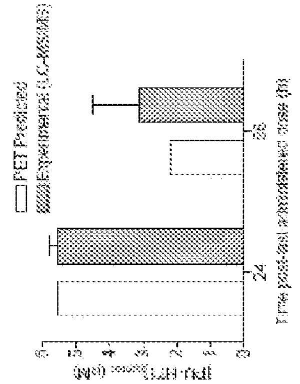
FIGURE 33E FIGURE 37A
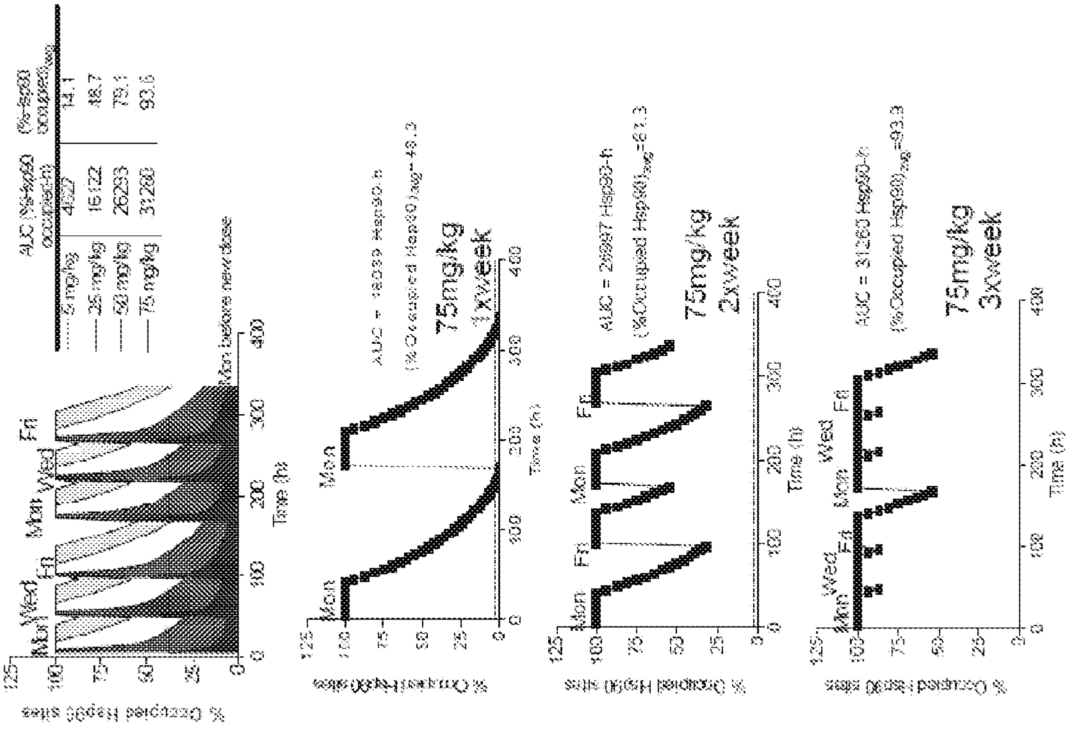
FIGURE 37B
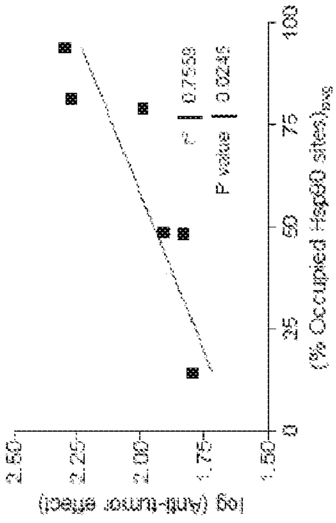
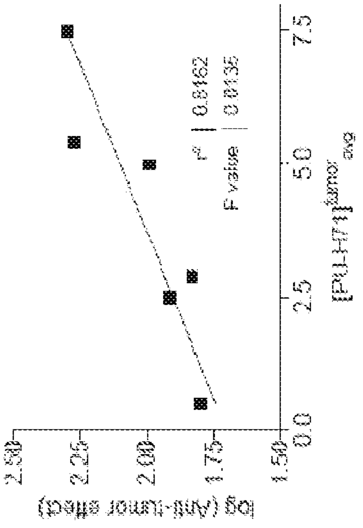
FIGURE 37C FIGURE 38A
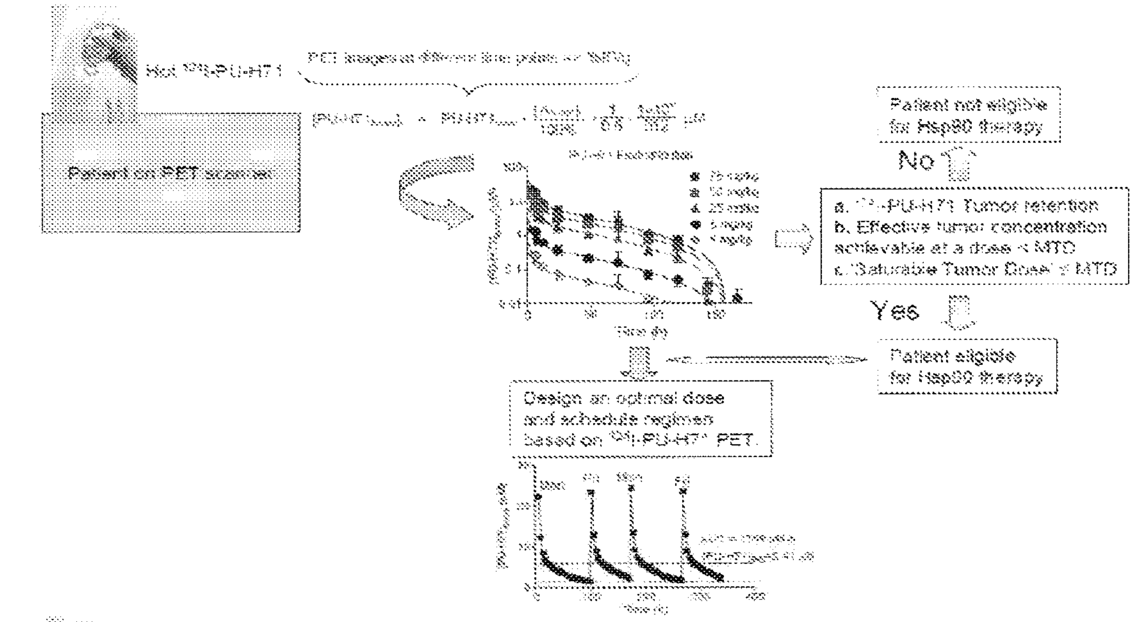
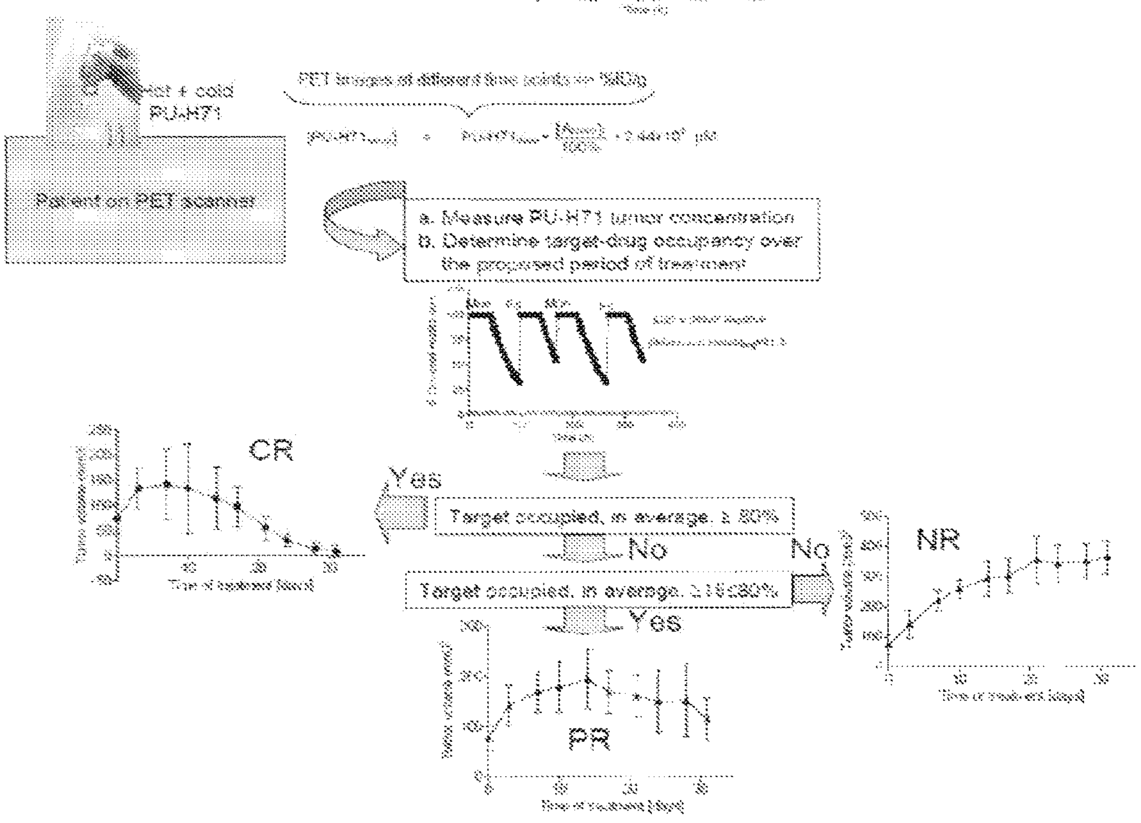
FIGURE 38B

USES OF LABELED HSP90 INHIBITORS

1. CROSS REFERENCE TO RELATED APPLICATIONS

This application is a continuation application of U.S. application Ser. No. 16/934,881, filed Jul. 20, 2020, now U.S. Pat. No. 11,607,465, which is a continuation of U.S. application Ser. No. 14/131,420, filed Jun. 12, 2014, which is a U.S. National Stage Application of International Application No. PCT/US2012/045861, filed Jul. 6, 2012, which claims the benefit under 35 U.S.C. § 119(e) of U.S. Provisional Application No. 61/506,010, filed Jul. 8, 2011, the contents of all of which are incorporated herein in their entireties by reference thereto.

SEQUENCE LISTING

The instant application contains a Sequence Listing which has been submitted electronically in XML format and is hereby incorporated by reference in its entirety. Said XML copy, created Sep. 7, 2023, is named 115872-1076_SequenceListing.xml and is 36,864 bytes in size.

2. BACKGROUND

To maintain homeostasis, cells employ intricate molecular machineries comprised of thousands of proteins programmed to execute well-defined functions. Dysregulation of these pathways, through protein mis-expression or mutation, can lead to biological advantages that confer a malignant phenotype. Although at the cellular level such dysregulation may be beneficial (i.e., favoring increased survival), at the molecular level this requires cells to invest energy in maintaining the stability and function of these proteins. It is believed that to maintain these proteins in a pseudo-stable state, cancer cells co-opt molecular chaperones, including HSP90[32,33].

In support of this hypothesis, HSP90 is recognized to play important roles in maintaining the transformed phenotype[32,33]. HSP90 and its associated co-chaperones assist in the correct conformational folding of cellular proteins, collectively referred to as “client proteins”, many of which are effectors of signal transduction pathways controlling cell growth, differentiation, the DNA damage response, and cell survival. Tumor cell addiction to deregulated proteins (i.e. through mutations, aberrant expression, improper cellular translocation etc) can thus become critically dependent on HSP90[33].

The rationale for HSP90 therapy in various forms of cancers is now well-supported by preclinical and clinical studies including in disease resistant to standard therapy[91-97]. For instance, studies have demonstrated a notable sensitivity of certain HER2+ tumors to HSP90 inhibitors[98,99]. In these tumors, 17-AAG (also called Tanespimycin) and 17-DMAG (Alvespimycin) elicited responses even, and in particular, in patients with progressive disease after trastuzumab therapy[98]. Other HSP90 inhibitors, such as PU-H71, when tested pre-clinically in a number of triple-negative breast cancer mouse models, delivered the most potent targeted single-agent anti-tumor effect yet reported in this difficult-to-treat breast cancer subtype[100].

While these data strongly support the use of HSP90 inhibitors in cancer, there is at the moment no clear consensus on how to identify those patients most-likely to benefit from HSP90 therapy[101,102]. This is especially problematic knowing that for a successful development of targeted agents it is essential to define the patient subpopulation that should receive the drug (i.e., tumors with EGFR mutations for tarceva). Such selection may reduce the number of patients receiving ineffective treatment and decrease the staggering number of targeted oncology agents that fail in late-stage clinical trials.

Further, there is no clinical assay that can non-invasively ascertain HSP90-target inhibition. While pharmacodynamic monitoring of peripheral blood lymphocytes has provided a readily accessible and reproducible index of in vivo biologic activity of HSP90 inhibitors in clinical trials, drug effects in normal tissue do not predict tumor-specific activity[97,101,102]. Judicious use of biopsies to measure pharmacodynamic changes has remained an important way to assay for target modulation, but this method remains limited because of the logistical and ethical issues associated with invasive assays. As an alternative, changes in the levels of tumor HER2 and VEGF levels is now being investigated using zirconium 89 labeled antibodies[103,104] and of soluble HER2 extracellular domain levels in patient sera by ELISA[105], but these studies are restricted to the subset of breast tumors that express these biomarkers.

Accordingly, there exists a strong need for biomarkers in HSP90 targeted therapy: The majority of cancer patients are treated with novel, experimental therapies, in many cases with little insight into the mechanism of action of the specific agent, the suitability of a particular treatment for different disease subsets, and little knowledge into optimal dose and scheduling of therapeutics in different malignant settings. The end result is empiric clinical investigation, in which patients with refractory malignancies are treated with a spectrum of novel agents without knowledge of which therapeutic approaches are best for different clinical contexts.

HSP90 is a highly sought target in cancer because of its critical role in stabilizing and folding proteins involved in oncogenic transformation. Given their potential to degrade a number of different oncoproteins and affect multiple signaling pathways, HSP90 inhibitors (HSP90i) have been hypothesized to be active in a wide variety of cancers. Early clinical trials have confirmed the therapeutic potential of this approach in a subset of tumors, but finding biomarkers to predict which cancers and patient populations will be most sensitive to such treatment has proven challenging. Such poor understanding and selection of the adequate patient population has led to a large number of emerging HSP90 cancer therapeutics progressing slowly or failing to continue development. Immediate efforts to identify the responsive population and to develop a companion diagnostic assay for HSP90 therapy are therefore urgently needed.

The design of a proper dose and schedule needed to achieve anti-tumor efficacy is also poorly understood in HSP90 therapy. Plasma pharmacokinetics generally provide data informative for the design of therapeutic dosing, with the plasma area under the curve (AUC) often as a metric of systemic drug exposure. However, for HSP90 inhibitors, the concentration and duration of retention of drugs in tumor tissues, and not in blood, determines their anti-tumor effect[106-109]. Specifically, most HSP90 inhibitors are characterized by an atypical pharmacokinetic profile of rapid clearance from plasma and normal tissues but relatively prolonged drug retention in tumors (i.e. for over 12-48 h post-administration). As such, clinical understanding of tumor response to HSP90 therapy remains severely limited if response is correlated with the injected dose, rather than the tumor dose. The limited value of plasma pharmacokinetics and the importance of tumor dose for tumor response suggest the need for the clinical development of an assay of tumor pharmacokinetics for HSP90 inhibitors. A validated, clinically practical non-invasive assay of tumor HSP90 would enable therapeutic dosing to focus upon achieving a steady-state tumor drug concentration, rather than a surrogate steady-state plasma concentration. Such assay could indicate if at or below a maximum permitted dosage, therapeutically effective tumor concentrations could be achieved. In case of contrary, patients could pursue an alternative treatment sparing them needless exposure to potential drug toxicity without a clinical benefit.

To overcome these limitations associated with HSP90 therapy, we here design and develop a non-invasive assay that we propose will facilitate the optimal clinical implementation, development and use of HSP90 inhibitors in cancers.

3. SUMMARY OF DISCLOSURE

This invention provides methods of using labeled HSP90 inhibitors to improve treatment of cancer patients with HSP90 inhibitors.

The disclosure provides evidence that the abundance of this particular "oncogenic HSP90" species, which is not dictated by HSP90 expression alone, predicts for sensitivity to HSP90 inhibition therapy, and thus is a biomarker for HSP90 therapy. The disclosure also provides evidence that identifying and measuring the abundance of this oncogenic HSP90 species in tumors predicts of response to HSP90 therapy. "Oncogenic HSP90" is defined herein as the HSP90 fraction that represents a cell stress specific form of chaperone complex, that is expanded and constitutively maintained in the tumor cell context, and that may execute functions necessary to maintain the malignant phenotype. Such roles are not only to regulate the folding of overexpressed (i.e. HER2), mutated (i.e. mB-Raf) or chimeric proteins (i.e. Bcr-Abl), but also to facilitate scaffolding and complex formation of molecules involved in aberrantly activated signaling complexes (i.e. STAT5, BCL6). While the tumor becomes addicted to survival on a network of HSP90-oncoproteins, these proteins become dependent on "oncogenic HSP90" for functioning and stability. This symbiotic interdependence suggests that addiction of tumors to HSP90 oncoproteins equals addiction to "oncogenic HSP90". Measuring the abundance of the latter is a read-out of the first, and therefore, in accordance with the present disclosure, is a biomarker for HSP90 therapy enrichment.

Furthermore, we show that HSP90 forms biochemically distinct complexes in malignant cells. A major fraction of cancer cell HSP90 retains "housekeeping" chaperone functions similar to normal cells, whereas a functionally distinct HSP90 pool enriched or expanded in cancer cells (i.e., "oncogenic HSP90") specifically interacts with oncogenic proteins required to maintain tumor cell survival, aberrant proliferative features and invasive and metastatic behavior.

To measure in a tumor-by-tumor manner the abundance of the "oncogenic HSP90", the invention also provides chemical tools. Such tools include fluorescently labeled and ANCA-labeled HSP90 inhibitors, biotinylated HSP90 inhibitors and radiolabeled inhibitors that specifically identify and interact with this tumor "oncogenic HSP90" species, making it feasible to measure the abundance of the "oncogenic HSP90" species in different types of tumors, tumor cells, tumor-supporting cells and tumor-associated biological formations, such as in hematologic malignancies, solid tumors and liquid tumors, and thus, measure and predict sensitivity to HSP90 inhibition therapy. These may be in the form of but not limited to cancer cells in a solid or liquid tumor, cancer stem cells, circulating tumor cells, tumor supporting immune cells, exosomes and tumor-supporting progenitor cells.

In one aspect, the disclosure provides a method for determining whether a tumor will likely respond to therapy with an HSP90 inhibitor which comprises the following steps:

(a) contacting the tumor or a sample containing cells from the tumor with a detectably labeled HSP90 inhibitor which binds preferentially to a tumor-specific form of HSP90 present in a tumor or tumor cells;

(b) measuring the amount of labeled HSP90 inhibitor bound to the tumor or the tumor cells in the sample; and (c) comparing the amount of labeled HSP90 inhibitor bound to the tumor or the tumor cells in the sample measured in step (b) to the amount of labeled HSP90 inhibitor bound to a reference;

wherein a greater amount of labeled HSP90 inhibitor bound to the tumor or the tumor cells measured in step (b) as compared with the reference amount indicates the tumor will likely respond to the HSP90 inhibitor.

In one embodiment the reference is from cells of the same patient with the tumor. The reference can be normal cells from the cancer patient. For instance, the normal cells can be lymphocytes from a patient with a blood tumor, leukocytes from a patient with circulating tumor cells or normal tissue surrounding a solid tumor. In another embodiment the reference is a tumor cell or another cell from the cancer patient with little to no expression of the oncogenic HSP90. In another embodiment, the reference is from cells of a different patient than the patient with the tumor. For instance, the reference can be from cells of a healthy individual or cells with little to no expression of the oncogenic HSP90 from a cancer patient other than the patient with the tumor to be measured.

In one aspect, the disclosure provides a method for determining whether a tumor will likely respond to therapy with an HSP90 inhibitor which comprises the following steps:

(a) contacting the tumor or a sample containing cells from the tumor with a first detectably labeled HSP90 inhibitor which binds preferentially to a tumor-specific form of HSP90 present in a tumor or tumor cells and a second detectably labeled inhibitor which has minimal or no binding to the tumor-specific form of HSP90;

(b) measuring the amount of first labeled inhibitor and second labeled inhibitor bound to the tumor or the tumor cells in the sample; and (c) comparing the amount of first labeled inhibitor bound to the tumor or the tumor cells with the amount of second labeled inhibitor bound to the tumor or tumor cells, wherein a greater amount of first labeled inhibitor bound to the tumor or tumor cells as compared with the second labeled inhibitor bound to the tumor or tumor cells indicates the tumor will likely respond to the HSP90 inhibitor.

In one embodiment, the labeled HSP90 inhibitor is fluorescently labeled or ANCA-labeled inhibitor that is cell permeable and that selectively binds to "oncogenic HSP90". For example, different fluorescently labeled and ANCA-labeled versions of the HSP90 inhibitor PU-H71 are provided that have been optimized for use in flow cytometry and for the analysis of cancer cells found in or isolated from a solid or liquid tumor, cancer stem cells, circulating tumor cells, tumor supporting immune cells, exosomes and tumor-supporting progenitor cells, and for use in tissue staining for samples obtained by several interventional methods such as biopsies, surgeries and fine needle aspirates.

In one such embodiment, we show that fluorescently labeled inhibitors such as PU-H71-FITC2 (Section 5.2.1.1.) can be used to measure the abundance of "oncogenic HSP90" in tissues obtained from such sources as biopsies and surgery specimens. In another embodiment, we show that fluorescently labeled inhibitors such as PU-H71-FITC2 can be used to measure the abundance of "oncogenic HSP90" in established cancer cell lines or in primary cancer cells. In still another embodiment we show that fluorescently labeled inhibitors can be used to measure the abundance of "oncogenic HSP90" in cells isolated from cancer specimens such as from tumors, in cancer stem cells, in circulating tumor cells and in cancer cells obtained from fine needle aspirates. In still other embodiments, we show that the other fluorescently labeled, ANCA-labeled and biotinylated HSP90 inhibitors that are also useful to perform the above mentioned measurements.

In another embodiment, the labeled HSP90 inhibitor is a radiolabeled inhibitor that selectively binds to "oncogenic HSP90". For example, different versions of radiolabeled PU-H71 have been optimized for PET imaging. In a particular embodiment, iodine 124 radiolabeled versions of PU-H71 are for PET imaging of solid and liquid tumors. The radiolabeled inhibitors can be used to image numerous types of primary and metastatic cancers including but not limited to colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, leukemias, myelomas, myeloproliferative neoplasms and gynecologic cancers including ovarian, cervical, and endometrial cancers.

The disclosure further provides means to measure in a tumor-by-tumor manner the abundance of the "oncogenic HSP90" in solid tumors such as, but not limited to, those tumors listed above and in liquid tumors, such as, but not limited to, those associated with lymphomas, leukemias, myelomas and myeloproliferative neoplasms. In one embodiment, the invention shows that by the use of Iodine 124 labeled HSP90 inhibitors that specifically interact with the "oncogenic HSP90" it is possible to use non-invasively PET imaging and quantify the "oncogenic HSP90" in patients, in solid tumors and liquid tumors.

In one aspect, the disclosure provides a method for determining whether a patient with hematologic malignancies such as blood cancer (e.g., leukemias) will likely respond to therapy with an HSP90 inhibitor which comprises contacting a sample containing cancer cells from the patient and reference non-cancer cells with a cell permeable fluorescently labeled HSP90 inhibitor that binds preferentially to a tumor-specific form of HSP90 present in the cancer cells of the patient, measuring the amount of fluorescently labeled HSP90 inhibitor bound to the cancer cells and non-cancer in the sample, and comparing the amount of the fluorescently labeled HSP90 inhibitor bound to the cancer cells with the amount of the fluorescently labeled HSP90 inhibitor bound to the non-cancer cells, wherein a greater amount of fluorescently labeled HSP90 inhibitor bound to the cancer cells than the non-cancer cells indicates the tumor will likely respond to the HSP90 inhibitor.

In one such embodiment the reference normal cells are normal cells (e.g., lymphocytes) which are from the same patient as the cancer cells. In another embodiment, the reference non-cancer cells are obtained from a different patient than the cancer patient.

In another aspect, the disclosure provides a method for determining whether a patient with a solid tumor will likely respond to therapy with an HSP90 inhibitor which comprises contacting a sample, such as obtained from biopsy, surgery, fine needle aspirates or other interventional procedure, containing cancer cells and non-cancer cells from the patient (e.g. surrounding stroma, benign cells or other types of normal cells in the specimen) with a cell permeable fluorescently labeled HSP90 inhibitor that binds preferentially to a tumor-specific form of HSP90 present in the cancer cells of the patient, measuring the amount of fluorescently labeled HSP90 inhibitor bound to the cancer cells and non-cancer cells in the sample, and comparing the amount of the fluorescently labeled HSP90 inhibitor bound to the cancer cells with the amount of the fluorescently labeled HSP90 inhibitor bound to the non-cancer cells, wherein a greater amount of fluorescently labeled HSP90 inhibitor bound to the cancer cells than the non-cancer cells indicate that the tumor will likely respond to the HSP90 inhibitor.

The disclosure also provides a method for determining whether a patient with a solid tumor will likely respond to therapy with an HSP90 inhibitor which comprises contacting a sample containing circulating cancer cells and non-cancer cells (e.g., leukocytes) from the patient with a cell permeable fluorescently labeled HSP90 inhibitor that binds preferentially to a tumor-specific form of HSP90 present in the cancer cells of the patient, measuring the amount of fluorescently labeled HSP90 inhibitor bound to the cancer cells and non-cancer in the sample, and comparing the amount of the fluorescently labeled HSP90 inhibitor bound to the cancer cells with the amount of the fluorescently labeled HSP90 inhibitor bound to the non-cancer cells, wherein a greater amount of fluorescently labeled HSP90 inhibitor bound to the cancer cells than the non-cancer cells indicates the tumor will likely respond to the HSP90 inhibitor.

In an alternative embodiment, the reference non-cancer cells are obtained from a patient other than the patient with the tumor In another aspect, the disclosure provides methods for using radiolabeled HSP90 inhibitors to determine patients who will be susceptible to HSP90 inhibition therapy.

In one such embodiment, the disclosure provides methods for determining whether a cancer patient with an imageable tumor will likely respond to therapy with an inhibitor of HSP90 which comprises the following steps:

(a) administering to the patient a radiolabeled HSP90 inhibitor which binds preferentially to a tumor-specific form of HSP90 present in the tumor or in tumor cells of the tumor;

(b) measuring uptake of the radiolabeled HSP90 inhibitor by the patient's tumor at one or more time points after the administration in step (a);

(c) measuring uptake of the radiolabeled HSP90 inhibitor by a predetermined healthy tissue or blood of the patient at said one or more time points after the administration in step (a);

(d) computing a ratio of the uptake measured at one or multiple time points in step (b) with the uptake measured at the same time points in step (c); and (e) determining the likelihood the cancer patient will respond to therapy with the inhibitor of HSP90, wherein a ratio greater than 2 computed in step (d) at one or multiple time points indicates that the patient will likely respond.

In another embodiment, the disclosure provides a method for determining whether a cancer patient with an imageable tumor will likely respond to therapy with an inhibitor of HSP90 which comprises the following steps:

(a) administering to the patient a radiolabeled HSP90 inhibitor which binds preferentially to a tumor-specific form of HSP90 present in the tumor or in tumor cells of the tumor;

(b) measuring uptake of the radiolabeled HSP90 inhibitor by the patient's tumor at one or more time points more than 4 hours after the administration in step (a), wherein an uptake of the inhibitor at said one or more time points relative to the uptake in healthy tissue surrounding the tumor indicates that the patient will likely respond to therapy with an inhibitor of HSP90.

In yet another embodiment, the disclosure provides a method for determining whether an imageable tumor will likely respond to therapy with an inhibitor of HSP90 which comprises the following steps:

(a) administering to the patient a radiolabeled HSP90 inhibitor which binds preferentially to a tumor-specific form of HSP90 present in the tumor or in tumor cells of the tumor;

(b) visually inspecting by PET the uptake of the radiolabeled inhibitor in the tumor or in tumor cells of the tumor at one or more time points 2 hours or more following administration of the radiolabeled HSP90 inhibitor in step (a), (c) comparing the PET image obtained in step (b) with the PET image obtained in healthy tissue surrounding the tumor at said one or more time points;

wherein the presence of an illuminated region in the PET image in the tumor or in tumor cells of the tumor at said one or more time points indicates that the patient will likely respond to HSP90 inhibition therapy.

In still another embodiment, the disclosure provides a method for determining whether a specific cancer patient with a tumor expressing the oncogenic HSP90 will likely respond to therapy with a defined dose of an inhibitor of HSP90 which comprises the following steps:

(a) administering to the patient a radiolabeled form of the HSP90 inhibitor which binds preferentially to a tumor-specific form of HSP90 present in the tumor or in tumor cells of the tumor;

(b) measuring uptake of the radiolabeled form of the HSP90 inhibitor by the patient's tumor at one or more time points after the administration in step (a);

(c) calculating for the defined dose of the HSP90 inhibitor, the concentrations of the HSP90 inhibitor which would be present in the patient's tumor at each of said one or more time points, based on the uptake measured at said one or more time points in step (b); and (d) comparing the concentrations of the HSP90 inhibitor calculated in step (c) with reference concentrations of the HSP90 inhibitor which would need to be present in the tumor at said one or more time points for the HSP90 inhibitor to be effective in treating the tumor, wherein the patient will likely respond to therapy with the defined dose of the HSP90 inhibitor if the concentrations of the HSP90 inhibitor calculated in step (c) would equal or exceed the concentrations of the HSP90 inhibitor needed to effectively treat the tumor.

In another aspect, we show that radiolabeled HSP90 inhibitors can be used to determine effective doses and dosing schedules of HSP90 inhibitors.

In one such embodiment, the disclosure provides a method for determining whether a specific cancer patient with a tumor expressing the oncogenic HSP90 will likely respond to therapy with a defined dose of an inhibitor of HSP90 which comprises the following steps:

(a) administering to the patient a radiolabeled form of the HSP90 inhibitor which binds preferentially to a tumor-specific form of HSP90 present in the tumor or in tumor cells of the tumor;

(b) measuring uptake of the radiolabeled form of the HSP90 inhibitor by the patient's tumor at one or more time points after the administration in step (a);

(c) calculating for the defined dose of the HSP90 inhibitor, the concentrations of the HSP90 inhibitor which would be present in the patient's tumor at each of said one or more time points, based on the uptake measured at said one or more time points in step (b); and (d) comparing the exposure of the tumor to the HSP90 inhibitor calculated in step (c) with a reference exposure to the HSP90 inhibitor which would need to be present in the tumor at said one or more time points for the HSP90 inhibitor to be effective in treating the tumor, wherein the patient will likely respond to therapy with the defined dose of the HSP90 inhibitor if the tumor exposure to the HSP90 inhibitor calculated in step (c) would equal or exceed the tumor exposure to the HSP90 inhibitor needed to effectively treat the tumor.

Additional embodiments include a method for determining, for a specific cancer patient with an imageable tumor, an effective dose and frequency of administration for therapy with an inhibitor of HSP90; a method for determining the concentration of a HSP90 inhibitor present in an imageable tumor in a cancer patient; and a method for determining or monitoring the responsiveness to therapy with an inhibitor of HSP90 of a tumor in a cancer patient.

In yet another embodiment, this disclosure provides a method for determining, for a specific cancer patient with a tumor that expresses the oncogenic HSP90, an effective dose and frequency of administration for therapy with an inhibitor of HSP90 which comprises the following steps:

(a) administering to the patient a radiolabeled form of the HSP90 inhibitor which binds preferentially to a tumor-specific form of HSP90 present in a tumor or tumor cells;

(b) measuring uptake of the radiolabeled form of the HSP90 inhibitor by the patient's tumor at one or more time points after the administration in step (a); and (c) calculating the dose and frequency of administration needed to maintain in the tumor at each of said one or more time points a concentration of the HSP90 inhibitor effective to treat the tumor, based on the uptake measured at said one or more time points in step (b), thereby determining, for the cancer patient, the effective dose and frequency of administration for therapy with the inhibitor of HSP90.

In still another embodiment, this disclosure provides a method for determining, for a specific cancer patient with a tumor expressing the oncogenic HSP90, an effective dose and frequency of administration for therapy with an inhibitor of HSP90 which comprises the following steps:

(a) administering to the patient a radiolabeled form of the HSP90 inhibitor which binds preferentially to a tumor-specific form of HSP90 present in a tumor or tumor cells;

(b) measuring uptake of the radiolabeled form of the HSP90 inhibitor by the patient's tumor at one or more time points after the administration in step (a); and (c) calculating the dose and frequency of administration needed to maintain in the tumor over the period of treatment an average tumor concentration of the HSP90 inhibitor effective to treat the tumor, based on the uptake measured at said one or more time points in step (b), thereby determining, for the cancer patient, the effective dose and frequency of administration for therapy with the inhibitor of HSP90.

In a still further aspect, the disclosure provides a method for determining the concentration of an HSP90 inhibitor present in a tumor expressing the oncogenic HSP90 in a cancer patient which comprises the following steps:

(a) co-administering to the patient a predetermined amount of the HSP90 inhibitor and an amount of a radiolabeled form of the HSP90 inhibitor which binds preferentially to a tumor-specific form of HSP90 present in a tumor or tumor cells;

(b) periodically measuring the uptake of the radiolabeled HSP90 inhibitor by the patient's tumor at one or more time point(s) after the co-administration in step (a); and (c) determining the concentration of the HSP90 inhibitor present in the tumor at any such time point based on the measurements of the uptake of the radiolabeled HSP90 inhibitor in step (b).

In yet another aspect, the disclosure provides a method for determining the responsiveness to therapy with an inhibitor of HSP90 of a tumor expressing the oncogenic HSP90 in a cancer patient which comprises the following steps:

(a) administering a radiolabeled form of the HSP90 inhibitor which binds preferentially to a tumor-specific form of HSP90 present in a tumor or tumor cells, to the patient at one or more time points within the period during which the patient is receiving the inhibitor of HSP90 as therapy;

(b) measuring the concentration of the radiolabeled HSP90 inhibitor in the patient's tumor at said one or more time points after the administration in step (a); and (c) comparing the concentrations of the radiolabeled HSP90 inhibitor measured in step (b) with the minimum concentration of the HSP90 inhibitor needed to effectively treat the tumor, wherein measured concentrations greater than the minimum needed to treat the tumor indicate that the patient is likely to respond to therapy with the HSP90 inhibitor.

In another aspect, the disclosure provides method for determining whether a patient suffering from a neurodegenerative disease will likely respond to therapy with an HSP90 inhibitor which comprises the following steps:

(a) contacting the brain with a radiolabeled HSP90 inhibitor which binds preferentially to a pathogenic form of HSP90 present in a brain cells of the patient;

(b) measuring the amount of labeled HSP90 inhibitor bound to the brain cells in the sample; and (c) comparing the amount of labeled HSP90 inhibitor bound to the brain cells in the sample measured in step (b) to a reference amount;

wherein a greater amount of labeled HSP90 inhibitor bound to the brain cells measured in step (b) as compared with the reference amount indicates the patient will likely respond to the HSP90 inhibitor.

In another aspect, the disclosure provides methods of treating HSP90 dependent cancers with the HSP90 inhibitor PU-H71. In particular embodiments, methods of treating HSP90 dependent cancers to achieve specific tumor exposures of PU-H71 are provided. In other embodiments, novel dosing regimens of PU-H71 are provided.

In another aspect, the disclosure provides a method for determining whether a human cancer present in a patient will likely respond to therapy with an HSP90 inhibitor which comprises:

(a) obtaining a sample containing cells from the patient's cancer, which cells express HSP90 protein alone or in addition to HSP70 protein;

(b) assessing for the cells present in the sample obtained in step (a) the presence of at least one of the following parameters: an activated AKT pathway, a defect in PTEN tumor suppressor function or expression, an activated STAT5 pathway, or Bcl-xL protein expression; and (c) comparing the assessment obtained in step (b) with a predetermined reference assessment of the same parameter or parameters assessed in step (b) for human cancer cells from one or more cancer patient(s) who responded to therapy with the HSP90 inhibitor so as to thereby determine whether the patient's cancer will likely respond to therapy with the HSP90 inhibitor.

In one embodiment, human cancers currently of considerable interest for use of this particular method are breast cancer, pancreatic cancer and acute myeloid leukemia.

Methods for assessing each of the parameters are well known in the art and readily available. However a correlation of one or more of these particular parameters with predicting the efficacy of a HSP90 inhibitor has not been shown previously. Although in theory a single parameter may be sufficient to enable a skilled practitioner to predict the efficacy of any given HSP90 inhibitor, it is more likely that at least 2, perhaps at least 3 or more or even all of these parameters will need to be taken into account to make a sound prediction of efficacy.

4. BRIEF DESCRIPTION OF FIGURES

FIGS. 1A, 1B, 1C, 1D, and 1E. PU-H71 preferentially interacts with a restricted fraction of HSP90 that is more abundant in cancer cells. FIG. 1A Sequential immunopurification steps with H9010, an anti-HSP90 antibody, deplete HSP90 in the MDA-MB-468 cell extract. Lysate=control cell extract. FIG. 1B HSP90 from MDA-MB-468 extracts was isolated through sequential chemical- and immuno-purification steps. The amount of HSP90 in each pool was quantified by densitometry and values were normalized to an internal standard. FIG. 1C Saturation studies were performed with $^{131}$I-PU-H71 in the indicated cells. All the isolated cell samples were counted and the specific uptake of $^{131}$I-PU-H71 determined. These data were plotted against the concentration of $^{131}$I-PU-H71 to give a saturation binding curve. Representative data of four separate repeats is presented (lower). Expression of HSP90 in the indicated cells was analyzed by Western blot (upper). FIG. 1D Primary AML and CML, CD34+ cord blood cells (CB), or K562 cells were pre-treated with the indicated doses of PU-H71 for 24 h. Post-treatment cells were treated with 1 μM PU-FITC. Binding of PU-FITC to the cells was evaluated by flow cytometry and is represented as mean fluorescence intensity (MFI). TEG-FITC is shown as a non-specific binding control. CD45 vs. SSC gating was used to distinguish binding to blast or lymphocytes from the primary specimens. FIG. 1E Percent viability relative to untreated control for primary AML and CML, CD34+CB or K562 cells after treatment at the indicated doses of PU-H71. Cell viability was evaluated by annexin V/7-AAD staining 96 h post-treatment. Data are presented as means±SE (n=3).

Figures 2A, 2B, 2C, 2D, 2E, 2F, 2G:
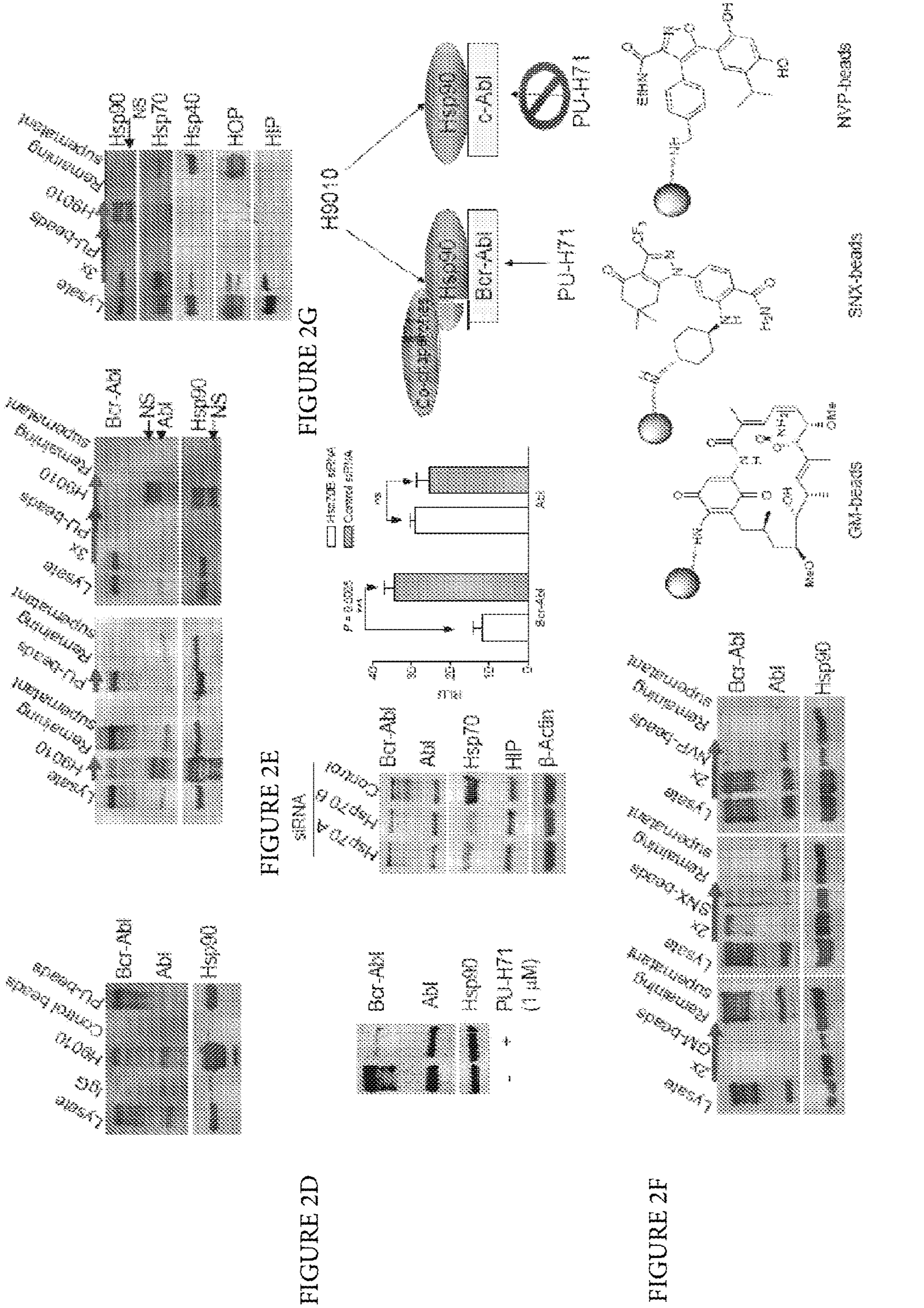

FIGS. 2A, 2B, 2C, 2D, 2E, 2F, and 2G. PU-H71 is selective for and isolates HSP90 in complex with oncoproteins and co-chaperones. FIG. 2A HSP90 complexes in K562 extracts were isolated by precipitation with H9010, anon-specific IgG, or by PU-H71- or Control-beads. Control beads contain ethanolamine, an HSP90-inert molecule. Proteins in pull-downs were analyzed by Western blot. FIGS. 2B and 2C Single or sequential immuno- and chemical-precipitations, as indicated, were conducted in K562 extracts with H9010 and PU-beads at the indicated frequency and in the shown sequence. Proteins in the pull-downs and in the remaining supernatant were analyzed by WB. NS=non-specific. FIG. 2D K562 cell were treated for 24 h with vehicle (−) or PU-H71 (+), and proteins analyzed by Western blot. FIG. 2E Expression of proteins in Hsp70-knocked-down cells was analyzed by Western blot (left) and changes in protein levels presented in relative luminescence units (RLU) (right). Control=scramble siRNA. FIG. 2F Sequential chemical-precipitations, as indicated, were conducted in K562 extracts with GM-, SNX- and NVP-beads at the indicated frequency and in the shown sequence. Proteins in the pull-downs and in the remaining supernatant were analyzed by Western blot. FIG. 2G HSP90 in K562 cells exists in complex with both aberrant, Bcr-Abl, and normal, c-Abl, proteins. PU-H71, but not H9010, selects for the HSP90 population that is Bcr-Abl onco-protein bound.

Figure 3A:
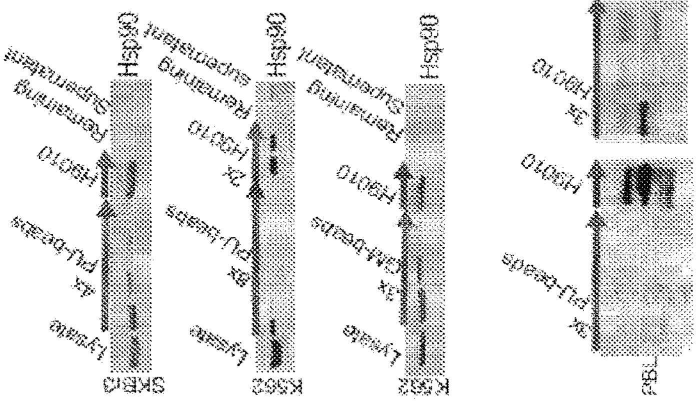
Figure 3B:
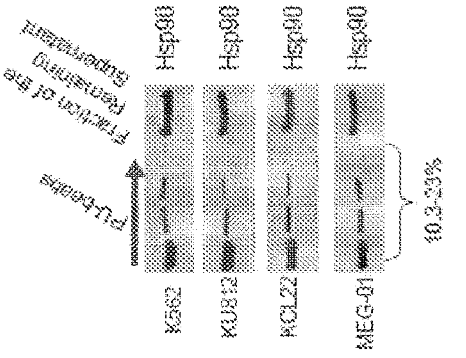
Figure 3C:
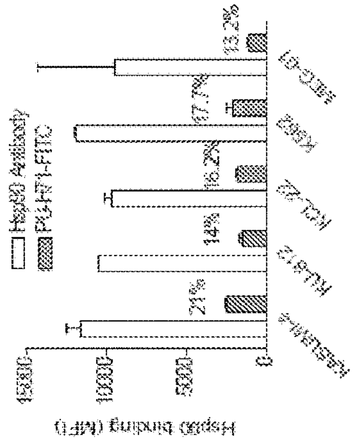
Figure 3D:
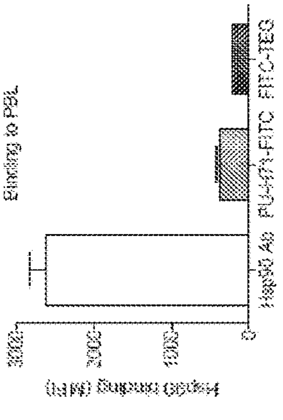
Figure 3E:
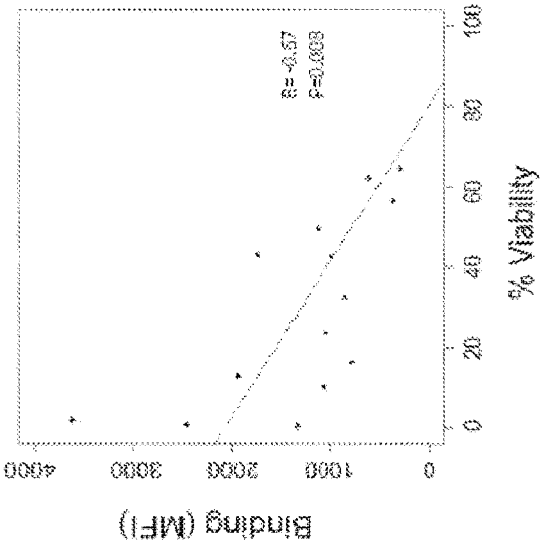

FIGS. 3A, 3B, 3C, 3D, and 3E. FIGS. 3A and 3B HSP90 from breast cancer and CML cell extracts (120 μg) was isolated through serial chemical- and immuno-purification steps, as indicated. The supernatant was isolated to analyze the left-over HSP90. HSP90 in each fraction was analyzed by Western blot. Lysate=endogenous protein content; PU-, GM- and Control-beads indicate proteins isolated on the particular beads. H9010 and IgG indicate protein isolated by the particular Ab. Control beads contain an HSP90 inert molecule. The data are consistent with those obtained from multiple repeat experiments (n≥2). FIG. 3C HSP90 binding of PE conjugated antibody vs PU-H71-FITC. The percent of total cellular HSP90 isolated by PU-H71 is indicated for each cell line above the data bar. FIG. 3D Sequential chemical- and immuno-purification steps were performed in peripheral blood leukocyte (PBL) extracts (250 μg) to isolate PU-H71 and H9010-specific HSP90 species. All samples were analyzed by Western blot. (upper). Binding to HSP90 in PBL was evaluated by flow cytometry using an HSP90-PE antibody and PU-H71-FITC. FITC-TEG=control for non-specific binding (lower). FIG. 3E Correlation for binding of PU-H71-FITC (1 μM) to HSP90 versus percent viability after treatment with PU-H71 in a panel of 14 leukemia cell lines: Kasumi-1, Kasumi-4, KCL-22, REH, TF-1, KG-1, HL-60, OCI-AML3, K562, MOLM-13, TUR, THP-1, U937 and MV4-11. Total HSP90 levels in these cells are similar, as demonstrated by Western blot (not shown).

Figures 4A, 4B, 4C:
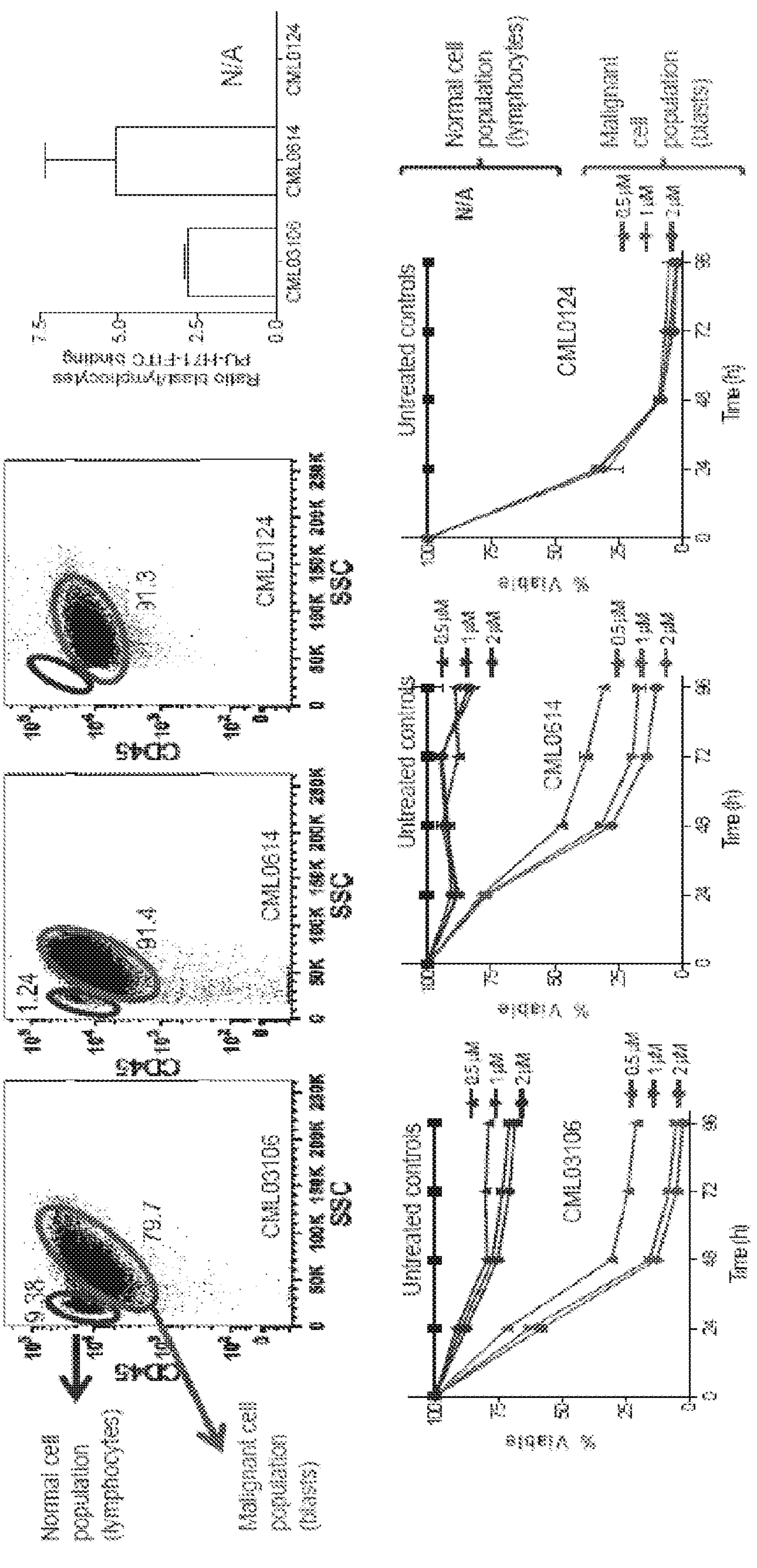

FIGS. 4A, 4B, 4C, 4D, 4E, 4F, 4G, and 4H. FIG. 4A Flow cytometric dot plots demonstrate the gating strategy used for primary chronic myeloid leukemia (CML) samples to distinguish blast (CD45dim, red circles) and non-malignant lymphocytes (blue circles). FIG. 4B Ratio for PU-H71-FITC binding to HSP90 in CML blasts to normal lymphocytes from the primary CML patient samples shown in FIG. 4A. FIG. 4C Percent viability of CML blasts (red) or normal lymphocytes (blue) relative to untreated control for the primary CML samples shown in A after treatment at the indicated time points and doses of PU-H71. FIG. 4D Flow cytometric dot plots demonstrate the gating strategy used for primary chronic phase CML (cpCML) samples to distinguish blast (CD45dim, red circle) and non-malignant lymphocytes (blue circle) and to analyze binding of CD34+ cells (red square) within the blast gate (CD45dim, red circle). CD45 vs. SSC dot plots were pre-gated on viable cells based on 7-AAD discrimination. FIG. 4E Ratio for PU-H71-FITC binding to HSP90 in chronic phase CML (cpCML) CD34+ cells and to normal lymphocytes. FIG. 4F Percent viability of cpCML CD34+ cells (red) and normal lymphocytes (blue) relative to untreated control after treatment for 48 h with 1 μM PU-H71-FITC or TEG-FITC. FIG. 4G Ratio for PU-H71-FITC binding to Hsp90 in CD34+ cells and lymphocytes from normal cord blood, chronic phase CML (cpCML) and blast phase (bpCML) cells (n=5). FIG. 4H Percent viability after 48 h treatment with PU-H71 (1 μM) of blast and chronic CML CD34+ cells, and normal CD34+ cells (from cord blood; CB) relative to untreated control. Cell viability in panels FIGS. 4C, 4F, and 4H was evaluated by annexin V/7-AAD staining. Data are presented as means±SE (n=3).

Figure 5B:
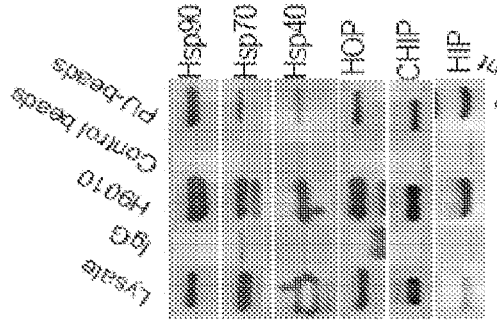
Figure 5C:
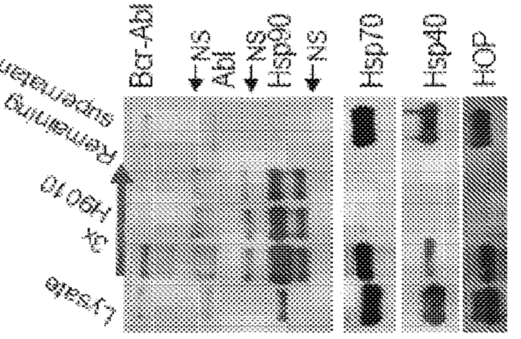
Figure 5A:
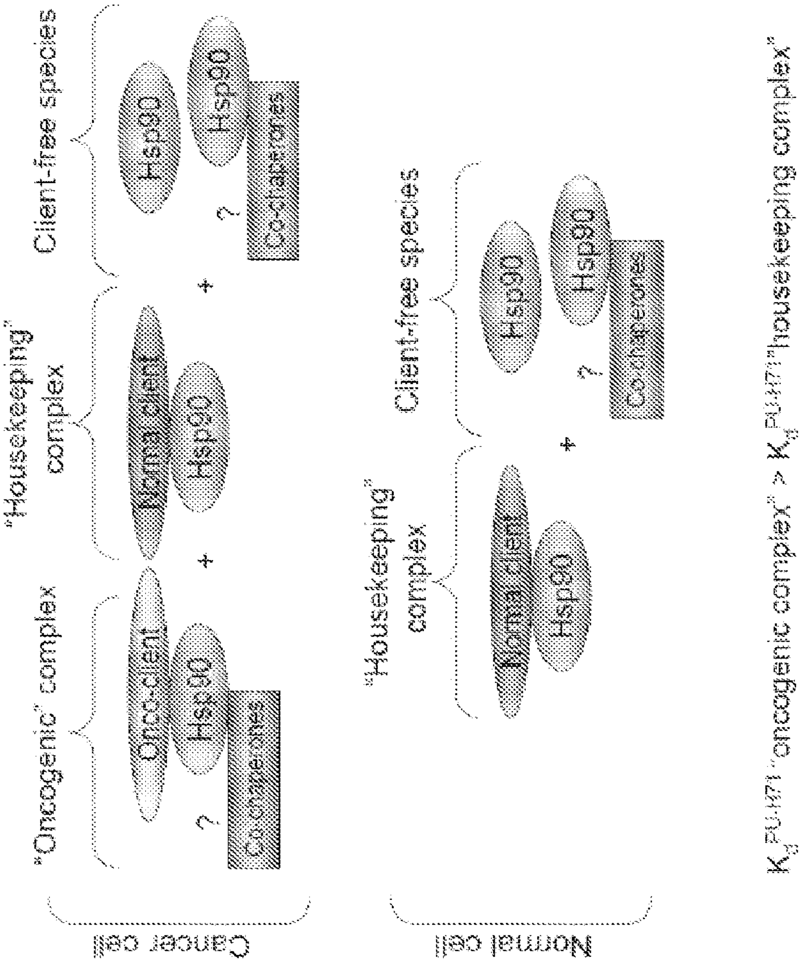

FIGS. 5A, 5B, and 5C. FIG. 5A Within normal cells, constitutive expression of HSP90 is required for its evolutionarily conserved housekeeping function of folding and translocating cellular proteins to their proper cellular compartment (“housekeeping complex”). Upon malignant transformation, cellular proteins are perturbed through mutations, hyperactivity, retention in incorrect cellular compartments or other means. The presence of these functionally altered proteins is required to initiate and maintain the malignant phenotype, and it is these oncogenic proteins that are specifically maintained by a subset of stress modified HSP90 (“oncogenic complex”). PU-H71 specifically binds to the fraction of HSP90 that chaperones oncogenic proteins (“oncogenic complex”). FIG. 5B HSP90 and its interacting co-chaperones were isolated in K562 cell extracts using PU- and Control-beads, and H9010 and IgG-immobilized Abs. Control beads contain an HSP90 inert molecule. FIG. 5C HSP90 from K562 cell extracts was isolated through three serial immuno-purification steps with the H9010 HSP90 specific antibody. The remaining supernatant was isolated to analyze the left-over proteins. Proteins in each fraction were analyzed by Western blot. Lysate=endogenous protein content. The data are consistent with those obtained from multiple repeat experiments (n≥2).

Figure 6A:
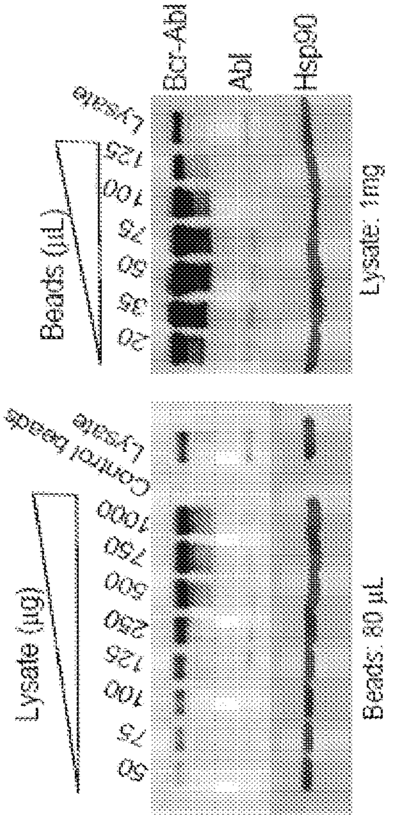
Figure 6B:
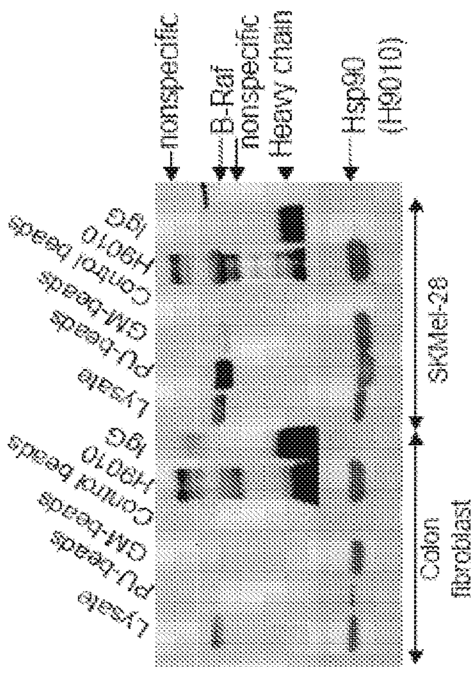
Figure 6C:
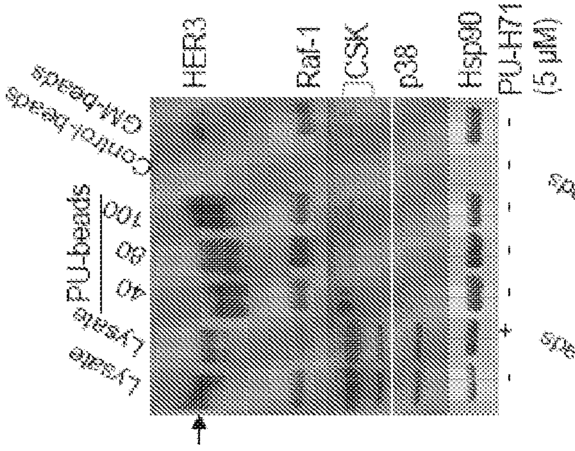
Figure 6D:
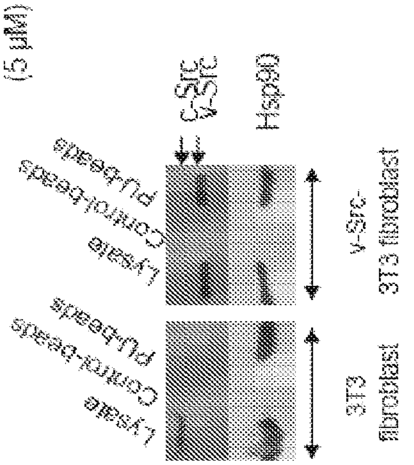

FIGS. 6A, 6B, 6C, and 6D. GM and PU-H71 are selective for aberrant protein/HSP90 species. FIG. 6A Bcr-Abl and Abl bound HSP90 species were monitored in experiments where a constant volume of PU-H71 beads (80 μL) was probed with indicated amounts of K562 cell lysate (left), or where a constant amount of lysate (1 mg) was probed with the indicated volumes of PU-H71 beads (right). FIG. 6B (left) PU- and GM-beads (80 μL) recognize the HSP90-mutant B-Raf complex in the SKMel28 melanoma cell extract (300 μg), but fail to interact with the HSP90-WT B-Raf complex found in the normal colon fibroblast CCD18Co extracts (300 μg). H9010 HSP90 Ab recognizes both HSP90 species. FIG. 6C In MDA-MB-468 cell extracts (300 μg), PU- and GM-beads (80 μl) interact with HER3 and Raf-1 kinase but not with the non-oncogenic tyrosine-protein kinase CSK, a c-Src related tyrosine kinase, and p38. FIG. 6D (right) PU-beads (80 μL) interact with v-Src/HSP90 but not c-Src/HSP90 species. To facilitate c-Src detection, a protein in lower abundance than v-Src, higher amounts of c-Src expressing 3T3 cell lysate (1,000 μg) were used when compared to the v-Src transformed 3T3 cell (250 μg), providing explanation for the higher HSP90 levels detected in the 3T3 cells (Lysate, 3T3 fibroblasts vs v-Src 3T3 fibroblasts). Lysate=endogenous protein content; PU-, GM- and Control-beads indicate proteins isolated on the particular beads. HSP90 Ab and IgG indicate protein isolated by the particular Ab. Control beads contain an HSP90 inert molecule. The data are consistent with those obtained from multiple repeat experiments (n≥2).

Figure 7B:
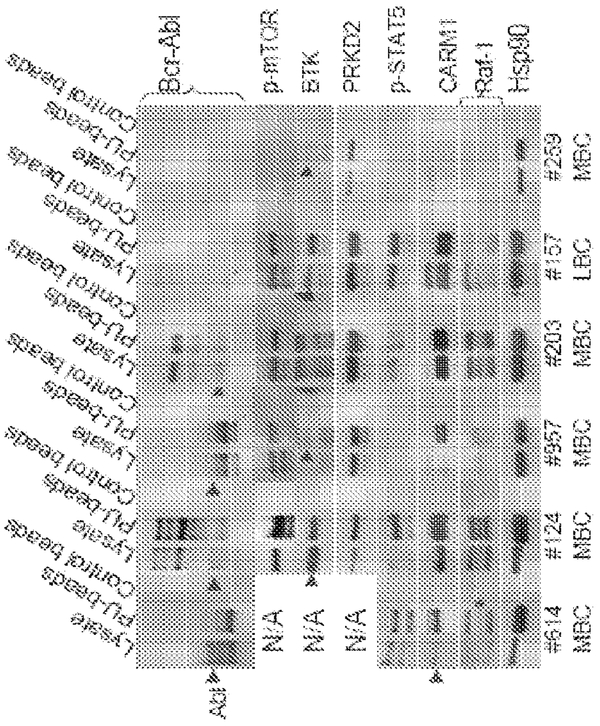
Figure 7A:
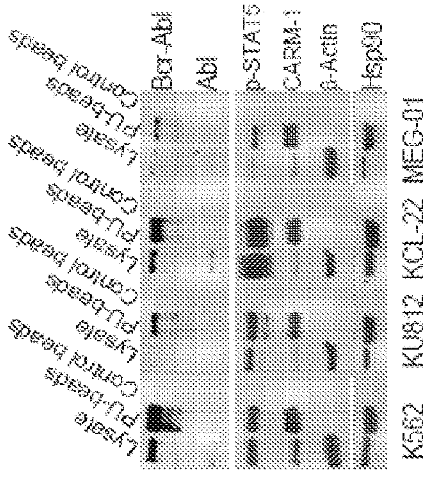

FIGS. 7A and 7B. Single chemical-precipitations were conducted in Bcr-Abl-expressing CML cell lines FIG. 7A and in primary CML cell extracts FIG. 7B with PU- and Control-beads. Proteins in the pull-downs were analyzed by Western blot. Several Bcr-Abl cleavage products are noted in the primary CML samples as reported[90]. N/A=not available.

Figure 8:
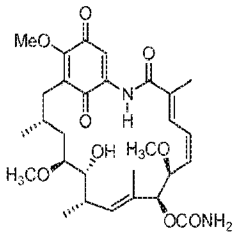
Figure 8:
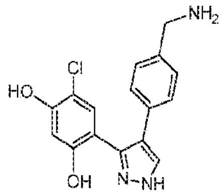
Figure 8:
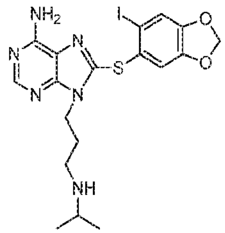
Figure 8:
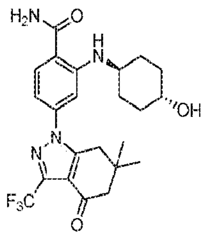
Figure 8:
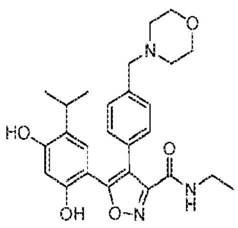
Figure 8:
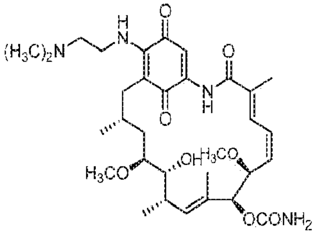
Figure 8:
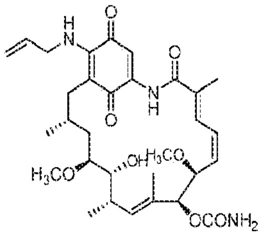
Figure 8:
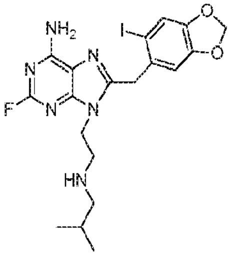
Figure 8:
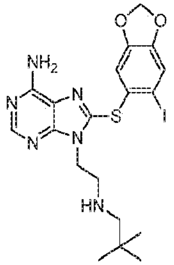

FIG. 8. Structures of several HSP90 inhibitors.

Figure 9:
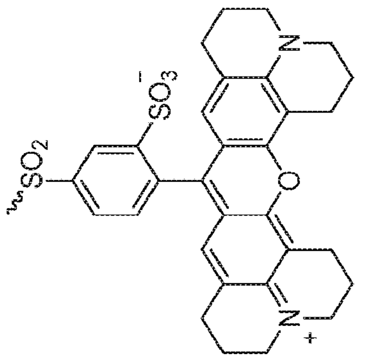
Figure 9:
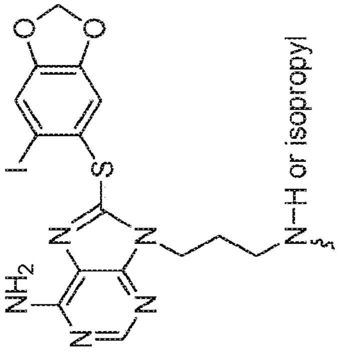
Figure 9:
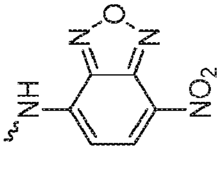
Figure 9:
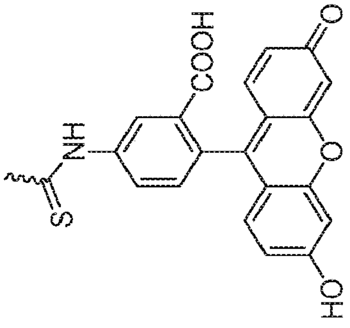

FIG. 9. Fluorescent ligands for the heat shock protein 90 (HSP90) synthesized containing either fluorescein isothiocyanate (FITC), 4-nitrobenzo[1,2,5]oxadiazole (NBD) or the red shifted dye sulforhodamine 101 (Texas Red) conjugated to PU-H71.

Figure 10:
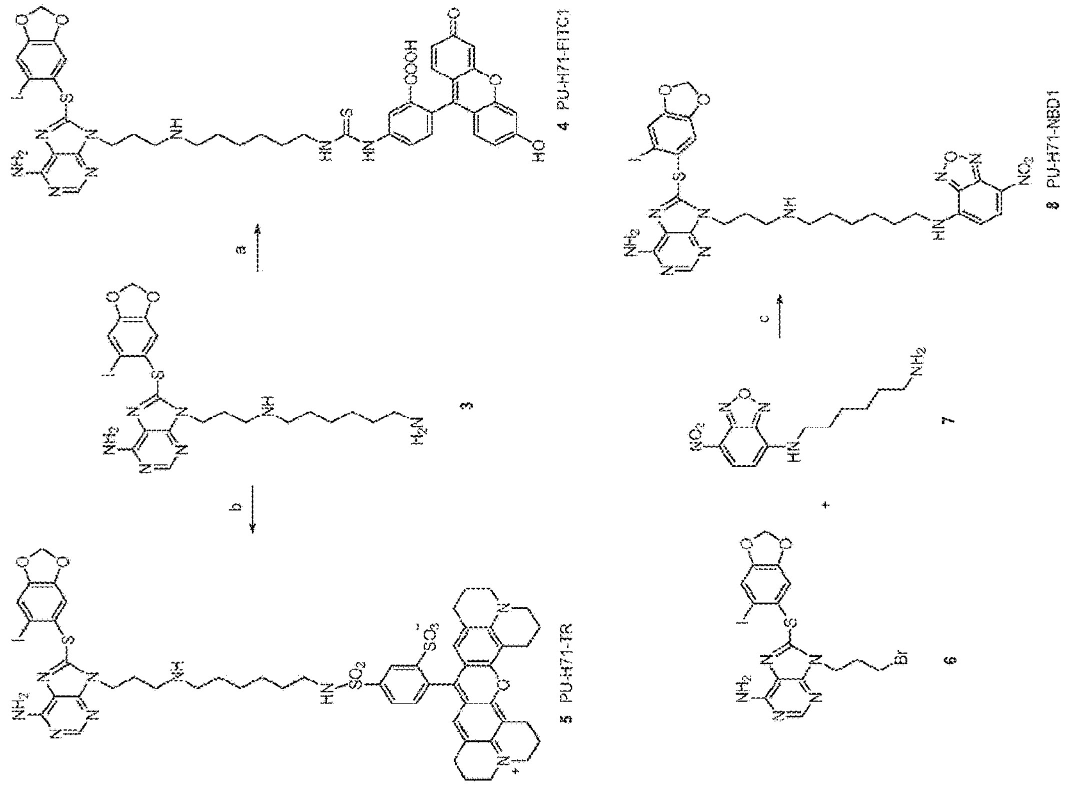

FIG. 10. Reagents and conditions for the reaction scheme shown: (a) FITC, $Et_3N$, DMF, rt, 12 h, 40%; (b) Texas Red sulfonyl chloride, DMF, 0-10° C., 12 h, 61%; (c) DMF, rt, 20 h, 47%.

Figure 11:
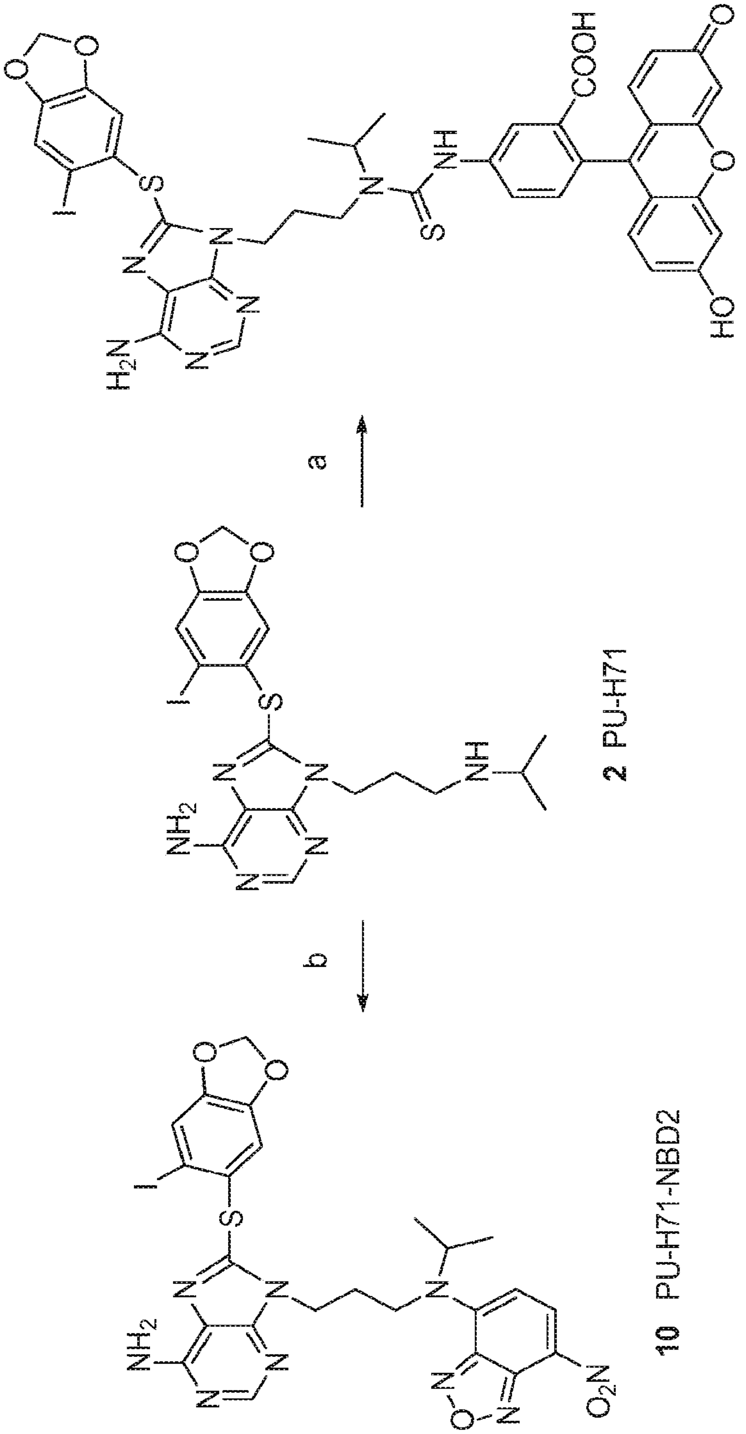

FIG. 11. Reagents and conditions for the reaction scheme shown: (a) FITC, $Et_3N$, DMF, rt, 5 h, 72%; (b) NBD-Cl, $Et_3N$, DMF, rt, 12 h, 40%.

Figure 12:
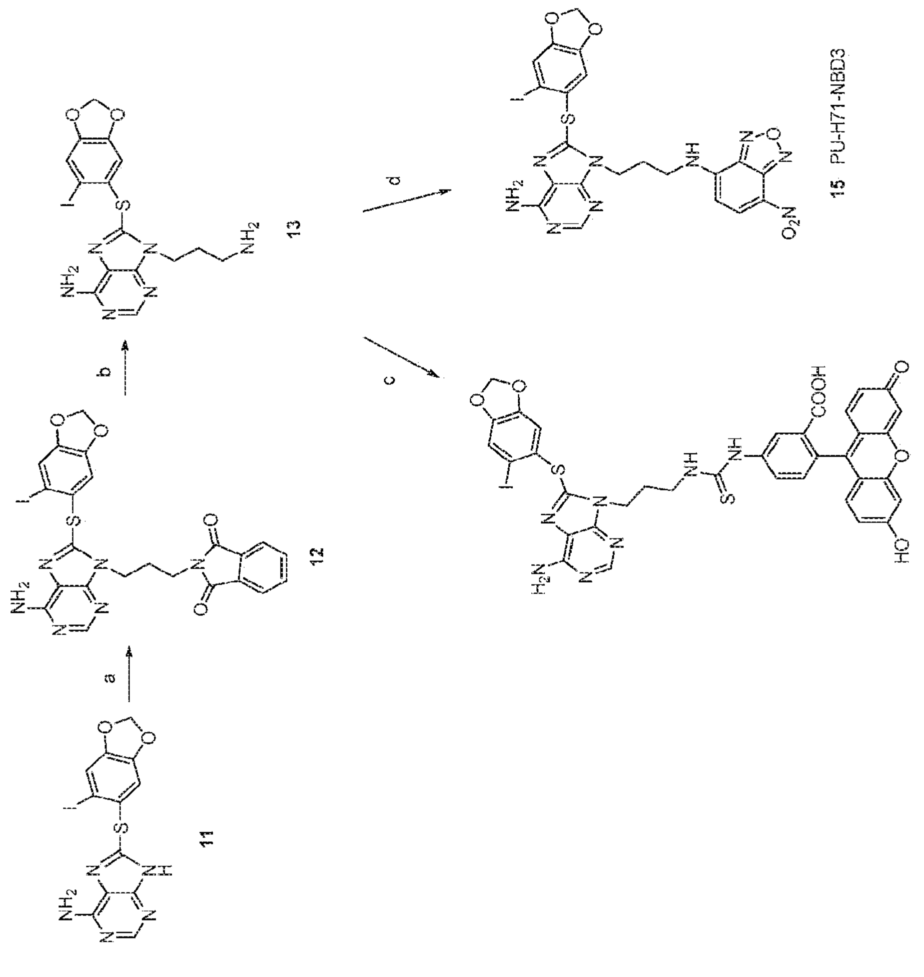

FIG. 12. Reagents and conditions for the reaction scheme shown: (a) N-(3-bromopropyl)-phthalimide, $Cs_2CO_3$, DMF, rt, 34%; (b) hydrazine hydrate, MeOH, $CH_2Cl_2$, rt, 64%; (c) FITC, $Et_3N$, DMF, rt, 12 h, 74%; (d) NBD-Cl, $Et_3N$, DMF, rt, 12 h, 42%.

Figure 13A:
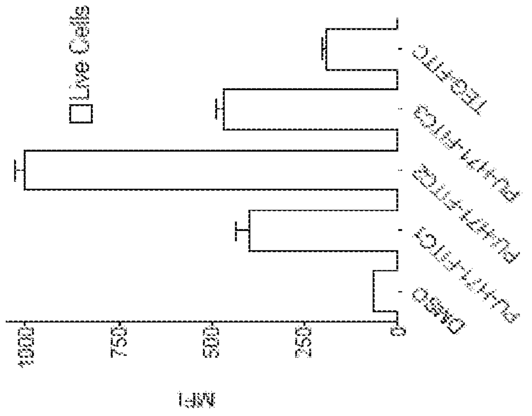
Figure 13A:
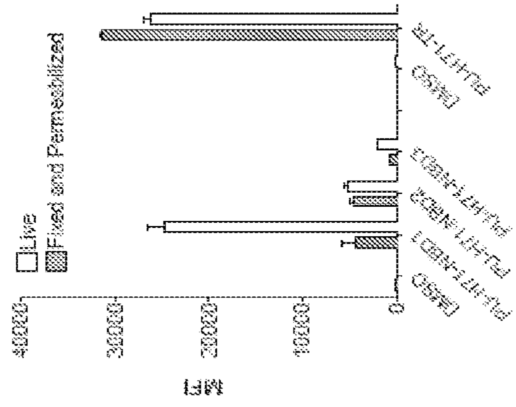
Figure 13B:
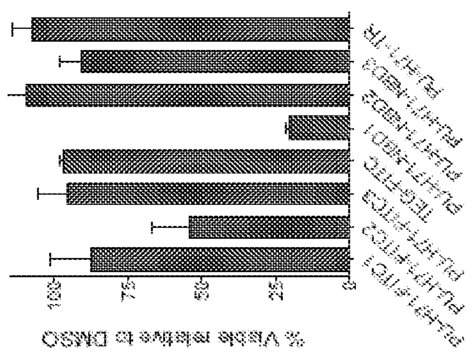
Figure 13C:
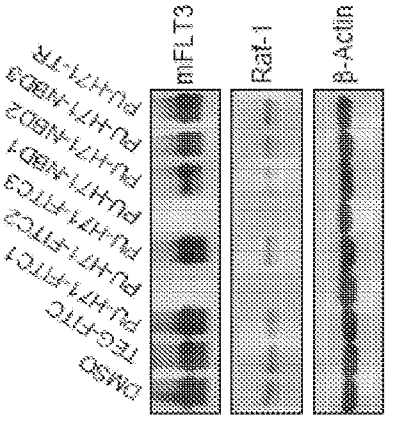

FIGS. 13A, 13B, and 13C. FIG. 13A MOLM-13 cells were treated with the indicated PU-H71-fluorescent derivatives (1 μM) at 37° C. for 4 h and binding to live cells (DAPI negative) measured by flow cytometry. The extent of binding is shown as mean fluorescence intensity (MFI). FIG. 13B MOLM-13 cells were treated with the indicated PU-H71-fluorescent derivatives (1 μM) at 37° C. for 24 h. Their viability was determined by DAPI exclusion. FIG. 13C MOLM-13 cells were treated with the indicated PU-H71-fluorescent derivatives (1 μM) for 24 h. The steady-state level of the HSP90 client proteins mFLT3 and Raf-1 was analyzed by Western blot. β-Actin was used to normalize for equal protein loading.

Figure 14A:
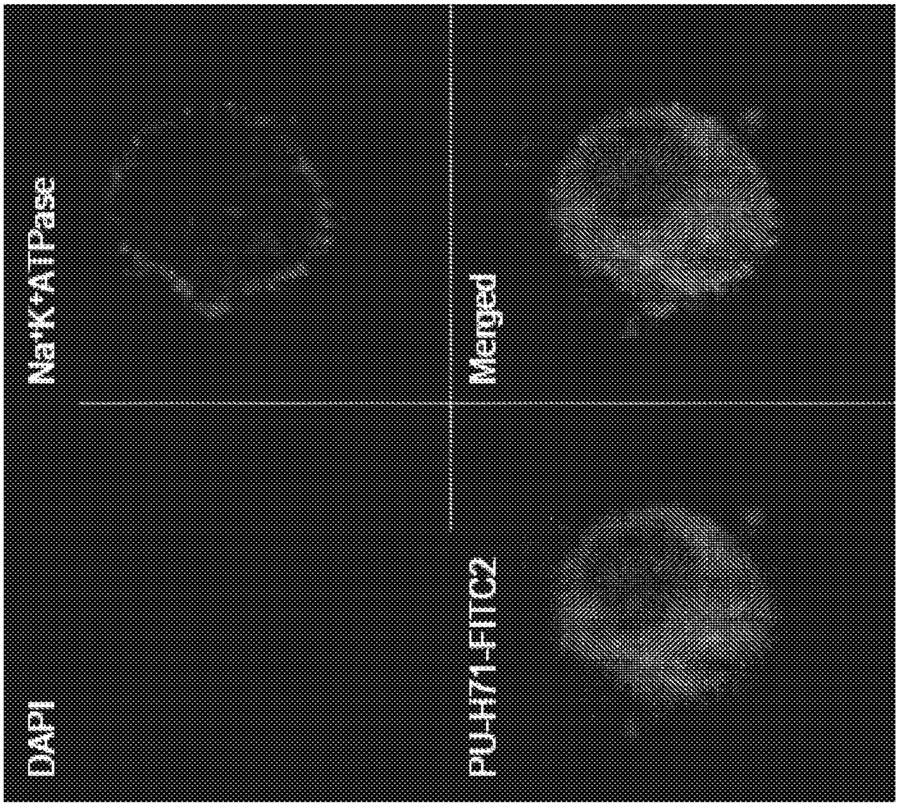
Figure 14B:
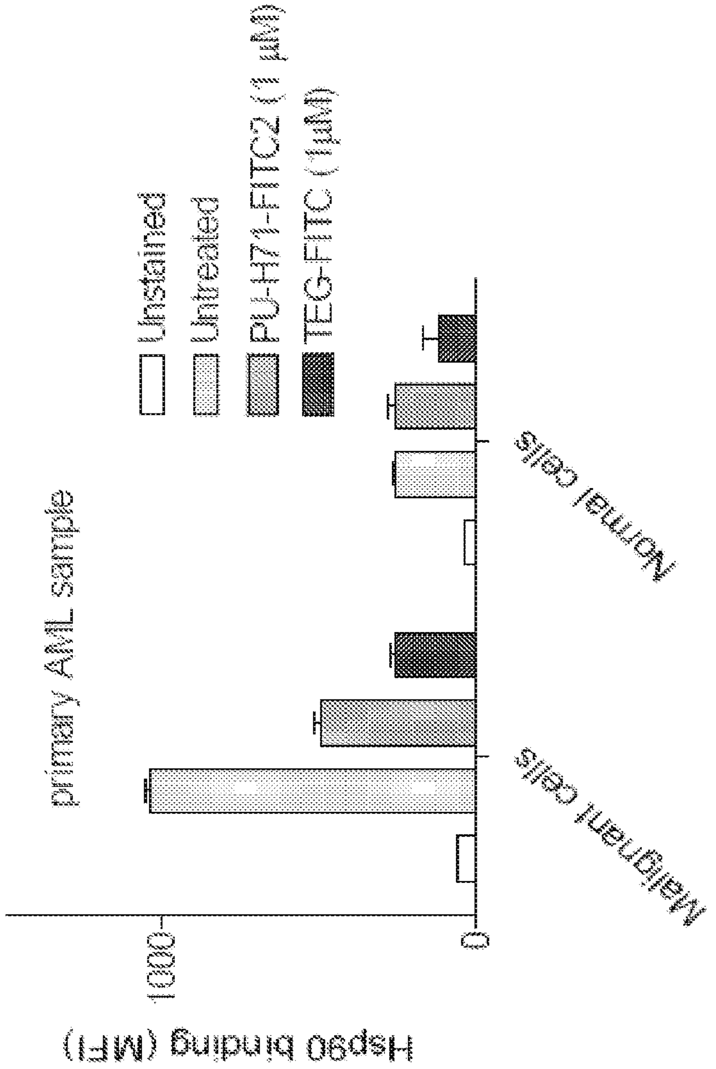

FIGS. 14A and 14B. FIG. 14A Confocal fluorescence microscopy of leukemia cells stained with PU-H71-FITC2 shows prominent intracellular localization. FIG. 14B A primary acute myeloid leukemia sample was pre-treated with the indicated dose of PU-H71 or vehicle (Untreated) for 24 h. Post-treatment cells were treated with 1 μM PU-H71-FITC2 or TEG-FITC. Binding of PU-H71-FITC2 and TEG-FITC to the cells was evaluated by flow cytometry and is represented as mean fluorescence intensity (MFI). TEG-FITC is shown as a non-specific binding control. CD45 vs. SSC gating was used to distinguish binding to blast (malignant cells) or lymphocytes (normal cells) from the primary specimens.

Figure 15:
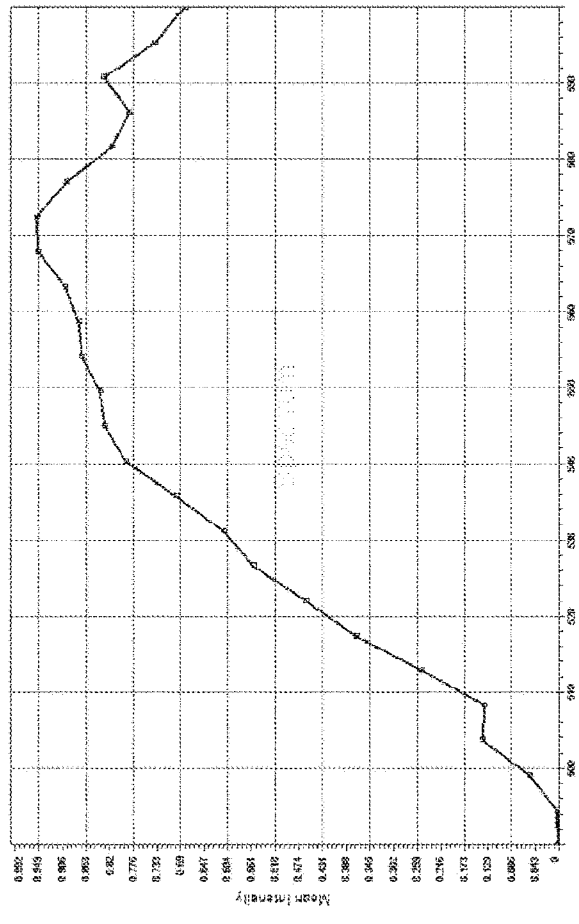
Figure 15:
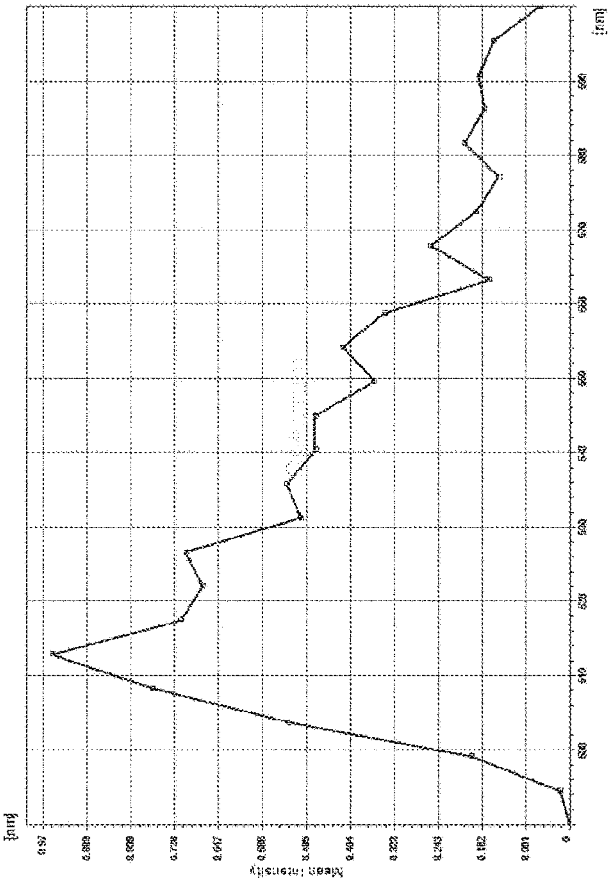

FIG. 15. Fluorescence emission spectrum of PU-ANCA in a normal cell (left) and a breast cancer cell (right). The spectral emission profile of breast cancer cells resulted in a fluorescent emission peak at approximately 530 nm wavelength, the representative fluorescence emission of the bound PU-H71-ANCA.

Figure 16A:
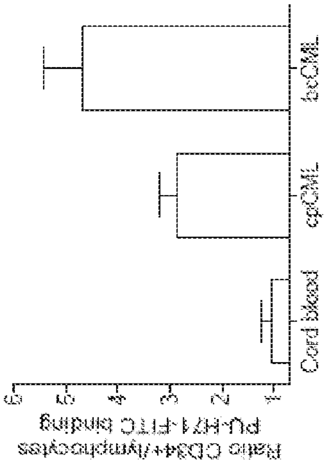
Figure 16B:
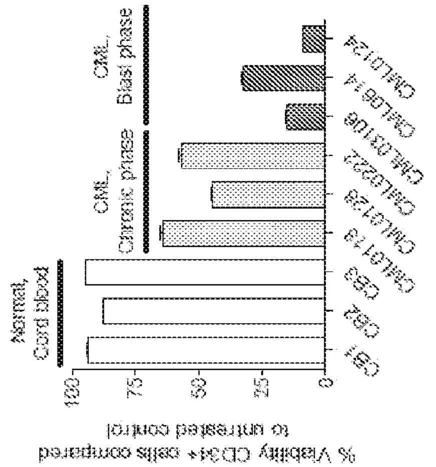
Figure 16C:
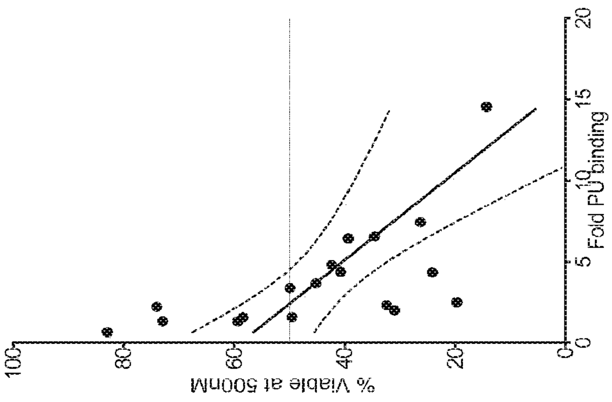

FIGS. 16A, 16B, and 16C. FIG. 16A Ratio for PU-H71-FITC binding to HSP90 in cord blood and CML blasts to normal lymphocytes from healthy donors (cord blood) and chronic and blast phase CML patients (cpCML and bpCML, respectively). Note no significant binding to cord blood from healthy patients vs increased binding in CML that correlates with disease progression. FIG. 16B Percent viability after 48 h treatment with PU-H71 (1 μM) of blast and chronic CML CD34+ cells, and normal CD34+ cells (from cord blood; CB) relative to untreated control. Cell viability was evaluated by annexin V/7-AAD staining. Data are presented as means±SE (n=3). FIG. 16C Correlation for binding of PU-H71-FITC (1 μM) to HSP90 versus percent viability after treatment with 500 nM PU-H71 for 48 h in a set of 19 primary AML patient samples. Each dot represents a primary AML sample. Each experiment was performed at least in duplicate. These cells express similar total HSP90 levels.

Figure 17A:
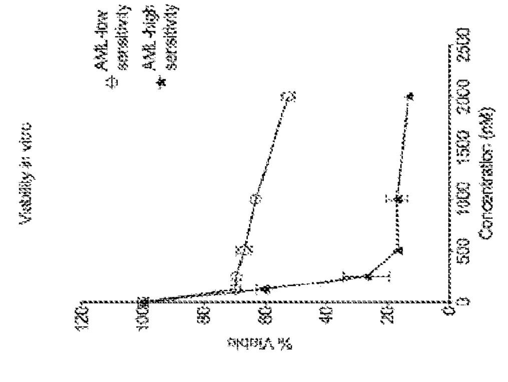
Figure 17B:
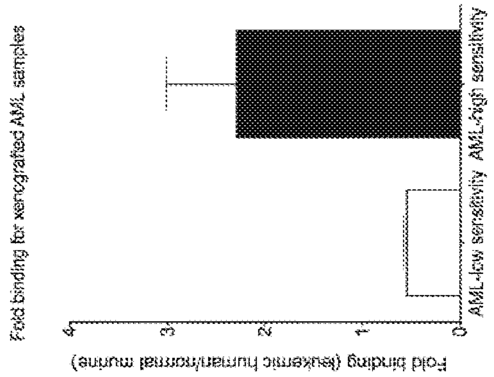
Figure 17C:
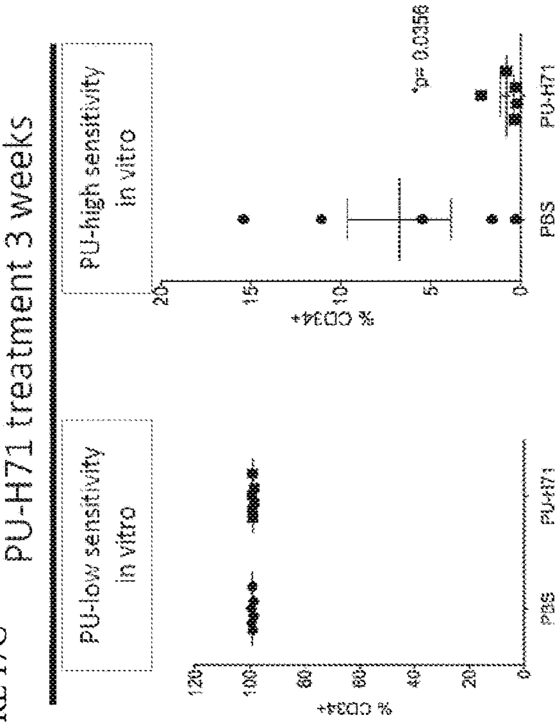

FIGS. 17A, 17B, and 17C. Xenotransplant assays suggest in vivo sensitivity to PU-H71 treatment of AML samples with high-PU-FITC binding. FIG. 17A Percent viability at 48 h for in vitro PU-H71 treatment of two primary AML samples that show low and high-PU-FITC uptake FIG. 17B. Viability was determined by Annexin/7AAD assays. FIG. 17B Bone marrow cells from xenotransplanted animals (for AML samples shown in panel FIG. 17A were stained with human specific antibodies to determine PU-FITC binding. PU-FITC binding is represented as a ratio of human (leukemia)/murine (normal) cells. FIG. 17C Percent CD34+ tumor cells in animals treated with 75 mg/kg PU-H71 3×week for 3 weeks.

Figure 18A:
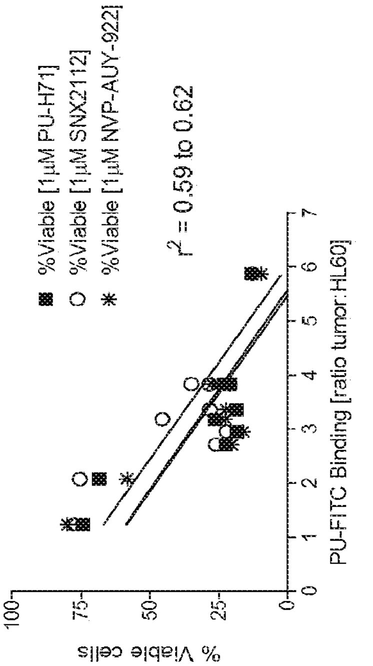
Figure 18B:
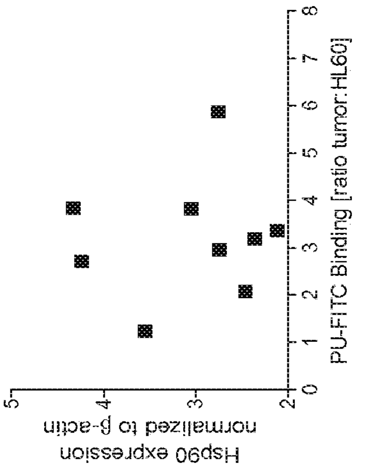
Figure 18C:
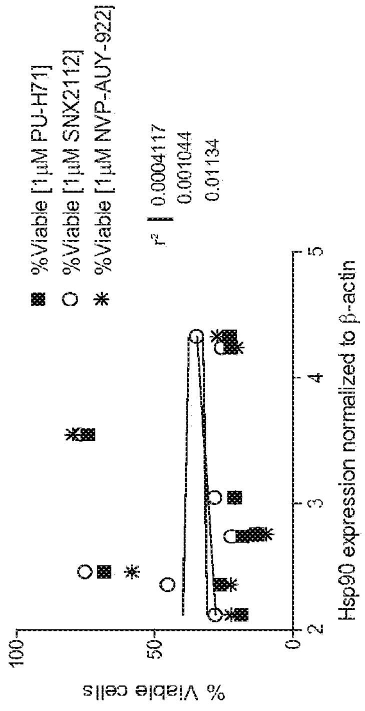
Figure 18D:
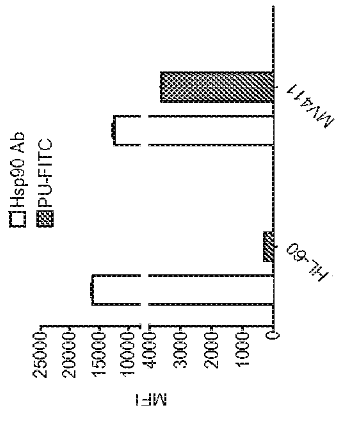

FIGS. 18A, 18B, 18C, and 18D. Use of labeled-PU-H71 to detect and quantify the "oncogenic HSP90" and predict sensitivity of tumor cells to HSP90 inhibitors. FIG. 18A Correlation for binding of PU-H71-FITC (1 μM) to HSP90 versus percent viability after treatment with 1 μM PU-H71, SNX-2112 or NVP-AUY922 for 48 h in a panel of pancreatic and breast cancer cell lines. Binding is measured as a ratio of PU-FITC uptake in the respective cancer cell and the uptake in the reference cells, the HSP90 resistant leukemia cells HL60 (see panel D). FIG. 18B Expression of total tumor HSP90 was measured by Western blot and plotted against PU-FITC binding. FIG. 18C Percent viability after treatment with 1 μM PU-H71, SNX-2112 or NVP-AUY922 for 48 h in a panel of pancreatic and breast cancer cell lines was plotted against expression of total tumor HSP90. FIG. 18D HSP90 binding of PE conjugated antibody vs PU-H71-FITC in a low-binding and sensitivity (HL-60) and high-binding and sensitivity (MV4-11) AML cell line. Data are presented as means±SE (n=3).

Figure 19:
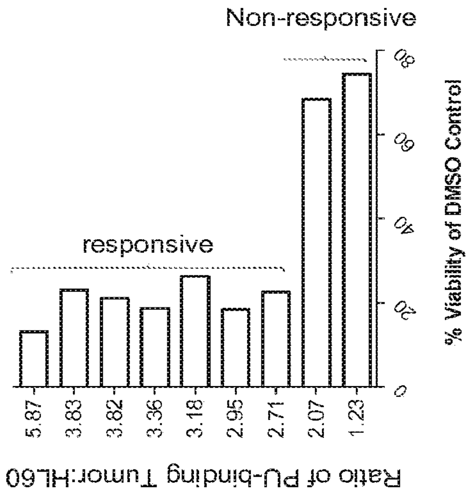

FIG. 19. Ratio of PU-H71-FITC2 binding to tumor cells and to reference HL-60 leukemia cells. A responsive (>50% reduced viability) from non-responsive (<50% reduced viability) cells could be differentiated by a ratio of binding to PU-H71-FITC2 from about 2.7 to about 5.87 or above for responsive cells compared to about 1.23 to about 2.07 or below for nonresponsive cells.

Figure 20A:
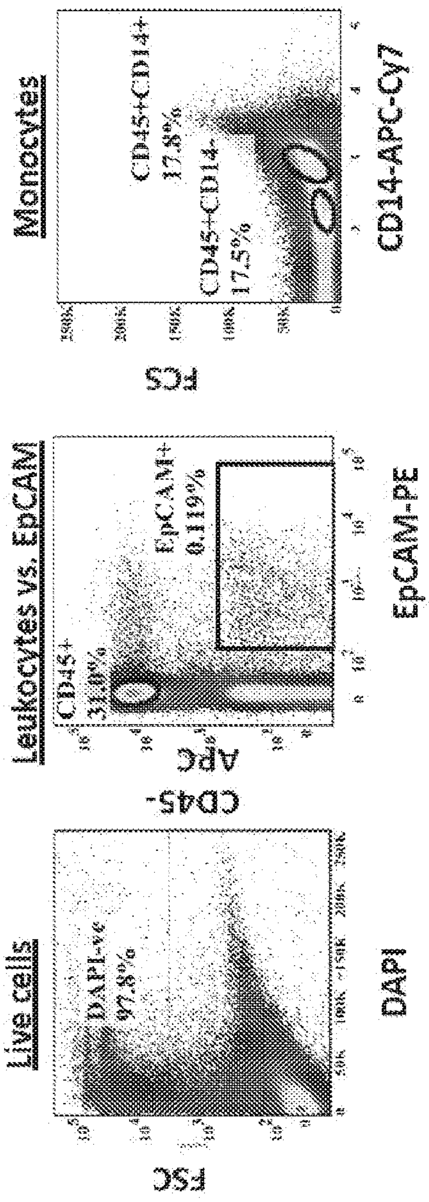
Figure 20B:
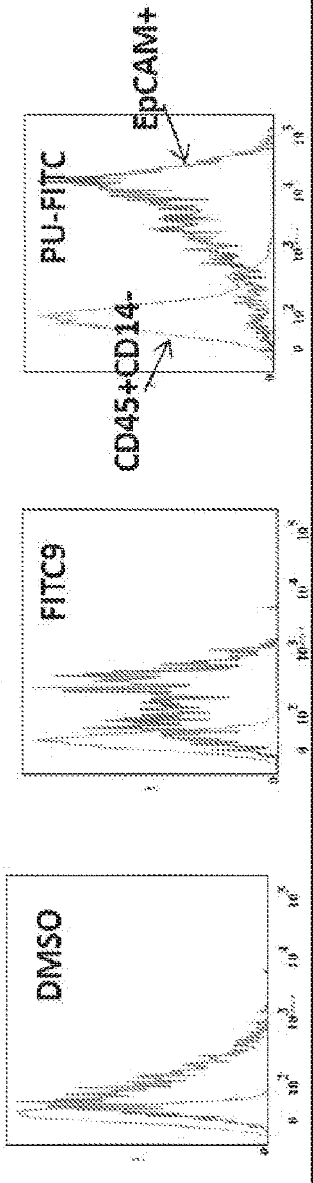

FIGS. 20A and 20B. PU-H71-FITC2 accumulation in EpCAM+ Circulating Tumor Cells: PBMC's isolated from whole blood were pre-treated with PU-FITC or controls (PU-FITC9, DMSO, 1 μM/2×$10^6$ cells/ml, 4 hrs). Cells were then stained with CD45, CD14 and EpCAM antibodies. FIG. 20A Cells are gated to exclude dead cells. Viable cells are then gated to determine EpCAM+vs CD45+ cells. Monocytes are excluded from the analysis by gating the CD45+ cells further as FSC vs. CD14. FIG. 20B Histogram plots showing the PU-FITC Median florescence intensity (MFI) of CD45+CD14− cells (blue) and EpCAM+ cells (Red). The drug accumulation in EpCAM+ cells is calculated as the ratio of MFI EpCAM+/MFI CD45+CD14− (circulating tumor cells/leukocytes) after subtracting the values of the DMSO and PU-FITC9 controls (used to control for non-specific and background binding).

Figure 21:
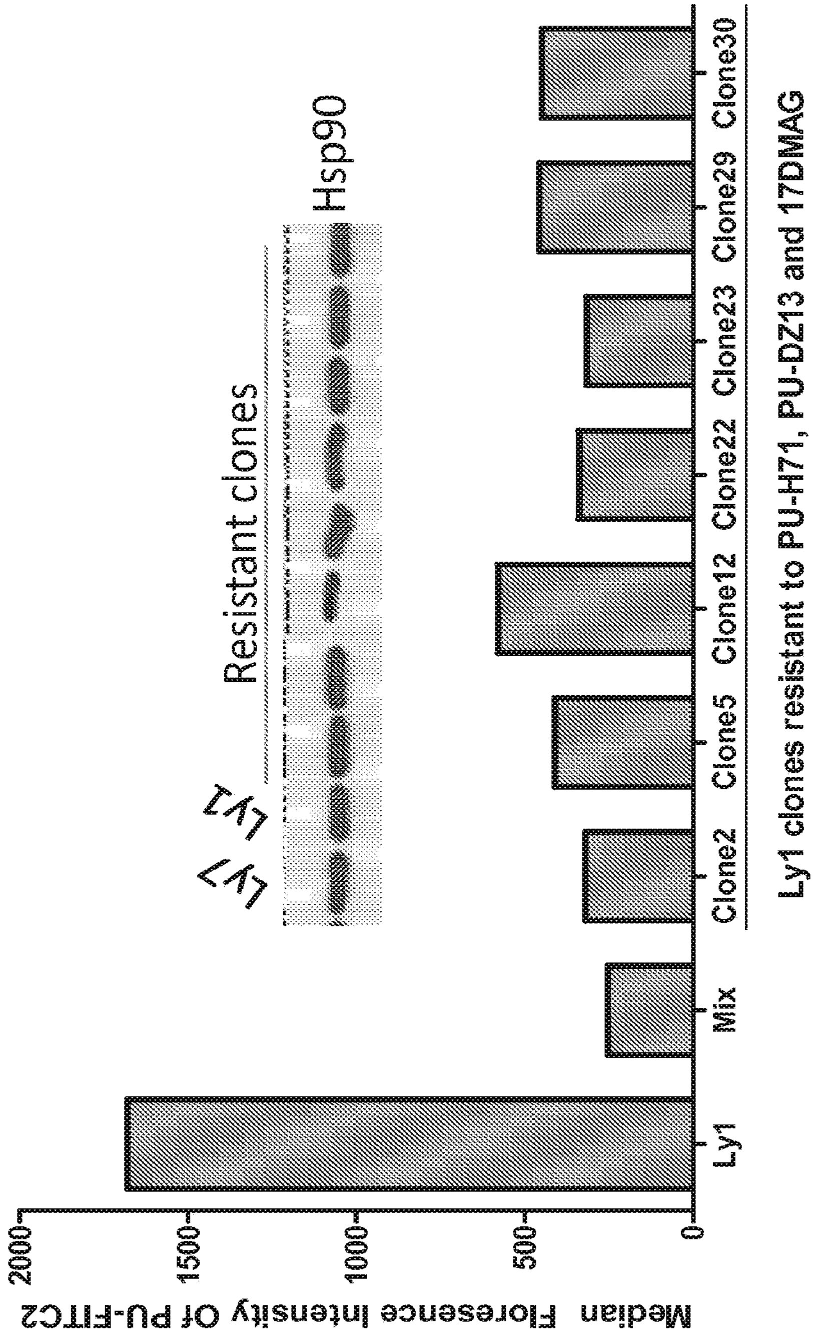

FIG. 21. Shows the uptake of PU-H71-FITC2 by different Ly1 clones and is expressed as median fluorescence intensity. The sensitivity of these cells to HSP90 inhibitors correlates with their uptake of labeled-PU-H71. Expression of total tumor HSP90 in these tumor cells was measured by Western blot (inset).

Figure 22A:
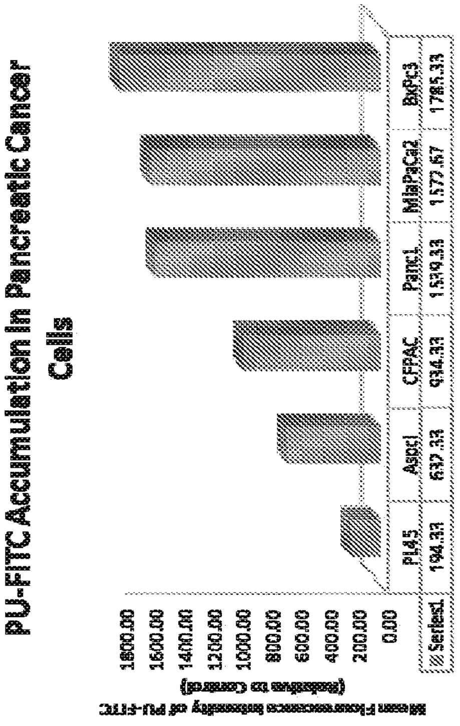
Figure 22B:
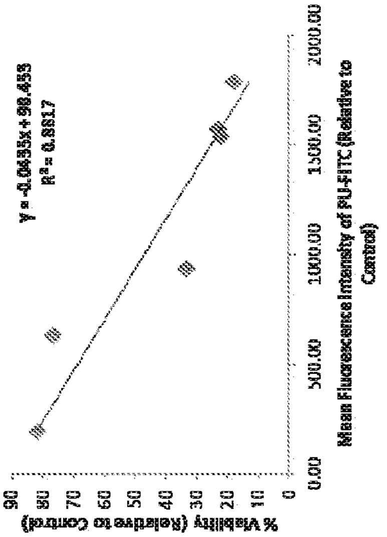
Figure 22C:
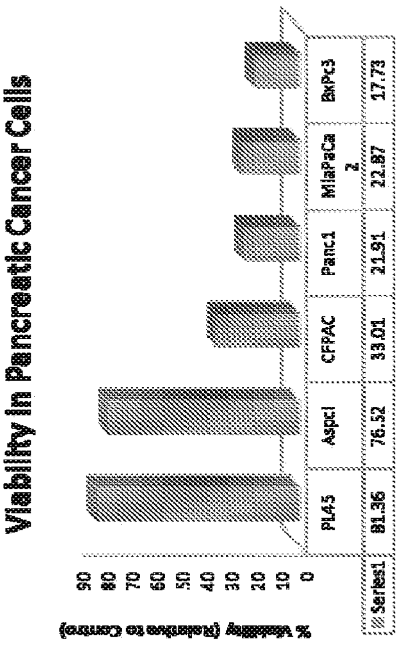

FIGS. 22A, 22B, and 22C. Correlation in PU-H71 Binding and Toxicity in Pancreatic Cancer Cells. FIG. 22A Binding in Live Cells; Pancreatic Cancer cells ($1\times10^6$ cells) were treated for 6 hrs with PUFITC2 (1 μM) or controls [TEG-FITC (1 μM) or DMSO]. Cells were washed twice with FACS buffer (PBS, 0.05% FBS), and stained with 1 μg/ml of DAPI (Invitrogen) in FACS buffer at room temperature, prior to analysis. The fluorescence intensities from live cells (DAPI negative) representing PU-H71-fluorescent derivative binding were captured by flow cytometry (LSR-II, BD Biosciences), and analyzed by FlowJo software (Tree Star, Ashland, OR). Value represent mean florescent intensities subtracted from the DMSO and TEG-FITC controls. FIG. 22B Toxicity: Pancreatic Cancer cells ($1\times10^6$ cells) were treated for 48 hrs with PU-FITC2 (1 μM). Cells were washed twice with FACS buffer (PBS, 0.05% FBS), and stained with 1 μg/ml of DAPI (Invitrogen) in FACS buffer at room temperature and captured by flow cytometry (LSR-II, BD Biosciences). Values represent the % live cells (DAPI negative) normalized to the values from the DMSO control. FIG. 22C Correlative analysis; MFI and toxicity obtained from A and B were plotted on the x and y axis respectively and a correlative linear regression analysis performed.

Figure 23A:
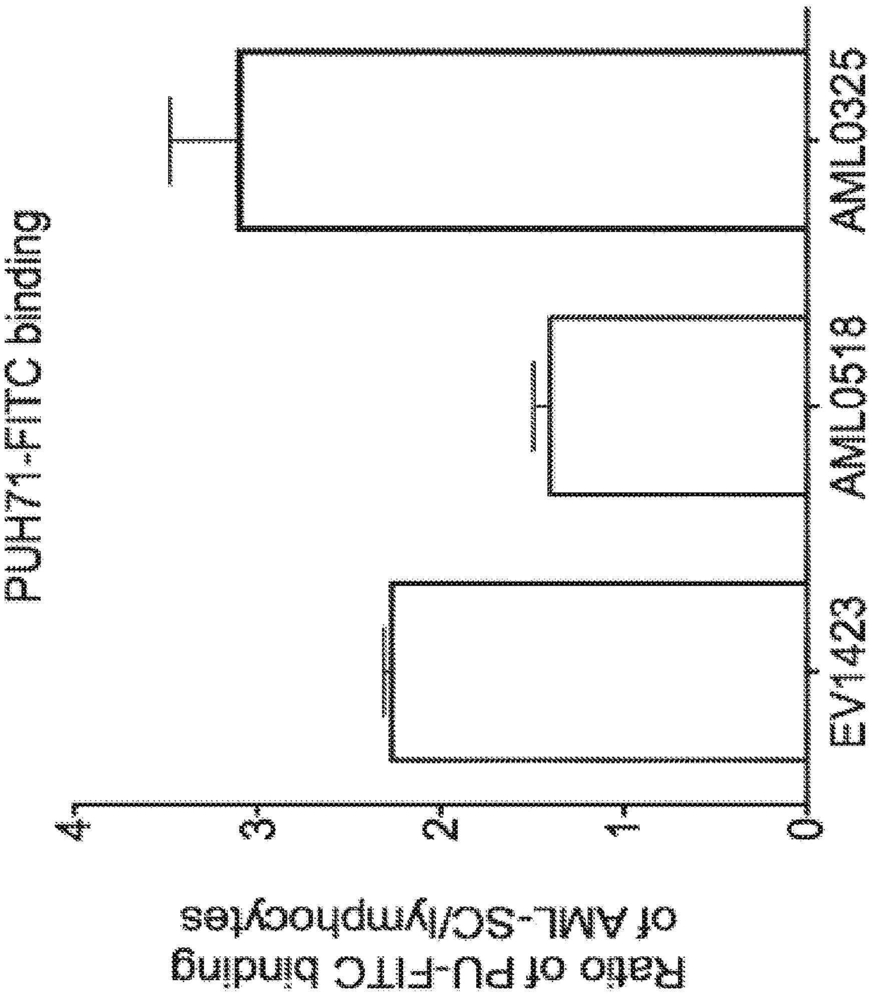
Figure 23B:
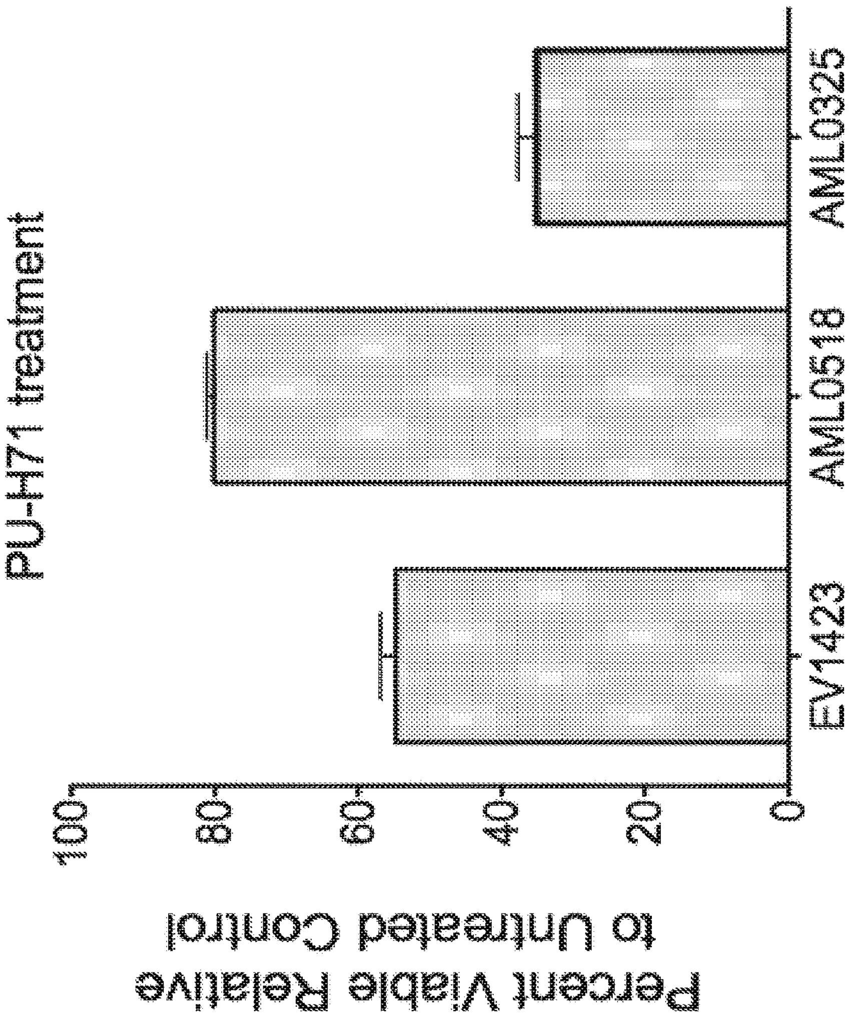

FIGS. 23A and 23B. FIG. 23A Binding of PUH71-FITC2 to leukemia stem cells (LSCs, CD34+CD38− CD45dim). Primary AML samples were incubated with 1 μM PU-H71-FITC2 at 37° C. for 4 h. Cells were stained with CD34, CD38, CD45 and 7-AAD followed by flow cytometry analysis. Binding of PU-H71 to LSCs is shown as the mean fluorescence intensity (MFI) in live cells (7-AAD negative). FIG. 23B Percent viability of LSCs relative to the untreated control from three primary AML samples after 48 hour treatment with 1 μM PUH71. Cells were stained with CD45, CD34 and CD38 prior to Annexin V and 7-AAD staining. Viability LSCs was measured by flow cytometry and determined as the percentage of AnnexinV-/7AAD- of the CD45dim CD34+CD38− gate.

Figure 24:
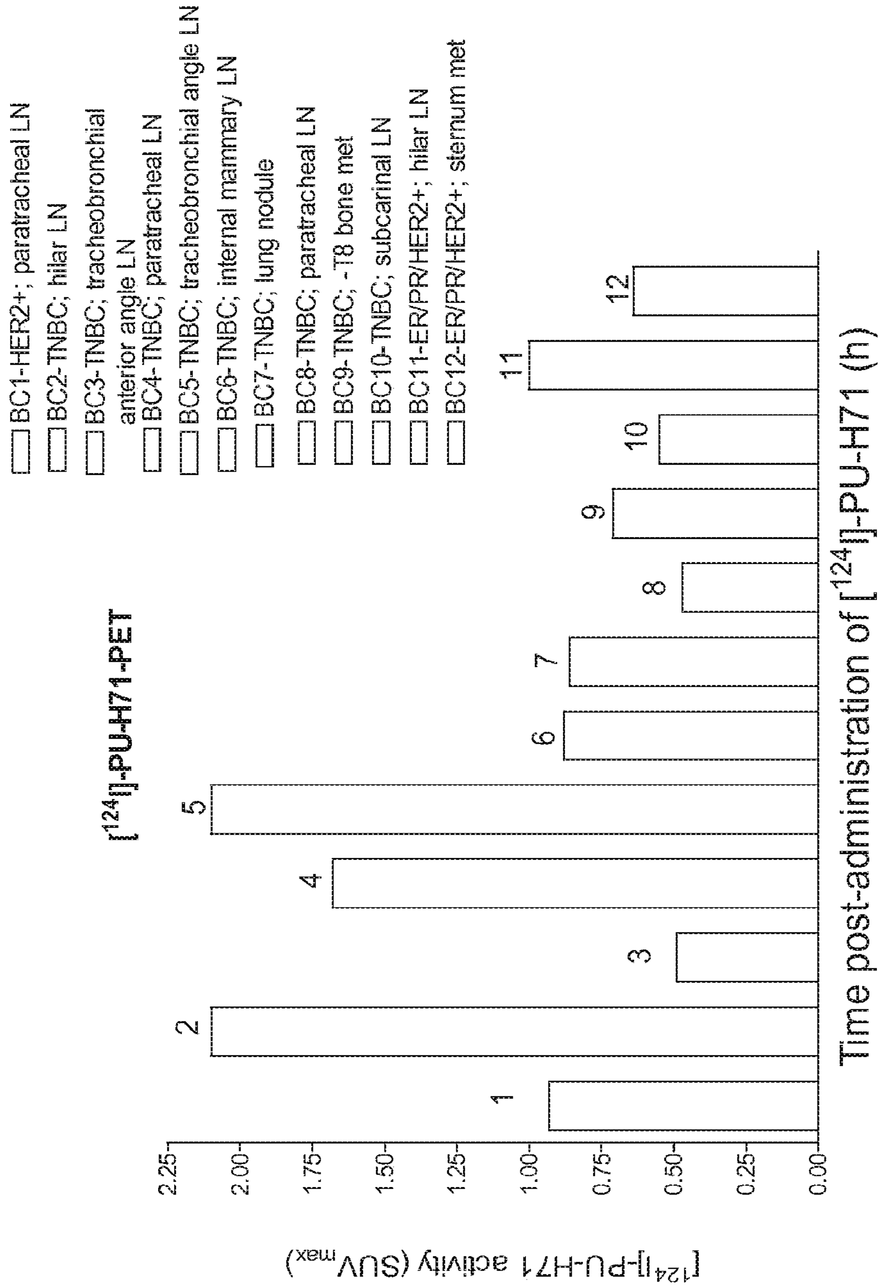

FIG. 24. Tumors have distinct [$^{124}$I]-PU-H71 uptake indicating differences in their "oncogenic HSP90" content and thus in their potential to respond to HSP90 therapy. [$^{124}$I]-PU-H71 PET images at 24 h post-[$^{124}$I]-PU-H71 injection were measured as Maximal Standardized Uptake Values ($SUV_{max}$) in several patients with breast cancer. BC=breast cancer. TNBC-triple-negative BC.

Figure 25:
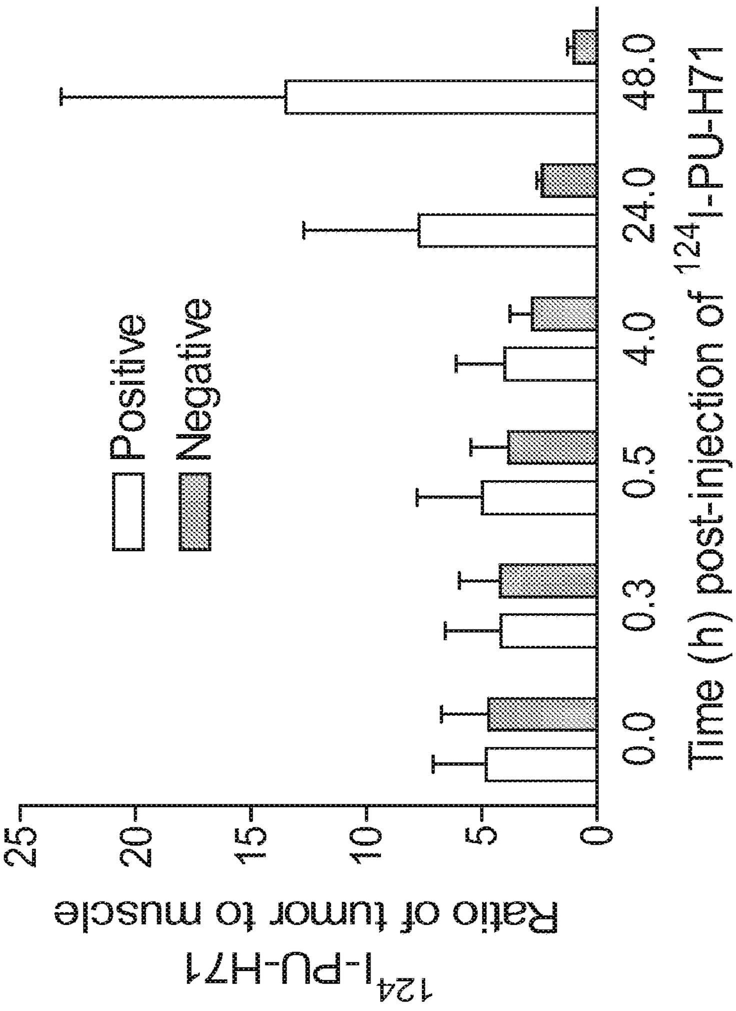

FIG. 25. Tumor:muscle SUV ratio for a select number of patients that are responsive to HSP90 inhibition therapy as determined by PET following administration of [$^{124}$I]-PU-H71. In these patients, the tumor:muscle SUV increases over time. Values averaged for several positive and negative tumors are presented.

Figure 26:
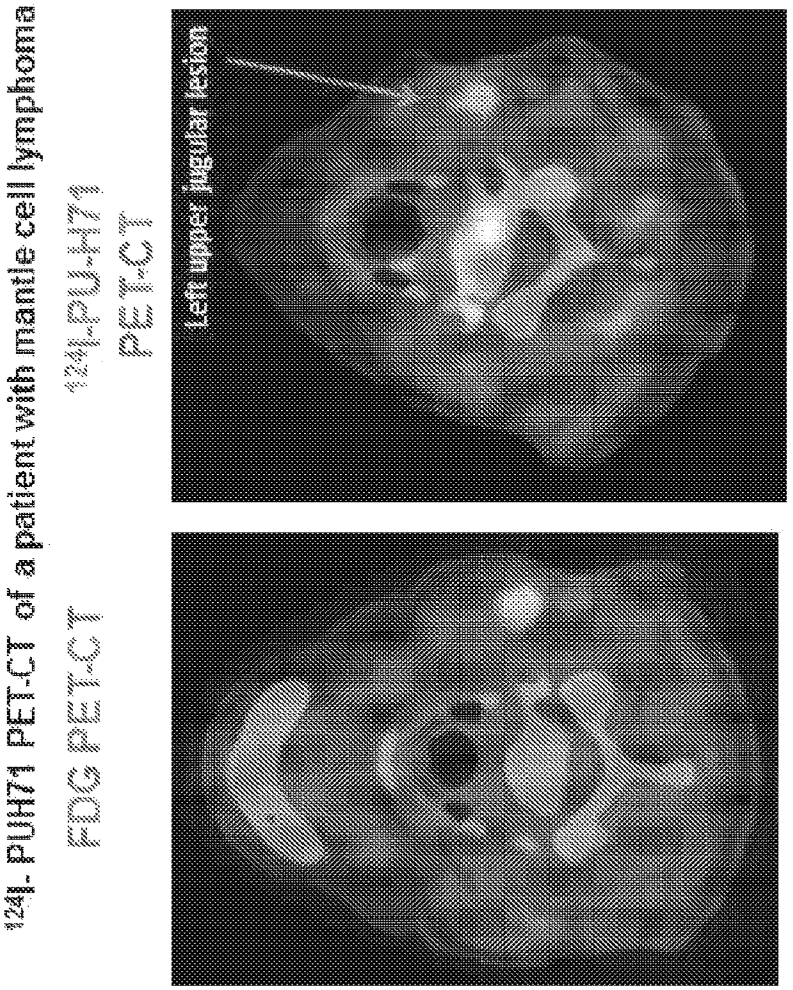

FIG. 26. FDG/CT and [$^{124}$I]-PU-H71 PET/CT of patient with mantle cell lymphoma. The patient shows clear visualization of the lesion at 30 min after [$^{124}$I]-PU-H71-injection. No [$^{124}$I]-PU-H71 uptake was seen in this tumor at later times (3.5-24 h and beyond).

Figure 27:
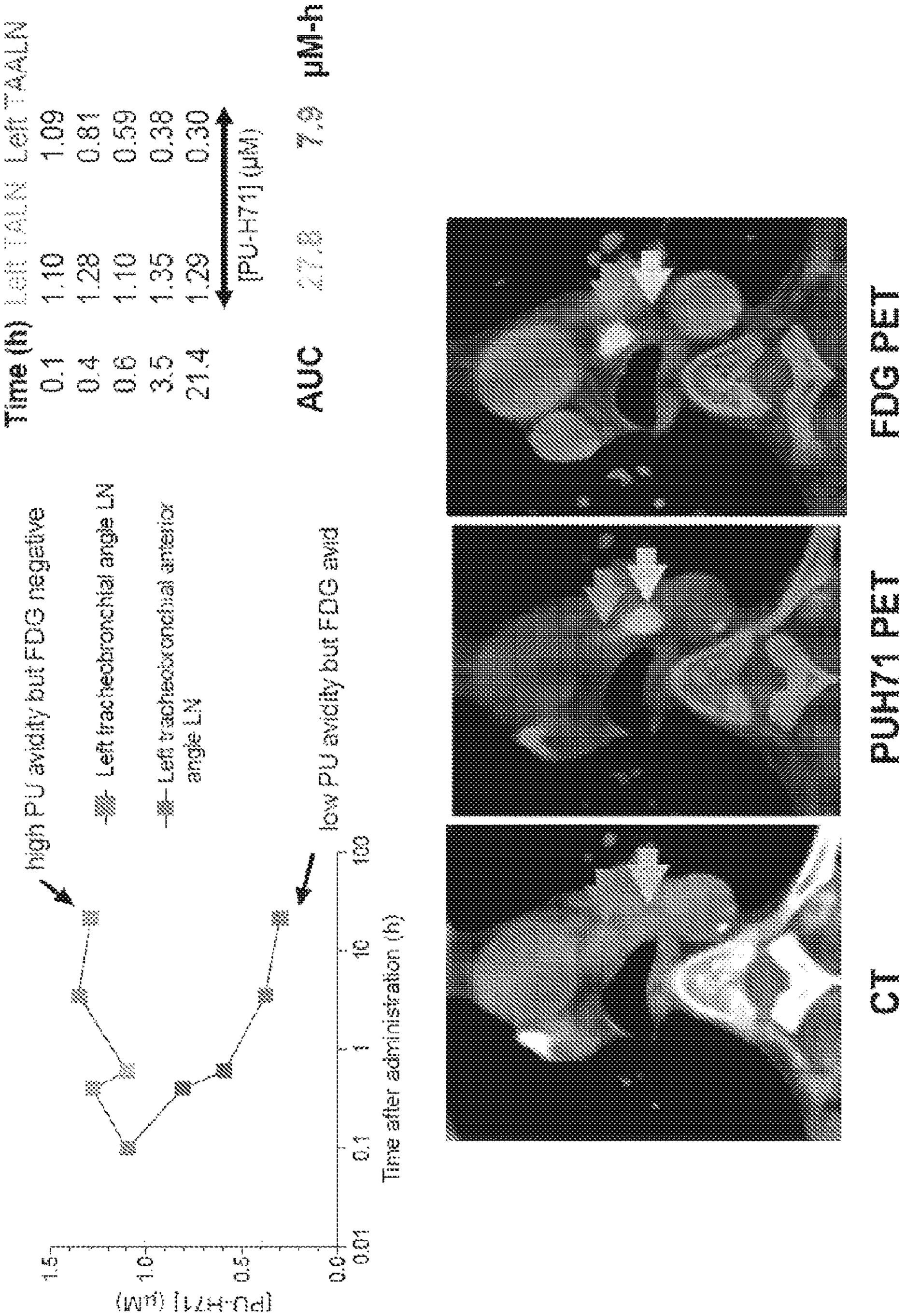
Figures 28A, 28B, 28C, 28D:
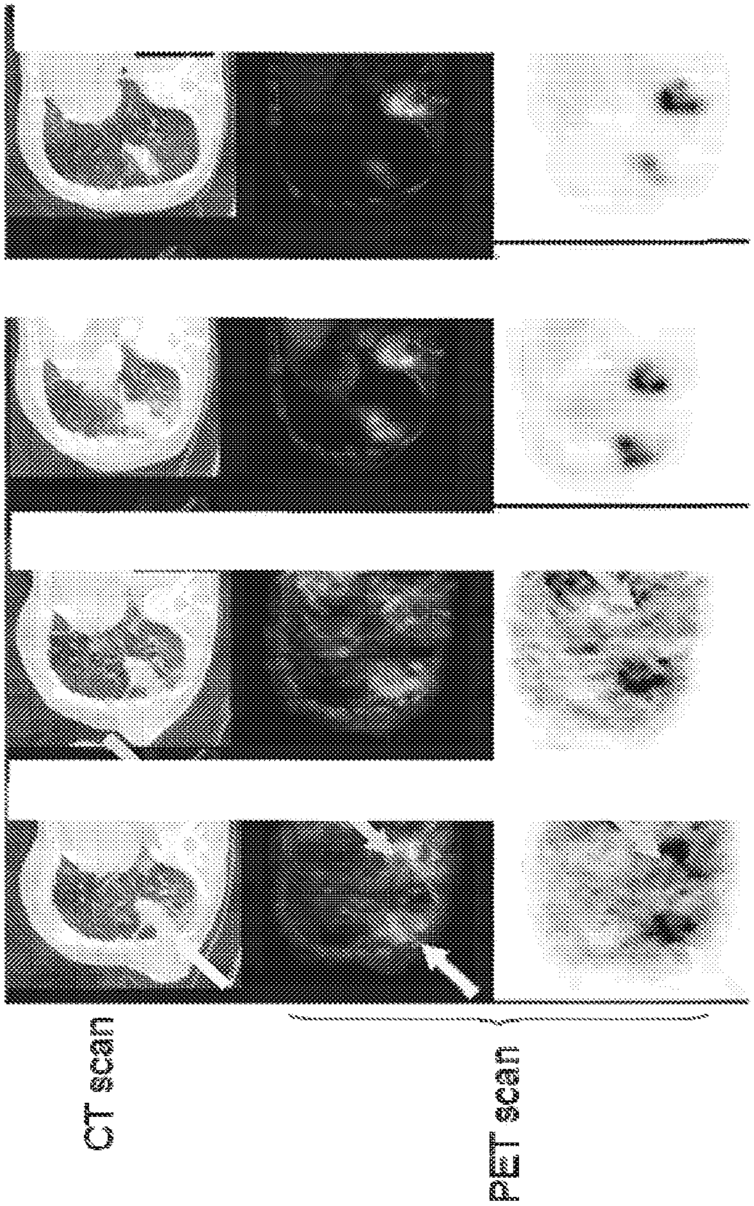

FIG. 27. [$^{124}$I]-PU-H71 PET/CT of patient with recurrent breast cancer in the two indicated lymph nodes (LN). PET images at several times post-[$^{124}$I]-PU-H71 injection (0.1, 0.4, 0.6, 3.5 and 21.4 h) were quantified and SUVmax data obtained for [$^{124}$I]-PU-H71 were converted to HSP90i concentrations for an administered dose of PU-H71 of 10 mg/m$^2$. The exposure of the two tumors to PU-H71 over the time of 0 to 24 h was also calculated and represented as the area-under-the-curve (AUC). CT (left), PU-PET/CT (middle), and FDG-PET/CT fusion (right) transaxial images demonstrate [$^{124}$I]-PU-H71-avidity in one of the diseased lymph nodes but not the other suggesting that the lesion in the left tracheobronchial anterior angle lymph node (TAALN) is less likely than the left tracheobronchial angle LN (TALN) to respond to HSP90 therapy.

FIGS. 28A, 28B, 28C, and 28D. A triple-negative breast cancer patient was imaged with $^{124}$I-PU-H71 PET. At 20 min post-injection, uptake is noted in a lung mass (left arrow), and a bone lesion (right arrow) FIG. 28A, but at 24 h uptake is seen only in the lung lesion FIG. 28B. Both the lung and bone tumors are confirmed by CT and FDG-scans FIG. 28C. The patient started treatment with the HSP90 inhibitor STA-9090. Twenty days post HSP90 inhibitor treatment, the lung but not the bone lesion is remarkably reduced in size, as evidenced by both CT and FDG-PET FIG. 28D.

Figure 29:
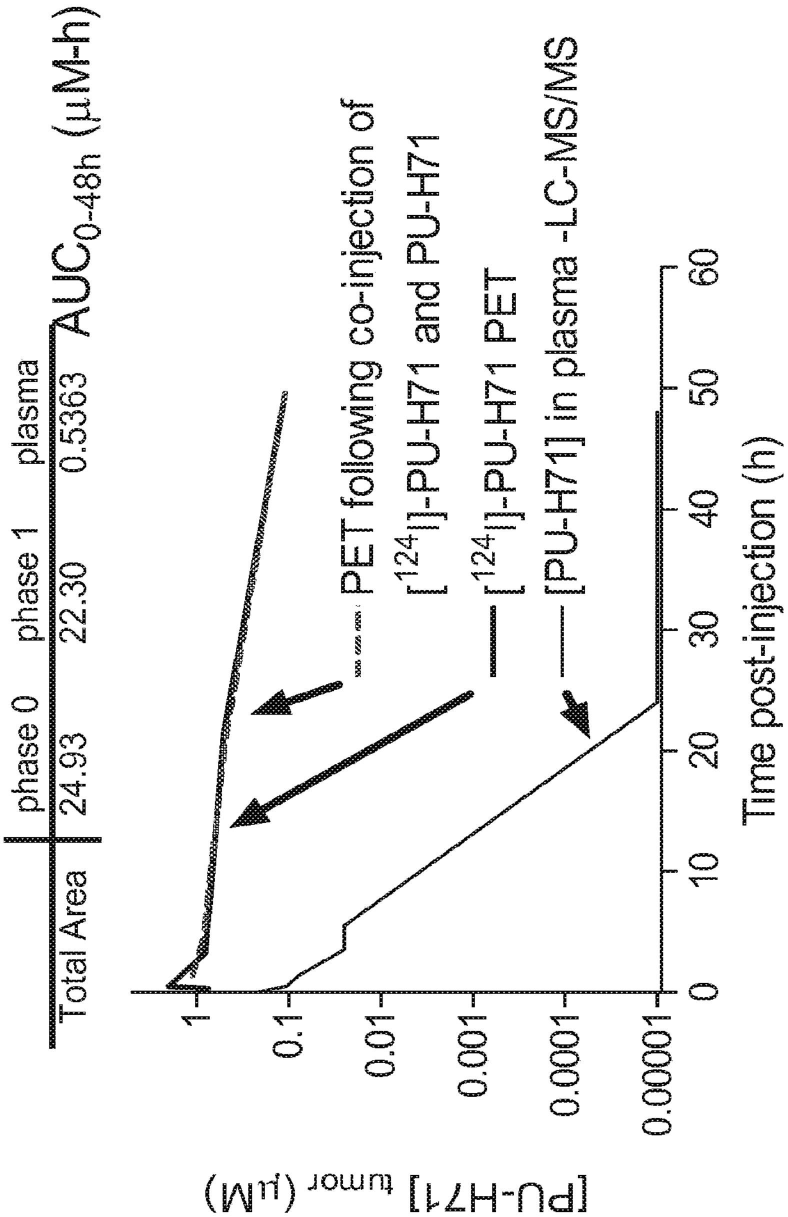

FIG. 29. [$^{124}$I]-PU-H71 PET/CT of a patient with metastatic HER2 breast cancer in the paratracheal node. PET images at the indicated times post-[$^{124}$I]-PU-H71 or post co-injection of [$^{124}$I]-PU-H71 with 10 mg/m2 PU-H71 were measured as Maximal Standardized Uptake Values ($SUV_{max}$). SUV data obtained for [$^{124}$I]-PU-H71 were converted to HSP90i concentrations for an administered dose of PU-H71 of 10 mg/m$^2$. The exposure of the tumor to PU-H71 over the time of 0 to 48 h was also calculated and represented as the area-under-the-curve (AUC). Tumor concentrations of PU-H71 (in micromolar values) as estimated from [$^{124}$I]-PU-H71 PET or as determined from [$^{124}$I]-PU-H71 PET after co-injection of [$^{124}$I]-PU-H71/PU-H71 are comparable.

Figure 30A:
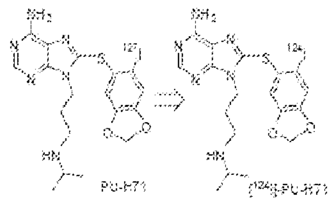
Figure 30B:
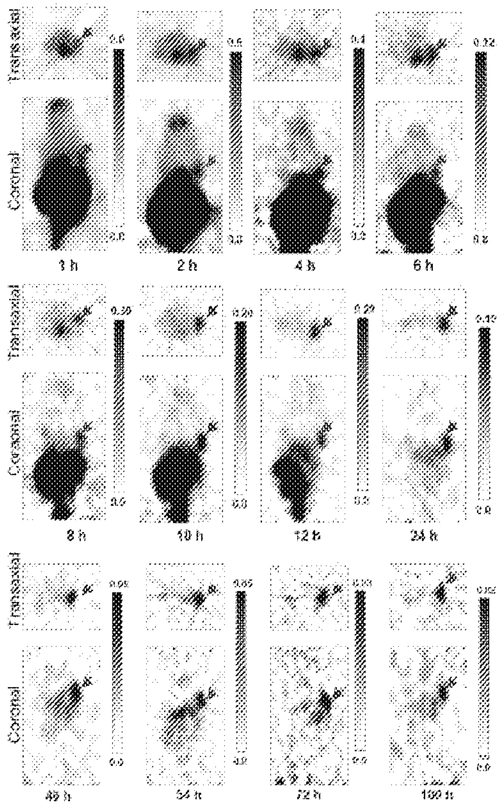
Figure 30C:
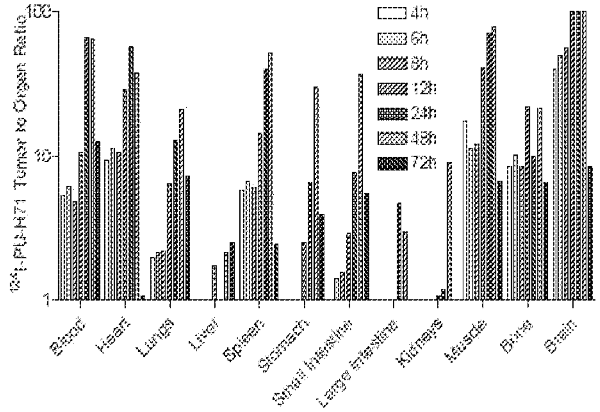
Figure 30D:
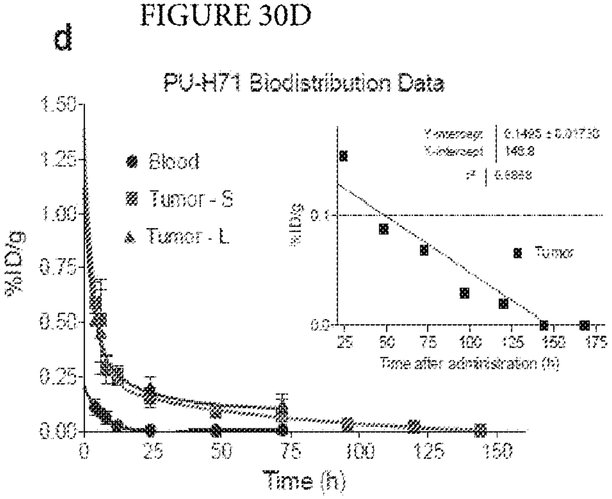

FIGS. 30A, 30B, and 30C. [$^{124}$I]-PU-H71 PET is a non-invasive assay for HSP90 inhibitors. FIG. 30A The chemical structure of PU-H71 and [$^{124}$I]-PU-H71. FIG. 30B Representative PET scan of [$^{124}$I]-PU-H71 in MDA-MB-468 tumor-bearing mice. Location of the tumor is indicated by a red arrow. FIG. 30C The [$^{124}$I]-PU-H71 tumor-to-organ activity concentration ratios for the indicated times post-administration. FIG. 30D Biodistribution of [$^{131}$I]-PU-H71 in MDA-MB-468 tumors and plasma (n=5). Tumor-S and Tumor-L, small and large tumors, respectively. (inset) The 24 to 140 h slow terminal clearance phase of PU-H71 from tumors was analyzed using a linear regression curve fit as implemented in GraphPad Prism.

FIGS. 31A, 31B, 31C, 31D, 31E, and 31F. [$^{124}$I]-PU-H71 PET accurately predicts the delivery of therapeutically effective PU-H71 concentrations in tumor. FIG. 31A Predicted PU-H71 tumor distribution based on the mean % ID/g generated by [$^{124}$I]-PU-H71 PET (lower). The predicted tumor concentration at indicated times p.a. of indicated PU-H71 doses (upper). FIG. 31B Tumor PU-H71 concentrations (n=5) following administration of 75 mg/kg agent as predicted by [$^{124}$I]-PU-H71 PET, and determined by LC-MS/MS and by [$^{124}$I]-PU-H71 PET following co-injection of [$^{124}$I]-PU-H71 and PU-H71. FIGS. 31C, 31D Representative Western blot analyses of MDA-MB-468 tumors administered PU-H71 at the indicated doses and analyzed at 24 h p.a. FIG. 31C and of MDA-MB-468 cells treated for 24 h with the indicated concentrations of PU-H71 FIG. 31D Blots (n=3) were quantified by densitometry and the change in protein levels graphed versus the concentration of PU-H71 (right panels). FIGS. 31E, 31F Target occupancy at 24 h p.a. as predicted by [$^{124}$I]-PU-H71 PET following co-administration of tracer amounts of [$^{124}$I]-PU-H71 mixed with the indicated doses of PU-H71.

FIGS. 32A, 32B, 32C, 32D, 32E, 32F, and 32G. [$^{124}$I]-PU-H71 PET predicts the design of an efficacious dose regimen for HSP90 therapy. FIG. 32A Predicted PU-H71 tumor distribution when administered for 2 weeks at the indicated doses on a 3×week (Mon-Wed-Fri with Sat/Sun off) schedule based on the mean tumor activity concentration (% ID/g) derived by [$^{124}$I]-PU-H71 PET. (inset) The AUCs for PU-H71 in tumors were calculated using GraphPad Prism. FIG. 32B The viability of MDA-MB-468 cells treated for 48 h with the indicated doses of PU-H71 was analyzed by Ethydium Bromide/Acridine Orange staining (upper). Estimated tumor apoptosis induced by the [$^{124}$I]-PU-H71 PET predicted indicated average and minimum PU-H71 tumor concentrations. FIG. 32C MDA-MB-468 tumor-bearing mice (n=5) were administered i.p. the indicated doses of PU-H71 on a 3×week schedule. Tumor volume and mouse weight were monitored over the indicated treatment period. FIG. 32D MDA-MB-468 tumor-bearing mice (n=5) were administered i.p. the indicated doses of PU-H71 on a 3×week schedule. Tumor volume and mouse weight were monitored over the indicated treatment period. FIG. 32E Predicted PU-H71 tumor distribution based on the mean tumor activity concentration (% ID/g) derived by [$^{124}$I]-PU-H71 PET when administered at the indicated dose on a 3×week (Mon-Wed-Fri with Sat/Sun off) schedule. FIG. 32F Western blot analysis of the Vehicle (Control) and PU-H71 (5 mg/kg)-treated tumors sacrificed on Thu, at 24 h p.a. of the last dose. PU-H71 tumor concentrations, as determined by LC-MS/MS, are indicated for each tumor. FIG. 32G Analysis of data (n=5) from panel FIG. 32D.

FIGS. 33A, 33B, 33C, 33D, and 33E. [$^{124}$I]-PU-H71 PET predicts the design of an efficacious schedule regimen for HSP90 therapy. FIG. 33A Predicted PU-H71 tumor distribution based on the mean tumor activity concentration (% ID/g) derived by [$^{124}$I]-PU-H71 PET when administered at 75 mg/kg on the indicated schedules. FIG. 33B Estimated tumor apoptosis induced by the indicated average and minimum PU-H71 tumor concentrations as predicted from in vitro analyses. FIG. 33C MDA-MB-468 tumor-bearing mice (n=5) were administered i.p. PU-H71 (75 mg/kg) on the indicated schedules. Tumor volume and mouse weight were monitored over the indicated treatment period. FIG. 33D Western blot and FIG. 33E LC-MS/MS analysis of the PU-H71 (75 mg/kg)-treated tumors on the 1×week schedule sacrificed on Thu, at 24 h and Thu, at 96 h p.a. of the last dose. Control; vehicle only treated mice.

Figure 34:
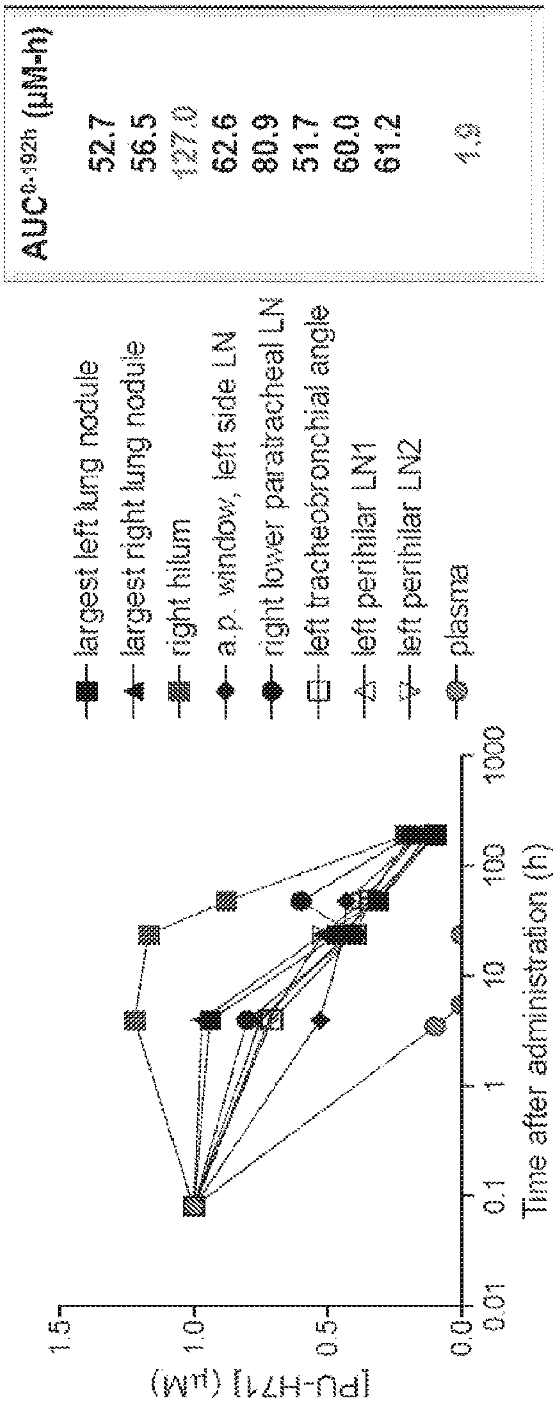

FIG. 34. Tumor exposure to PU-H71 as predicted by PU-PET for a pancreatic patient with metastatic disease to lung and indicated lymph nodes. Tumor concentrations are calculated based on an administered dose of 20 mg/m2. Plasma exposure is also shown in red. Calculated AUCs (μM-h) for the period 0 to 192 h are tabulated on the right.

Figure 35:
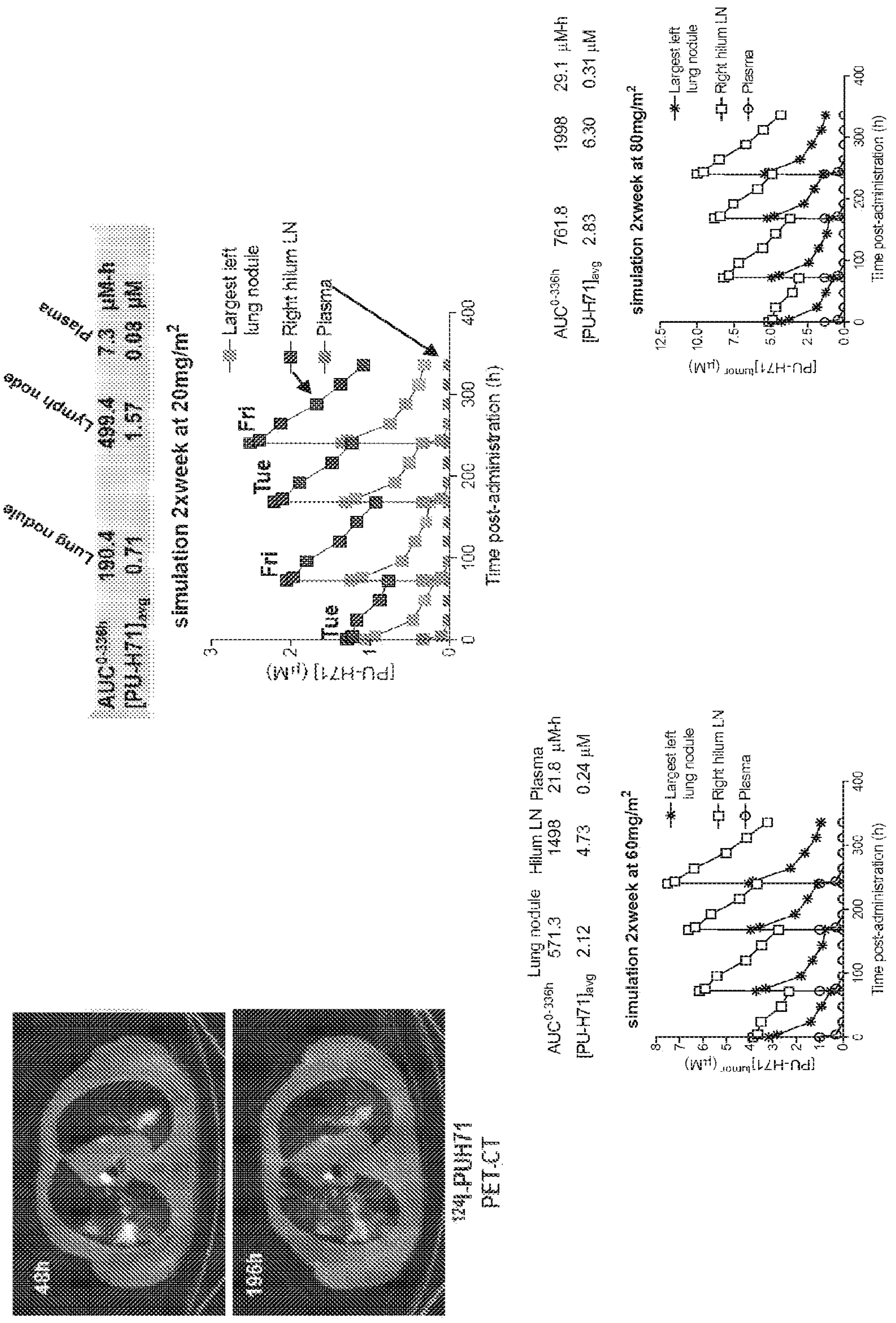

FIG. 35. [$^{124}$I]-PU-H71 PET/CT of a patient with pancreatic cancer with recurrent disease in the lung. PET images at the indicated times post-[$^{124}$I]-PU-H71 injection (48 and 196 h, left panels) were quantified and SVU data obtained for [$^{124}$I]-PU-H71 were converted to PU-H71 concentrations in the tumor for the indicated administered doses of PU-H71. The exposure of two tumors, one in the left lung and another in the right hilum LN, to PU-H71 over the time of 0 to 336 h for a two-week treatment on a twice-week (Tue and Fri) schedule and an administered dose of 20, 60 and 80 mg/m2 (upper right and bottom panels) was also calculated and represented as the area-under-the-curve (AUC) and as an average tumor concentration.

Figure 36A:
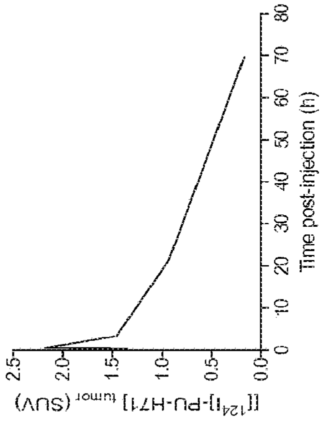
Figure 36B:
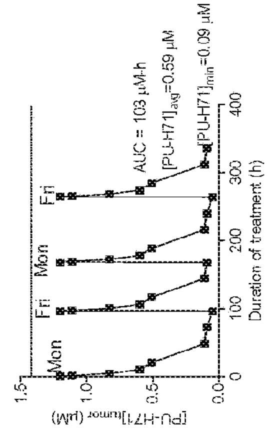
Figure 36C:
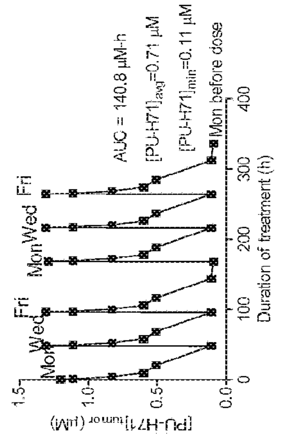
Figure 36D:
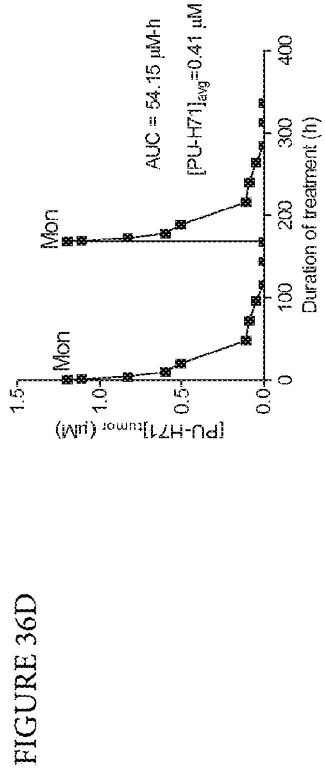
Figure 36E:
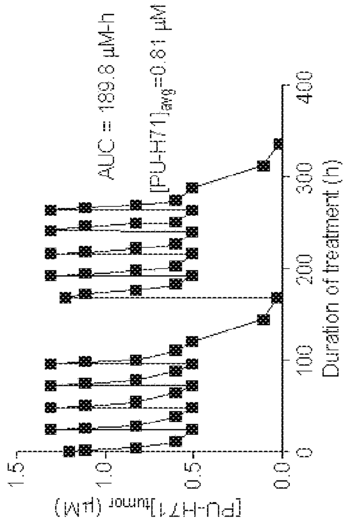

FIGS. 36A, 36B, 36C, 36D, and 36E. FIG. 36A shows the biodistribution of $^{124}$I-PU-H71 over 0 to 72 h in the tumor of a breast cancer patient as obtained from PU-PET. The data was used to simulate the tumor exposure to an administered dose of 10 mg/m2 when given twice a week for two weeks with weekend off (FIG. 36B), three times a week for two weeks with weekend off (FIG. 36C), once a week for two weeks with weekend off (FIG. 36D), and five times a week for two weeks with weekend off (FIG. 36E).

FIGS. 37A, 37B, and 37C. [$^{124}$I]-PU-H71 PET predicts the magnitude of response to HSP90 therapy. FIG. 37A Predicted average occupancy of tumor HSP90 sites by PU-H71 when administered at the indicated doses and on the indicated schedules. FIGS. 37B-37C Correlation of tumor HSP90 sites occupancy with the observed anti-tumor effect was analyzed in GraphPad Prism.

Figure 38C:
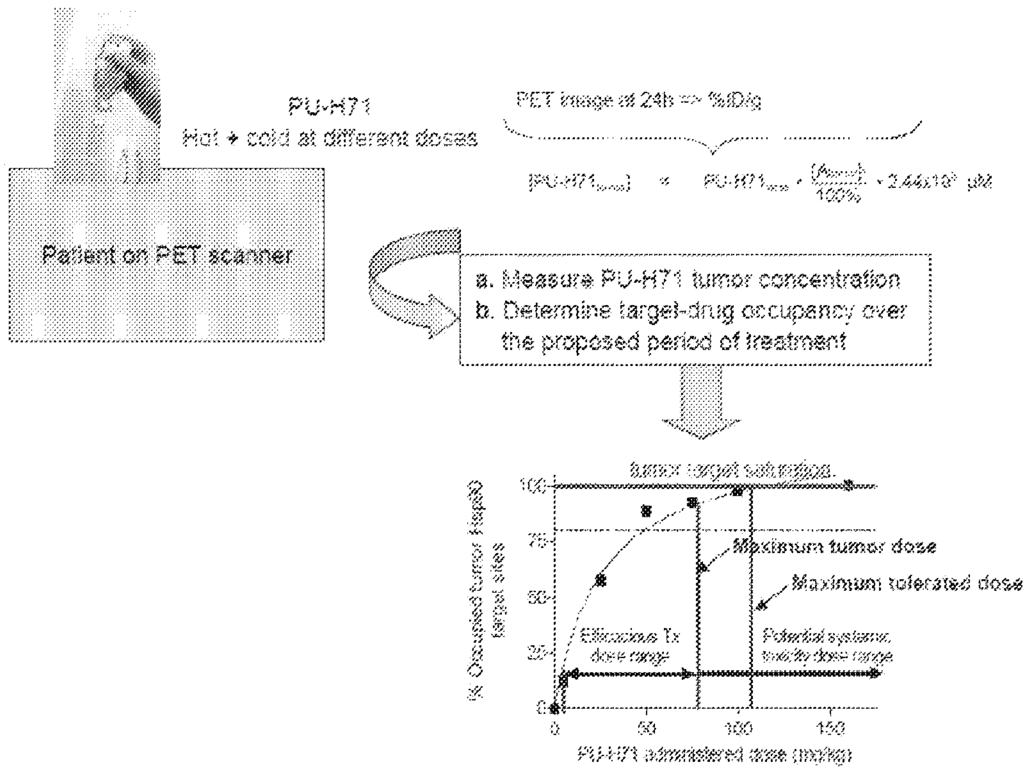

FIGS. 38A, 38B, and 38C. The use of $^{124}$I-PU-H71 PET assay in the clinical development of HSP90 inhibitors: FIG. 38A in determining the dose of HSP90 inhibitor needed to achieve effective tumor concentrations, selection of patient eligible for HSP90 therapy and in designing an efficacious dose and schedule regimen; FIG. 38B in assaying the actual concentration of the drug delivered to the tumor and predicting clinical outcome on HSP90 therapy and FIG. 38C in determining the "maximum tumor dose". CR=complete response, PR=partial response, NR=no response.

Figure 39:
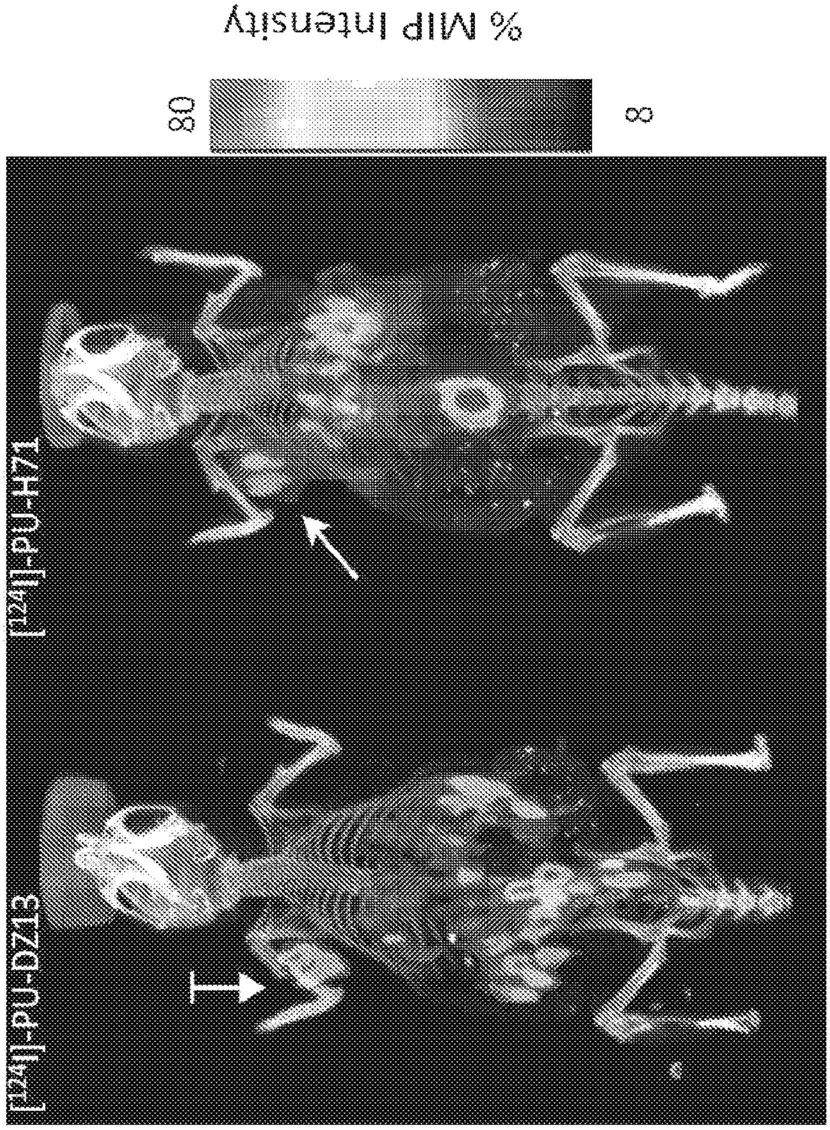

FIG. 39. In vivo PET imaging of [$^{124}$I]-PU-DZ13 and [$^{124}$I]-PU-H71 in MDA-MB-468 xenograft TNBC mice. PET imaging was conducted on either an R4 or a Focus 120 dedicated small animal PET scanner (Concord Microsystems, Inc., Knoxville, TN); separate anatomical imaging was conducted on a dedicated small animal CT scanner (ImTek, Inc., Oak Ridge, TN), using a custom built stereotactic restraint device. Maximum intensity projection (MIP) of CT and PET image datasets were anatomically registered, and overlay images were generated using an alpha transparency blend of PET and CT data.

Figure 40A:
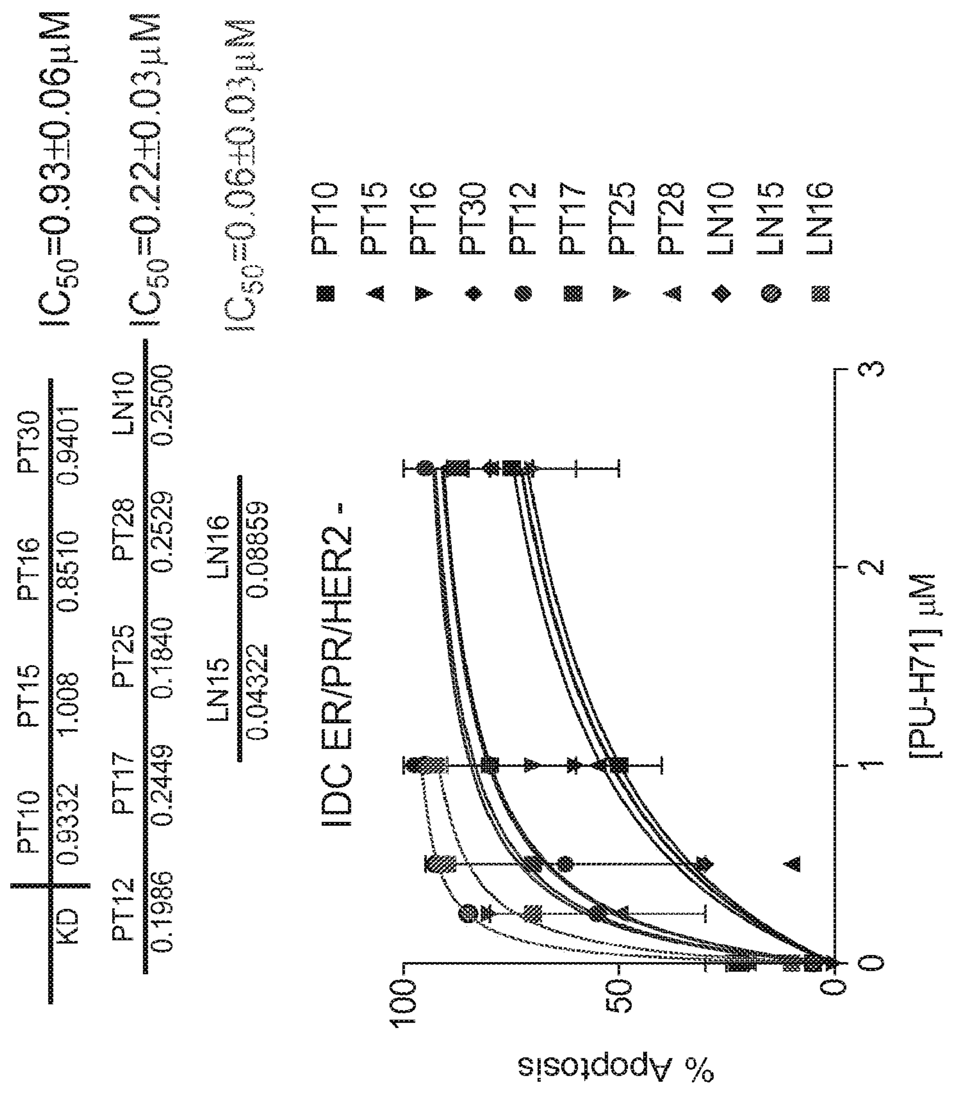
Figure 40B:
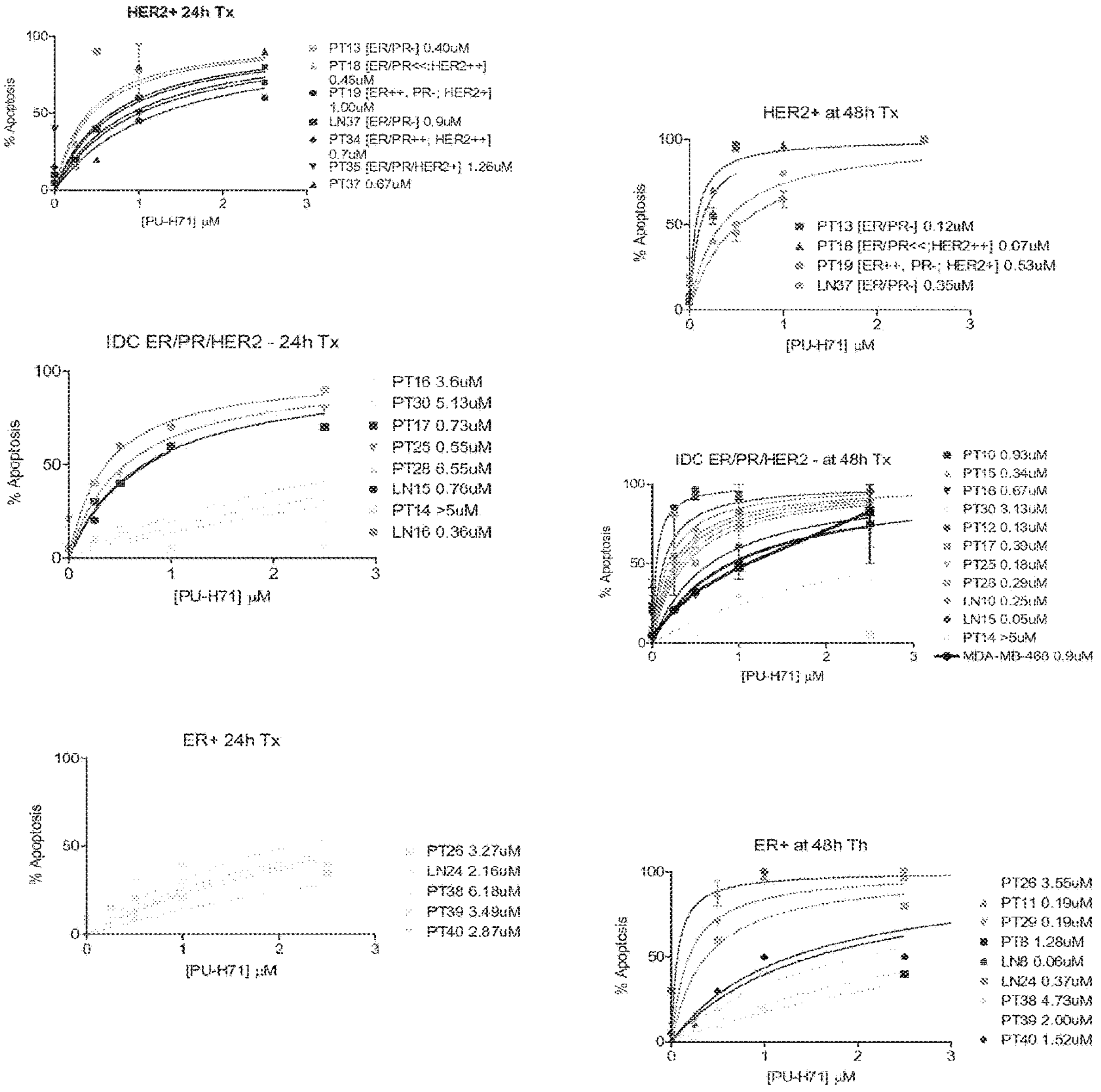

FIGS. 40A, and 40B. Cases of BC show a dose-dependent response to PU-H71. H&E stained slides display significant areas of apoptosis containing both pyknotic cells (indicative of early stage apoptosis) and karyorrhexic cells (representative of late phase apoptosis) when the tumor is highly sensitive to PU-H71. FIG. 40A: Apoptosis/cell death in TNBC specimens treated for 48 h with the indicated concentrations of PU-H71 was quantified and plotted against the concentration of PU-H71. Both apoptotic and necrotic/late apoptotic cells were counted and added to the % apoptosis as depicted on the y-axis. Note a clustering of cases in three sensitivity groups (steepest, top curves, most sensitive, LN15 and LN16; middle curves, sensitive, PT12, PT17, PT25, PT28 and LN10 and lower curves, less sensitive, PT10, PT15, PT16 and PT30). Interestingly, the lymph node metastases showed a higher sensitivity than the primary tumor at the equivalent dose. PT=primary tumor, LN=lymph node. Tumors most sensitive to PU-H71 also stain high for p-Akt. FIG. 40B: Same as for FIG. 40A with specimens from HER2+, TNBC and ER+BC patients treated for 24 or 48 h with PU-H71.

Figure 41A:
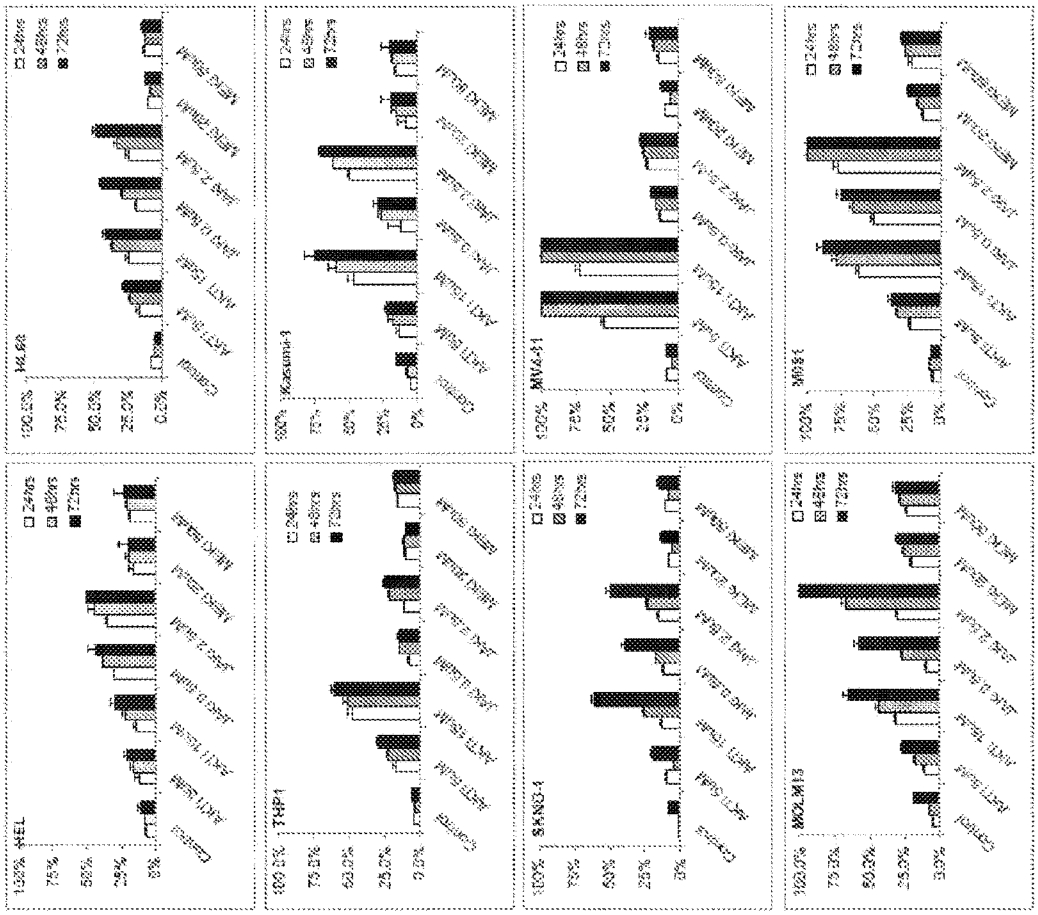
Figure 41B:
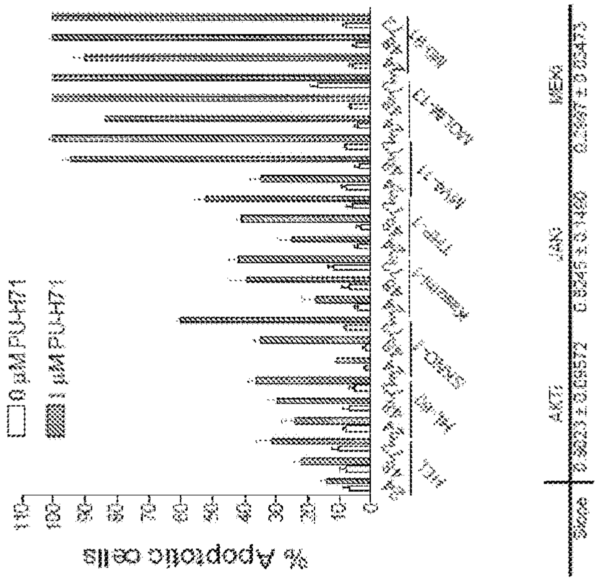
Figure 41C:
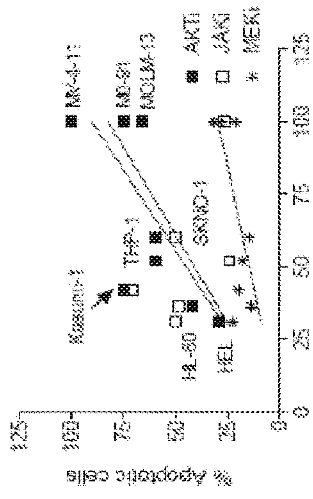

FIGS. 41A, 41B, and 41C. Apoptotic sensitivity to HSP90 inhibition correlates with addiction of cells for survival on the AKT- and STAT- but not MEK-pathways. FIGS. 40A-40B: Representative AML cells were incubated for the indicated times with the indicated concentrations of the HSP90, AKT, JAK and MEK inhibitors and apoptosis was assessed using the Acridine Orange/Ethydium Bromide method. The data are consistent with those obtained from multiple repeat experiments ($n \geq 3$). Points, mean; bars, s.d. FIG. 41C: % Apoptosis values from cell treated for 72 h with the AKTi, MEKi and JAKi alone were plotted against those obtained upon HSP90 inhibitor treatment and a linear regression analysis, as implemented in Prism 4.0 was performed.

Figure 42A:
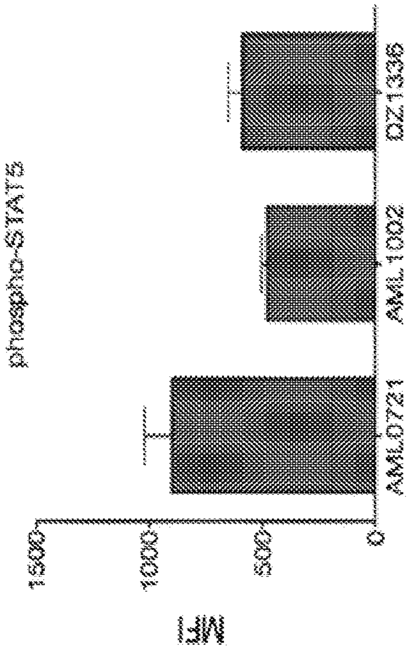
Figure 42B:
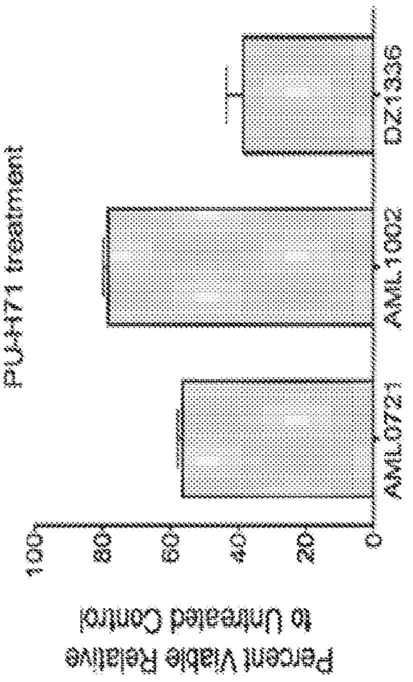

FIGS. 42A and 42B. AML primary cells with highest levels of p-STAT5 are also most sensitive to PU-H71. FIG. 42A: Phospho-STAT5 levels in blast cells (CD45dim gated) represented as mean fluorescence intensity (MFI) for three different primary AML samples. Phosphorylation level of Stat5 was assessed by flow cytometry. FIG. 42B: Percent viability of AML blast relative to the untreated control from three primary AML samples after 48 hour treatment with 1 μM PUH71. Cells were stained with CD45 prior to Annexin V and 7-AAD staining. Viability of AML blast cells was measured by flow cytometry and determined as the percentage of AnnexinV-/7AAD- of the CD45dim vs SSC gate for AML blast.

Figure 43B:
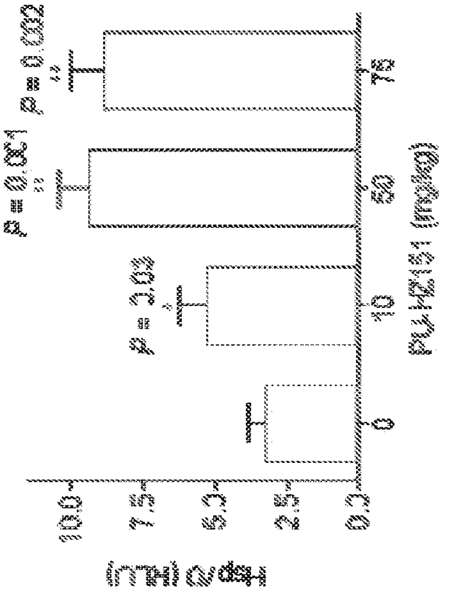
Figure 43A:
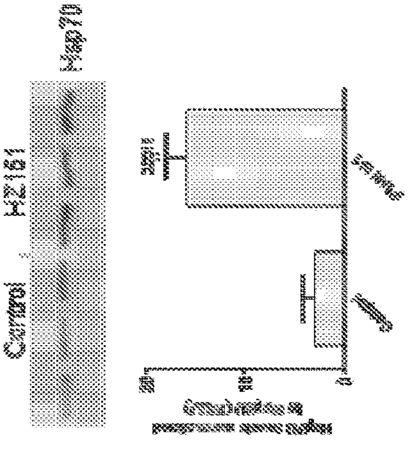
Figure 43C:
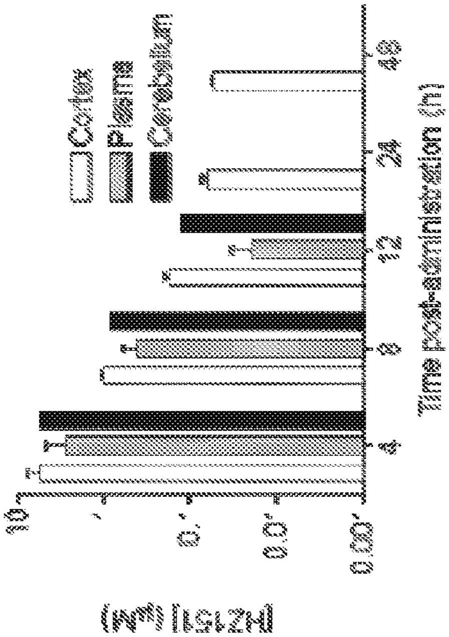

FIGS. 43A, 43B, and 43C. 8-10 mo 3×Tg mice were administered 75 mg/kg (FIG. 43A) or the indicated dose of the HSP90 inhibitor PU-HZ151 (FIG. 43B) and the PD marker, HSP70, was measured in hippocampus, an afflicted brain region in this model of AD, at 24 h post-administration. HSP70 is induced when HSP90 is inhibited and its induction is an indicator that therapeutic levels of the HSP90 inhibitor were delivered to the brain region of interest. FIG. 43C: Levels of the HSP90 inhibitor in the indicated brain regions and plasma were determined by LC-MS/MS after the administration of 50 mg/kg PU-HZ151. Hsp90 inhibitor levels at different times after single ip injection are shown in micromolar units. Brain exposure was also measured as the area under the curve (AUC).

Figure 44A:
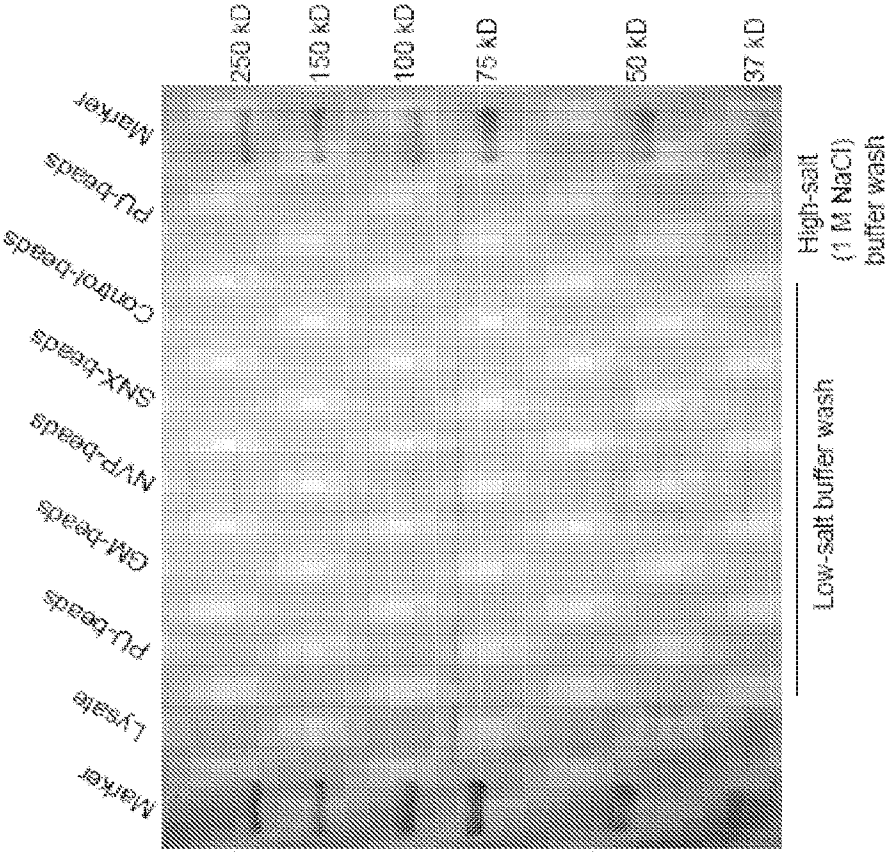
Figure 44B:
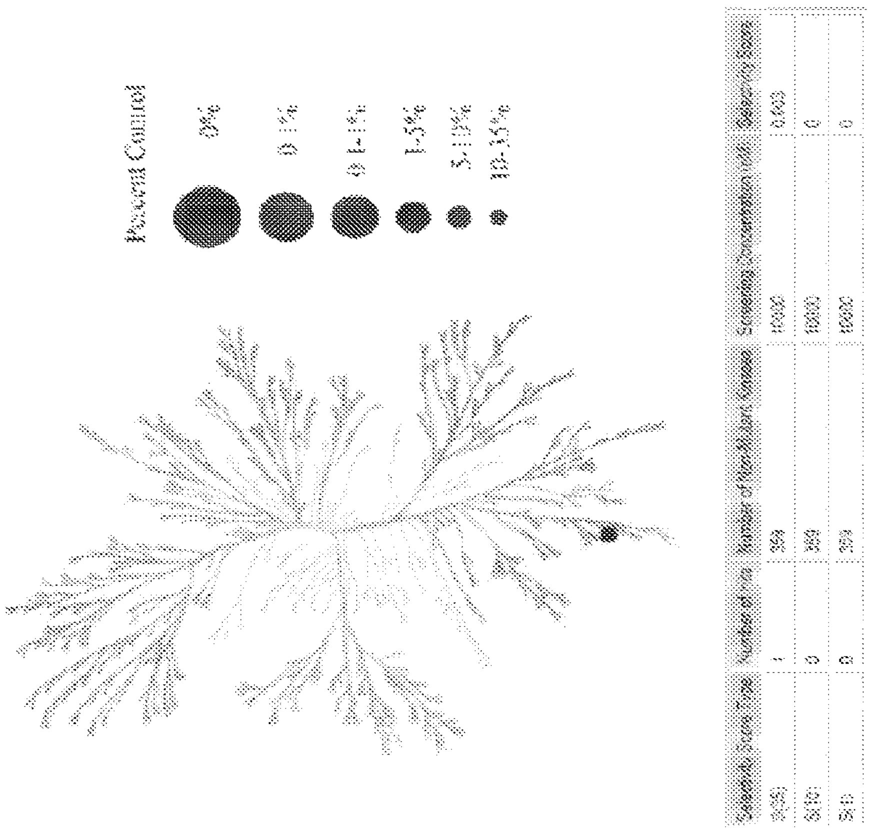

FIGS. 44A and 44B. PU-H71 is selective for HSP90. FIG. 44A: Coomassie stained gel of several HSP90 inhibitor bead-pulldowns. K562 lysates (60 μg) were incubated with 25 μL of the indicated beads. Following washing with the indicated buffer, proteins in the pull-downs were applied to an SDS-PAGE gel. FIG. 44B: PU-H71 (10 μM) was tested in the scanMAX screen (Ambit) against 359 kinases. The TREEspot™ Interaction Map for PU-H71 is presented. Only SNARK (NUAK family SNF1-like kinase 2) (red dot on the kinase tree) appears as a potential low affinity kinase hit of the small molecule.

5. DETAILED DESCRIPTION

5.1. Oncogenic HSP90 as a Tumor Specific Biomarker

The disclosure provides evidence that the abundance of this particular "oncogenic HSP90" species, which is not dictated by HSP90 expression alone, predicts for sensitivity to HSP90 inhibition therapy, and thus is a biomarker for HSP90 therapy. The invention also provides evidence that identifying and measuring the abundance of this oncogenic HSP90 species in tumors predicts of response to HSP90 therapy.

In the following sections, we show that the HSP90 inhibitor PU-H71 targets tumor-enriched HSP90 complexes and affinity-captures HSP90-dependent oncogenic client proteins. The compound PU-H71 was disclosed in U.S. Pat. No. 7,834,181, which is hereby incorporated by reference. PU-H71 has the following chemical structure:

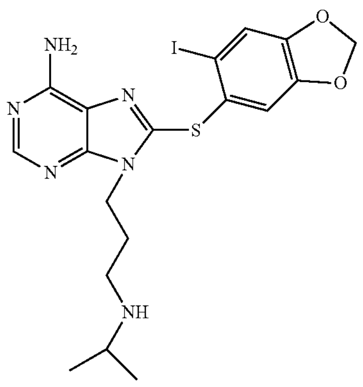

PU-H71

PU-H71 can be administered as a free base or as a pharmaceutically acceptable salt.

In addition, we show that the abundance of the PU-H71-enriched HSP90 species, which is not dictated by HSP90 expression alone, is predictive of the cell's sensitivity to HSP90 inhibition by PU-H71 and other HSP90 inhibitors.

5.1.1. Heterogeneous HSP90 Presentation in Cancer Cells

To investigate the interaction of small molecule HSP90 inhibitors with tumor HSP90 complexes, we made use of agarose beads covalently attached to either geldanamycin (GM) or PU-H71 (GM- and PU-beads, respectively) (FIGS. 1A-1E, 2A-2G) Both GM and PU-H71, chemically distinct agents, interact with and inhibit HSP90 by binding to its N-terminal domain regulatory pocket[35]. For comparison, we also generated G protein agarose-beads coupled to an anti-HSP90 antibody (H9010).

First we evaluated the binding of these agents to HSP90 in breast cancer and in chronic myeloid leukemia (CML) cell lysates. Four consecutive immunoprecipitation (IP) steps with H9010, but not with a non-specific IgG, efficiently depleted HSP90 from these extracts (FIG. 1A, 4×H9010 and not shown). In contrast, sequential pull-downs with PU- or GM-beads removed only a fraction of the total cellular HSP90 (FIGS. 1B, 3A, 3B). Specifically, in MDA-MB-468 breast cancer cells, the combined PU-bead fractions represented approximately 20-30% of the total cellular HSP90 pool, and further addition of fresh PU-bead aliquots failed to precipitate the remaining HSP90 in the lysate (FIG. 1B, PU-beads). This PU-depleted, remaining HSP90 fraction, while inaccessible to the small molecule, maintained affinity for H9010 (FIG. 1B, H9010). From this we conclude that a significant fraction of HSP90 in the MDA-MB-468 cell extracts was still in a native conformation but not reactive with PU-H71.

To exclude the possibility that changes in HSP90 configuration in cell lysates make it unavailable for binding to immobilized PU-H71 but not to the antibody, we analyzed binding of radiolabeled $^{131}$I-PU-H71 to HSP90 in intact cancer cells (FIG. 1C, lower). The chemical structures of $^{131}$I-PU-H71 and PU-H71 are identical: PU-H71 contains a stable iodine atom ($^{127}$I) and $^{131}$I-PU-H71 contains radioactive iodine; thus, isotopically labeled $^{131}$I-PU-H71 has identical chemical and biological properties to the unlabeled PU-H71. Binding of $^{131}$I-PU-H71 to HSP90 in several cancer cell lines became saturated at a well-defined, although distinct, number of sites per cell (FIG. 1C, lower). We quantified the fraction of cellular HSP90 that was bound by PU-H71 in MDA-MB-468 cells. First, we determined that HSP90 represented 2.66-3.33% of the total cellular protein in these cells, a value in close agreement with the reported abundance of HSP90 in other tumor cells[33]. Approximately $41.65\times10^{6}$ MDA-MB-468 cells were lysed to yield 3875 μg of protein, of which 103.07-129.04 μg was HSP90. One cell, therefore, contained $(2.47\text{-}3.09)\times10^{-6}$ μg, $(2.74\text{-}3.43)\times10^{-11}$ μmols or $(1.64\text{-}2.06)\times10^{7}$ molecules of HSP90. In MDA-MB-468 cells, $^{131}$I-PU-H71 bound at most to $5.5\times10^{6}$ of the available cellular binding sites (FIG. 1C, lower), which amounts to 26.6-33.5% of the total cellular HSP90 (calculated as $5.5\times10^{6}/(1.64\text{-}2.06)\times10^{7}*100$). This value is remarkably similar to the one obtained with PU-bead pull-downs in cell extracts (FIG. 1B), confirming that PU-H71 binds to a fraction of HSP90 in MDA-MB-468 cells that represents approximately 30% of the total HSP90 pool and validating the use of PU-beads to efficiently isolate this pool. In K562 and other established t(9; 22)+ CML cell lines, PU-H71 bound 10.3-23% of the total cellular HSP90 (FIGS. 1C, 3B, 3C).

Next, we extended our studies to several primary leukemia cells and to normal blood cells. Among these were primary chronic and blast phase CML and acute myeloid leukemia (AML) samples that contained both blasts (malignant cell population) and lymphocytes (normal cell population), CD34+ cells isolated from the cord blood of healthy donors, total mononuclear cells from peripheral blood and also peripheral blood leukocytes (PBLs) (FIGS. 1C, 1D, 1E, 3, 4). We used a fluorescein labeled PU-H71 (PU-FITC). This chemical tool allows for the flow cytometric analysis, in heterogeneous cell populations, of PU-H71 binding to distinct cell populations using cell surface markers, as well as the investigation of cells' sensitivity to PU-H71. A tetraethylene glycol derivatized FITC (FITC-TEG) was used to control for non-specific binding (FIG. 1D).

PU-H71 efficiently bound to HSP90 in K562 cells and in CML and AML blasts with a half relative binding affinity ($EC_{50}$) of 116, 201 and 425 nM, respectively (FIG. 1D). In contrast, its affinity for normal blood cells was weaker, with $EC_{50s}$ higher than 2,000 nM (FIGS. 1D, 3D). HSP90 remains highly expressed in these normal blood cells as indicated by substantial binding to the HSP90 antibody (FIG. 3D).

Cells with highest avidity for PU-H71 were also most sensitive to killing by the agent (FIGS. 1E, 3E, 4). When evaluated in a panel of CML and AML cell lines and primary samples, a significant correlation between the ability of PU-H71 to bind HSP90 and the cell killing potential of PU-H71 against these cells was noted (FIGS. 3E, 4).

Collectively, these data show that certain HSP90 inhibitors, such as PU-H71, preferentially bind to a subset of HSP90 species that is more abundant in cancer cells than in normal cells (FIG. 5A). The abundance of this HSP90 species, which is not dictated by HSP90 expression level alone, is predictive of the cell's sensitivity to HSP90 inhibition, thus the abundance of this tumor HSP90 species can be used as a biomarker predictive of response to HSP90 therapy.

5.1.2. Onco- and WT-Protein Bound HSP90 Species Co-Exist in Cancer Cells, but PU-H71 Selects for the Onco-Protein/HSP90 Species To explore the biochemical functions associated with these HSP90 species, we performed immunoprecipitations (IPs) and chemical precipitations (CPs) with antibody- and HSP90-inhibitor beads, respectively, and we analysed the ability of HSP90 bound in these contexts to co-precipitate with a chosen subset of known clients. K562 CML cells were first investigated because this cell line co-expresses the aberrant Bcr-Abl protein, a constitutively active kinase, and its normal counterpart c-Abl. These two Abl species are clearly separable by molecular weight and thus easily distinguishable by Western blot (FIG. 2A, Lysate), facilitating the analysis of HSP90 onco- and wild type (WT)-clients in the same cellular context. We observed that H9010, but not a non-specific IgG, isolated HSP90 in complex with both Bcr-Abl and Abl (FIGS. 2A, SC, H9010). Comparison of immunoprecipitated Bcr-Abl and Abl (FIGS. 2A, 2B, left, H9010) with the fraction of each protein remaining in the supernatant (FIG. 2B, left, Remaining supernatant), indicated that the antibody did not preferentially enrich for HSP90 bound to either mutant or WT forms of Abl in K562 cells.

In contrast, PU-bound HSP90 preferentially isolated the Bcr-Abl protein (FIGS. 2A, 2B, right, PU-beads). Following PU-bead depletion of the HSP90/Bcr-Abl species (FIG. 2B, right, PU-beads), H9010 precipitated the remaining HSP90/Abl species (FIG. 2A, 2B, right, H9010). PU-beads retained selectivity for HSP90/Bcr-Abl species at substantially saturating conditions (i.e. excess of lysate, FIG. 6A, left, and beads, FIG. 6A, right). As further confirmation of the biochemical selectivity of PU-H71 for the Bcr-Abl/HSP90 species, Bcr-Abl was much more susceptible to degradation by PU-H71 than was Abl (FIG. 2D). The selectivity of PU-H71 for the aberrant Abl species extended to other established t(9; 22)+ CML cell lines (FIG. 7A), as well as to primary CML samples (FIG. 7B).

5.1.3. The Onco- but not WT-Protein Bound HSP90 Species are Most Dependent on Co-Chaperone Recruitment for Client Protein Regulation by HSP90

To further differentiate between the PU-H71- and antibody-associated HSP90 fractions, we performed sequential depletion experiments and evaluated the co-chaperone constituency of the two species[32]. The fraction of HSP90 containing the HSP90/Bcr-Abl complexes bound several co-chaperones, including Hsp70, Hsp40, HOP and HIP (FIG. 2C, PU-beads). PU-bead pull-downs were also enriched for several additional HSP90 co-chaperone species. These findings strongly suggest that PU-H71 recognizes co-chaperone-bound HSP90. The PU-beads-depleted, remaining HSP90 pool, shown to include HSP90/Abl species, was not associated with co-chaperones (FIG. 2C, H9010), although their abundant expression was detected in the lysate (FIG. 2C, Remaining supernatant). Co-chaperones are however isolated by H9010 in the total cellular extract (FIGS. 5B, SC).

These findings suggest the existence of distinct pools of HSP90 preferentially bound to either Bcr-Abl or Abl in CML cells (FIG. 2). H9010 binds to both the Bcr-Abl and the Abl containing HSP90 species, whereas PU-H71 is selective for the Bcr-Abl/HSP90 species. Our data also suggest that HSP90 may utilize and require more acutely the classical co-chaperones Hsp70, Hsp40 and HOP when it modulates the activity of aberrant (i.e. Bcr-Abl) but not normal (i.e. Abl) proteins (FIG. 5A). In accord with this hypothesis, we find that Bcr-Abl is more sensitive than Abl to knock-down of Hsp70, an HSP90 co-chaperone, in K562 cells (FIG. 2E).

5.1.4. The Onco-Protein/HSP90 Species Selectivity and the Complex Trapping Ability of PU-H71 are not Shared by all HSP90 Inhibitors We next evaluated whether other inhibitors that interact with the N-terminal regulatory pocket of HSP90 in a manner similar to PU-H71, including the synthetic inhibitors SNX-2112 and NVP-AUY922, and the natural product GM[35], could selectively isolate similar HSP90 species (FIG. 2F). SNX-beads demonstrated selectivity for Bcr-Abl/HSP90, whereas NVP-beads behaved similarly to H9010 and did not discriminate between Bcr-Abl/HSP90 and Abl/HSP90 species (see SNX- versus NVP-beads, respectively; FIG. 2F). While GM-beads also recognized a subpopulation of HSP90 in cell lysates (FIG. 3A), they were much less efficient than were PU-beads in co-precipitating Bcr-Abl (FIG. 2F, GM-beads). Similar ineffectiveness for GM in trapping HSP90/client protein complexes was previously reported[36].

5.1.5. The Onco-Protein/HSP90 Species Selectivity and the Complex Trapping Ability of PU-H71 is not Restricted to Bcr-Abl/HSP90 Species To determine whether selectivity towards onco-proteins was not restricted to Bcr-Abl, we tested several additional well-defined HSP90 client proteins in other tumor cell lines (FIGS. 6B-6D)[37-38]. In agreement with our results in K562 cells, H9010 precipitated HSP90 complexed with both mutant B-Raf expressed in SKMel28 melanoma cells and WT B-Raf expressed in CCD18Co normal colon fibroblasts (FIG. 6B, H9010). PU- and GM-beads however, selectively recognized HSP90/mutant B-Raf, showing little recognition of HSP90/WT B-Raf (FIG. 6B, PU-beads and GM-beads). However, as was the case in K562 cells, GM-beads were significantly less efficient than PU-beads in co-precipitating the mutant client protein. Similar results were obtained for other HSP90 clients (FIGS. 6C, 6D).

In summary, PU-H71 enriches a broad cross-section of proteins that participate in signaling pathways vital to the malignant phenotype in CML. The interaction of PU-bound HSP90 with the aberrant CML signalosome was retained in primary CML samples.

5.1.6. PU-H71 Identified Proteins and Networks are Those Important for the Malignant Phenotype We hypothesize that the presence of these proteins in the PU-bead pull-downs is functionally significant and suggests a role for HSP90 in broadly supporting the malignant signalosome in CML cells.

To demonstrate that the networks identified by PU-beads are important for transformation in K562, we next showed that inhibitors of key nodal proteins from individual networks Bcr-Abl, NFκB, mTOR, MEK and CAMIIK) diminish the growth and proliferation potential of K562 cells.

Next we demonstrated that PU-beads identified HSP90 interactors with yet no assigned role in CML, also contribute to the transformed phenotype. The histone-arginine methyltransferase CARM1, a transcriptional co-activator of many genes[57], was validated in the PU-bead pull-downs from CML cell lines and primary CML cells. This is the first reported link between HSP90 and CARM1, although other arginine methyltransferases, such as PRMT5, have been shown to be HSP90 clients in ovarian cancer cells[58]. While elevated CARM1 levels are implicated in the development of prostate and breast cancers, little is known on the importance of CARM1 in CML leukomogenesis[57]. We found CARM1 essentially entirely captured by the HSP90 species recognized by PU-beads and also sensitive to degradation by PU-H71. CARM1 therefore, may be a novel HSP90 onco-protein in CML. Indeed, knock-down experiments with CARM1 but not control shRNAs, demonstrate reduced viability and induction of apoptosis in K562 but not in normal CD34+ cells (not shown), supporting this hypothesis. qPCR data confirmed that the CARM1 mRNA levels were markedly reduced by the two different shRNAs (data not shown).

To demonstrate that the presence of proteins in the PU-pulldowns is due to their participation in aberrantly activated signaling and not merely their abundant expression, we compared PU-bead pulldowns from K562 and Mia-PaCa-2, a pancreatic cancer cell line. While both cells express high levels of STAT5 protein, activation of the STAT5 pathway, as demonstrated by STAT5 phosphorylation and DNA-binding[59], was noted only in the K562 cells. In accordance, this protein was identified only in the K562 PU-bead pull-downs. In contrast, activated STAT3 was identified in PU-HSP90 complexes from both K562 and Mia-PaCa-2 cells extracts.

The mTOR pathway was identified by the PU-beads in both K562 and Mia-PaCa-2 cells, and indeed, its pharmacologic inhibition by PP242, a selective inhibitor that targets the ATP domain of mTOR[60], is toxic to both cells. On the other hand, the Abl inhibitor Gleevec[61] was toxic only to K562 cells. Both cells express Abl but only K562 has the oncogenic Bcr-Abl and PU-beads identify Abl, as Bcr-Abl, in K562 but not in Mia-PaCa-2 cells.

5.1.7. PU-H71 Identifies a Novel Mechanism of Oncogenic STAT-Activation

PU-bead pull-downs contain several proteins, including Bcr-Abl[41], CAMKIIγ[52], FAK[53], vav-1[62] and PRKD2[48] that are constitutively activated in CML leukemogenesis. These are classical HSP90-regulated clients that depend on HSP90 for their stability because their steady-state levels decrease upon HSP90 inhibition[32,33]. Constitutive activation of STAT3 and STAT5 is also reported in CML[41,46]. These proteins, however, do not fit the criteria of classical HSP90 client proteins because STAT5 and STAT3 levels remain essentially unmodified upon HSP90 inhibition. The PU-pull-downs also contain proteins isolated potentially as part of an active signaling mega-complex, such as mTOR, VSP32, VSP15 and RAPTOR[44]. mTOR activity, as measured by cellular levels of p-mTOR, also appears to be more sensitive to HSP90 inhibition than are the complex components (i.e. compare the relative decrease in p-mTOR and RAPTOR in PU-H71 treated cells. Further, PU-HSP90 complexes contain adapter proteins such as GRB2, DOCK, CRKL and EPS15, which link Bcr-Abl to key effectors of multiple aberrantly activated signaling pathways in K562[30,41]. Their expression also remains unchanged upon HSP90 inhibition. We therefore wondered whether the contribution of HSP90 to certain oncogenic pathways extends beyond its classical folding actions. Specifically, we show that HSP90 also acts as a scaffolding molecule that maintains signaling complexes in their active configuration, as has been previously postulated[40,63].

5.1.8. HSP90 Binds to and Influences the Conformation of STAT5.

To investigate this hypothesis further we focused on STAT5, which is constitutively phosphorylated in CML[64]. The overall level of p-STAT5 is determined by the balance of phosphorylation and dephosphorylation events. Thus, the high levels of p-STAT5 in K562 cells may reflect either an increase in upstream kinase activity or a decrease in protein tyrosine phosphatase (PTPase) activity. A direct interaction between HSP90 and p-STAT5 could also modulate the cellular levels of p-STAT5.

To dissect the relative contribution of these potential mechanisms, we first investigated the effect of PU-H71 on the main kinases and PTPases that regulate STAT5 phosphorylation in K562 cells. Bcr-Abl directly activates STAT5 without the need for JAK phosphorylation[64]. Concordantly, STAT5-phosphorylation rapidly decreased in the presence of the Bcr-Abl inhibitor Gleevec. While HSP90 regulates Bcr- Abl stability, the reduction in steady-state Bcr-Abl levels following HSP90 inhibition requires more than 3 h[65]. Indeed no change in Bcr-Abl expression or function, as evidenced by no decrease in CRKL phosphorylation, was observed with PU-H71 in the time interval it reduced p-STAT5 levels. Also, no change in the activity and expression of HCK, a kinase activator of STAT5 in 32Dcl3 cells transfected with Bcr-Abl[66], was noted.

Thus reduction of p-STAT5 phosphorylation by PU-H71 in the 0 to 90 min interval is unlikely to be explained by destabilization of Bcr-Abl or other kinases.

We therefore examined whether the rapid decrease in p-STAT5 levels in the presence of PU-H71 may be accounted for by an increase in PTPase activity. The expression and activity of SHP2, the major cytosolic STAT5 phosphatase[57], were also not altered within this time interval. Similarly, the levels of SOCS1 and SOCS3, which form a negative feedback loop that switches off STAT-signaling[61] were unaffected by PU-H71.

Thus no effect on STAT5 in the interval 0-90 min can likely be attributed to a change in kinase or phosphatase activity towards STAT5 upon HSP90 inhibition. As an alternative mechanism, and because the majority of p-STAT5 but not STAT5 is HSP90 bound in CML cells, we hypothesized that the cellular levels of activated STAT5 are fine-tuned by direct binding to HSP90.

The activation/inactivation cycle of STATs entails their transition between different dimer conformations. Phosphorylation of STATs occurs in an anti-parallel dimer conformation that upon phosphorylation triggers a parallel dimer conformation. Dephosphorylation of STATs on the other hand require extensive spatial reorientation, in that the tyrosine phosphorylated STAT dimers must shift from parallel to anti-parallel configuration to expose the phosphotyrosine as a better target for phosphatases[68]. We find that STAT5 is more susceptible to trypsin cleavage when bound to HSP90, indicating that binding of HSP90 directly modulates the conformational state of STAT5, potentially to keep STAT5 in a conformation unfavorable for dephosphorylation and/or favorable for phosphorylation.

To investigate this possibility we used a pulse-chase strategy in which orthovanadate ($Na_3VO_4$), a non-specific PTPase inhibitor, was added to cells to block the dephosphorylation of STAT5. The residual level of p-STAT5 was then determined at several later time points. In the absence of PU-H71, p-STAT5 accumulated rapidly, whereas in its presence, cellular p-STAT5 levels were diminished. The kinetics of this process were similar to the rate of p-STAT5 steady-state reduction.

5.1.9. HSP90 Maintains STAT5 in an Active Conformation Directly within STAT5-Containing Transcriptional Complexes.

In addition to STAT5 phosphorylation and dimerization, the biological activity of STAT5 requires its nuclear translocation and direct binding to its various target genes[64,68]. We wondered therefore, whether HSP90 might also facilitate the transcriptional activation of STAT5 genes, and thus participate in promoter-associated STAT5 transcription complexes. Using an ELISA-based assay, we found that STAT5 is constitutively active in K562 cells and binds to a STAT5 binding consensus sequence (5'-TTCCCGGAA-3'). STAT5 activation and DNA binding is partially abrogated, in a dose-dependent manner, upon HSP90 inhibition with PU-H71. Furthermore, quantitative ChIP assays in K562 cells revealed the presence of both HSP90 and STAT5 at the critical STAT5 targets MYC and CCND2. Neither protein was present at intergenic control regions (not shown). Accordingly, PU-H71 (1 μM) decreased the mRNA abundance of the STAT5 target genes CCND2, MYC, CCND, BCL-XL and MCL1[62], but not of the control genes HPRT and GAPDH.

Collectively, these data show that STAT5 activity is positively regulated by HSP90 in CML cells. Our findings are consistent with a scenario whereby HSP90 binding to STAT5 modulates the conformation of the protein and by this mechanism it alters STAT5 phosphorylation/dephosphorylation kinetics, shifting the balance towards increased levels of p-STAT5. In addition, HSP90 maintains STAT5 in an active conformation directly within STAT5-containing transcriptional complexes. Considering the complexity of the STAT-pathway, other potential mechanisms however, cannot be excluded. Therefore, in addition to its role in promoting protein stability, HSP90 promotes oncogenesis by maintaining client proteins in an active configuration.

More broadly, the data reveal that it is the PU-H71-HSP90 fraction of cellular HSP90 that is most closely involved in supporting oncogenic protein functions in tumor cells, and a labeled PU-H71 can be used to identify this tumor HSP90 species that is bound to a broad cross-section of the protein pathways required to maintain the malignant phenotype in specific tumor cells.

5.1.10. HSP90 is Present in Two Distinct Forms in Tumor Cells

The methods presented above take advantage of several properties of PU-H71 which i) binds preferentially to the fraction of HSP90 that is associated with oncogenic client proteins, and ii) locks HSP90 in an onco-client bound configuration.

Identification of HSP90 clients required for tumor cell survival may also serve as tumor-specific biomarkers for selection of patients likely to benefit from HSP9 therapy and for pharmacodynamic monitoring of HSP90 inhibitor efficacy during clinical trials (i.e., clients whose expression or phosphorylation changes upon HSP90 inhibition). Tumor specific HSP90 client profiling provide one approach for personalized therapeutic targeting of tumors.

This work substantiates and significantly extends the work of Kamal et al, providing a more sophisticated understanding of the original model in which HSP90 in tumors is described as present entirely in multi-chaperone complexes, whereas HSP90 from normal tissues exists in a latent, uncomplexed state[34]. We show that HSP90 forms biochemically distinct complexes in cancer cells (FIG. 5A). In this view, a major fraction of cancer cell HSP90 retains “housekeeping” chaperone functions similar to normal cells, whereas a functionally distinct HSP90 pool enriched or expanded in cancer cells specifically interacts with oncogenic proteins required to maintain tumor cell survival. Perhaps this HSP90 fraction represents a cell stress specific form of chaperone complex that is expanded and constitutively maintained in the tumor cell context. Our data suggest that it may execute functions necessary to maintain the malignant phenotype. One such role is to regulate the folding of mutated (i.e., mB-Raf) or chimeric proteins (i.e., Bcr-Abl)[32,33]. We now present experimental evidence for an additional role; that is, to facilitate scaffolding and complex formation of molecules involved in aberrantly activated signaling complexes. Herein we describe such a role for HSP90 in maintaining constitutive STAT5 signaling in CML. These data are consistent with previous work in which we showed that HSP90 was required to maintain functional transcriptional repression complexes by the BCL6 oncogenic transcriptional repressor in B cell lymphoma cells[70].

What distinguishes the PU-binding fraction of HSP90 from the non-PU-binding fraction? This is a very complex question that remains under active investigation. Although both HSP90α and HSP90β isoforms are recognized by PU-H71, our data provide evidence for at least one difference between Bcr-Abl/HSP90 (PU-preferring) and Abl/HSP90 (PU-non-preferring) chaperone complexes. That is, Bcr-Abl/HSP90 chaperone complexes contain a number of co-chaperones (suggesting that an active chaperoning process is underway, further supported by the sensitivity of Bcr-Abl to the silencing of Hsp70), while Abl/HSP90 complexes lack associated co-chaperones (likely representing sequestered but not actively chaperoned Abl, supported by the insensitivity of Abl to Hsp70 knockdown) (see FIG. 2E). Furthermore, we have observed that HSP90 that is mutated to more avidly bind to its client proteins also binds more avidly than does wild type HSP90 to PU-beads (manuscript in preparation). Finally, we have observed a differential impact of HSP90 phosphorylation on PU-H71 and geldanamycin binding. These findings, which are being pursued further, suggest that various HSP90 inhibitors may be uniquely affected by specific post-translational modifications to the chaperone. Taken together, these preliminary observations show that PU-H71 recognizes an HSP90 fraction that is participating in an active chaperone cycle, and that this characteristic is not necessarily shared by other HSP90 inhibitors.

5.2. Labeled HSP90 Inhibitors for Diagnostic and Prognostic Applications

To measure in a tumor-by-tumor manner the abundance of the "oncogenic HSP90", the disclosure provides several chemical tools (see Sections 5.2.1. and 5.2.2.) that can be used for diagnostic and prognostic purposes. Additionally, the chemical tools provide new insight into the heterogeneity of tumor associated HSP90 and harnesses the biochemical features of a particular HSP90 inhibitor to identify tumor-specific HSP90 that regulates the tumor-promoting biological pathways and proteins. Such tools include labeled HSP90 inhibitors that specifically identify and interact with this tumor "oncogenic HSP90" species, making it feasible to measure the abundance of the "oncogenic HSP90" species in different subpopulations in tumors and thus, measure and predict sensitivity to HSP90 inhibition therapy. Moreover, measuring the abundance of "oncogenic HSP90" provides a means of determining whether a tumor is dependent on HSP90.

In one aspect, the disclosure provides a method for determining whether a tumor will likely respond to therapy with an HSP90 inhibitor which comprises the following steps:

(a) contacting the tumor or a sample containing cells from the tumor with a detectably labeled HSP90 inhibitor which binds preferentially to a tumor-specific form of HSP90 present in a tumor or tumor cells;
(b) measuring the amount of labeled HSP90 inhibitor bound to the tumor or the tumor cells in the sample; and
(c) comparing the amount of labeled HSP90 inhibitor bound to the tumor or the tumor cells in the sample measured in step (b) to a reference amount of the labeled HSP90 inhibitor bound to normal cells;

wherein a greater amount of labeled HSP90 inhibitor bound to the tumor or the tumor cells measured in step (b) as compared with the reference amount indicates the tumor will likely respond to the HSP90 inhibitor.

The method involves measuring in a tumor the abundance of an HSP90 species, the "oncogenic HSP90", as a biomarker for HSP90 therapy. The abundance of this HSP90 species does not necessarily correspond with the total HSP90 expression in the tumor. The disclosure provides several solutions to measuring the abundance of "oncogenic HSP90". In one such embodiment, labeled derivatives of certain HSP90 inhibitors can be used as tools to measure its presence and its abundance.

Further, in this particular method the greater the ratio of the amount of labeled HSP90 inhibitor bound to the tumor or tumor cells measured in step (b) as compared to the reference amount, the greater the magnitude of the likely response to the HSP90 inhibitor therapy.

Still, further in this particular method the greater the amount of labeled HSP90 inhibitor bound to the tumor or the tumor cells measured in step (a), the greater the magnitude of the likely response to the HSP90 inhibitor therapy.

In one embodiment of this particular method, the reference amount of the labeled HSP90 inhibitor bound to normal cells is the amount of the labeled HSP90 inhibitor bound to normal cells in the sample containing cells from the tumor.

In another embodiment, the reference amount of the labeled HSP90 inhibitor bound to normal cells is a predetermined amount of the labeled HSP90 inhibitor bound to normal cells in a reference sample.

In another aspect, the disclosure provides a method for determining whether a tumor will likely respond to therapy with an HSP90 inhibitor which comprises the following steps:

(a) contacting the tumor or a sample containing cells from the tumor with a detectably labeled HSP90 inhibitor which binds preferentially to a tumor-specific form of HSP90 present in a tumor or tumor cells;
(b) measuring the amount of labeled HSP90 inhibitor bound to the tumor or the tumor cells in the sample; and
(c) comparing the amount of labeled HSP90 inhibitor bound to the tumor or the tumor cells in the sample measured in step (b) to a reference;

wherein a greater amount of labeled HSP90 inhibitor bound to the tumor or the tumor cells measured in step (b) as compared with the reference amount indicates the tumor will likely respond to the HSP90 inhibitor.

In one embodiment of this particular method, the reference sample are cancer cells with no to little "oncogenic HSP90" expression In another embodiment the reference is a correspondingly labeled compound with little to no binding to the "oncogenic HSP90".

The detectably labeled HSP90 inhibitor may be labeled with any detectable label, and many such labels are well known in the art. For example, the detectably labeled HSP90 inhibitor may be fluorescently labeled, biotin labeled, ANCA-labeled or radioactively labeled.

In the practice of this particular method, the tumor may be any tumor or tumor-derived biological formation that contain the "oncogenic HSP90", such as exosomes. For example, the tumor and the other cells or tumor-derived biological formations that contain the "oncogenic HSP90" may be associated with, indicative of, or derived from any cancer selected from the group consisting of colorectal cancer, pancreatic cancer, thyroid cancer, a leukemia including acute myeloid leukemia, acute lymphoblastic leukemia and chronic myeloid leukemia, lymphoid leukemia, multiple myeloma, basal cell carcinoma, melanoma, renal cell carcinoma, bladder cancer, prostate cancer, a lung cancer including small cell lung cancer and non-small cell lung cancer, breast cancer, neuroblastoma, myeloproliferative disorders, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers.

In the practice of this particular method, the tumor, the tumor cell or the tumor-associated cell or biological formation may be present in a subject or may be isolated from a subject. Thus, the tumor, tumor cell or tumor-associated cell to be contacted may be in the form of a solid tumor per se in vivo or in the form of an attached cell such as in a tissue sample or as within a liquid tumor or biological fluid; a sample obtained during a blood draw, bone marrow aspirate, biopsy, a fine needle aspiration or a surgical procedure; a biological fluid; blood or bone marrow. The cells to be contacted with the labeled HSP90 inhibitor may be present in any form including as disrupted cells, live cells, frozen cells, fixed and permeabilized cells, or formalin-fixed paraffin-embedded cells.

The detectably labeled HSP90 inhibitor may be a labeled form of the HSP90 inhibitor which is to be administered as therapy, or may be a labeled form of a different HSP90 inhibitor including a chemically unrelated HSP90 inhibitor or a labeled form of an analog, homolog or derivative of the HSP90 inhibitor to be administered. Subject only to the requirement that the detectably labeled HSP90 inhibitor and most likely the unlabeled HSP90 inhibitor to which is corresponds binds preferentially to a tumor-specific form of HSP90 present in many tumor and tumor cells. In this regard, "preferentially" means the HSP90 inhibitor binds with substantially greater affinity to the tumor-specific form of HSP90 as compared to the affinity, if any, with which it binds to HSP90 characteristic of normal or non-tumor cells.

Currently, one HSP90 inhibitor considered likely to be administered as therapy is PU-H71 or an analog, homolog or derivative of PU-H71. See for example, U.S. Pat. Nos. 7,820,658 B2; 7,834,181 B2; and 7,906,657 B2, which are all hereby incorporated by reference in their entireties, for descriptions of illustrative HSP90 inhibitors.

In one embodiment the HSP90 inhibitor is PU-H71 and the detectably labeled HSP90 inhibitor is a form of PU-H71 or of an analog, homolog, or derivative of PU-H71. Examples of forms of PU-H71 which may be the detectably labeled HSP90 inhibitor include, but are not limited to, [$^{124}$I]-PU-H71, PU-H71-FITC2 or PU-H71-NBD1, or a biotinylated analog of PU-H71 such as PU-H71-biotin-5, PU-H71-biotin-6, PU-H71-biotin-8 or PU-H71-biotin-9, which are described below.

A labeled derivative of PU-H71, such as radiolabeled [$^{124}$I]-PU-H71, [$^{31}$I]-PU-H71, [$^{134}$I]-PU-H71, fluorescently-labeled PU-H71, biotin-labeled-PU-H71, or ANCA-labeled inhibitor can therefore be employed as a tool to identify and quantify the tumor-specific HSP90 species. The abundance of this tumor HSP90 species can be used as a biomarker predictive of response to HSP90 therapy.

5.2.1. Fluorescent, Biotinylated and ANCA-Labeled Probes for Detecting Oncogenic HSP90

The disclosure provides fluorescently labeled, biotinylated probes and ANCA-labeled probes that are capable of detecting oncogenic HSP90 in cancer cells. Section 5.2.1.1. describes the production of various types of probes to be used in accordance with the present disclosure. Section 5.2.1.2. describes the use of such probes in prognostic and diagnostic assays.

5.2.1.1. Production of Probes

The disclosure provides fluorescently labeled, biotinylated and ANCA-labeled inhibitors that are cell permeable and that selectively bind to "oncogenic HSP90". Cell permeable inhibitors are capable of penetrating the cell membrane of a cell and binding HSP90 within the cytoplasm of the cell. To be useful in the methods of the invention, the labeled inhibitor has to penetrate the cells in an amount that is measurable by the methods of detection known to the person skilled in the art. Section 5.2.1.1.1. describes the development of different fluorescently labeled probes that are cell permeable and are capable of selectively binding to "oncogenic HSP90". Section 5.2.1.1.2. describes the development of different biotinylated probes that are cell permeable and are capable of selectively binding to "oncogenic HSP90". Section 5.2.1.1.3. describes the development of different ANCA-labeled probes that are cell permeable and are capable of selectively binding to "oncogenic HSP90".

5.2.1.1.1. Fluorescently Labeled Probes

Fluorescently labeled inhibitors of HSP90 have already been reported, with analogs of geldanamycin (GM-FITC,[13] GM-Bodipy,[13] GM-cy3b[14]) as well as pyrazole 1 (fluorescein analog, VER-00045864)[15] used as ligands in fluorescence polarization assays (FIG. 8). A cell-impermeable GM-FITC derivative was used to identify cell surface HSP90 by fluorescence microscopy.[16] HSP90 however, is mainly a cytoplasmic protein with cell surface expression detected only in certain cells.[1,2] Fluorescent probes are thus needed to analyze both intracellular and cell surface HSP90.

An HSP90 cell-permeable probe that specifically and tightly interacts with "oncogenic HSP90" is favored for flow cytometry measurements of this potential biomarker because fixation/permeabilization methods used for the detection of intracellular antigens by flow cytometry may result in the destruction of the "oncogenic HSP90 complexes" and of the cellular morphology and surface immunoreactivity, properties useful in flow cytometry for the characterization of cells in heterogeneous populations. To solve this issue the disclosure provides methods for the synthesis, characterization and evaluation of fluorescently labeled HSP90 inhibitors that permeate live cells and bind to the target.

This present disclosure provides various new fluorescently labeled derivatives of PU-H71 (2), a purine-scaffold inhibitor of HSP90 (FIG. 8) and describes their biological application as probes for studying HSP90 by fluorescence-activated flow cytometry and fluorescence microscopy. Several HSP90 inhibitors based on the purine-scaffold, including BIIB021, MPC-3100, PU-H71 and Debio 0932 (formerly CUDC-305) are currently in clinical development for cancers.[18,19]

Fluorescent ligands for the heat shock protein 90 (HSP90) were synthesized containing either fluorescein isothiocyanate (FITC), 4-nitrobenzo[1,2,5]oxadiazole (NBD) or the red shifted dye sulforhodamine 101 (Texas Red) conjugated to PU-H71 (FIG. 9). Two of the compounds, PU-H71-FITC2 (9) and PU-H71-NBD1 (8), were shown to be suitable for fluorescence-activated flow cytometry and fluorescence microscopy. Thus these molecules serve as useful probes for studying HSP90 in heterogeneous live cell populations.

For the development of small dye-labeled ligands, the selection of an optimal fluorophore and its site of attachment are relevant. Particularly in small molecules the introduced dye can significantly affect the biochemical and pharmacologic characteristics of the ligand. According to the X-ray crystal structure of PU-H71 (2) bound to HSP90,[20] the N9-alkylamino chain of the ligand is oriented towards solvent. As a result of this, as well as previous SAR, several of the compounds synthesized in the present disclosure contain the fluorescent label attached to the N9 position. In particular embodiments, as described below, derivatives of PU-H71 with different linkers were labeled with either FITC, NBD or Texas Red (TR) (see FIG. 1).

In one embodiment of the present disclosure, a six carbon spacer was appended to the constituent amine of an inhibitor based on the purine scaffold, thereby providing Compound 3 (Scheme 1 and FIG. 10). We had previously used this linker to attach PU-H71 to solid support and showed that Compound 3 retains good affinity for HSP90.[21] As depicted in Scheme 1, Compound 3 was reacted with FITC in DMF/$Et_3N$ to give Compound 4 (PU-H71-FITC1) in 40% yield following purification by HPLC.

Scheme 1: Synthesis of PU-H71-FITC and PU-H71-NBD1

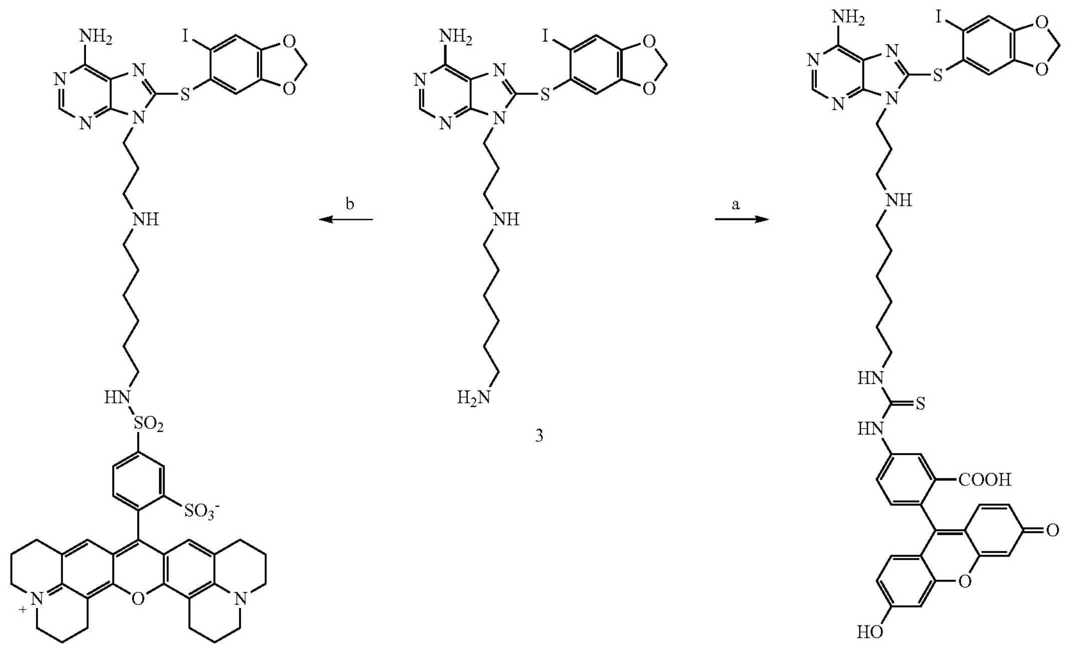

3

5

PU-H71-TR

4

PU-H71-FITC1

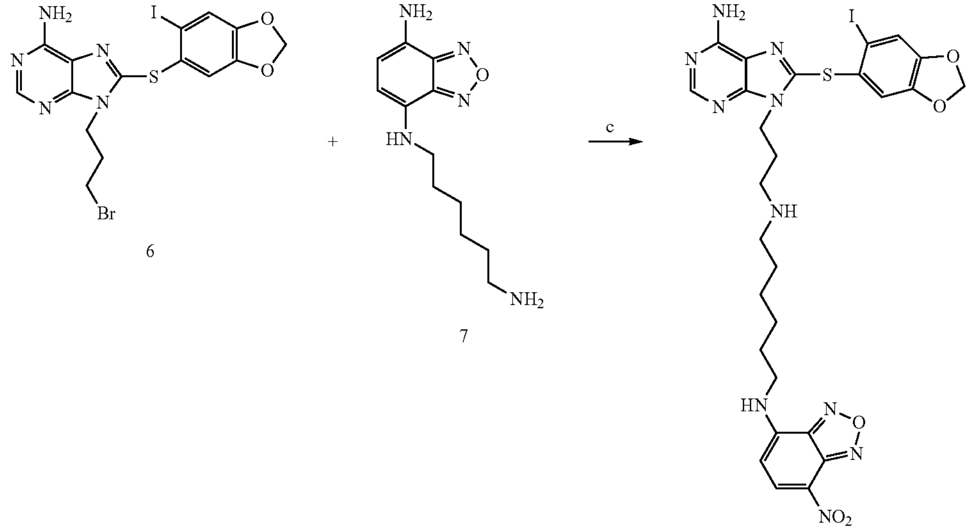

6

7

8

PU-H71-NBD1

In another embodiment, PU-H71-Texas Red (Compound 5; PU-H71-TR) was synthesized by the reaction of 3 with sulforhodamine 101 sulfonyl chloride in DMF to give Compound 5 in 61% yield following purification by HPLC (Scheme 1). In the case of the NBD analog, bromide 6 was reacted with Compound 7 in DMF to give Compound 8 (PU-H71-NBD1) in 47% yield (Scheme 1). Compound 6[21] and NBD derivative 7[22] were prepared as previously described.

In another embodiment, we took advantage of the secondary amine present in PU-H71[23] and reacted it directly with FITC or NBD-Cl to give Compound 9 (PU-H71-FITC2) (72%) or Compound 10 (PU-H71-NBD2) (40%), respectively (Scheme 2 and FIG. 11). It was hypothesized that attachment of the dye directly to the amine would result in more cell permeable analogs, owing to the presence of the ionizable amine functionality. Additionally, derivatives containing an isopropyl group (e.g., Compound 9 and Compound 10) in place of a hydrogen render the compounds more lipophilic and enhance their cell permeability.

Scheme 2: Synthesis of PU-H71-FITC2 and PU-H71-NBD2

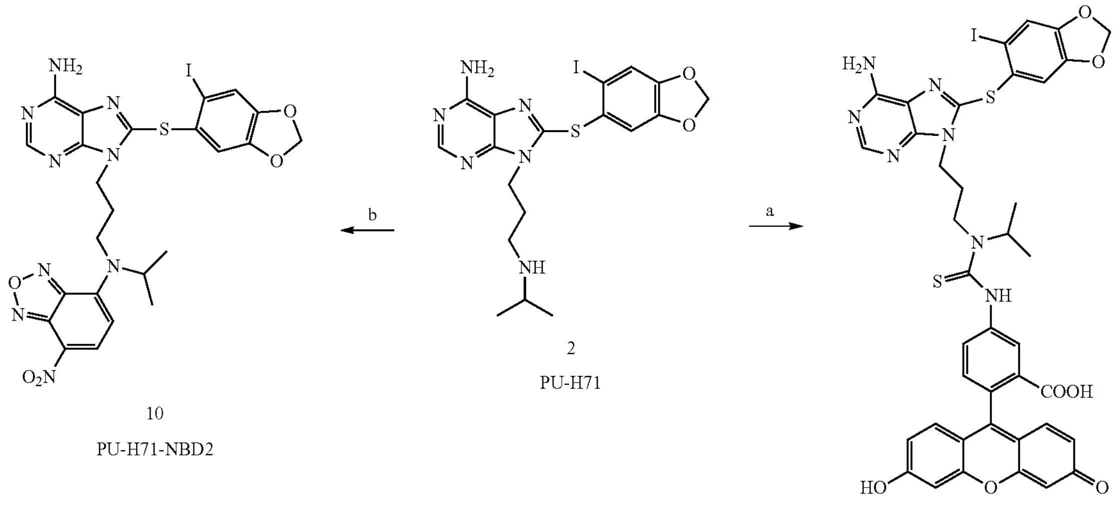

10

PU-H71-NBD2

2

PU-H71

9

PU-H71-FITC2

In yet another embodiment, as depicted in Scheme 3 and FIG. 12, desisopropyl-PU-H71 (Compound 13) was reacted with FITC or NBD-Cl to give Compound 14 (PU-H71-FITC3) (74%) or Compound 15 (PU-H71-NBD3) (42%), respectively. Compound 13 was synthesized by N9-alkylation of Compound 11 with N-(3-bromopropyl)-phthalimide and subsequent removal of phthalimide with hydrazine (Scheme 3).

Scheme 3: Synthesis of PU-H71-FITC3 and PU-H71-NBD3.

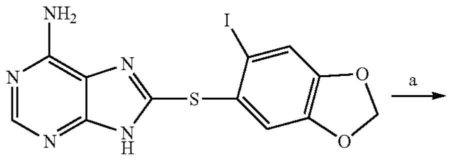

11

-continued
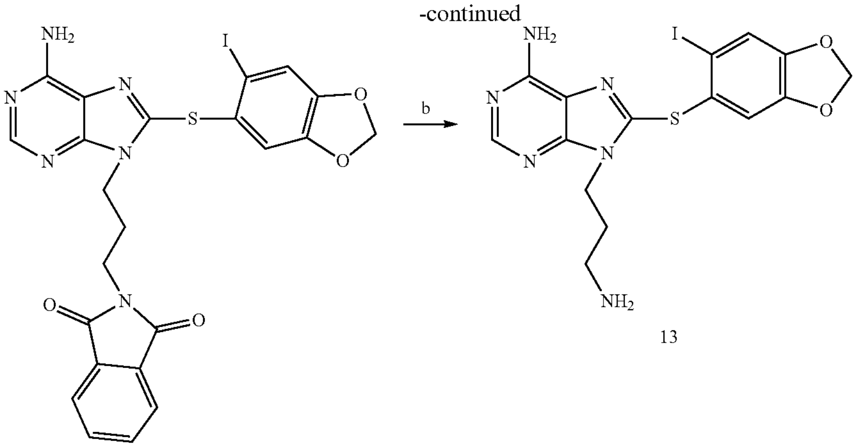
12
13
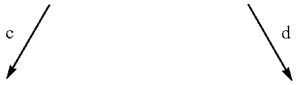
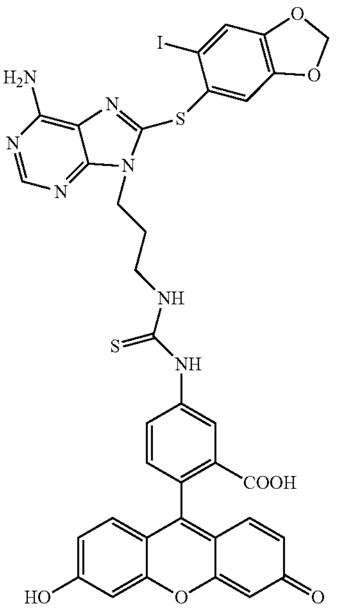
14
PU-H71-FITC3
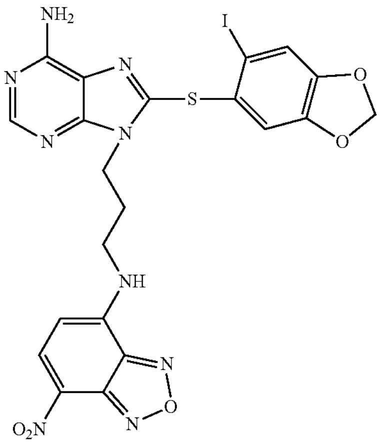
15
PU-H71-NBD3

Additional compounds analogous to PU-H71-FITC3 (shown in Scheme 3) but with different linker lengths were prepared, as depicted in Scheme 4.

Scheme 4:
Synthesis of PU-H71-FITC4, PU-H71-FITC5, and PU-71-FITC6

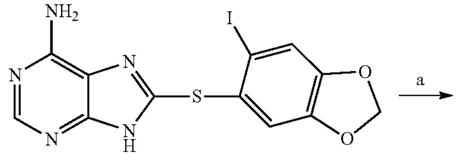

11

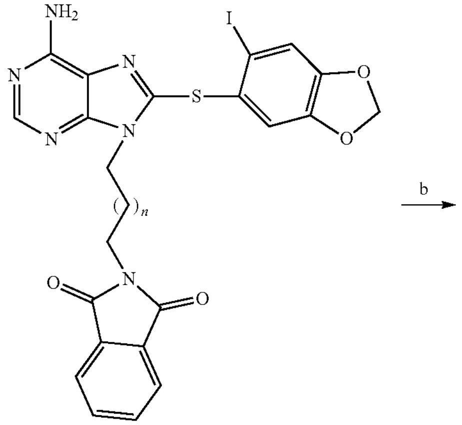

16a n = 2
16b n = 4
16c n = 6

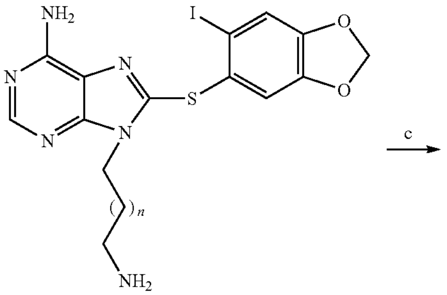

17a n = 2
17b n = 4
17c n = 6

-continued

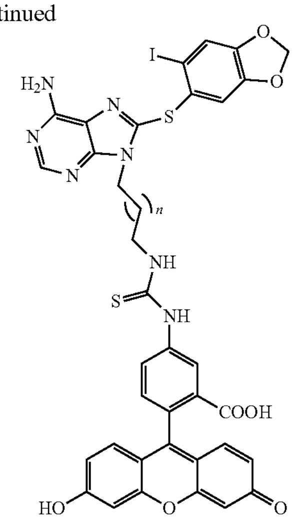

18a PU-H71-FITC4 n = 2
18b PU-H71-FITC5 n = 4
18c PU-H71-FITC6 n = 6

The compounds prepared in Schemes 1-4 were assessed for their ability to permeate cells and bind to HSP90 within the cells. Cell permeable probes are favored because fixation/permeabilization methods used for the detection of intracellular antigens by flow cytometry often result in the destruction of cellular morphology and surface immunoreactivity, properties useful in flow cytometry for the characterization of cells in heterogeneous populations. Thus, it is of particular interest to find cell-permeable ligands that interact with the target in live cells without the requirement of fixation and permeabilization steps.

To investigate which of the above synthesized fluorescently labeled PU-H71 derivatives retained the cells permeability profile of the parent compound PU-H71, we examined the cellular permeability of these HSP90 probes in human acute myelogenous leukemia (AML) cell lines, MV4-11 and MOLM-13. Of the ten fluorescent derivatives of PU-H71 prepared in Schemes 1-4, we find that PU-H71I-FITC2 (9) and PU-H71I-NBD1 (8) have the highest ability to permeate cells and bind to HSP90 (FIG. 13). Specifically, we show efficient staining of live cells by these two derivatives (FIG. 13A) as well as biological activity in these cells indicative of target (HSP90) inhibition (FIGS. 13B, 13C). In particular, we show that both PU-H71-FITC2 (9) and PU-H71-NBD1 (8) decrease the viability of MOLM-13 cells (FIG. 13B), effect associated with degradation of HSP90-client proteins such as mutant FLT3 and Raf-1 (FIG. 13C) indicating intracellular HSP90 inhibition in these cancer cells.[1-3]

Furthermore, confocal fluorescence microscopy of leukemia cells stained with PU-H71-FITC2 (9) showed prominent intracellular localization (FIG. 14A). In these experiments, DAPI was used as a viability dye to discriminate between viable and non-viable cells. This dye is impermeable in live cells at the tested concentration, but permeates non-viable cells and binds specific regions of DNA. DAPI is excited in most instruments with a UV laser. Similar data were generated with PU-H71-NBD1 (8) (not shown).

Flow cytometry is commonly used to separate and distinguish different cell populations in normal and malignant hematopoiesis by the use of specific markers. As an example, blast cells are often quantified and characterized by dim CD45 staining (CD45dim), in contrast to the circulating non-blast cell populations, which are bright for CD45 staining (CD45hi).[24] These cells, gated and separated by the presence of their identifying markers, we show here can also be stained for the target, HSP90, with PU-H71-FITC2 (FIG. 14B). In accord with previous reports indicating the selective binding of PU-H71 to tumor cell HSP90,[23] PU-H71-FITC2 preferentially stained the malignant cell (blasts) and not the normal cell (lymphocytes) population in a primary acute myeloid leukemia sample (FIG. 14B).

Accordingly, we show that PU-H71-FITC2 (9) and PU-H71-NBD1 (8) permeate live cells and bind to the target. Specifically, we show that PU-H71-FITC2 and PU-H71-NBD1 stain live cells (FIG. 13A), reduce the viability of leukemia cells (FIG. 13B), inhibit the intracellular HSP90 as indicated by degradation of HSP90 client proteins (FIG. 13C), are localized intracellularly as indicated by confocal microscopy (FIG. 14A) and bind specifically to tumor versus normal cell HSP90 as indicated by flow cytometry (FIG. 14B), to provide ample evidence that these probes permeate the cell and bind specifically to the tumor HSP90 target, similarly to PU-H71. Examples such as provided in FIGS. 4A-4H, FIG. 15, FIGS. 16A-16C, and FIGS. 18A-18D also demonstrate that these fluorescent derivatives of PU-H71 interact with the "oncogenic HSP90" species and moreover provide a means to quantify this species in a large spectrum of cancer cells. As discussed in Section 5.2.1.2., these fluorescent derivatives of PU-H71 can be applied as probes for fluorescence-activated flow cytometry or as tools for monitoring real-time interaction of HSP90 with the target by fluorescence microscopy.

Based on the results discussed above, we designed various other cell permeable probes that can interact with HSP90 and thus, can be used as diagnostic and/or prognostic tools. In one embodiment, compounds similar to PU-H71-FITC2 but with a different substituent on the benzo[d][1,3] dioxole ring were synthesized in a manner similar to PU-H71-FITC2, as shown in Scheme 5.

-continued

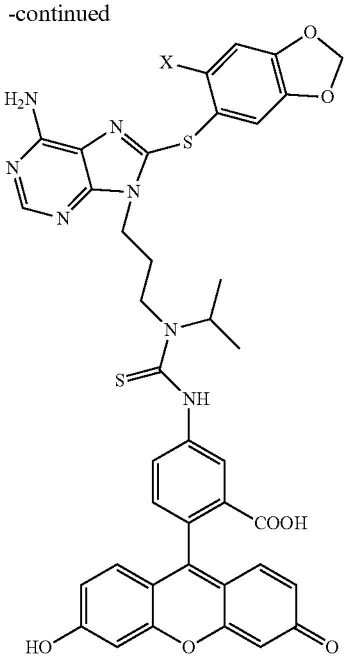

Scheme 5: Synthesis of Compounds Analogous to PU-H71-FITC2

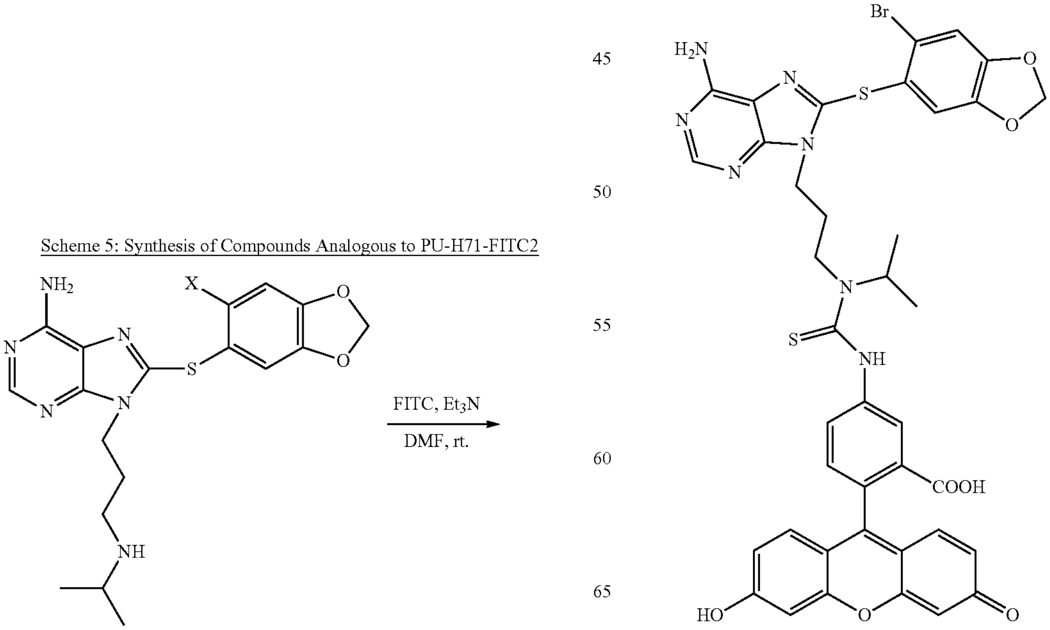

-continued
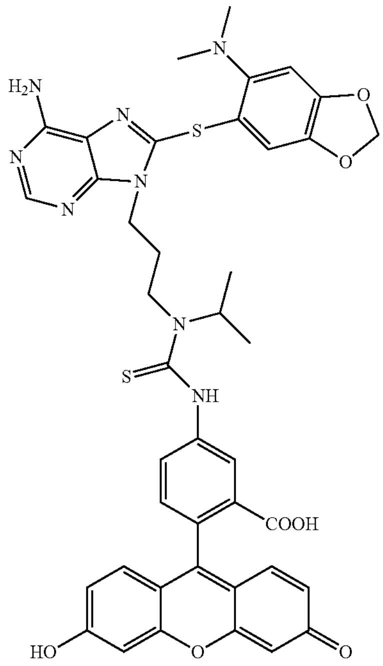
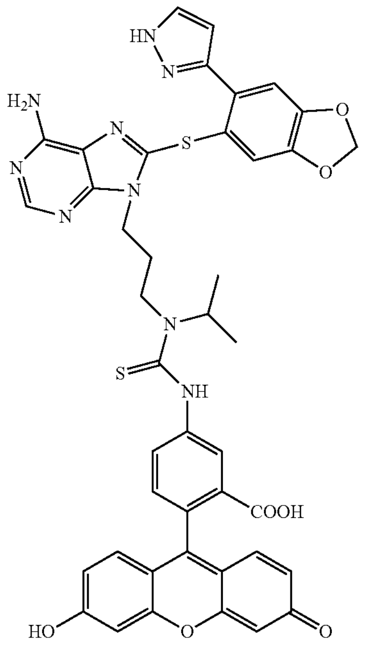
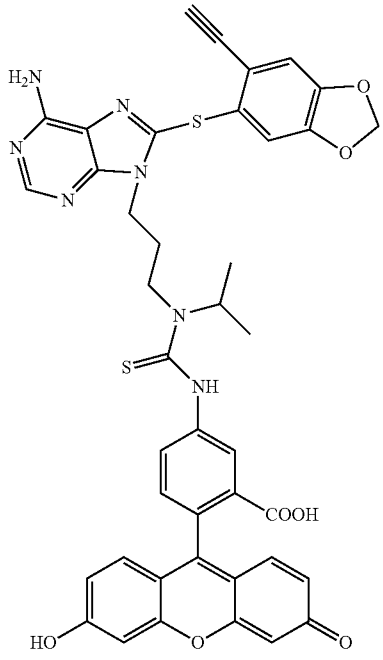
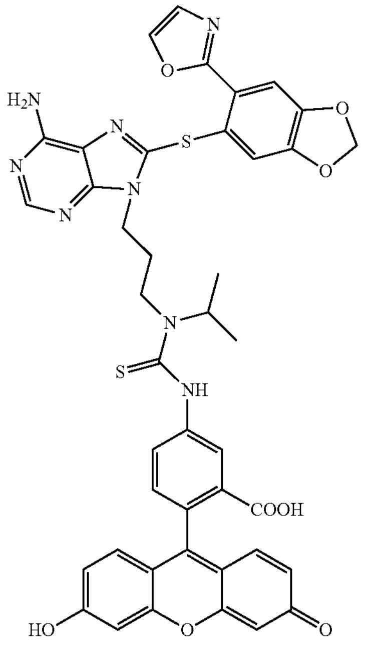

-continued
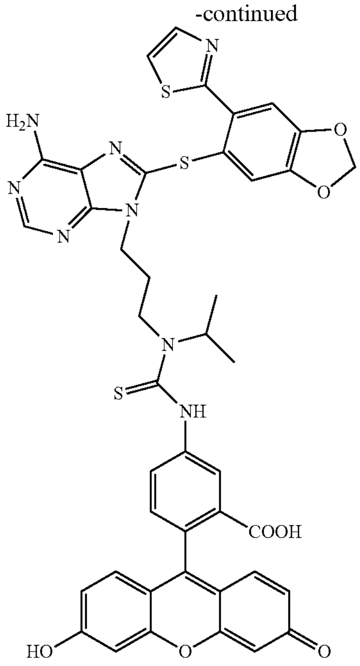
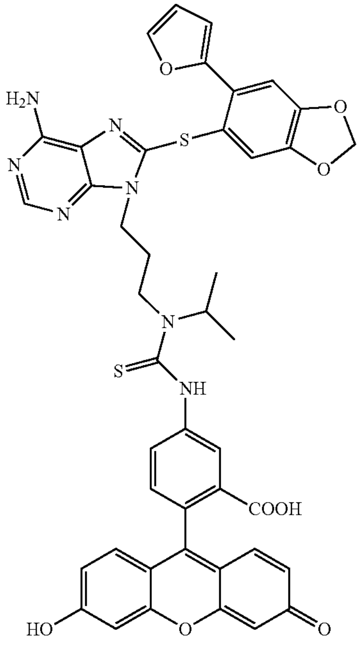
-continued
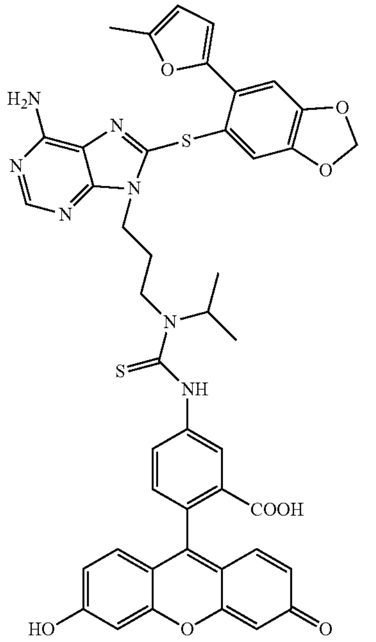 [SMILES: Cc1ccc(-c2cc3c(cc2Sc2nc4c(N)ncnc4n2CCCN(C(=S)Nc2ccc(-c4c5ccc(=O)cc-5oc5cc(O)ccc45)c(C(=O)O)c2)C(C)C)OCO3)o1]
In another embodiment, compounds similar to compounds depicted in Scheme 5 but where the pyrimidine ring on the purine-scaffold is replaced with a pyridine ring, were synthesized in a manner similar to PU-H71-FITC2, as shown in Scheme 6.
Scheme 6: Synthesis of Compounds Analogous to PU-H71-FITC2
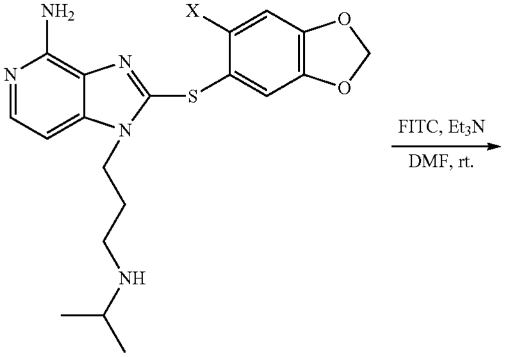

-continued
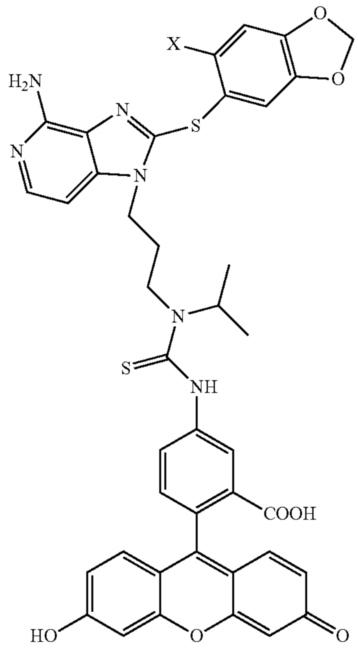
-continued
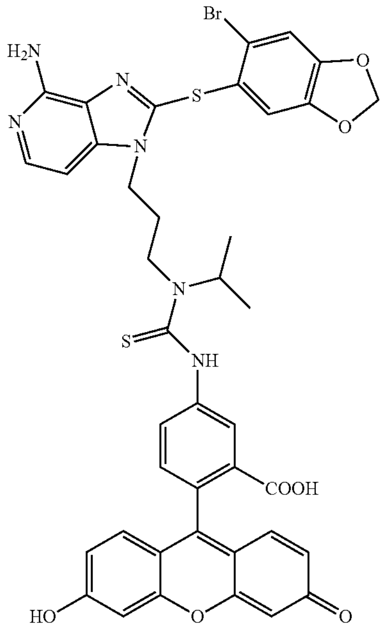
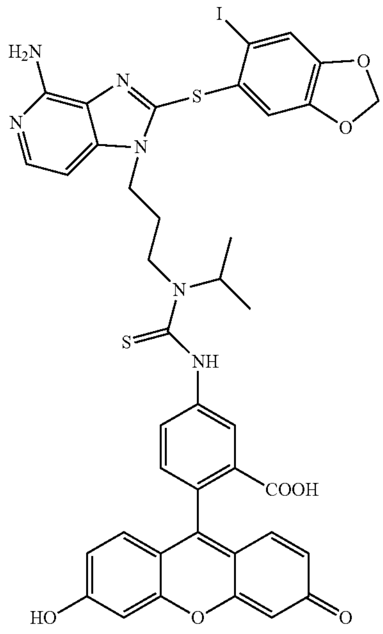
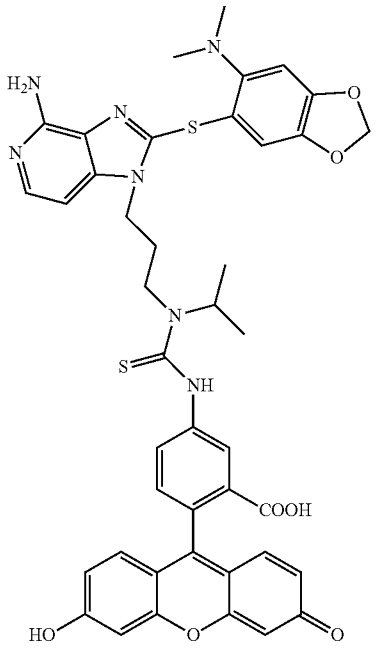

-continued
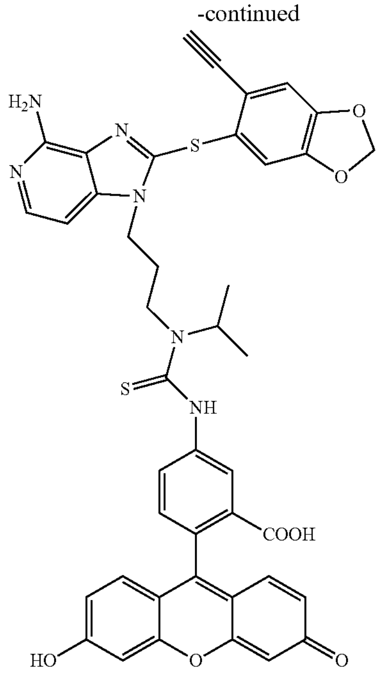
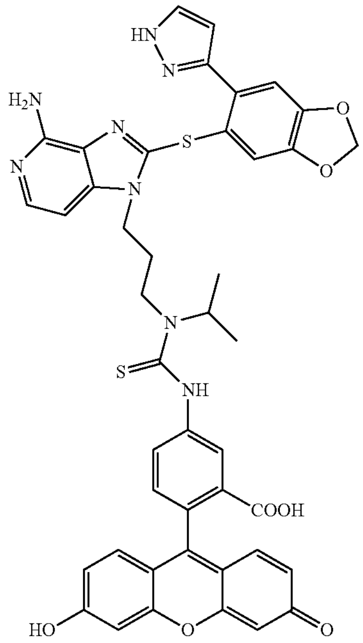
-continued
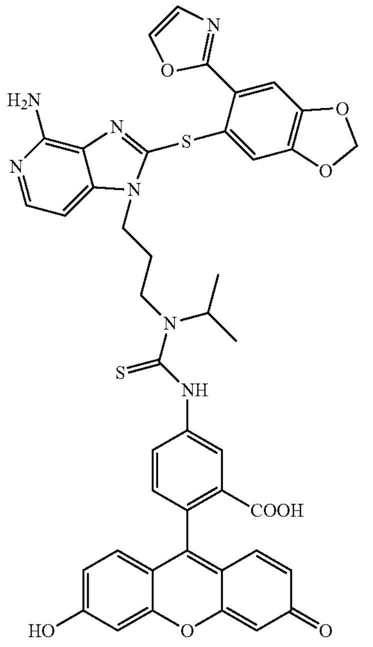
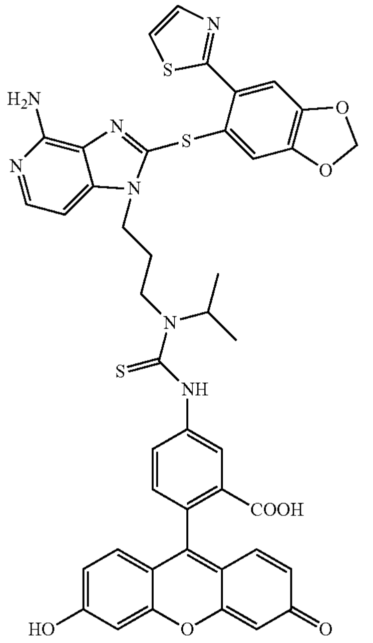

-continued
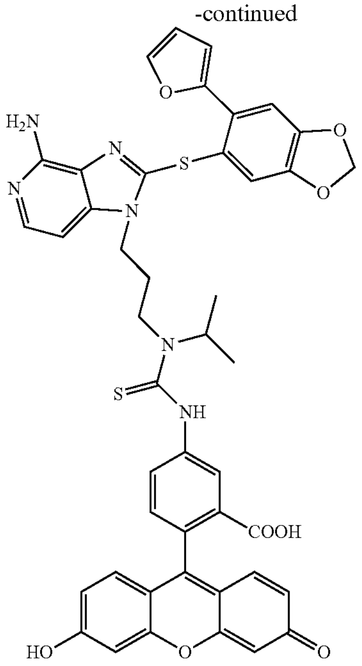
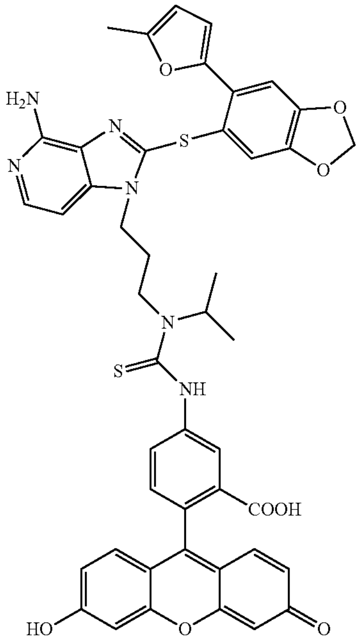
In another embodiment, Compound PU-FITC7 is prepared, as depicted in Scheme 7.
Scheme 7: Synthesis of PU-FITC7
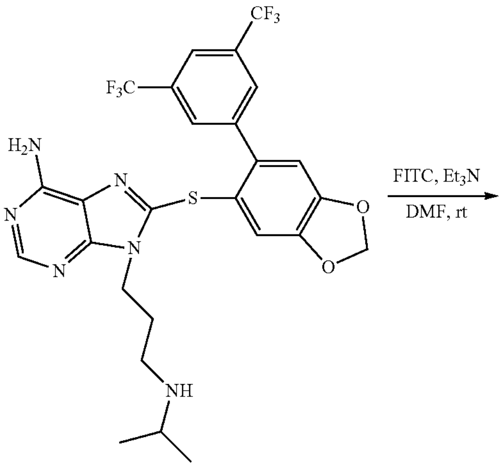
19
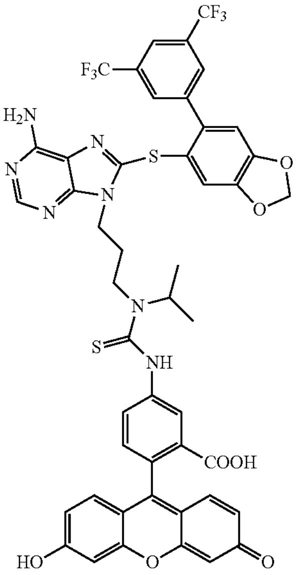
20
PU-FITC7

In another embodiment, Compound PU-FITC8 is prepared, as depicted in Scheme 8.
Scheme 8: Synthesis of PU-FITC8
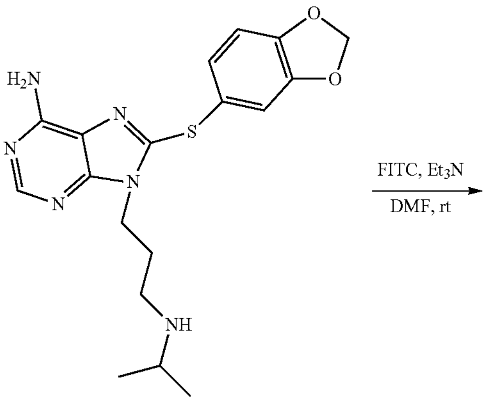
21
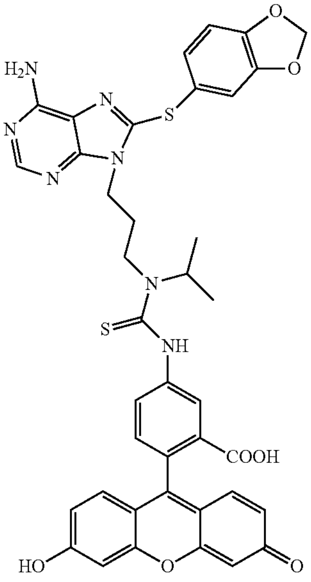
22
PU-FITC8
In another embodiment, Compound PU-FITC9 is prepared, as depicted in Scheme 9.
Scheme 9: Synthesis of PU-FITC9
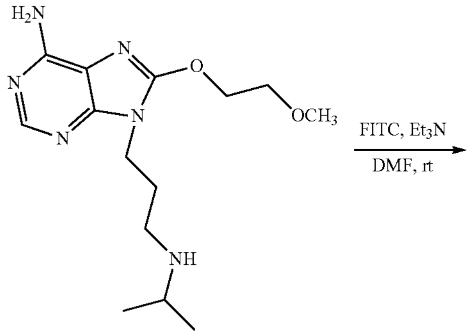
23
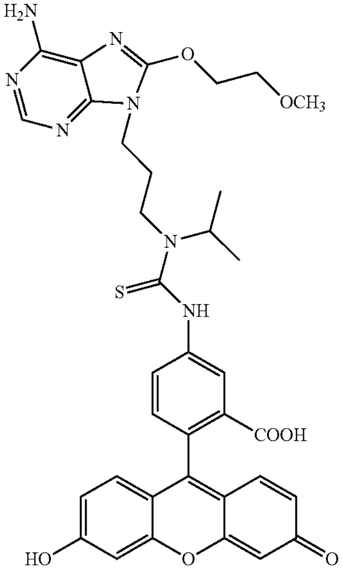
24
PU-FITC9
In still another embodiment, Compound DZ13-FITC1 (PU-DZ13-FITC) is prepared, as depicted in Scheme 10.
Scheme 10: Synthesis of Compound DZ13-FITC1
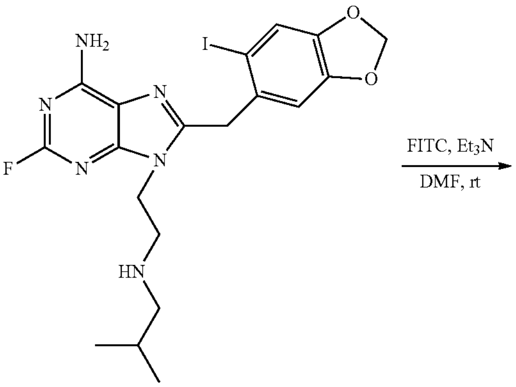
PU-DZ13

-continued

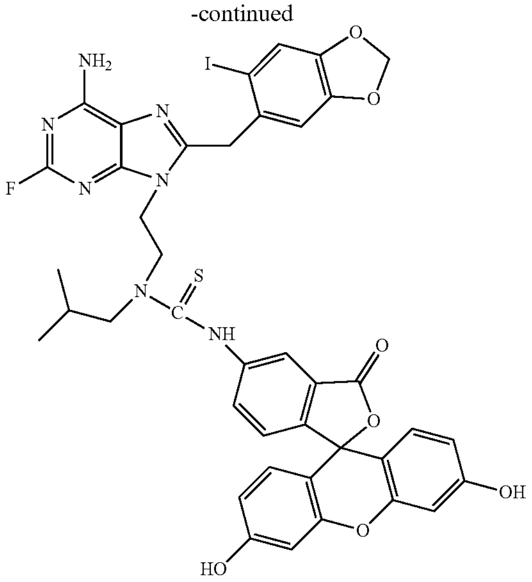

DZ13-FITC1

In still another embodiment, Compound SNX-FITC is prepared, as depicted in Scheme 11.

Scheme 11: Synthesis of Compound SNX-FITC

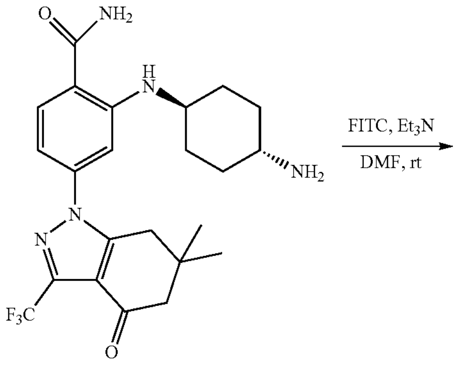

25

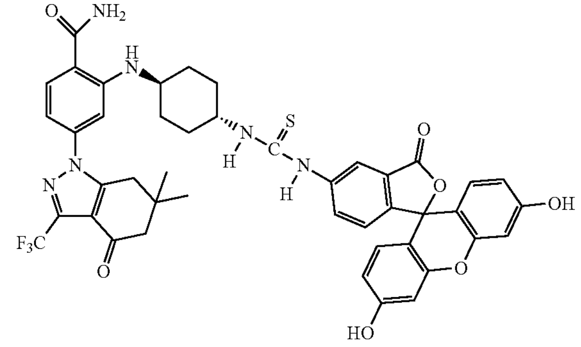

SNX-FITC 5.2.1.1.2. Synthesis of Biotinylated Probes for Detecting Oncogenic HSP90

A series of biotinylated analogs of PU-H71 (2) and desisopropyl-PU-H71 (13) were prepared with the purpose of obtaining compounds that are capable of permeating cell membranes and bind to intracellular HSP90 in live cells. The HSP90 inhibitors 13 and 2 were conjugated to biotin through a linker. The type of linker, as well as its length, were systematically altered so as to identify compounds capable of permeating into live cells and binding to HSP90.

The biotin tag enables for pull down experiments through subsequent binding to streptavidin. The linker should be of sufficient length to enable the concomitant binding to HSP90 and streptavidin.

The biotin tag also enables for detection using a labeled streptavidin or avidin antibody, and thus the biotinylated HSP90 inhibitors can be useful in staining tissues to detect the "oncogenic HSP90".

Compound 13 and Compound 2 contain an amine functionality which enables for the direct attachment of biotin and biotin containing linkers through the formation of an amide bond. In one embodiment, biotinylated molecules were prepared with no linker (i.e., direct attachment to biotin). The synthesis of two such compounds, referred to as PU-H71-biotin2 and PU-H71-biotin3, is depicted in Scheme 12. The compounds may be prepared from Compound 13 or Compound 2, respectively, by DCC coupling with D-biotin under sonication.

Scheme 12: Synthesis of PU-H71-biotin2 and PU-H71-biotin3

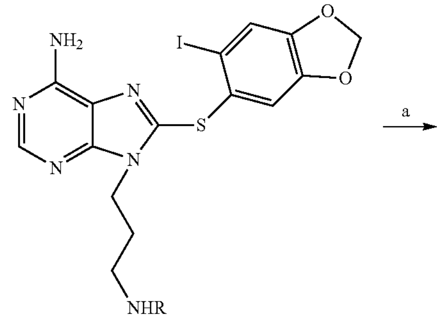

13 R = H
2 R = isopropyl

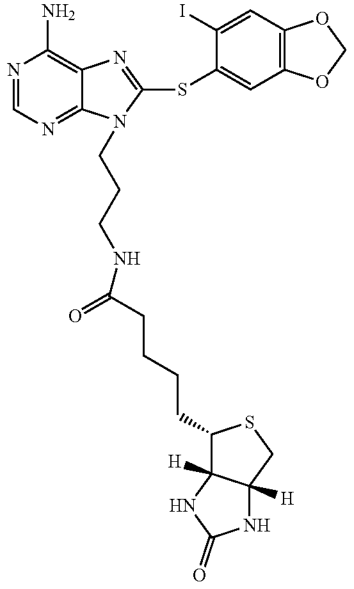

PU-H71-biotin3 R = H
PU-H71-biotin2 R = Isopropyl

In another embodiment, biotinylated molecules were prepared by covalently attaching PU-H71 (2) or desisopropyl-PU-H71 (13) to biotin through a 6-carbon chain spacer group to produce PU-H71-biotin4 or PU-H71-biotin7, as depicted in Scheme 13. PU-H71-biotin4 and PU-H71-biotin7 may be prepared by reacting Compound 13 or Compound 2, respectively, with the commercially available N-hydroxysuccinimide active ester containing biotin molecule referred to as EZ-Link® NHS-LC-Biotin, in the presence of a base.

Scheme 13: Synthesis of PU-H71-biotin4 and PU-H71-biotin7

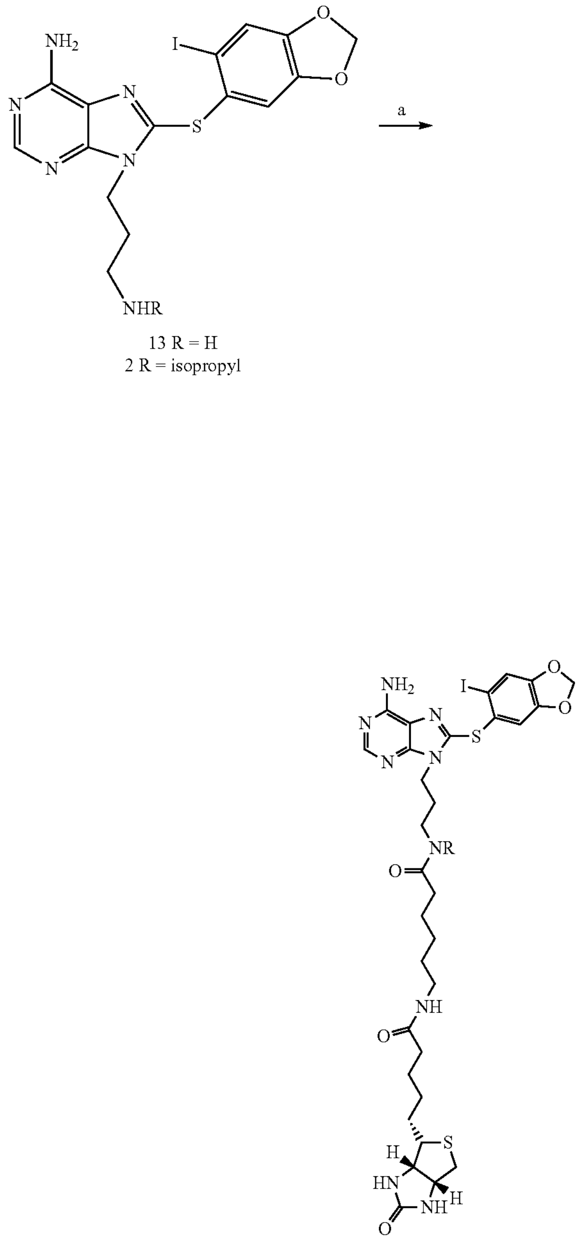

13 R = H
2 R = isopropyl

PU-H71-biotin4 R = H
PU-H71-biotin7 R = Isopropyl

In still another embodiment, biotinylated molecules were prepared by covalently attaching PU-H71 (2) or desisopropyl-PU-H71 (13) to biotin through an extended carbon chain spacer group to produce PU-H71-biotin5 or PU-H71-biotin8, as depicted in Scheme 14. PU-H71-biotin5 and PU-H71-biotin8 may be prepared by reacting Compound 13 or Compound 2, respectively, with the commercially available N-hydroxysuccinimide active ester containing biotin molecule referred to as EZ-Link® NHS-LC-LC-Biotin, in the presence of a base.

Scheme 14: Synthesis of PU-H71-biotin5 and PU-H71-biotin8

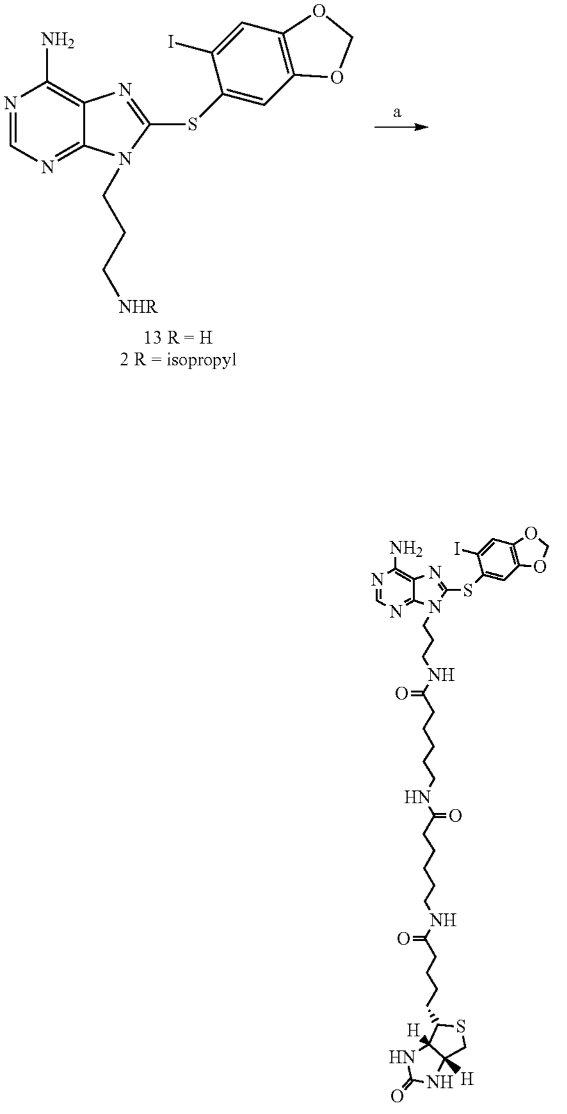

13 R = H
2 R = isopropyl

PU-H71-biotin5 R = H
PU-H71-biotin8 R = Isopropyl

In yet another embodiment, biotinylated molecules were prepared by covalently attaching PU-H71 (2) or desisopropyl-PU-H71 (13) to biotin through a polyethylene glycol chain to produce PU-H71-biotin6 or PU-H71-biotin9, as depicted in Scheme 15. PU-H71-biotin6 and PU-H71-biotin9 may be prepared by reacting Compound 13 or Compound 2, respectively, with the commercially available N-hydroxysuccinimide active ester containing biotin molecule referred to as EZ-Link® NHS-$PEG_4$-Biotin, in the presence of a base.

Scheme 15: Synthesis of PU-H71-biotin6 and PU-H71-biotin9

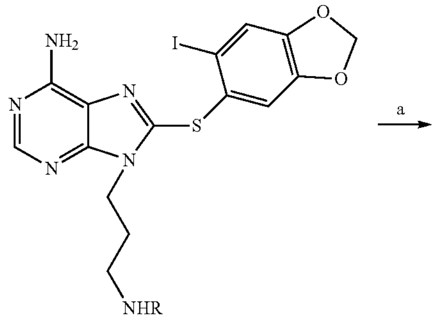

13 R = H
2 R = isopropyl

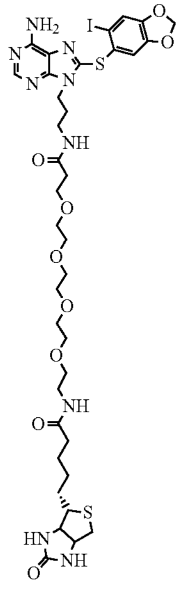

PU-H71-biotin6 R = H
PU-H71-biotin9 R = Isopropyl

In yet another embodiment depicted in Scheme 16, an amine linked biotin analog, referred to as PU-H71-biotin, was synthesized by the reaction of bromide compound 6 with EZ-Link® Amine-$PEO_3$-Biotin Scheme 16: Synthesis of PU-H71-biotin

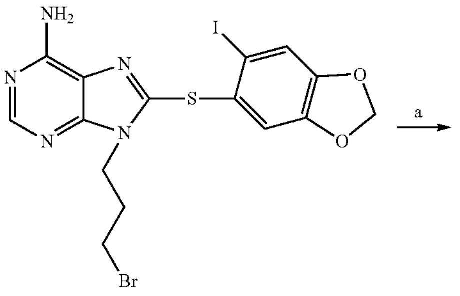

6

-continued

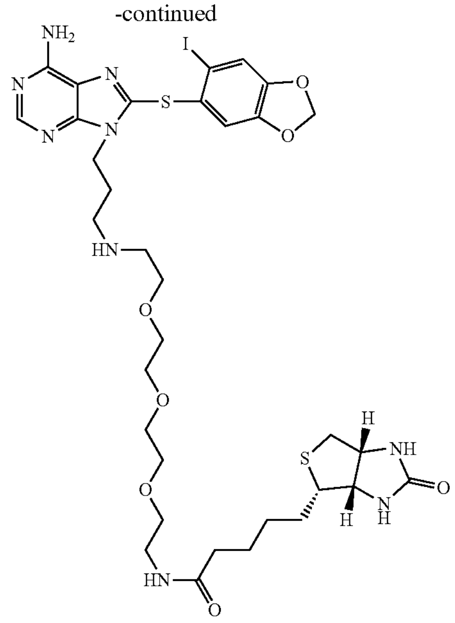

PU-H71-biotin

To ensure the biotinylated compounds still retain affinity for HSP90, they were each evaluated in a fluorescence polarization assay using SKBr3 cancer cell lysate. As can be seen each of the compounds retain good affinity for HSP90 with $IC_{50}$'s in the range 31-154 nM (Table 1; PU-H71, $IC_{50}$=25 nM).

TABLE 1

Properties of Biotinylated compounds

| Compound | $EC_{50}$ (nM); SKBr3 HSP90 binding assay | HSP90-streptavidin binding with K562 lysate | cells | MW | TPSA | ClogP |
|---|---|---|---|---|---|---|
| PU-H71 | 24.5 | n.a. | n.a. | 512 | 96.8 | 3.09 |
| PU-H71-biotin | 58.9 | Yes | No | 871.81 | 194.75 | 1.69 |
| PU-H71-biotin2 | 153.5 | No | No | 738.66 | 146.24 | 3.12 |
| PU-H71-biotin3 | 44.3 | No | No | 696.58 | 155.03 | 1.93 |
| PU-H71-biotin4 | 34.8 | No | No | 809.74 | 184.13 | 3.49 |
| PU-H71-biotin5 | 31.4 | Yes | Yes | 922.90 | n.d | n.d. |
| PU-H71-biotin6 | 66.2 | Yes | Yes | 943.87 | n.d. | n.d. |
| PU-H71-biotin7 | 72.8 | No | No | 851.82 | n.d. | n.d. |
| PU-H71-biotin8 | 76.9 | Yes | Yes | 964.98 | n.d. | n.d. |
| PU-H71-biotin9 | 110.1 | Yes | Yes | 985.95 | n.d. | n.d. |

n.a. = not applicable
n.d. = not determined; TPSA and Clog P values were determined with Chemdraw and n.d. Indicates that it was not possible to determine a value for the given structure.

Two general trends can be observed. First, compared to PU-H71 analogs the desisopropyl analogs bind on average with approximately 2-fold greater affinity (i.e. PU-H71-biotin3 vs -2, -4 vs -7, -5 vs -8, -6 vs -9). Second, in terms of the linkers the carbon series is more potent than the ethylene glycol series (i.e. PU-H71-biotin4 and -5 vs -6, -7 and -8 vs -9). In sum, all of the compounds prepared retain good affinity with HSP90 and were suitable for further analysis.

Having shown that each of the prepared biotinylated molecules retain good affinity to HSP90 we next wanted to determine whether the chain length was sufficient to maintain concomitant binding to HSP90 and streptavidin. K562 lysate (500 µg protein) was treated overnight with a mixture of streptavidin beads and 100 µM of each of the compounds. Following sufficient washing to remove any unbound material, the remaining bead pellet was analyzed by SDS-PAGE. The gel was washed and stained with coomasie blue for 1 h. PU-H71-biotin-5, -6, -8, -9 as well as PU-H71-biotin show a band at approximately 90 kDa, indicating concomitant binding to HSP90 and streptavidin. Analogs without a linker (PU-H71-biotin2 and -3) and with a 6-carbon spacer group (PU-H71-biotin4 and -7) did not show a band at 90 kDa, indicating that the linker was too short. In contrast, compounds containing an extended carbon chain spacer group (PU-H71-biotin5 and -8 and a polyethylene chain (PU-H71-biotin6 and -9) were of sufficient length to enable concomitant binding.

Having shown that some of the molecules bind concomitantly to HSP90 and streptavidin, we next investigated whether this can similarly be accomplished in live cells. In this case, binding in K562 cells was first determined by treatment with 100 µM of PU-H71-biotin-5, -6, -8, -9 as well as PU-H71-biotin for 4 h then analyzed by SDS-PAGE. Of the compounds evaluated only PU-H71-biotin failed to maintain binding in live cells. Interestingly, PU-H71-biotin contains an ionizable amine which limits its permeability and may be a primary factor for its failure to bind. In contrast, PU-H71-biotin-5, -6, -8, -9 do not contain an ionizable amine and are able to permeate the cell membrane. The active compounds were evaluated at 50, 25, and 10 µM and show that PU-H71-biotin-6 and 9 maintain good binding even at 10 µM. These two compounds were further evaluated at 5, 2.5 and 1 µM and even at the lowest concentration a faint band is still present at approximately 90 kDa. PU-H71-biotin-6 still shows a faint band at 0.5 µM, indicating concomitant binding is still maintained at this low concentration.

It appears that compounds containing extended carbon chain spacer groups (PU-H71-biotin-5, -8) or polyethylene glycol chain linkers (PU-H71-biotin-6, -9), irrespective of whether 13 or 2 is attached, are able to permeate the membrane of K562 cells, bind to HSP90 and subsequently bind to streptavidin beads. Furthermore, it appears as if compounds containing polyethylene glycol chain linkers (PU-H71-biotin-6, -9) may be preferred.

5.2.1.1.3. Synthesis of ANCA-Labeled Probes

The present disclosure further provides probes for detecting oncogenic HSP90 by labeling inhibitors with amino naphthalenyl-2-cyano-acrylate (ANCA). ANCA is a fluorescent probe that can bind to and stain amyloid plaques in human tissue. ANCA is often referred to as a molecular rotor. Molecular rotors are probes where the fluorescence quantum yield is dependent on the surrounding environment. The structural motif of the molecular rotor is such that when brought in to close proximity of a macromolecule the internal molecular rotation is hindered (increase in rigidity) resulting in a change in fluorescent emission i.e. bound and unbound molecular rotors have different fluorescence emission peaks (see FIG. 15). This physical aspect can be exploited when conjugated to PU-H71, which has specificity to the “oncogenic Hsp90”. The molecular rotor conjugated to PU-H71 allows one to discern in a heterogeneous population of cancer cells, the cells with “oncogenic Hsp90” and allows the quantitation of such species in the cells present in specimens obtained from interventions such as biopsy, surgery or fine needle aspirates.

In one embodiment, desisopropyl-PU-H71 (13), PU-H71 (2) or compounds analogs of 13 or 2 may be labeled with ANCA, as depicted in Scheme 17. In Scheme 17, desisopropyl-PU-H71 (13) is reacted with cyanoacetic acid to produce Compound 26 In the next step, Compound 26 is reacted with Compound 27 at elevated temperature to afford Compound 28 (PU-ANCA).

Scheme 17: Synthesis of PU-ANCA

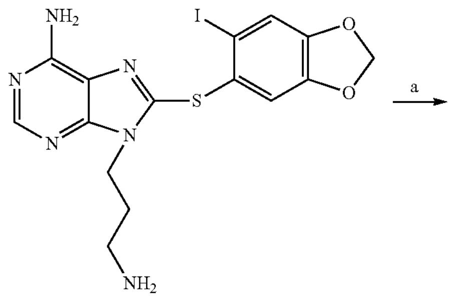

13

-continued
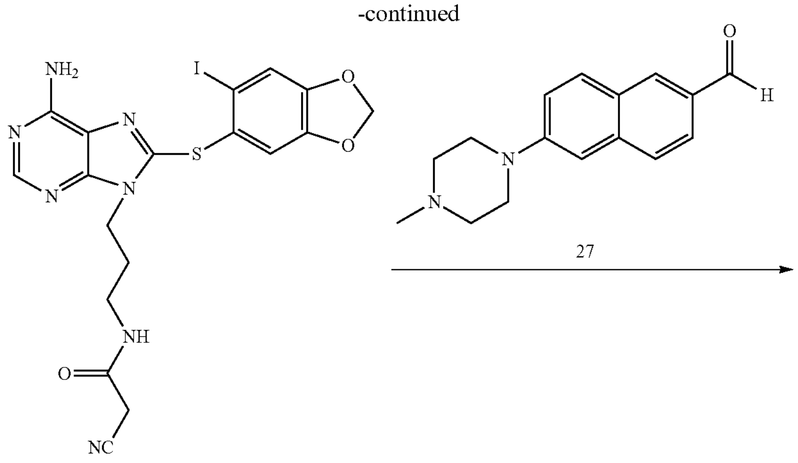
26
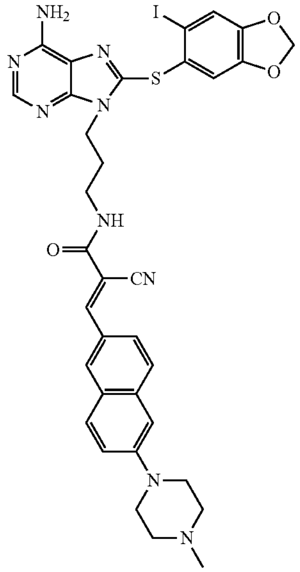
28
PU-ANCA
In yet another embodiment, ANCA labeled HSP90 inhibitors useful in the invention, such as those based on purine are shown in Scheme 18.
Scheme 18: Synthesis of ANCA-labeled HSP90 inhibitors based on purine
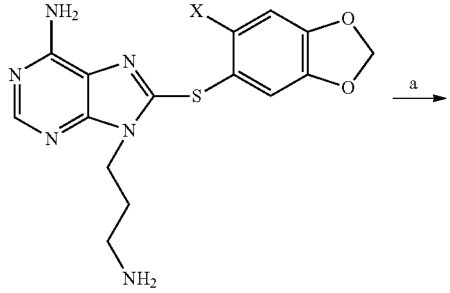

-continued
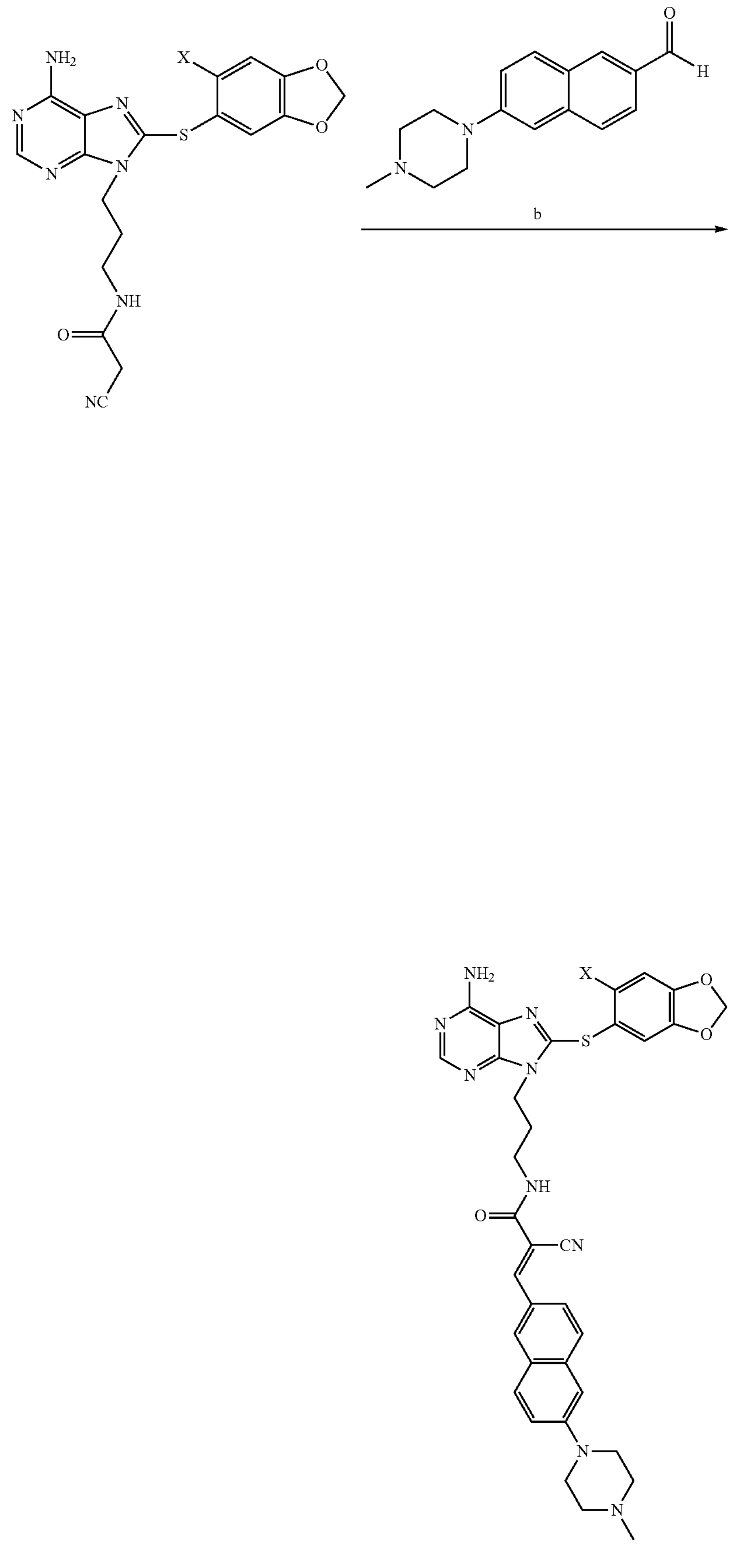

-continued
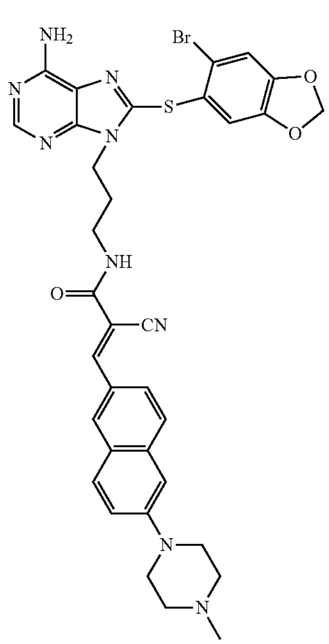
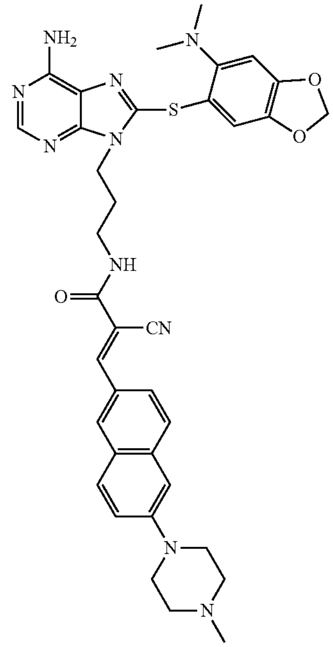
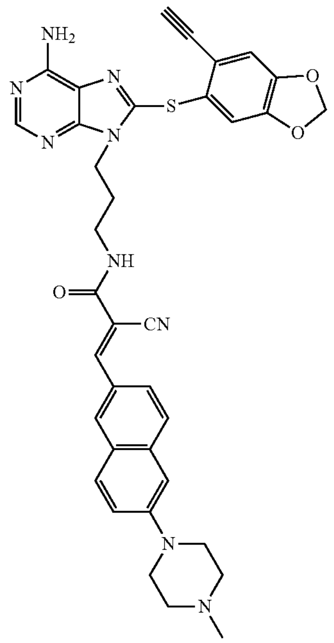
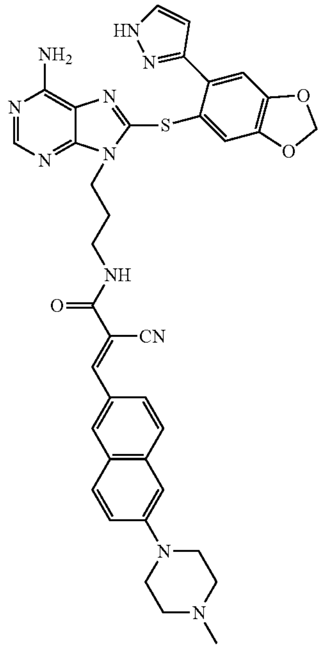
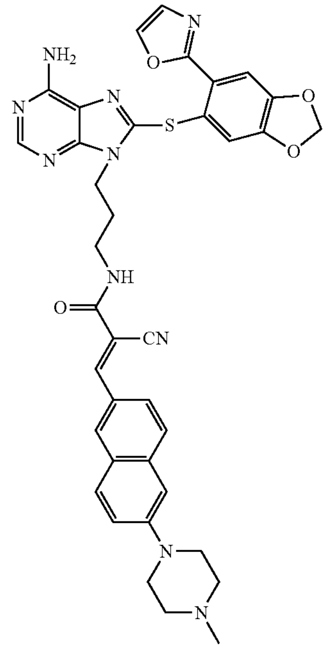
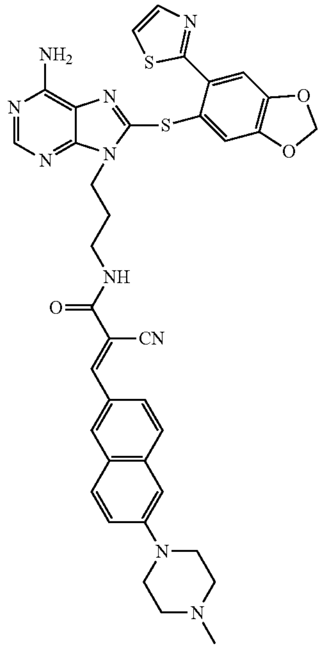

-continued
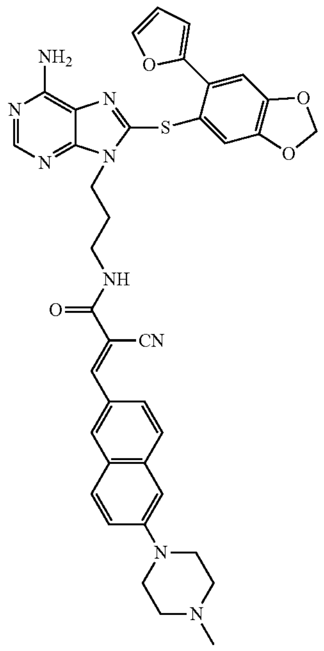
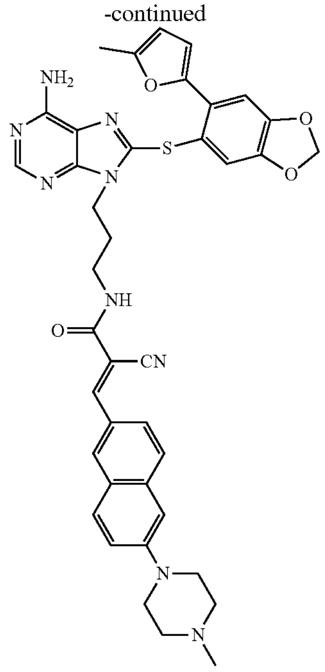
In yet another embodiment, ANCA labeled HSP90 inhibitors useful in the invention, such as those based on imidazopyridine are shown in Scheme 19.
Scheme 19: Synthesis of ANCA-labeled HSP90 inhibitors based on imidazopyridine
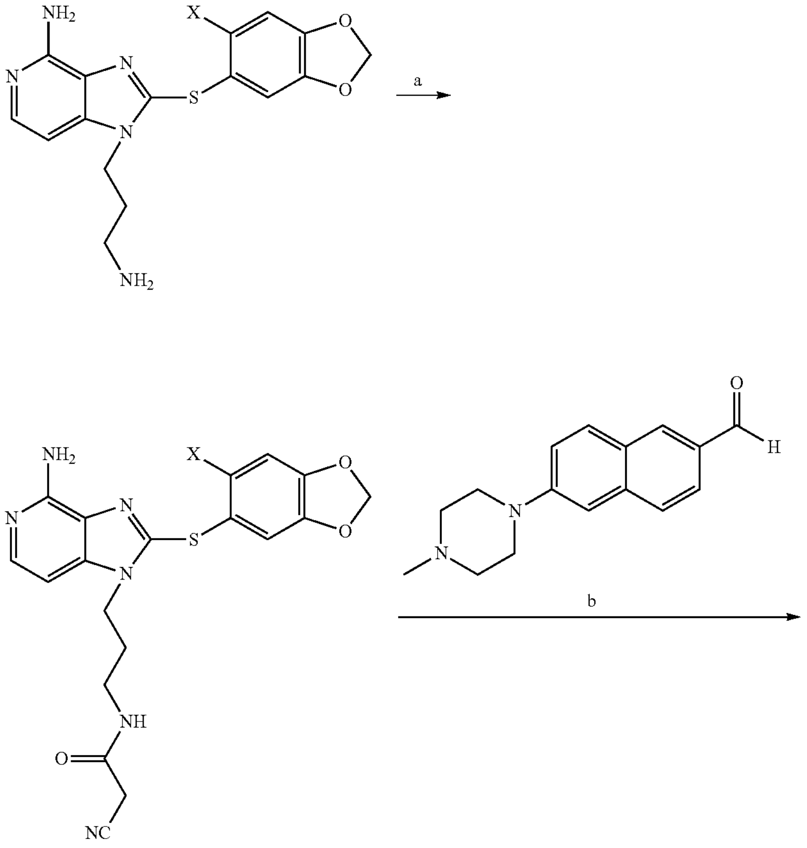

-continued
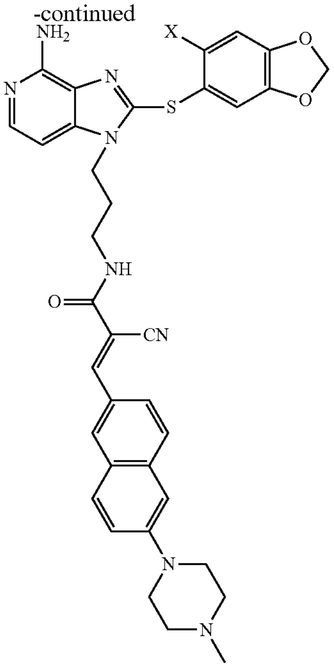
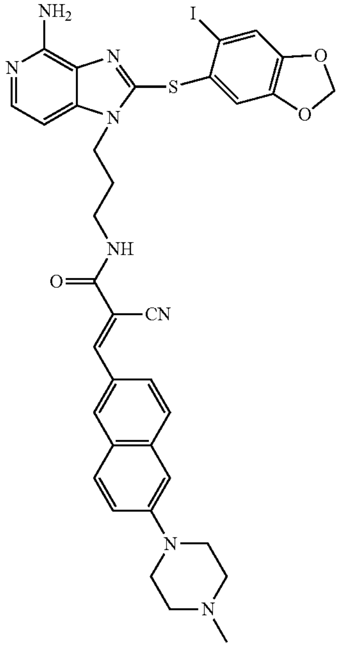
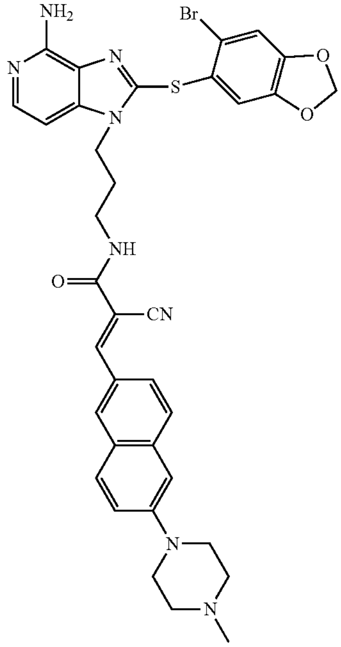
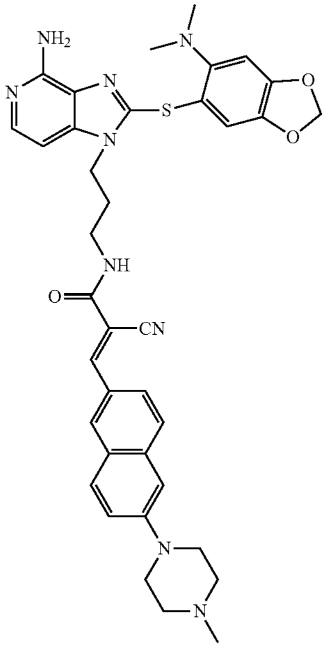

-continued

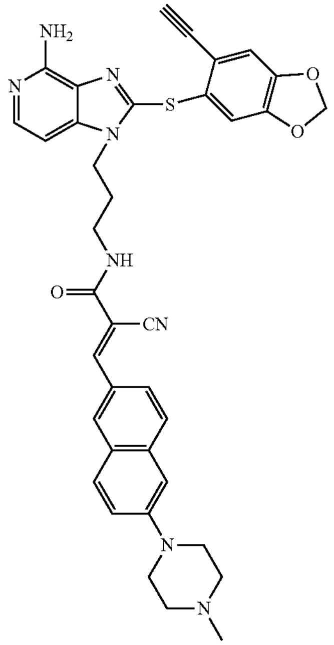

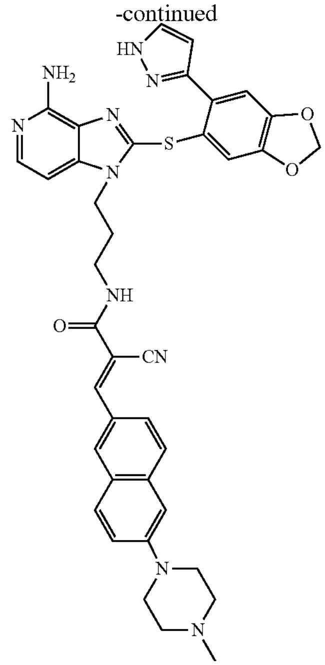

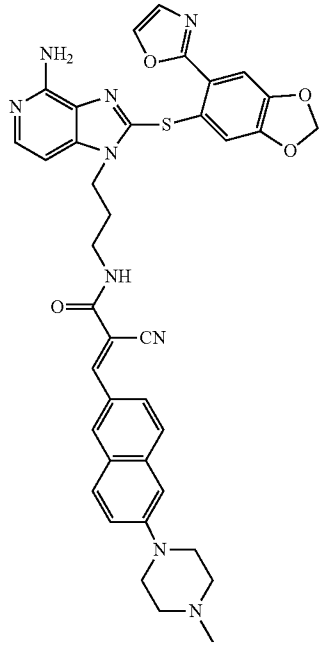

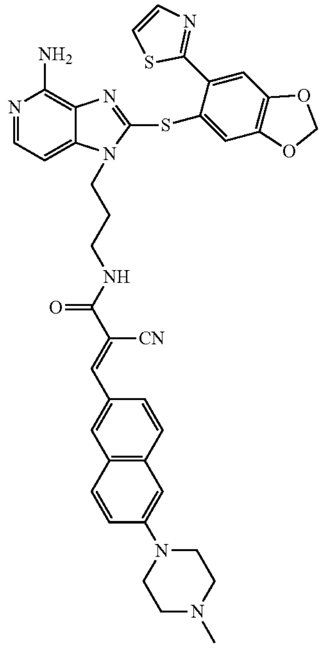

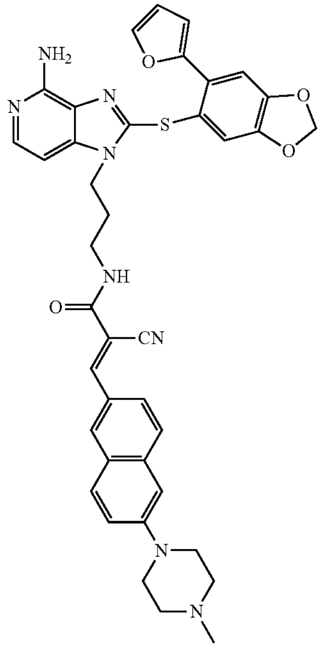

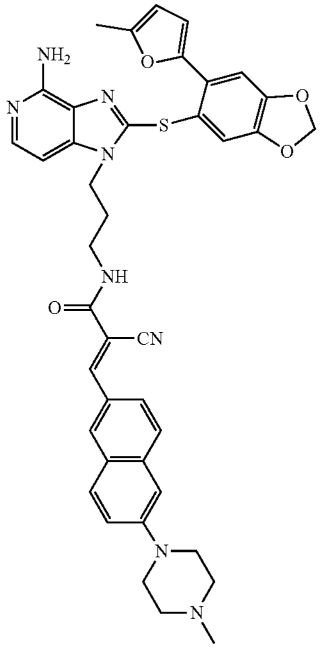

5.2.1.2. Utilization of Probes in Cancer Prognosis and Treatment 5.2.1.2.1. Hematologic Malignancies Studies discussed in Section 5.1, confirm that certain HSP90 inhibitors bind preferentially to a subset of HSP90 species, the "oncogenic HSP90" that is more abundant in cancer cells than in normal cells. Abundance of this species is not dictated solely by the amount of HSP90 expression and is predictive of cellular sensitivity to HSP90 inhibition. Thus, determining the proportion of the HSP90 population in a patient's cancer cells that is available for binding to a tagged inhibitor that selects for this "oncogenic HSP90", such as PU-H71, predicts sensitivity to HSP90 inhibitors in the clinic and reveals the level to which the cancer cells are dependent on HSP90.

Specifically, the disclosure shows that cell permeable fluorescently labeled HSP90 inhibitors such as PU-H71-FITC derivatives (e.g., PU-FITC; PU-H71-FITC2) label live cells as early as one hour after exposure, reduces the viability of leukemia cells at 24-48 h, inhibits the intracellular tumor HSP90 as indicated by degradation of HSP90 client oncoproteins, are localized intracellularly as indicated by confocal microscopy and bind specifically to tumor versus normal cell HSP90 as indicated by flow cytometry. Furthermore, the fluorescently labeled compounds of the present disclosure bind to the "oncogenic HSP90" species, which provide ample evidence that this probe permeates the cell and binds specifically to the tumor "oncogenic HSP90" target, similarly to PU-H71.

The methods of the present disclosure may be used to determine if a patient with a hematologic malignancy (e.g., leukemia) or a myeloproliferative disorder will be responsive to HSP90 inhibition therapy. The method may be applied to different hematologic malignancies including, but not limited to, leukemia including acute myeloid leukemia, acute lymphoblastic leukemia and chronic myeloid leukemia, to lymphoid leukemias, to multiple myeloma and myeloproliferative neoplasms and disorders.

The disclosure provides a method for determining whether a patient with a blood cancer will likely respond to therapy with an HSP90 inhibitor which comprises contacting a sample containing cancer cells and non-cancer cells (e.g., lymphocytes) from the patient with a cell permeable fluorescently labeled HSP90 inhibitor which binds preferentially to a tumor-specific form of HSP90 present in the cancer cells of the patient, measuring the amount of fluorescently labeled HSP90 inhibitor bound to the cancer cells and non-cancer cells in the sample, and comparing the amount of the fluorescently labeled HSP90 inhibitor bound to the cancer cells with the amount of the fluorescently labeled HSP90 inhibitor bound to the non-cancer cells, wherein a greater amount of fluorescently labeled HSP90 inhibitor bound to the cancer cells than the non-cancer cells indicates the tumor will likely respond to the HSP90 inhibitor. In certain embodiments, the amount of binding to the cell permeable fluorescently labeled HSP90 inhibitor is determined using flow cytometry.

In some embodiments, a ratio of binding blood cancer cells to normal lymphocytes of about 1.5 or greater indicates that a cancer patient will be susceptible to HSP90 inhibition therapy. In other embodiments, a ratio of binding blood cancer cells to normal lymphocytes of about 2 or greater indicates that a cancer patient will be susceptible to HSP90 inhibition therapy. In still other embodiments, a ratio of binding blood cancer cells to normal lymphocytes of about 2.5 or greater indicates that a cancer patient will be susceptible to HSP90 inhibition therapy. In still other embodiments, a ratio of binding blood cancer cells to normal lymphocytes of about 3 or greater indicates that a cancer patient will be susceptible to HSP90 inhibition therapy. In still other embodiments, a ratio of binding blood cancer cells to normal lymphocytes of about 4 or greater indicates that a cancer patient will be susceptible to HSP90 inhibition therapy. In still other embodiments, a ratio of binding blood cancer cells to normal lymphocytes of about 5 or greater indicates that a cancer patient will be susceptible to HSP90 inhibition therapy.

A large number of established cell lines and primary tumor samples were investigated by conducting a correlative analysis between binding of a cell permeable fluorescently labeled HSP90 inhibitor (e.g., PUH71-FITC2) and cell viability in vitro upon exposure to HSP90 inhibitors. To determine PUH71-FITC2 binding to a panel of cell lines and primary leukemia samples, we used multiparameter flow cytometry analysis. We also tested the sensitivity of these cells to HSP90 inhibitors by performing viability assays 48 h after drug exposure.

Fluorescence-activated flow cytometry, remains a method of choice for enumerating, purifying and analyzing cells.[9,10] In fact, a multitude of measurements can be performed now by flow cytometry, and recent technical advances allow these measurements to be made simultaneously on individual cells within heterogeneous populations.[11] Such multiparameter analysis is quite powerful as it provides more data from less sample, a key consideration when patient samples are limited. Multiparameter analysis also allows more accurate identification of populations, by excluding unwanted cells that bind some reagents.[9,10] The method is thus optimal for analyzing the binding of HSP90 ligands, when fluorescently labeled, to distinct cell populations.

Fluorescently labeled ligands have historically had a wide variety of uses in biology and pharmacology,[12] and offer the advantage of retaining the pharmacological properties of the unlabeled ligand. In addition to in vitro investigations of ligand-receptor binding, small molecule fluorescent probes allow for real time and non-invasive monitoring of the interaction between the target and the ligand in living cell populations, such as by means of flow cytometry.

Fluorescent dyes absorb light at certain wavelengths and in turn emit their fluorescence energy at a higher wavelength. Each dye has a distinct emission spectrum, which can be exploited for multicolor analysis by flow cytometry. Among the most used are fluorescein isothiocyanate (FITC), 4-nitrobenzo[1,2,5]oxadiazole (NBD) or the red shifted dye sulforhodamine 101 (Texas Red). FITC and NBD are detected in the FL1 channel on most instruments and are also a good choice for fluorescence microscopy (excitation 495 and 466 nM and emission 519 and 539 nM, respectively), whereas Texas Red is detected in FL3 on single laser instruments (excitation 589 nM and emission 615 nM).

In Section 5.1.1., we discussed studies with several primary leukemia cells and normal blood cells. In particular, we analyzed primary chronic and blast phase CML and acute myeloid leukemia (AML) samples that contained both blasts (malignant cell population) and lymphocytes (normal cell population), CD34+ cells isolated from the cord blood of healthy donors, total mononuclear cells from peripheral blood and also peripheral blood leukocytes (PBLs) (FIGS. 1C, 1E, 3, 4). We used a fluorescein labeled PU-H71 (PUH71-FITC2) as a tool to perform multiparameter flow cytometric analysis, in heterogeneous cell populations. As shown in FIG. 4A, a gating strategy is used to distinguish between the normal cell population (lymphocytes) and the malignant cell population (blasts). The flow cytometric dot blots are shown for three different patients. In FIG. 4B, the ratio of PU-H71-FITC2 binding to HSP90 in CML blasts to normal lymphocytes from the primary patient samples is shown.

In FIG. 4D, flow cytometry is again used to distinguish between blasts and normal lymphocytes and to analyze binding of CD34+ cells within the blast gate. In FIGS. 4E and 4G, the ratio of PU-H71-FITC2 binding to HSP90 CD34+ blasts to normal lymphocytes in six leukemia patients and in three healthy patients was determined. The nine patients were treated with either PU-H71-FITC2 or a control (TEG-FITC) (FIGS. 4F and 4H). As shown in FIG. 4H, patients who had the highest ratio (referred to as CML03106, 0614 and 0124; ratios averaged in FIG. 4G as "bcCML") were more sensitive than those with a lower ratio (referred to as CML0118, 0128 and 0222; ratios averaged in FIG. 4G as "cpCML"). It is noted that healthy patients had a ratio nearing one (FIG. 4G) and their cells in cord blood were not significantly sensitive to PU-H71 (FIG. 4H, referred to as CB1,2,3). The results displayed in FIG. 4F indicate that the viability of the CD34+ blasts was significantly reduced in the patients while the normal lymphocytes were not affected. Similarly, the control compound (TEG-FITC) did not reduce the viability of either the CD34+ blasts or the normal lymphocytes.

In primary samples, we analyzed both the blast populations and normal lymphocytes within the same patient. We found that in a panel comprised of primary leukemia cells (primary chronic- and blast-phase chronic myelogenous leukemia (CML) and acute myelogenous leukemia (AML) samples), and healthy blood cells (including CD34+ cord blood cells, and total peripheral blood mononuclear cells isolated from healthy donors), cells with the highest avidity for PUH71-FITC2 were also the most sensitive to killing by this agent (FIGS. 16A-16C). Importantly, normal lymphocytes present within the leukemia blood samples, show low binding to PU-FITC and were not affected by PU-H71. Thus, we rationalized that the use of the relative binding of PU-FITC in leukemia cells compared to normal lymphocytes within the same patient can be used as a normalized value to compare PUH71-FITC2 binding across samples. Specifically, when evaluated in CML samples, blast crisis CML (bcCML) cells presented the highest binding to PU-FITC (over 4 fold relative to normal lymphocytes) and demonstrated the highest sensitivity to PU-H71 treatment when compared to chronic phase (cpCML) (FIG. 16A) In contrast, PU-H71 bound weakly to HSP90 in normal blood cells ($IC_{50}$ values higher than 2,000 nM vs ~100 nM in bcCML) and was non-toxic in these cells at concentrations that were toxic to the cancer cells (FIGS. 1D, 1E and 16B, 16C). FIG. 16C shows the graph correlating the ratios obtained by analyzing the binding of PU-H71-FITC2 to blasts and to normal lymphocytes in 19 primary AML samples (reported as Fold PU binding on the X-axis) and the measured viability of the blasts when treated with PU-H71. Responsive (>50% reduced viability) from non-responsive (<50% reduced viability) tumors cells could be differentiated by a ratio of about 2.31 to about 7.43 or above compared to about 0.65 to about 2.22 or below, respectively.

Furthermore, in a panel of 14 leukemia cell lines we also noted a significant correlation between PU-H71-FITC2 binding (as presented in mean fluorescence intensity) and the sensitivity of these cells to HSP90 inhibition by PU-H71 (FIG. 3E).

Based on the data collected for the 19 primary AML specimens, we have calculated the sensitivity and accuracy curves to determine the probability of the assay to correctly identify the sensitive and resistant AML specimens. We performed a classification performance analysis using an arbitrary cut-off value of 2 or higher for PU-FITC binding (blast/lymphocyte) and less than 50% viability as a predicted outcome, and observed the following values: Accuracy: 83.3% (53.2-93.8%; 95% CI); Sensitivity: 91.7% (72.8-99.5%; 95% CI); Specificity: 66.7% (28.9%-82.4%; 95% CI); Positive predictive value: 84.6% (67.2-91.9%; 95% CI); Negative predictive value: 80% (34.7%-98.9%; 95% CI); Fisher exact test, p=0.022. These calculations suggest that PU-FITC has a good classification performance; this evaluation will be repeated with a larger cohort of samples to obtain more accurate and precise performance estimates. To minimize assay differences due to experimental or instrument variation, we will use the following: (1) BD Cytometer Setup & Tracking (CST) beads to allow for automated performance adjustments and improve day-to-day cytometer performance and consistency. CST beads will be run prior every new experimental set. (2) Positive control MV411 (sensitive cell line-high binding) and a negative control HL60 (low sensitivity cell line-low binding) will be included in the assays.

To determine whether the in vitro observations in leukemia cells can be confirmed in animal preclinical models, we set up xenotransplants using primary AML samples with different sensitivities (high and low) to PU-H71 evaluated in vitro and or predicted by PU-FITC binding. Primary AML cells were injected into sub-lethally irradiated NOD/SCID mice (n=8). Three to four weeks after injection, when the human leukemia cells have engrafted in the bone marrow (BM) of the mouse, treatment with PU-H71 or vehicle control was started (75 mg/kg 3×week) and continued for four weeks. Mice were sacrificed and leukemia engraftment evaluated using anti-human CD45 and CD34. To determine the ability of the surviving cells to give rise to disease, we transplanted equal numbers of human cells into sub-lethally irradiated NOD/SCID mice. This experiment determines whether PU-H71 treatment for the high binding-high in vitro sensitivity cells prevents further tumor initiation. If that is the case, it will suggest that treatment will decrease the likelihood of relapse. Because the xenografts may alter the biology of the leukemia sample, PUH71-FITC2 binding to the primary cells was evaluated prior to injection of the engrafted cells (4 weeks after transplant).

Results from the xenotransplant experiments are depicted in FIGS. 17A-17C. In experiments using two primary AML samples (high sensitivity and low sensitivity, FIG. 17A), we found that the high sensitivity sample has higher PUH71-FITC2 binding than the low sensitivity sample in the xenografted AML sample (FIG. 17B) and responds significantly better to treatment with an HSP90 inhibitor (FIG. 17C). In addition we found that cells from the PU-high sensitivity AML showed significantly decreased engraftment in secondary transplants (p=0.016). The results show that HSP90 involvement in the survival and proliferation of leukemia cells of patients at similar stages of the disease may be substantially different. Additionally, the effect of HSP90 inhibition therapy may be predicted from using fluorescently labeled probes of the present disclosure.

5.2.1.2.2. Solid and Liquid Tumors

Fluorescently labeled, ANCA-labeled and biotinylated probes of the present disclosure also have prognostic and diagnostic applications for solid tumors and lymphomas and other liquid tumor associated cancers. Examples of such tumors are those associated with a cancer selected from the group consisting of colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers, particularly breast cancer, gastric cancer, or pancreatic cancer. A person skilled in the art will recognize that labeling can be performed on tumor cells that are part of a tissue slice such as obtained from a biopsy or surgical resection of a tumor. In this case, tumor cells will be surrounded by cells of the stroma, benign tissue, vessels and other cells such as lymphocytes, macrophages. Labeling can also be performed in dissociated tumor cells such as those obtained from tissues that contain such tumor cells. Labeling can also be performed in tumor cells such as those obtained from established cancer cell lines. Not last, labeling can also be performed in tumor cells such as those obtained from biological fluids that contain such tumor cells including plasma and pleura. In one embodiment, labeling can be performed in tumor cell and tumor-associated cells and biologic bodies such as those found in the circulation of cancer patients, cells obtained by fine needle aspirates or other interventional procedures that result in a biospecimen containing cancer cells or other types of cells or biological formations that contain the “oncogenic HSP90”. In yet another embodiment, labeling can be performed in other cells associated with malignant transformation or biologic bodies that incorporate the oncogenic HSP90, such as the tumor exosomes. For instance, Section 6.3.8. describes isolating tissue for staining from a patient with gastric cancer and breast cancer after surgical resection and Section 5.2.1.2.4. describes isolating circulating tumor cells from a cancer patient.

Experiments in pancreatic and breast cancer cell lines indicate that analyses conducted in blood tumors are also valid in solid tumors and lymphomas. Thus labeled cell permeable HSP90 inhibitors, can detect and quantify the "oncogenic HSP90" present in the solid tumor cells or lymphoma cells. Moreover, the inhibitors can be used to predict the sensitivity of solid or liquid tumor cells to HSP90 inhibition therapy. A person skilled in the art will recognize that liquid tumors are associated but not limited to leukemias, lymphomas, myelomas and myeloproliferative neoplasms. Such person will also recognize that certain liquid tumors can also form solid tumors, and that in addition to the blood, cancer cells associated with these diseases can spread to the lymph nodes, spleen, liver, bone marrow and other sites.

In one example, a panel of pancreatic and breast cancer cells were tested for (1) sensitivity to several distinct HSP90 inhibitors such as PU-H71, SNX-2112 and NVP-AUY922 (see FIGS. 2A-2F); (2) binding to PU-H71-FITC2; and (3) expression of total HSP90 in these tumor cells. FIG. 18A shows a significant correlation between PU-H71-FITC2 binding and sensitivity of these cells to PU-H71, SNX-2112 and NVP-AUY922 ($r^2$=0.59, 0.62 and 0.61, respectively FIG. 18A). In contrast no significant correlation was determined between the sensitivity to HSP90 inhibitors and the expression of total tumor HSP90 in these cells (FIG. 18C). Similarly, no significant correlation could be established between the expression of "oncogenic HSP90" as determined by PU-FITC and the expression of total tumor HSP90 in these cells (FIG. 18B). The HL-60 leukemia cells are resistant to PU-H71 and other HSP90 inhibitors and show low to no binding to PU-FITC. Thus, we rationalized that the use of the relative binding of a labeled HSP90 inhibitor (e.g., PU-H71-FITC2) in cancer cells compared to HL-60 can also be used as a normalized value to compare PU-FITC binding across samples and experiments (FIG. 18D). FIG. 18C shows such analysis using the ratio of labeled-PUH71 (e.g., PU-H71-FITC2) binding to the respective cancer cell and to HL60 in several pancreatic and breast cancer cells. Collectively, these data indicate that: (1) PU-FITC is an appropriate tool to measure the abundance of the "oncogenic HSP90"; (2) measuring the abundance of the "oncogenic HSP90" predicts for sensitivity to HSP90i; and (3) the abundance of total tumor HSP90 is not predictive of response to HSP90 inhibitors nor it correlates with the abundance of the "oncogenic HSP90" as measured by labeled PU-H71.

The labeled HSP90 inhibitors of the present disclosure can be used to determine if a patient will benefit from HSP90 inhibition therapy. In one embodiment, binding of the labeled HSP90 inhibitor to the patient's tumor cells can be compared with binding to control cells. Increased binding relative to the control indicates that the patient will be amenable to HSP90 inhibition therapy. As shown in FIG. 19, responsive (>50% reduced viability) from non-responsive (<50% reduced viability) cells could be differentiated by a ratio of PU-H71-FITC2 binding to tumor cells and reference HL60 cells from about 2.7 to about 5.87 or above for responsive cells compared to about 1.23 or about 2.07 or below for nonresponsive cells. It will be understood that these ratios for determining responsiveness to the HSP90 inhibitor will depend on the nature of the labeled HSP90 inhibitor and the reference specimen (i.e. HL60 cells, normal leukocytes, CD45+CD14− cells, or normal lymphocytes in the blood) and/or control derivative (i.e. PUFITC9 or FITC-TEG used to account for non-specific/background binding) used in the assay.

A more detailed description of the invention in labeling the oncogenic HSP90 in circulating tumor cells is given in section 5.2.1.2.4. FIGS. 20A-20B show the use of PUFITC9 as a PU derivative designed to have low to no binding to oncogenic HSP90, and thus to account for non-specific/background binding. It also shows the use of the patient's leukocytes (CD45+CD14− cells) as a reference cell (cells with low to no oncogenic HSP90).

Experiments in diffuse large B-cell lymphoma (DLBCL) cells also indicate that sensitivity of these cells to HSP90 inhibitors correlates with their uptake of labeled-PU-H71 but not with the expression of total tumor HSP90 in the cell (FIG. 21). Specifically, OCI-Ly7 and OCI-Ly1 are two DLBCL cells highly sensitive to HSP90 inhibition (Cerchietti et al Nature Medicine 2009). They are both avid PU-H71 binders. We treated these cells for an extended period of time with sub-therapeutic concentrations of HSP90 inhibitors and were able to select clones that exhibited 5 to 10-times lower sensitivity than the parental cells to several tested HSP90 inhibitors, such as PU-H71, PU-DZ13 and 17DMAG (FIG. 8). FIG. 21 shows that, while these clones express total tumor HSP90 levels similar to the parental Ly1 cells, they have lower "oncogenic HSP90" levels as measured by labeled PU-H71-uptake. The binding experiment was carried out in the presence and absence of PSC833 (2.5 μM), a P-gP inhibitor, to demonstrate that differential uptake was a result of distinct "oncogenic HSP90" levels and not an indirect measure of drug pump-mediated efflux.

5.2.1.2.2.1. Pancreatic Ductal Adenocarcinoma

Pancreatic ductal adenocarcinoma (PDAC) is the fourth most common cause of cancer-related mortality in the United States. The five-year survival rate is the lowest among all cancers, with estimates ranging from 0.4 to 4 percent. In 2009, an estimated 42,470 new cases of PDAC were diagnosed, and an estimated 35,240 patients died as a result of their disease. Because of the aggressiveness of this cancer, the inability to diagnose it early, and the current lack of outcome altering therapies, mortality rates from PDAC closely mirror incidence rates. The only potentially curative treatment for PDAC is surgical resection. Because the disease is generally advanced at presentation, only 10 to 20% of patients are eligible for curative resection. In these patients who undergo pancreaticoduodenectomy, five-year survival remains dismal, approximately 20%. Development of effective chemotherapeutic agents to treat PDAC has been enormously challenging. Traditional cytotoxic agents are largely ineffective at controlling tumor growth, improving quality of life and prolonging patient survival.

To tolerate the complex load of aberrant pathways and molecules, PDACs become dependent for survival on molecular chaperones. The major chaperone, heat shock protein 90 (HSP90), assists and abets onco-proteins driving malignant processes in PDAC, such as proliferation, survival and metastasis, and allow for the development of a cancer phenotype. In addition, HSP90 helps cancer cells build resistance to other therapies by increasing the apoptotic threshold. These comprehensive biological functions propose an important role for anti-HSP90-targeted therapy in PDAC. Consequently, these tumors are appropriate candidates for treatment with inhibitors of one of the major cancer chaperones, HSP90.

Identification of the abundance of tumor HSP90 species required for pancreatic cancer survival by means of HSP90 inhibitors, such as PU-H71 that preferentially bind the oncogenic HSP90 species, will serve as a tumor-specific biomarker for selection of patients likely to benefit from HSP90-therapy and to personalize therapeutic targeting of tumors.

Indeed, the sensitivity of pancreatic cell lines to HSP90 inhibitors correlates with tumor HSP90 species abundance, as measured by cellular uptake of fluorescein labeled PU-H71 (PU-H71-FITC2) (FIGS. 22A-22C). Cells that take up the highest amount of PU-H71-FITC2 are also those most sensitive to the HSP90 inhibitors.

Similar to studies with blood cancers (Section 5.2.1.2.1.), the higher the relative binding of the labeled HSP90 inhibitor (e.g. PU-H71-FITC2) in pancreatic cancer cells compared to reference derivative or reference cells (e.g., HL60 or normal cells), the more susceptible the pancreatic tumor or tumor cells will be to HSP90 inhibitor therapy (FIG. 19). In some embodiments, a ratio of binding tumor cells to reference cells of about 2 or greater indicates that a pancreatic cancer patient will be susceptible to HSP90 inhibition therapy. In other embodiments, a ratio of binding pancreatic cancer tumor or tumor cells to reference cells of 2.5 or greater indicates that a cancer patient will be susceptible to HSP90 inhibition therapy. In other embodiments, a ratio of binding pancreatic cancer tumor or tumor cells to reference cells of 3 or greater indicates that a cancer patient will be susceptible to HSP90 inhibition therapy.

5.2.1.2.3. Cancer Stem Cells

The present disclosure provides methods of determining the amount of "oncogenic HSP90" in cancer stem cells (CSCs) relative to normal cells (e.g., lymphocytes) and thereby determining if CSCs are responsive to HSP90 inhibitor therapy. Recent evidence suggests that cancer stem cells (CSCs) are able to originate and maintain disease for a diverse type of cancers. Moreover, it has been shown that these cells are resistant to common chemotherapeutic agents and thus more likely to result in disease relapse or metastasis. Therefore, it is critical to identify therapies that can ablate CSCs in order to obtain better therapeutic outcomes. Heat shock proteins (HSPs) play an important surveillance role in protein synthesis, maintenance and degradation. In FIGS. 23A-23B, we provide data in acute myeloid leukemia (AML) stem cells that shows that CSC populations are sensitive to HSP90 inhibition and that sensitivity correlates with the abundance of the oncogenic tumor HSP90 species, as recognized by a labeled PU-H71.

FIG. 23A displays the ratio of binding of PU-FITC to leukemia stem cells (LSCs, CD34+CD38− CD45dim) and to lymphocytes. Primary AML samples were incubated with 1 μM PU-H71-FITC2 at 37° C. for 4 h. Cells were stained with CD34, CD38, CD45 and 7-AAD followed by flow cytometry analysis. FIG. 23B displays the percent viability of LSCs relative to the untreated control from three primary AML samples after 48 hour treatment with 1 μM PU-H71. Cells were stained with CD45, CD34 and CD38 prior to Annexin V and 7-AAD staining. Viability in LSCs was measured by flow cytometry and determined as the percentage of AnnexinV-/7AAD- of the CD45dim CD34+CD38− gate. Notably, the cells with the higher binding to PU-H71-FITC2 were most susceptible to treatment with the HSP90 inhibitor.

Similar to studies with blood cancers (Section 5.2.1.2.1.), the higher the relative binding of the fluorescently labeled HSP90 inhibitor (e.g. PU-H71-FITC2) in CSCs compared to normal cells (e.g., lymphocytes) within the same patient, the more susceptible the CSCs will be to HSP90 inhibitor therapy. In some embodiments, a ratio of binding CSCs to normal lymphocytes of 1.5 or greater indicates that a cancer patient will be susceptible to HSP90 inhibition therapy. In other embodiments, a ratio of binding CSCs to normal lymphocytes of 2 or greater indicates that a cancer patient will be susceptible to HSP90 inhibition therapy.

5.2.1.2.4. Circulating Tumor Cells

Circulating tumor cells (CTCs) are cells that have detached from a primary tumor and circulate in the bloodstream. CTCs may constitute seeds for subsequent growth of additional tumors (metastasis) in different tissues. FIG. 20 shows labeling of CTCs isolated from a patient with HER2+ metastatic breast cancer. The tumor cells isolated from her plasma bind around 84-fold more PUFITC than the leukocytes (CD45+CD14− cells) also isolated from her plasma, indicating that these tumor cells have high levels of the oncogenic HSP90 and that therapy with an HSP90 inhibitor would be effective at killing them. Indeed, twenty-four hours after this patient received a dose of 20 mg/m2 PU-H71, a 6-fold drop in the number of CTCs in the blood was measured.

5.2.2. Radiolabeled Probes for Detecting Oncogenic HSP90

The disclosure provides for using radiolabeled probes that are capable of detecting oncogenic HSP90 in cancer cells. Section 5.2.2.1 describes the various types of probes to be used in accordance with the present disclosure. Section 5.2.2.2 describes the use of such probes in prognostic and diagnostic assays.

5.2.2.1. Radiolabeled Probes

HSP90 inhibitors that can be labeled without changing the affinity, selectivity or biodistribution profile of the inhibitor are ideal probes for prognostic and/or diagnostic purposes. In one embodiment, the probe is an iodine 124 radiolabeled versions of the HSP90 inhibitor. In another embodiment, the probe is an iodine 131 radiolabeled version of the HSP90 inhibitor. In another embodiment, the probe is an iodine 123 radiolabeled version of the HSP90 inhibitor. In another embodiment, the probe is an iodine 125 radiolabeled version of the HSP90 inhibitor.

In one embodiment, the radiolabeled probe is a compound of the following formula:

(IA)

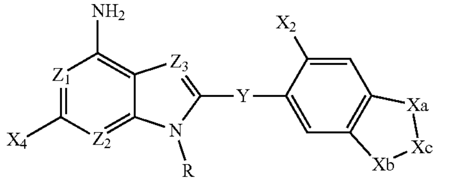

(IB)

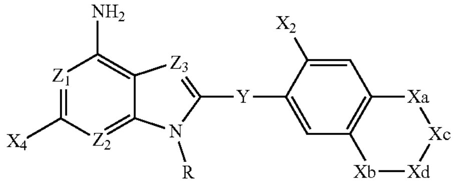

or a pharmaceutically acceptable salt thereof, wherein:

(a) each of $Z_1$, $Z_2$ and $Z_3$ is independently CH or N;

(b) Y is $CH_2$, O, or S;

(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;

(d) $X_2$ is $^{123}I$, $^{124}I$, $^{125}I$ or $^{131}I$;

(e) $X_4$ is hydrogen or halogen; and (f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl, wherein the R group is optionally interrupted by —S(O)N($R_A$)—, —$NR_A$S(O)—, —$SO_2N(R_A)$—, —$NR_ASO_2$—, —C(O)N($R_A$)—, or —$NR_A$C(O)—, and/or the R group is optionally terminated by —S(O)$NR_AR_B$, —$NR_AS(O)R_B$, —$SO_2NR_AR_B$, —$NR_ASO_2R_B$, —C(O)$NR_AR_B$, or —$NR_AC(O)R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

In another embodiment, the radiolabeled probe is a compound of the following formula:

(IA)

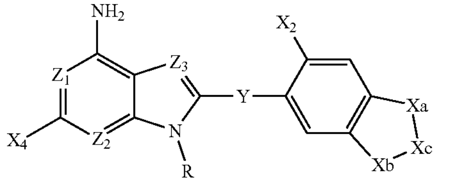

(IB)

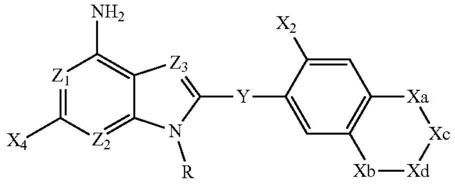

or a pharmaceutically acceptable salt thereof, wherein:

(a) each of $Z_1$, $Z_2$ and $Z_3$ is independently CH or N;

(b) Y is $CH_2$, O, or S;

(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;

(d) $X_2$ is $^{123}I$, $^{124}I$, $^{125}I$ or $^{131}I$;

(e) $X_4$ is hydrogen or halogen; and (f) R is —$(CH_2)_m$—N—$R_{10}R_{11}R_{12}$ or —$(CH_2)_m$—N—$R_{10}R_{11}$, where m is 2 or 3 and where $R_{10}$-$R_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen or a 6-membered ring including the N and optionally an additional heteroatom with substituents to satisfy valence, with the proviso that when all of $R_{10}$-$R_{12}$ are present the compound further comprises a pharmaceutically acceptable counter ion.

In another embodiment, the radiolabeled probe is a compound of the following formula:

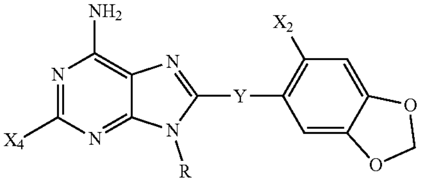

or a pharmaceutically acceptable salt thereof, wherein:

Y is $CH_2$ or S;

$X_4$ is H or halogen $X_2$ is $^{123}I$, $^{124}I$, $^{125}I$ or $^{131}I$; and R is —$(CH_2)_m$—N—$R_{10}R_{11}R_{12}$ or —$(CH_2)_m$—N—$R_{10}R_{11}$, where m is 2 or 3 and where $R_{10}$-$R_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen or a 6-membered ring including the N and optionally an additional heteroatom with substituents to satisfy valence, with the proviso that when all of $R_{10}$-$R_{12}$ are present the compound further comprises a pharmaceutically acceptable counter ion.

In one embodiment, the radiolabeled probe is a compound of the following formula:

(1)

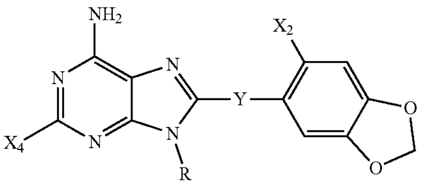

or a pharmaceutically acceptable salt thereof, wherein:

Y is $CH_2$ or S;

$X_4$ is H or halogen;

$X_2$ is $^{123}I$, $^{124}I$, $^{125}I$ or $^{131}I$; and

R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide.

In another embodiment, the radiolabeled probe is a compound of the following formula:

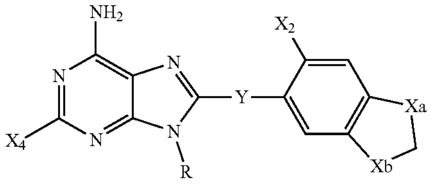

or a pharmaceutically acceptable salt thereof, wherein:

one of Xa and Xb is O and the other is $CH_2$;

Y is $CH_2$ or S;

$X_4$ is hydrogen or halogen; and $X_2$ is $^{123}I$, $^{124}I$, $^{125}I$ or $^{131}I$; and R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide.

In another embodiment, the radiolabeled probe is a compound of the following formula:

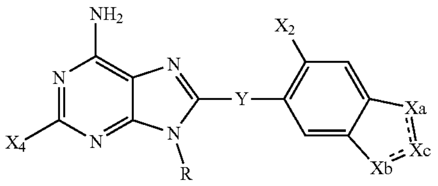

or a pharmaceutically acceptable salt thereof, wherein:

Xa-Xc-Xb is $CH_2$—$CH_2$—$CH_2$, CH═CH—$CH_2$, or $CH_2$—CH═CH;

Y is $CH_2$ or S;

$X_2$ is $^{123}I$, $^{124}I$, $^{125}I$ or $^{131}I$; and

R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide.

In another embodiment, the radiolabeled probe is a compound of the following formula:

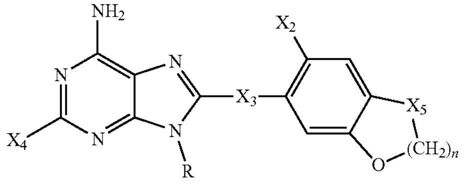

or a pharmaceutically acceptable salt thereof, wherein:

$X_3$ is $CH_2$, $CF_2$, S, SO, $SO_2$, O, NH, or $NR^2$, wherein $R^2$ is alkyl;

$X_2$ is $^{123}I$, $^{124}I$, $^{125}I$ or $^{131}I$;

$X_4$ is hydrogen or halogen;

$X_5$ is O or $CH_2$;

R is 3-isopropylaminopropyl, 3-(isopropyl(methyl)amino)propyl, 3-(isopropyl(ethyl)amino)propyl, 3-((2-hydroxyethyl)(isopropyl)amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2-hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)

amino)ethyl, 2-(isobutyl(methyl)amino)ethyl, or 2-(methyl(prop-2-ynyl)amino)ethyl; and
n is 1 or 2.
In another embodiment, the radiolabeled probe is selected from a compound having the following formulas:
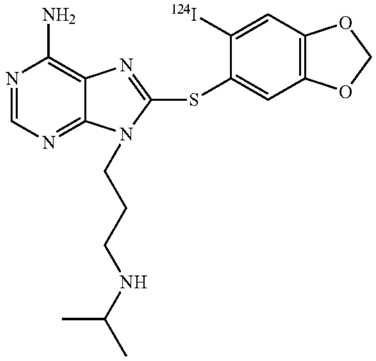
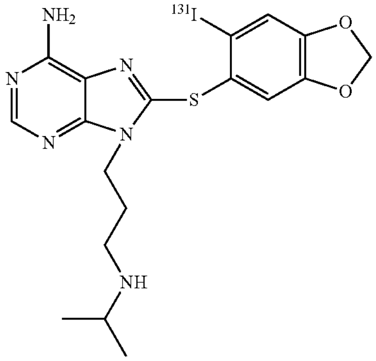
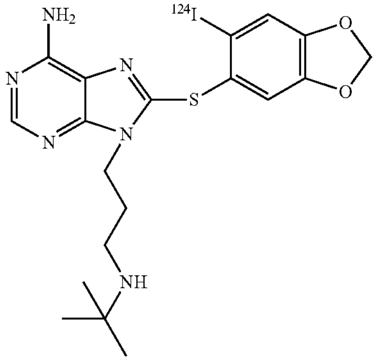
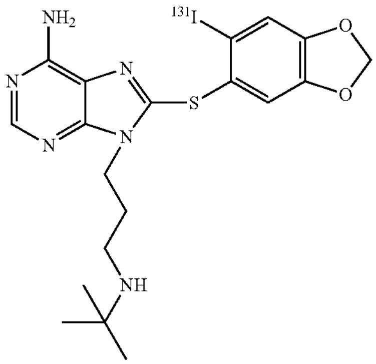
-continued
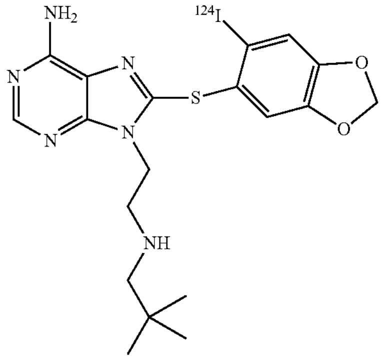
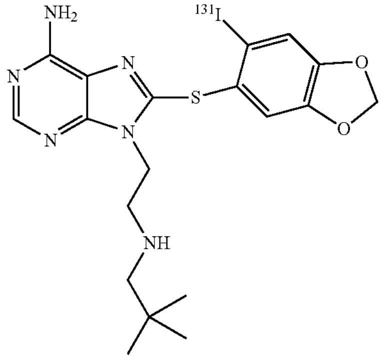
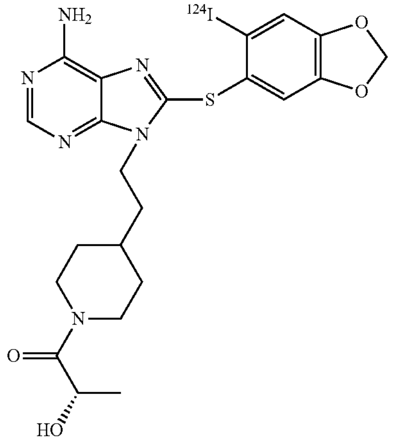
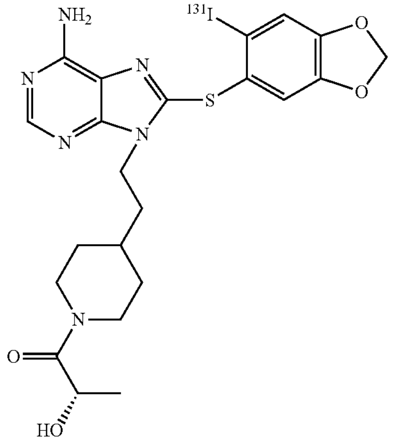

-continued
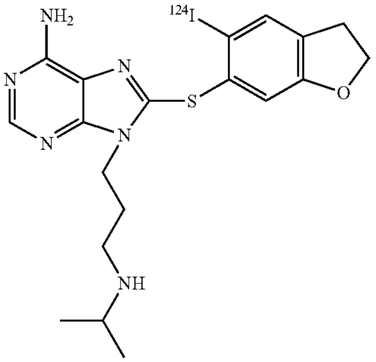
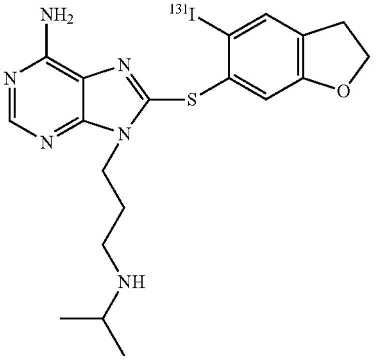
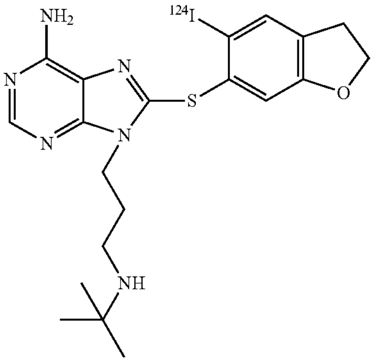
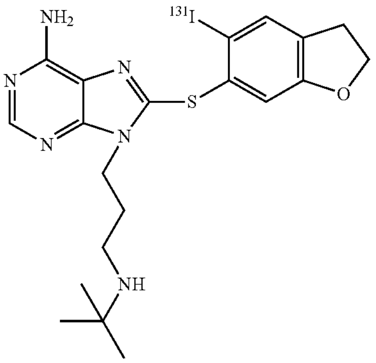
-continued
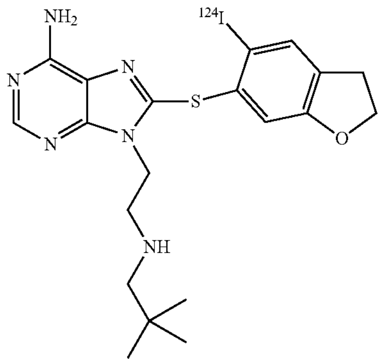
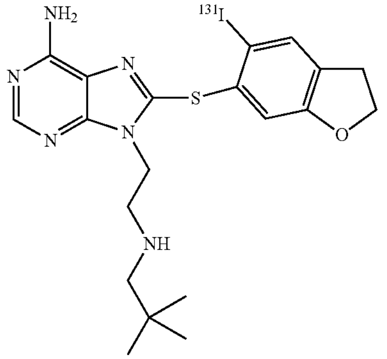
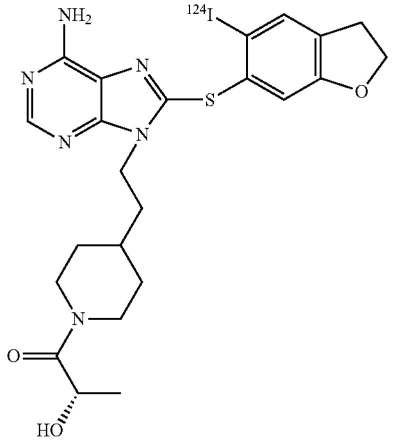
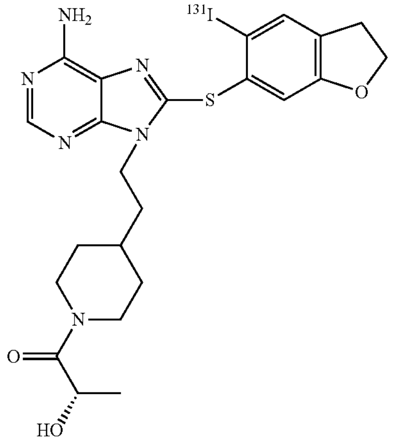

-continued
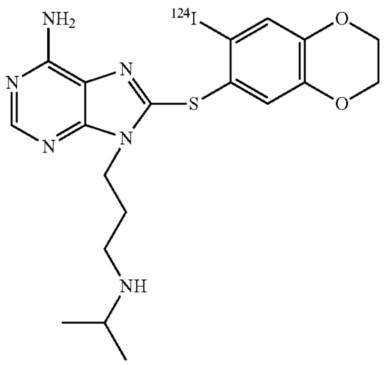
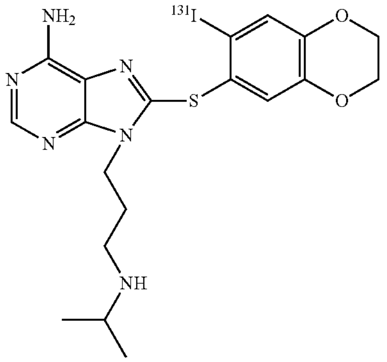
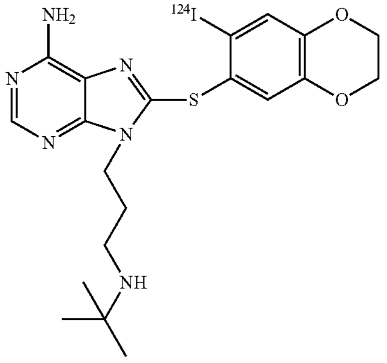
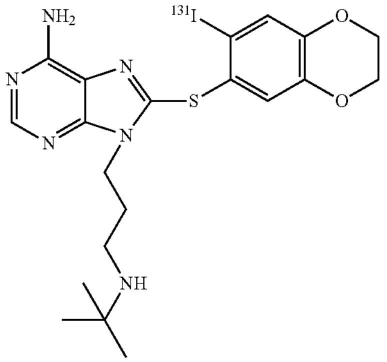
-continued
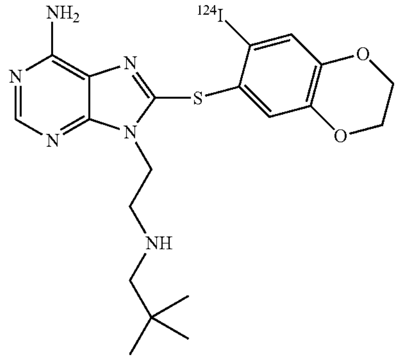
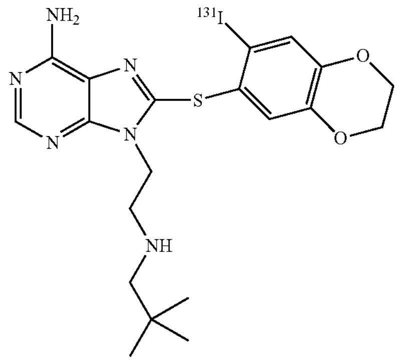
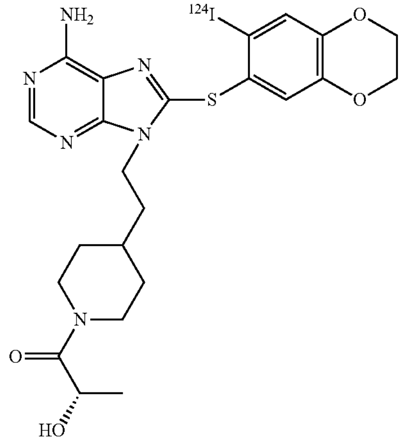 [SMILES: C[C@H](O)C(=O)N1CCC(CCn2c(Sc3cc4c(cc3[131I])OCCO4)nc3c(N)ncnc32)CC1]
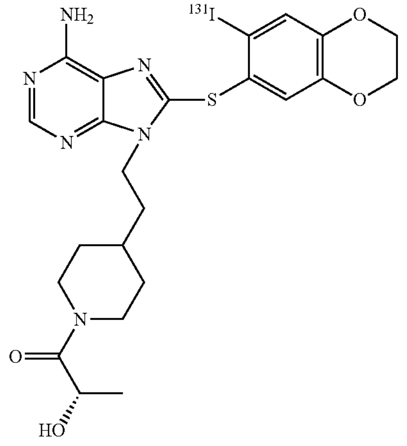

In another embodiment, the radiolabeled probe is selected from a compound having the following formulas:
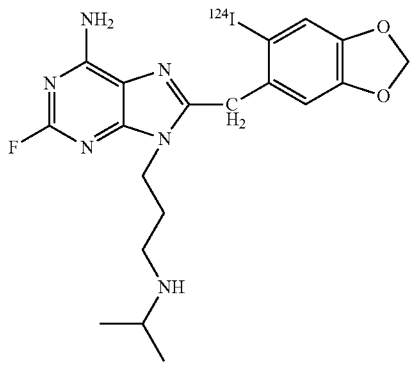
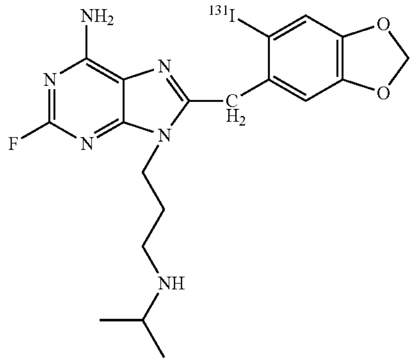
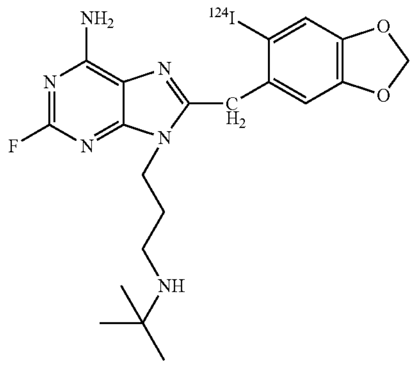
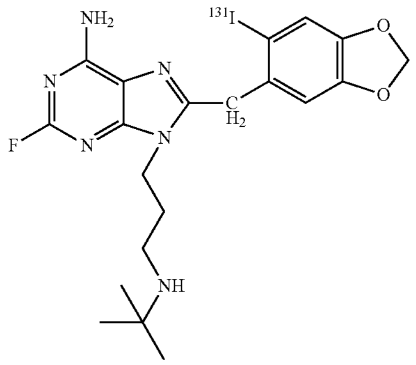
-continued
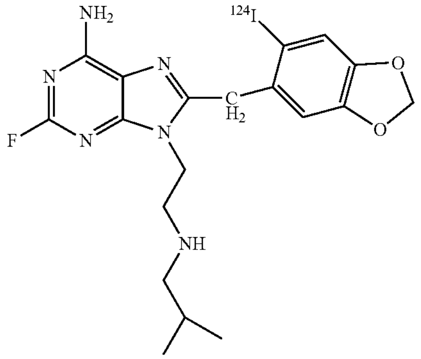
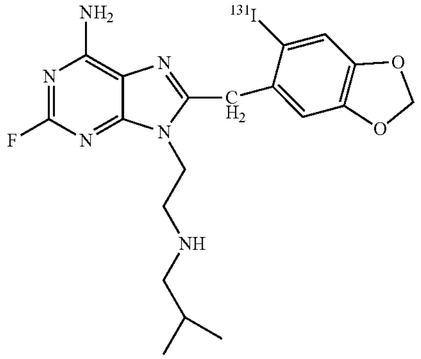
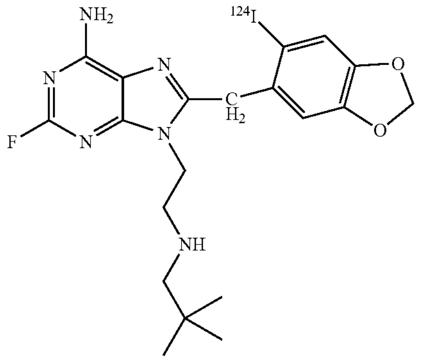
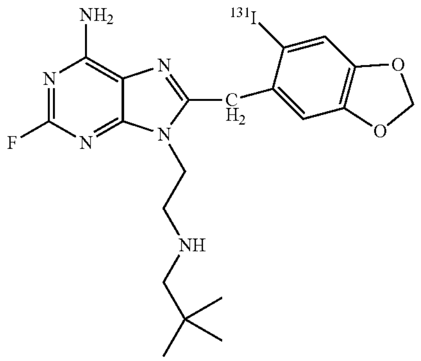

-continued
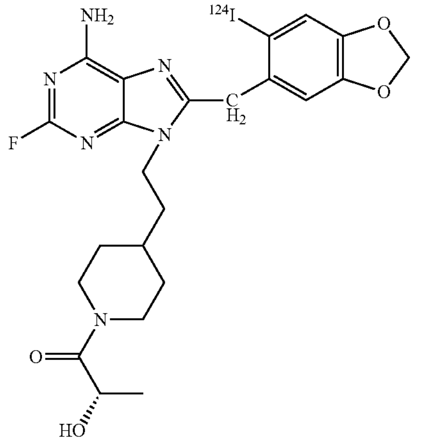
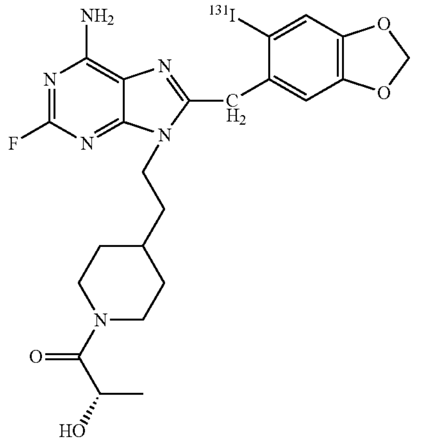
In still another embodiment, the radiolabeled probe is selected from a compound having the following formulas:
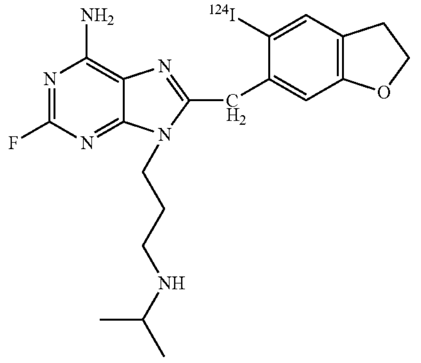
-continued
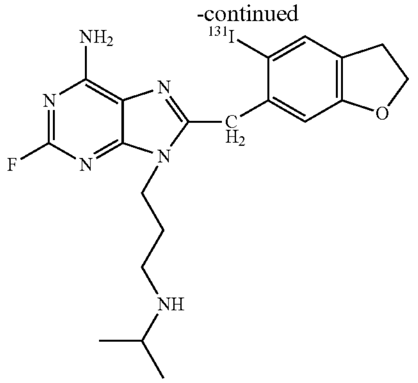
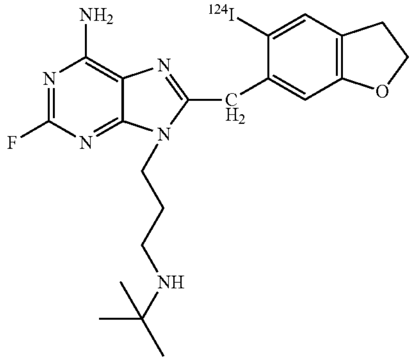
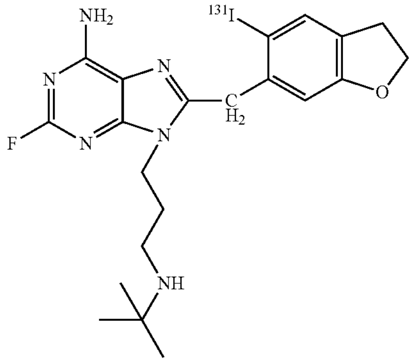
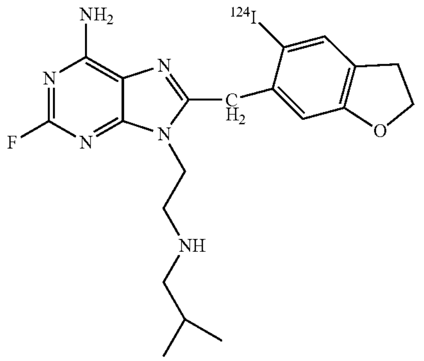

-continued
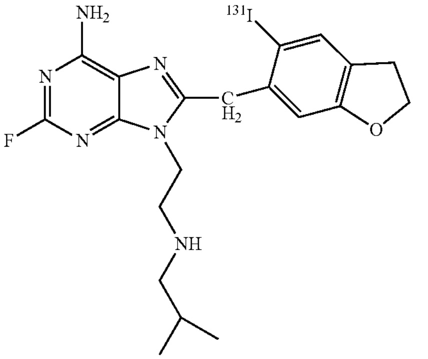
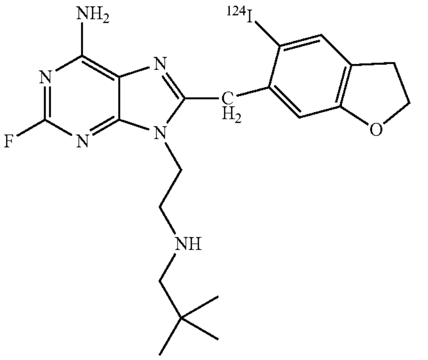
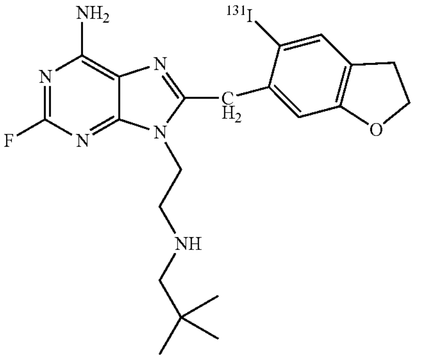
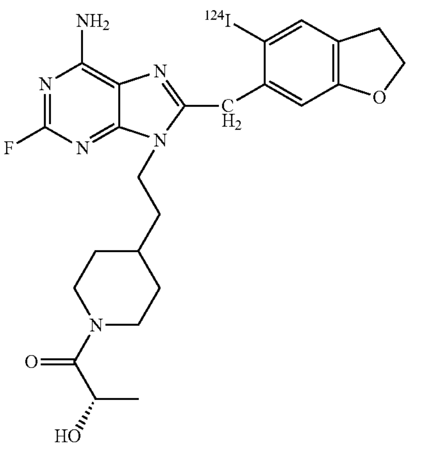
-continued
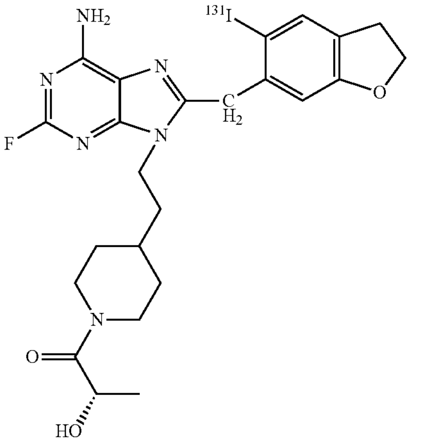
In still another embodiment, the radiolabeled probe is selected from a compound having the following formulas:
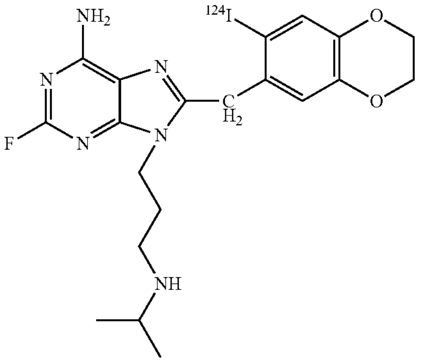
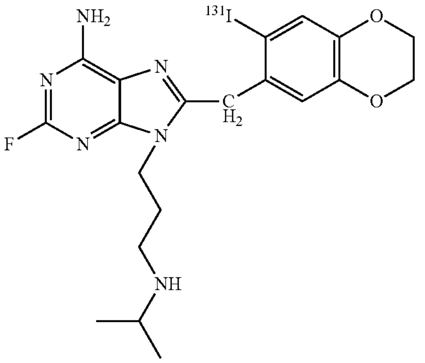
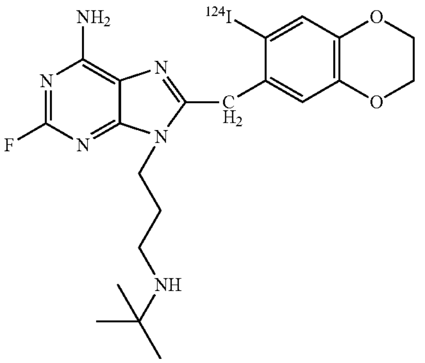

-continued
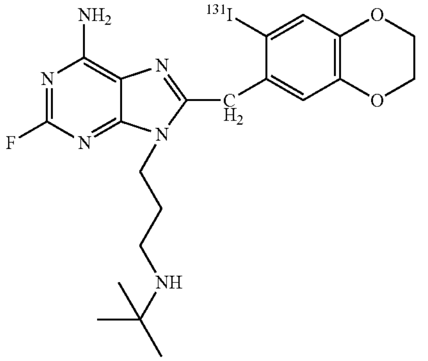
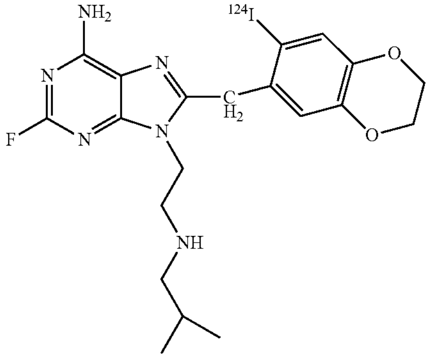
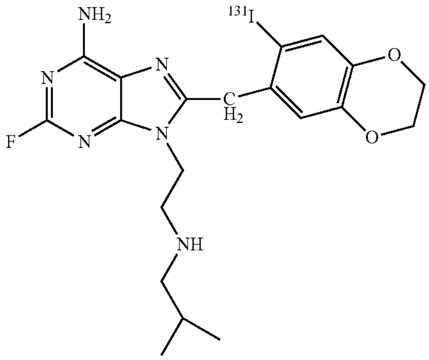
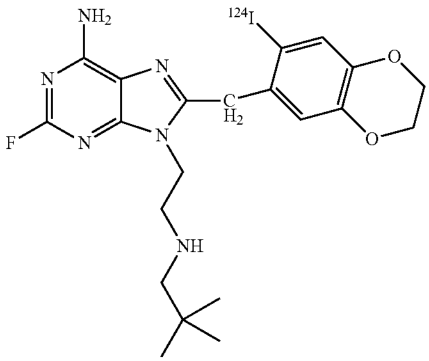
-continued
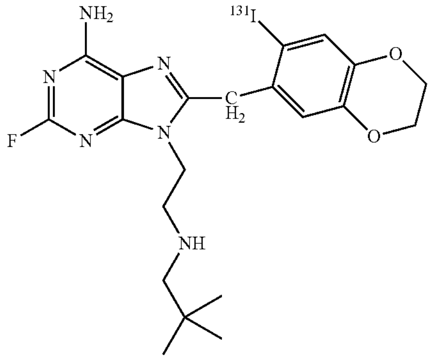
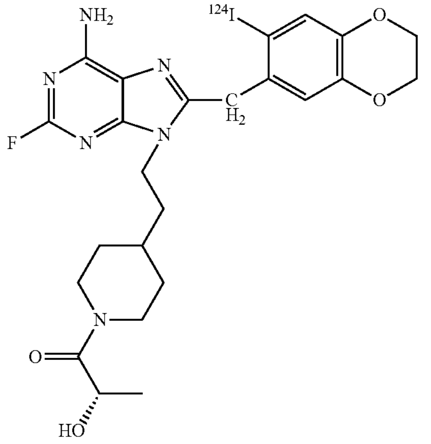
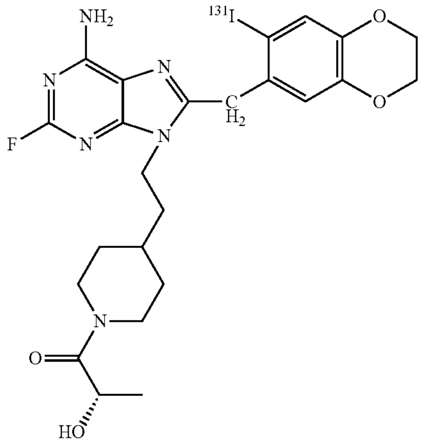

In still another embodiment, the radiolabeled probe is selected from a compound having the following formulas:
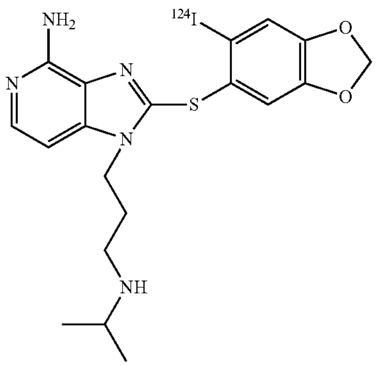
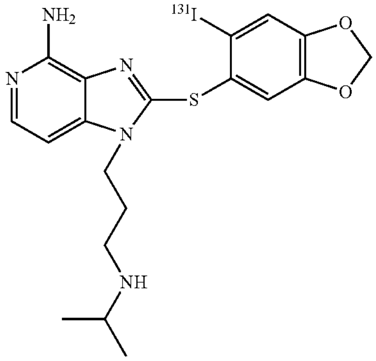
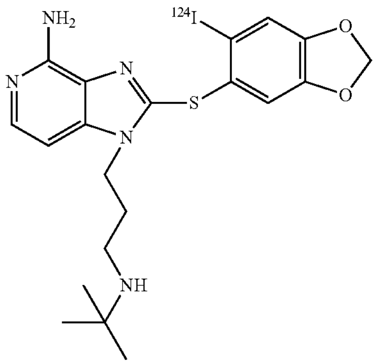
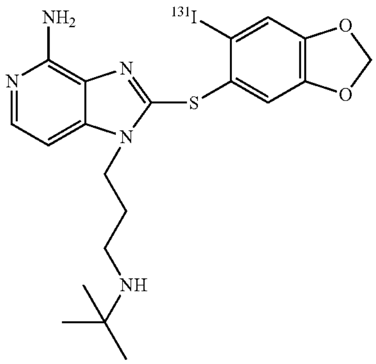
-continued
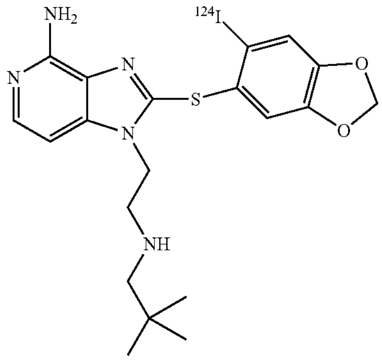
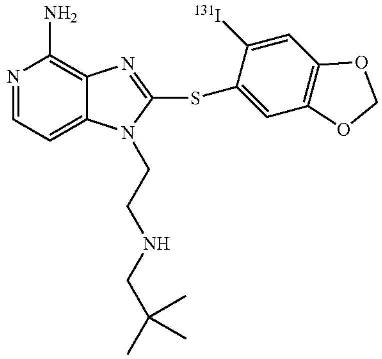
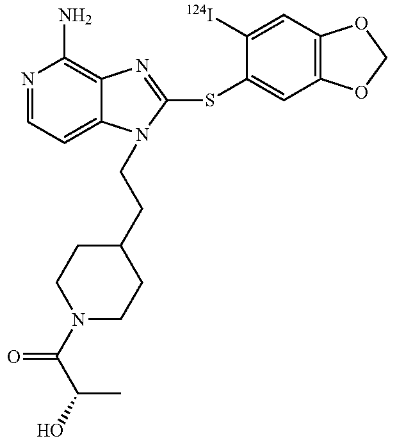
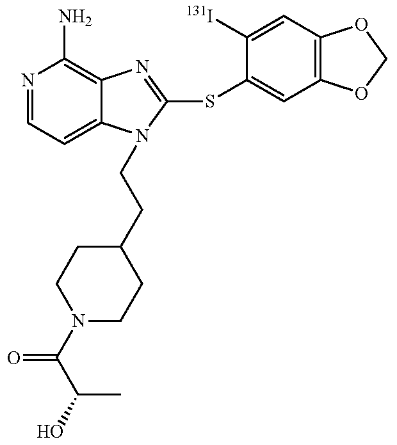

-continued
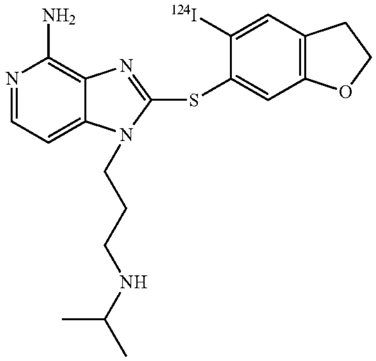
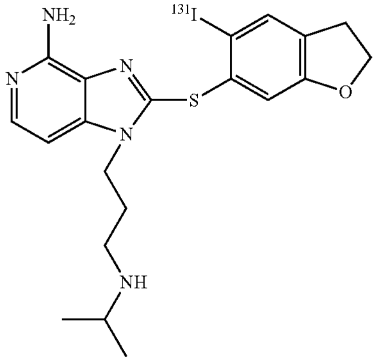
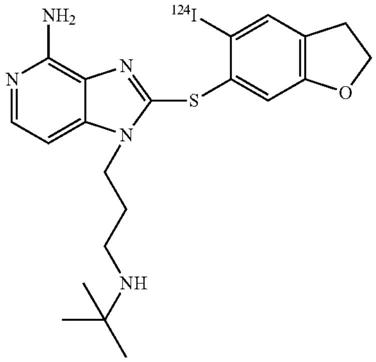
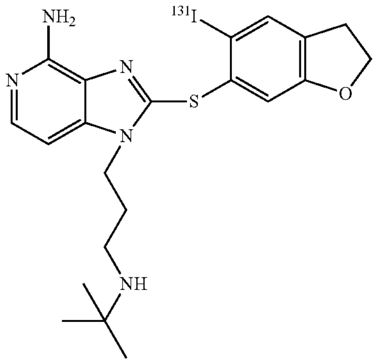
-continued
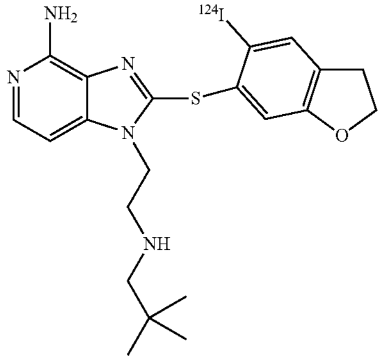
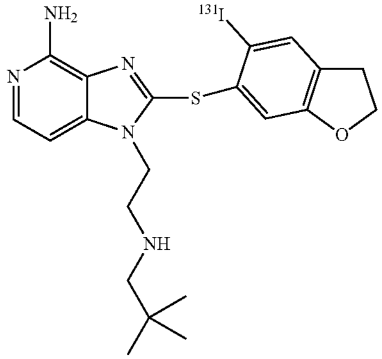
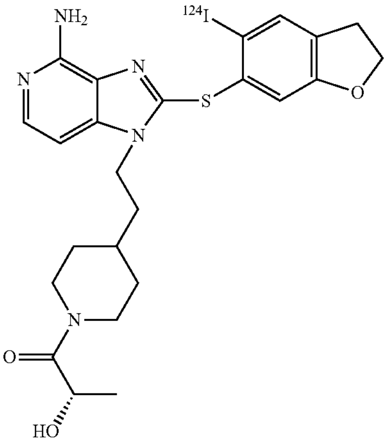
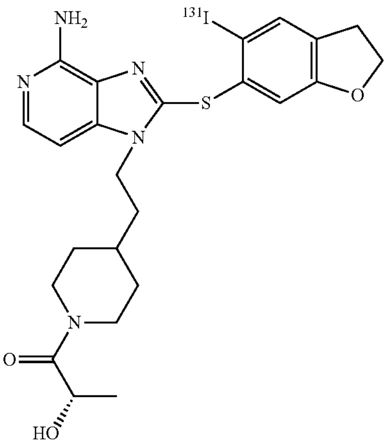

-continued
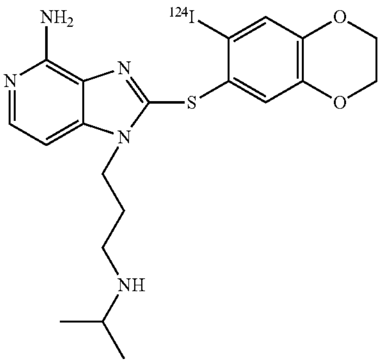
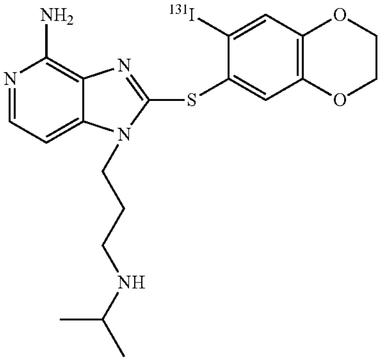
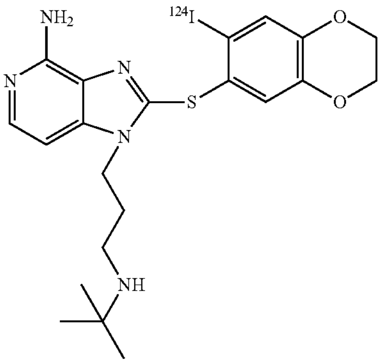
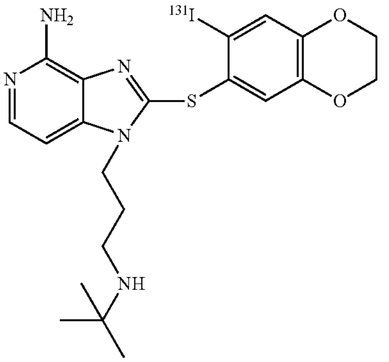
-continued
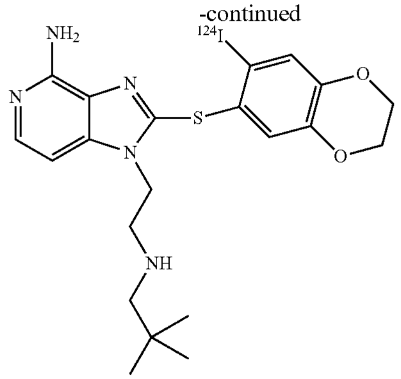
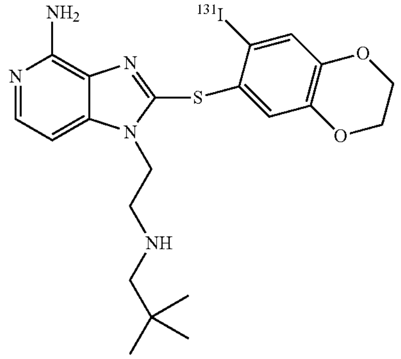
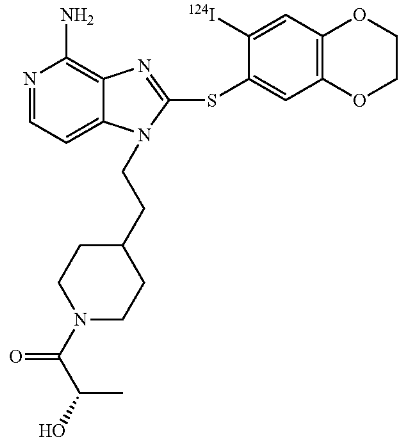
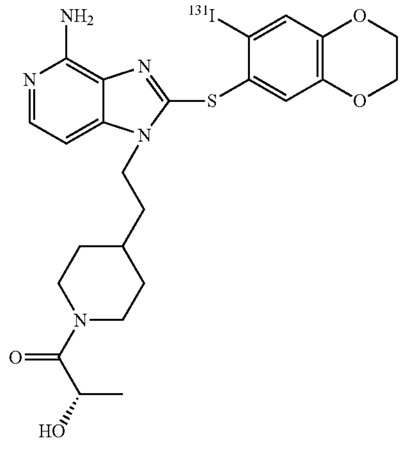 [SMILES: C[C@H](O)C(=O)N1CCC(CCn2c(Sc3cc4c(cc3[131I])OCCO4)nc3c(N)nccc32)CC1]

In still another embodiment, the radiolabeled probe is selected from a compound having the following formulas:

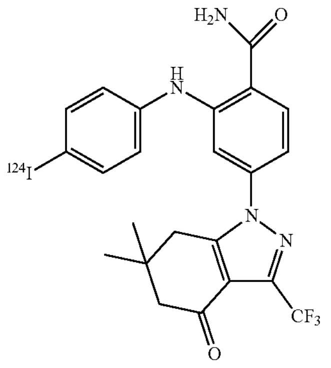

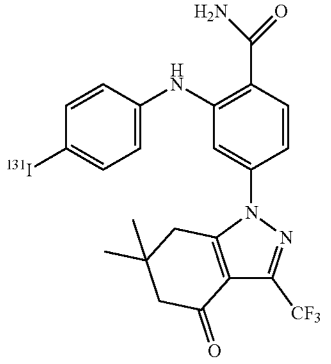

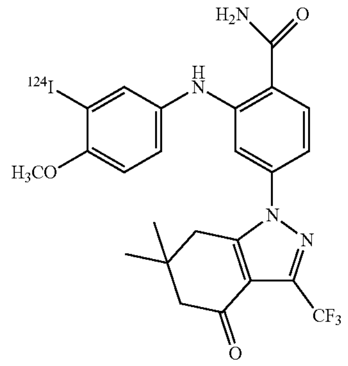

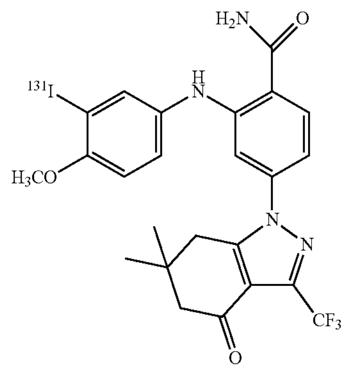

-continued

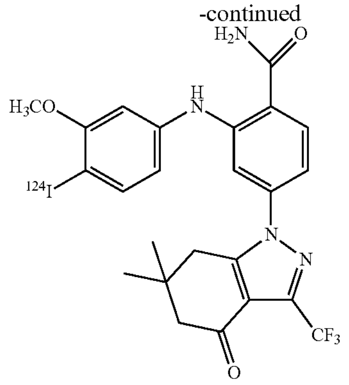

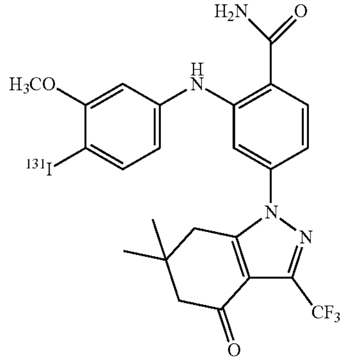

Methods of synthesizing the radiotracers in the above embodiments can be found for instance in U.S. Pat. No. 7,834,181, WO 2011/044394, WO 2008/005937 and PCT application PCT/US2012/032371, the contents of all of which are hereby incorporated by reference in their entirety. Specific examples of radiolabeled probes are described in Sections 5.2.2.2.1. and 5.2.2.2.2.

5.2.2.2. Utilization of Radiolabeled Probes in Cancer Treatment

To non-invasively measure the expression of the HSP90 tumor species ("oncogenic HSP90"), determine the dependence of the tumor on HSP90 and to ascertain target inhibition, a positron emission tomography (PET) assay, that is based on HSP90 specific inhibitors that selectively bind to "oncogenic HSP90" in cancer cells is used. For a number of compelling reasons, positron emission tomography (PET) is well-suited for measuring the pharmacokinetics and retention of drug in tumor in individual patients[110-113]. PET is a quantitative method with higher resolution and sensitivity compared with other forms of nuclear imaging. It allows non-invasive three-dimensional imaging, yielding reliable estimates of tissue concentrations (e.g. μCi or percent of the injected dose per gram (% ID)) of an administered radiolabeled compound in tumors and normal organs, regardless of their depth in the body[110-113]. PET can therefore provide spatially and temporally resolved tumor uptake, concentration and clearance, as well as whole-body distribution of the tracer. Since PET does not necessarily provide detailed anatomical information, the PET assay is often combined with a CAT scan. The CAT scan provides a comprehensive view of the structural anatomy of the body. The PET scan imagery can be overlaid on top of the CAT scan to determine exactly where in the body the radiolabeled inhibitor goes. The combined use of a PET scan and CAT scan will be referred to herein as PET/CT.

Detection and quantification methods other than PET may also be used. In one embodiment, SPECT imaging (Single Photon Emission Computed Tomography) tracers, such as iodine 131, iodine 123, and iodine 125 can be used. In particular embodiments, $^{131}$I-PU-H71, $^{123}$I-PU-H71 or $^{125}$I-PU-H7 can be used as radiolabeled inhibitors for SPECT imaging.

Methods of the present disclosure are applicable to any tumor which may be imaged with the clearest applicability being for solid and liquid tumors or lymphomas. Examples of such tumors are those associated with a cancer selected from the group consisting of colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, leukemias, lymphomas, multiple myeloma, myeloproliferative neoplasms and gynecologic cancers including ovarian, cervical, and endometrial cancers, particularly breast cancer, gastric cancer, or pancreatic cancer. As discussed below, we show that the uptake and exposure of tumors to the radiolabeled HSP90 inhibitor (e.g., $^{124}$I-PU-H71) varies in a manner that is predictive of response to HSP90 therapy and will distinguish patients likely to have either a favorable or unfavorable therapeutic response to PU-H71 or other HSP90 therapies. Specifically, tumors that demonstrate minimal uptake and/or rapid clearance of the radiolabeled HSP90 inhibitor (e.g., $^{124}$I-PU-H71) may be inaccessible or resistant to PU-H71 or other HSP90 inhibitors. Alternatively, such tumors may not depend on HSP90 for survival (i.e., "low abundance of "oncogenic HSP90"), making HSP90 therapy inappropriate. Conversely, tumors with high uptakes and long retention of the radiolabeled HSP90 inhibitor (e.g., corresponding to high tumor-to-blood ratios at later time points or high tumor AUC for the interval of 0 to 24 or 48 h or beyond) would be predicted to be more sensitive to targeting by HSP90 inhibitors. Patient selection can be further guided if the therapeutic doses and schedules required to achieve effective tumor concentrations, as predicted by PET, would result in prohibitive toxicities (e.g., the effective dose is higher than the maximum tolerated dose (MTD) or if 15 to 100% of the "oncogenic HSP90" is occupied only by doses higher than the MTD.

The abundance of the HSP90 oncogenic complex (i.e., "oncogenic HSP90") as measured by uptake of the radiolabeled inhibitor, is reflective of the sensitivity of the tumor to HSP90 inhibition. Thus, in accordance with one aspect of the present disclosure, the abundance of "oncogenic HSP90" in tumors is used as a biomarker of response to HSP90 inhibition. As discussed above, PET allows for non-invasive, reliable estimates of tissue concentrations of radiolabeled compound in tumors and normal organs. [$^{124}$I]-PU-H71 and other HSP90 inhibitors that preferentially bind to the HSP90 oncogenic species can thus be used to measure non-invasively their tumor uptake, a feature that allows, similarly to the above described use of fluorescently labeled PU-H71, the quantification of "oncogenic complex HSP90". Thus, high tumor uptake of the radiolabeled inhibitor will identify patients with tumors that are most likely to respond to HSP90 inhibitors. PU-H71 tracer accumulation in tumors is quantified from PET imagery using techniques known to persons skilled in the art. Tumor accumulation of PU-H71 tracer can be quantified from analysis of tumor tracer concentrations at a single time-point or multiple time points. Tracer concentration refers to the amount of tracer present in a particular volume of tissue. There are various mathematical forms for expression of tracer concentration widely-known in the state of the art as known to persons skilled therein. Tracer-amount and/or tissue-volume each may be expressed as a fraction of a reference value. For example, the commonly used standardized uptake value, SUV, expresses the tracer-amount as a fraction of the total tracer-dose administered to the patient; and expresses the tissue-volume as a fraction of a body reference value (e.g., body mass or body surface area).

In the present disclosure, we show that cancer patients demonstrate variable 'avidity' (uptake and retention) for radiolabeled inhibitors that bind selectively to "oncogenic HSP90". Cancer patients with similar types and stages of cancer can have substantially different uptakes of the radiolabeled inhibitor, which indicates different levels of involvement of HSP90 in the survival and proliferation of cancer cells. As an example, twelve breast cancer patients were evaluated for their uptake of [$^{124}$I]-PU-H71 after 24 hours. The results of these studies are depicted in FIG. 24. Each bar on the graph indicates the maximal standardized uptake value ($SUV_{max}$) of [$^{124}$I]-PU-H71, as determined through PET. The $SUV_{max}$ varies significantly from patient to patient, which indicates differences in the amount of "oncogenic HSP90" in the patients' tumors. Patients with higher $SUV_{max}$ values are more likely to respond to HSP90 inhibition therapy. For instance, patients with an $SUV_{max}$ of [$^{124}$I]-PU-H71 of about 0.25 or greater when measured 24 hours following administration of the radiotracer are potential candidates for HSP90 inhibition therapy. Patients with an $SUV_{max}$ of [$^{124}$I]-PU-H71 of about 0.75 or greater when measured 24 hours after administration of the compound are strong candidates for HSP90 inhibition therapy. Patients with an $SUV_{max}$ of [$^{124}$I]-PU-H71 of about 1.5 or greater when measured 24 hours after administration of the compound are very strong candidates for HSP90 inhibition therapy.

Based on our finding that cancer patients demonstrate variable avidity for particular HSP90 inhibitors (i.e., those that bind preferentially to "oncogenic HSP90"), radiolabeled HSP90 inhibitors can be used to distinguish patients likely to respond to HSP90 inhibition therapy from patients who are unlikely to respond. Accordingly, the present disclosure provides a method for determining whether a tumor will likely respond to therapy with an HSP90 inhibitor which comprises contacting the tumor or a sample containing cells from the tumor with a detectably labeled HSP90 inhibitor which binds preferentially to a tumor-specific form of HSP90 present in a tumor or tumor cells, measuring the amount of labeled HSP90 inhibitor bound to the tumor or the tumor cells in the sample, and comparing the amount of labeled HSP90 inhibitor bound to the tumor or the tumor cells in the sample to a reference amount. A greater amount of labeled HSP90 inhibitor bound to the tumor or the tumor cells as compared with the reference amount indicates the tumor will likely respond to the HSP90 inhibitor.

Measuring the amount of labeled HSP90 inhibitor bound to the tumor or tumor cells may be conducted in a number of different ways. For instance, in one embodiment, as discussed above, the $SUV_{max}$ (or $SUV_{avg}$) of the radiolabeled compound is calculated at a particular time point. For instance, the SUV may be calculated at a time 4 hours or more following administration of the radiolabeled inhibitor. In some embodiments, the SUV may be calculated at a time 8 hours or more following administration of the radiolabeled inhibitor. In particular embodiments, the SUV may be calculated at a time 16 hours or more following administration of the radiolabeled inhibitor (e.g., 16 hours, 20 hours, 24 hours, 48 hours, 72 hours, 192 hours). The SUV may be calculated in a range bounded by any of the two foregoing values, e.g., at a time ranging from 8 hours to 16 hours, from 16 hours to 24 hours, from 16 hours to 48 hours, etc.

The SUV may be compared to a reference amount of the labeled HSP90 inhibitor bound to normal cells. In one embodiment, the reference SUV may be an average level taken from healthy individuals or from measurements on the normal cells and tissues of cancer patients in a control population at a particular time point. As discussed in Section 5.1., normal cells have minimal or no "oncogenic HSP90". Hence, the uptake of the radiolabeled inhibitor specific for "oncogenic HSP90" in the cells of healthy individuals or the healthy tissues or organs of a cancer patient is minimal. It will be appreciated by a person skilled in the art that a measurement at the time the labeled inhibitor has cleared the blood circulation is preferred. It is also appreciated by a person skilled in the art that the measurement can be performed in any normal tissues but that those that are not involved in the labeled inhibitor metabolism and clearance are preferred. In one embodiment, such preferred measurement is from one or more areas as selected from skeletal muscle, bone or heart blood pool.

In another embodiment, the maximum uptake (i.e., $SUV_{max}$) of the radiolabeled inhibitor in a patient's tumor (referred to herein as "tumor SUV') may be compared with the uptake of the radiolabeled inhibitor in the patient's healthy cells. For example, in one embodiment, the SUV data from the tumor of a patient taken at a particular time point may be compared to the SUV from the blood or select areas from the bone or from the muscle of the patient. The term "blood SUV" refers to the average SUV of the contents of the heart derived from the PET assay. The term "muscle SUV" refers to the average SUV of the skeletal musculature of the patient derived from the PET assay. The heart and the skeletal musculature were chosen because they are representative of the 'background' activity surrounding tumor sites.

Use of PET Assay for Patient Selection and Treatment

We have found that in patients with tumors dependent on HSP90, the tumor:muscle and the tumor:blood SUV ratios derived from PET increase in a time dependent manner following injection or a radiolabeled inhibitor that specifically binds "oncogenic HSP90" (e.g., [$^{124}$I]-PU-H71). In these patients, the tumor:muscle and the tumor:blood SUV ratios are generally close to 1:1 following injection of the radiolabeled inhibitor and the ratio increases over time. Data derived from PET on a select number of patients with various types of solid tumors and liquid tumors who are responsive to HSP90 inhibition therapy are shown in FIG. 25. For each patient, the maximum tumor SUV ($SUV_{max}$) and average muscle SUV at multiple times following administration of [$^{124}$I]-PU-H71 were obtained from the PET assay. FIG. 25 shows the mean tumor:muscle SUV ratio and standard deviation values for the cancer patients. The tumor: muscle SUV ratio increases from 0 to 48 hours.

In addition to solid tumors, the method allowed the imaging of liquid tumors such as is the case for a patient diagnosed with marginal zone lymphoma and chronic lymphocytic leukemia stage IV who presented massive splenomegaly imageable by PU-PET.

Based on this accumulation of data, we have determined that cancer patients with a tumor:muscle SUV and/or tumor: blood SUV ratios greater than 2 following administration of an HSP90 inhibitor that specifically binds "oncogenic HSP90" are likely to respond to HSP90 inhibition therapy. The ratio is preferably calculated at one or more times at more than 4 hours following administration of the radiolabeled inhibitor. For instance, the ratio may be calculated at a time 8 hours, 16 hours, 24 hours or 48 hours following administration of the radiolabeled inhibitor. In particular embodiments, a tumor:muscle or tumor:blood SUV ratio of 2.5 or greater at a time of 24 hours following administration of the radiolabeled inhibitor indicates that the patient is likely to respond to HSP90 inhibition therapy. In other embodiments, a tumor:muscle or tumor:blood SUV ratio of 4 or greater at a time of 24 hours following administration of the radiolabeled inhibitor indicates that the patient is likely to respond to HSP90 inhibition therapy. In still other embodiments, a tumor:muscle or tumor:blood SUV ratio of 5 or greater at a time of 24 hours following administration of the radiolabeled inhibitor indicates that the patient is likely to respond to HSP90 inhibition therapy. In these embodiments, the SUV in the tumor is the $SUV_{max}$ and the SUV in the muscle or blood is the average SUV (i.e., $SUV_{avg}$).

In another embodiment, the PET image obtained in the tumor is compared to healthy (i.e., non-cancerous) tissue of the patient. Preferably, in this embodiment, the reference PET scan is taken in the same organ as the tumor. For instance, if the patient has a tumor in the spine, the spinal tumor is compared to normal spinal bones. If the tumor is dependent upon HSP90, a greater concentration of the radiolabeled inhibitor will be found in the tumor than in the healthy tissue. The amounts of the radiolabeled inhibitor can be determined quantitatively using the PET scan. The SUV values for the tumor can be compared to the SUV values for the healthy surrounding tissue at a particular time point or at a plurality of time points following injection of the radiolabeled inhibitor. Alternatively, the PET image from the tumor and the PET image from the healthy tissue can be compared by visual inspection. If the tumor retains the radiolabeled inhibitor, then, visually, on the PET imagery, the tumor will 'light up' and look like a 'hotspot' (see, for example. FIG. 26 and FIG. 27).

We have determined that the presence of a 'hotspot' or 'hotspots' at particular times following administration of the radiolabeled inhibitor implicates HSP90 involvement in the patient's cancer and provides an indication that the patient will be amenable to HSP90 inhibition therapy. The presence of hotspots in the PET imagery is preferably determined at a time at least 1.5 hours following administration of the radiolabeled inhibitor. For instance, the hot spot may be detected at 2 hours, 4 hours, 6 hours, 8 hours, 16 hours, 24 hours, 48 hours, 72 hours, 165 hours or 192 hours following administration of the radiolabeled inhibitor. The presence of a hot spot may be detected between a range bounded by any of the two foregoing values, e.g., at a time ranging from 2 hours to 4 hours, from 4 hours to 8 hours, from 16 hours to 24 hours, etc. The presence of a hotspot in a patient's tumor at time points less than 2 hours does not necessarily indicate that the patient will be a good candidate for HSP90 inhibition therapy. For instance, FIG. 26 (right panel) depicts a [$^{124}$I]-PU-H71 PET/CT of a patient with mantle cell lymphoma taken 30 minutes after [$^{24}$I]-PU-H71 injection. The PET scan shows clear visualization after 30 minutes. However, no uptake of [$^{124}$I]-PU-H71 was observed at later times (3.5-24 hours). Accordingly, the patient is not a likely candidate for HSP90 therapy.

The PET assay of the present disclosure may also be used to determine which metastatic or primary solid tumors and liquid tumors are more susceptible to HSP90 inhibition therapy. For example, FIG. 27 shows the [$^{124}$I]-PU-H71

PET/CT of patient with recurrent breast cancer in the two indicated lymph nodes (LN). PET images at the indicated times post-[$^{124}$I]-PU-H71 injection were quantified and SUV data obtained for [$^{124}$I]-PU-H71 were converted to HSP90 inhibitor concentrations for a hypothetical administered dose of PU-H71 of 10 mg/m$^2$. The exposure of the two tumors to PU-H71 over the time of 0 to 24 h was also calculated and represented as the area-under-the-curve (AUC). In the lower panel of FIG. 27, CT (left), PU-PET/CT (middle), and FDG-PET/CT fusion (right) transaxial images demonstrate [$^{124}$I]-PU-H71-avidity in one of the lymph nodes but not the other. PU-PET imaging is at 24 h post-[$^{124}$I]-PU-H71 injection. Interestingly, PU-avidity does not overlap with FDG-avidity in this case. This is not a unique case, and in several of the analyzed patient's FDG- and PU-avidity correlated for some tumors but not all. Location of the tumors is indicated by arrows. PET images at the indicated times post-[$^{124}$I]-PU-H71 injection were measured as Maximal Standardized Uptake Values ($SUV_{max}$). The results from the PET assay indicate that the left tracheobronchial angle lymph node is expected to be more susceptible to HSP90 inhibition therapy than the lesion of the left tracheobronchial anterior angle lymph node.

In another aspect of the present invention, patients who are identified as being candidates for HSP90 therapy are treated with a pharmaceutically effective amount of an HSP90 inhibitor. We have determined that cancer patients that are determined to be candidates to HSP90 inhibition therapy respond highly favorably to HSP90 inhibition therapy. If a patient has multiple tumors, then only those tumors with a sufficient avidity for the radiolabeled HSP90 inhibitor are expected to respond to HSP90 inhibition therapy. For example, FIGS. 28A-28D shows the image obtained for a 48 year old breast cancer patient with lung and bone metastases who was imaged with [$^{124}$I]-PU-H71 and then treated with an HSP90 inhibitor. Specifically, when the patient was imaged with [$^{124}$I]-PU-H71 PET, the scan showed HSP90-targeting in dominant right lung metastasis but not in the spine metastasis. When the patient went on HSP90 therapy with STA9090 (ganetespib), an HSP90 inhibitor chemically distinct from PU-H71, early partial response was demonstrated by FDG PET-CT studies in the lung mass but not in the spinal lesion, in accord with the prediction by [$^{124}$I]-PU-H71 PET. Similar results were obtained in patients with lymphoma, pancreatic cancer and neuroblastoma patients.

Use of PET Assay for Dosage Determination

The present disclosure provides methods of determining an effective dose and frequency of administration for therapy with an inhibitor of HSP90 which comprises administering to the patient a radiolabeled form of the HSP90 inhibitor which binds preferentially to a tumor-specific form of HSP90 present in a tumor or tumor cells, measuring uptake of the radiolabeled form of the HSP90 inhibitor by the patient's tumor at one or more time points, and calculating the dose and frequency of administration needed to maintain in the tumor at each time point a concentration of the HSP90 inhibitor effective to treat the tumor. The uptake of the radiolabeled form of the HSP90 inhibitor can be determined using a PET assay, as discussed above. The methodology can be applied to numerous types of solid and liquid tumors including but not limited to colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, leukemias, myelomas and myeloproliferative neoplasms and gynecologic cancers including ovarian, cervical, and endometrial cancers.

In one embodiment of the disclosure, the SUV of the radiolabeled inhibitor derived from PET can be converted to molar concentrations of the drug in the tumor according to the following equation:

$$[HSP90\ \text{inhibitor}_{tumor}]t = HSP90\ \text{inhibitor (dose)} \times \frac{[A_{tumor}]t}{100\%} \times \frac{1}{W} \times \frac{1}{\text{MW}}$$

In the above equation, [HSP90 inhibitor]t is the molar concentration of the inhibitor in the tumor at a time t following injection of the radiolabeled inhibitor. The term HSP 90 inhibitor (dose) is the injected therapeutic dose. The term W is the tumor water space. The term MW is the molecular weight of the injected drug. The term [$A_{tumor}$]t is the %-injected radiolabeled dose in the tumor at time t, a value obtained from the SUV obtained from the PET image. Specifically, the term [$A_{tumor}$] can be derived from the SUV in the tumor ($SUV_{tumor}$) by the following equation:

$$[A_{tumor}]/100\% = SUV_{tumor}/[\text{body weight (g)}]$$

In the above equation, [body weight] refers to the body weight of the patient.

In one aspect, the present disclosure provides a method for determining the concentration of an HSP90 inhibitor present in an imageable tumor in a cancer patient. A solution of the radiolabeled inhibitor (also referred to herein as "hot" drug) can be injected into the patient without concomitant injection of the drug (i.e., non-radiolabeled form of the drug, also referred to herein as "cold" drug). In such cases, the concentration of the drug [HSP90 inhibitor$_{tumor}$]t can be determined using the equation above. In one embodiment, the radiolabeled inhibitor ("hot drug") is the labeled form of the injected drug ("cold drug"). For instance, the radiolabeled inhibitor can be [$^{124}$I]-PU-H71 and the administered drug can be PU-H71. In another embodiment, the radiolabeled inhibitor can be different than the injected drug. The determination of the concentration of the drug in the tumor [HSP90 inhibitor$_{tumor}$]t can be determine at a single time point or a plurality of time points following injection of the radiolabeled inhibitor and the therapeutic drug. By comparing the concentration of the drug in the tumor [HSP90 inhibitor$_{tumor}$]t with known efficacious doses obtained from preclinical studies (e.g., half-inhibitory concentrations ($IC_{50}$)), one can determined if the administered dose will be efficacious. A doctor can then adjust the dose accordingly to ensure that the desired amount of the drug is in the tumor.

In the embodiment where the radiolabeled inhibitor is the radiolabeled form of the drug to be administered to the patient, the concentration of the drug in the tumor [HSP90 inhibitor$_{tumor}$]t can be determined without actually administering the cold drug. In such cases, following determination of [$A_{tumor}$]t from the PET assay, different hypothetical injected dose values (D) can be imputed into the equation above to determine the concentration of the drug in the tumor [HSP90 inhibitor$_{tumor}$]t. An effective dose can thereby be determined by comparing the concentration of the drug in the tumor [HSP90 inhibitor$_{tumor}$]t with known efficacious doses obtained from preclinical studies, as discussed above.

Moreover, as discussed in detail in Section 5.2.1.2.1., the methodology can be utilized to design an efficacious dosing regimen for HSP90 therapy.

We have determined that calculations of tumor concentration or drug exposure (e.g., AUC) following administration of just the hot drug and inputting hypothetical amount of the HSP90 inhibitor provide similar results to experiments in which the cold and the hot drug are co-administered. As an example, FIG. 29 shows the concentration of PU-H71 in a diseased paratracheal node over the time of imaging (0-72 h) as obtained by the two methods. Remarkably similar tumor concentrations and thus tumor exposure to PU-H71 is measured by the two methods ($AUC_{0-48\,h}$, 24.9 vs. 22.3 μM-h).

The present disclosure also provides methods of determining the dose of an HSP90 inhibitor that is needed to saturate the oncogenic HSP90 receptors in the tumor. As described above, the PET assay can be conducted by co-injecting a radiolabeled HSP90 inhibitor (i.e., hot drug) and a specific amount of the therapeutic drug (i.e., cold drug). If the dose of the injected drug is sufficiently high to occupy most or all of the "oncogenic HSP90" in the tumor, then the uptake of the radiolabeled inhibitor is suppressed. The point at which uptake of the radiolabeled inhibitor is suppressed can be used to determine the target-saturating dose of the inhibitor, which would also be the 'maximum tumor dose' that a single dose of the drug can deliver or the maximally effective single dose of the drug. As shown in Equation (4) of Section 5.2.2.2.1., below, the number of tumor sites occupied by the HSP90 inhibitor can be calculated and converted to a percent occupancy. If the HSP90 inhibitor is delivered in an amount that approaches full occupancy of the HSP90 sites, additional drug would not be expected to provide increased levels of efficacy. Hence, the methodology provides a means of determining a dose of the inhibitor that can occupy most or all of the oncogenic HSP90 in the tumor. As discussed in more detail in Section 5.2.2.2.1., the above described methodology provides a more rational and effective dosing strategy that is based on PET-derived maximally effective tumor concentration rather than conventional maximum tolerated dose (MTD). The approach avoids dose escalation and limits the toxicological problems associated with the drug.

5.2.2.2.1. [$^{124}$I]-PU-H71

In one aspect of the present disclosure, the radiolabeled HSP90 inhibitor to be employed for PET imaging is a radiolabeled form of PU-H71, such as [$^{124}$I]-PU-H71. As discussed below, PET imaging with [$^{124}$I]-PU-H71 can be used to inform doctors if cancer patients will be susceptible to HSP90 therapy. Moreover, the results obtained from PET imaging with [$^{124}$I]-PU-H71 can be used to determine the dose of an HSP90 inhibitor that should be administered to a particular cancer patient. Additionally, the results obtained from PET imaging with [$^{124}$I]-PU-H71 can be used to determine a dosing schedule of an HSP90 inhibitor. The HSP90 inhibitor to be administered as therapy is PU-H71 or an analog, homolog, or derivative of PU-H71.

[$^{124}$I]-PU-H71 PET Assay as a Potential Non-Invasive Tumor HSP90 Assay

Introduction of PET for non-invasive assay of HSP90 inhibitors is feasible because one of the HSP90 inhibitors, PU-H71, contains an endogenous iodine atom, the naturally occurring stable isotope iodine-127 ($^{127}$I) (FIG. 30A)[114]. This can be isotopically substituted for PET with the long-lived positron emitter iodine-124 ($^{124}$I), an isotope with a four-day physical half-life (FIG. 30A). Such isotopic labeling does not change the affinity, selectivity or biodistribution profile of this compound. In fact, the PET radiopharmaceutical, [$^{124}$I]-PU-H71, is the same molecule as the therapeutic compound, PU-H71, and should therefore predict its pharmacokinetics. A single administration of trace (microgram) amounts of radiolabeled drug is also completely non-perturbing biologically, and allows serial PET imaging for monitoring tissue tracer-concentrations over multiple days.

The relatively long half-life of $^{14}$1 is ideal for monitoring the reported prolonged tumor pharmacokinetics of HSP90 inhibitors because it allows for satisfactory quantitative PET imaging for up to one week following administration. In addition, $^{124}$I is now commercially available in the United States, and its half-life ensures that [$^{124}$I]-PU-H71 can be made available in medical centers worldwide.

Hence, [$^{124}$I]-PU-H71 is well-suited for use as a true 'tracer' of PU-H71 and as a target biomarker for other HSP90 inhibitors.

The HSP90 inhibitors are a promising class of targeted cancer therapy, but their optimal clinical development requires co-development of pharmacometric assays specific to the HSP90 target. Because of its endogenous iodine, we use the HSP90 inhibitor PU-H71 to develop a first-of-its-kind non-invasive imaging assay for tumor HSP90 based on positron emission tomography. We show in mouse models of breast cancer that [$^{124}$I]-PU-H71 is a true tracer for the intratumoral pharmacokinetics and pharmacodynamics of the parent drug. We demonstrate its use in determining the dose of HSP90 inhibitor needed to achieve effective tumor concentrations, in assaying the actual concentration of the drug delivered to the tumor and in designing an efficacious dose and schedule regimen. The assay also informs on a tumor target saturating dose, promising to lead HSP90 therapy beyond the conventional maximum tolerated dose. Based on this work we propose that the assay will provide clinicians an improved ability for trial enrichment and to tailor drug dosage and schedule to the individual patient, promising to fill an unmet clinical need and to positively-impact clinical decision-making with HSP90-targeted agents.

[$^{124}$I]-PU-H71 Biodistribution and Clearance Mirrors that of PU-H71

To evaluate the use of [$^{124}$I]-PU-H71 in predicting and monitoring the in vivo kinetic profile of PU-H71 and other HSP90 inhibitors, we have produced [$^{124}$I]-PU-H71 and performed serial small animal PET imaging studies of tumor-bearing mice (human breast cancer MDA-MB-468 xenografts), deriving time-activity (ie % ID/g versus time post-administration) curves for tumors and various normal tissues. Corroborative biodistribution studies of [$^{131}$I]-PU-H71 or [$^{124}$I]-PU-H71 were performed by sacrificing cohorts of animals at selected times post-injection and harvesting and gamma counting of tumors and selected normal tissues (FIGS. 30B-C). Following intravenous (i.v.) or intraperitoneal (i.p.) administration, the agent rapidly distributed to tissues (FIG. 30B; 1-2 h), with subsequent fast clearance from blood and other normal tissues (FIG. 30B; 4 to 100 h). At 4 h post administration (p.a.), it was present at 40-, 9-, 18-, 6- and 10-fold higher concentrations in tumor than in brain, bone, muscle, spleen and heart, respectively (FIG. 30C). By 24 h, the tumor-to-normal tissue ratios increased to 50 to 100 for brain, muscle, spleen, heart and blood. Uptakes (% ID/g) in both smaller (~100 $mm^3$ in volume) and larger (~200 $mm^3$ in volume) tumors were similar (FIG. 30D).

[$^{124}$I]-PU-H71 cleared from tumors in a bi-exponential fashion (FIG. 30D). An initial rapid phase, attributable to clearance of blood-borne activity (FIGS. 30B, 30D), was followed by a slow terminal clearance phase (half time ~60 h) attributable to specific tumor retention (FIG. 30D, inset), consistent with the previously reported tandem liquid chromatography mass spectrum (LC-MS/MS)-based tumor pharmacokinetic data for PU-H71[100,115-118]. These data support the concept that within the tumor, the therapeutic and the radiotracer forms of the drug behave identically.

In contrast to tumors, [$^{124}$I]-PUH71 cleared rapidly from the total body in a monoexponential fashion, with no evidence of plasma protein-binding (FIGS. 30B-D). [$^{124}$I]-PU-H71 excretion occurred via the hepatobiliary and urinary routes (FIG. 30B). Hepatic activity was cleared more slowly than total-body activity, presumably due to hepatic drug metabolism and hepatobiliary excretion. Activity in the hepatic region likely represented both intact tracer and metabolites in the biliary tree and not [$^{124}$I]-PU-H71 in hepatocytes, consistent with previously reported findings that intact PU-H71 disappears rapidly from the mouse liver[100,117]. Activity in the gastrointestinal tract accounted for over 50% of the administered activity (FIG. 30B) but was almost entirely excreted activity (not shown).

Activity in non-gastrointestinal and non-genitourinary organs (i.e., the kidneys, ureters and urinary bladder) accounted for ~1% of the administered activity. The remaining 49% (50% in gastrointestinal organs minus 1% in genitourinary organs) were likely excreted via the urinary tract. This observation is supported by the 4 h in vivo [$^{124}$I]-PU-H71 PET data (FIG. 30B) derived using a region-of-interest (ROI) circumscribing the entire mouse and accounting for only 40-50% of the administered activity. Because intestinal transit time in mice is usually longer than 4 h[119], it is likely that the balance of the administered activity (i.e., the 40-50% not in the 4 h whole-body ROI) was excreted via the urinary tract.

Radioactivity was visualized in the thyroid region which was suppressed if mice received a saturating dose of potassium iodide prior to administration of the radiotracer (FIG. 30B), indicating production of free radioiodine (i.e. radioiodide) in vivo. In mice that did not receive potassium iodide, the maximum thyroid activity between 4 and 28 h postinjection was <0.4% of the administered activity. The normal mouse thyroid accumulates up to ~4-7% of administered radioiodide[120,121]. Thus, a thyroid uptake of <0.4% suggests that the amount of free radioiodine released in vivo from [$^{124}$I]-PU-H71 is small (~5-10% of the administered activity). The release of a small amount of free radioiodine is not uncommon for radioiodinated tracers, and in clinical practice, thyroid uptake is routinely and effectively blocked using oral administration of a saturated solution of potassium iodide prior to a radiotracer administration.

[$^{124}$I]-PU-H71 Allows for Clear Tumor HSP90 Visualization by PET

In vivo PET imaging of [$^{124}$I]-PU-H71 in tumor-bearing mice provided clear tumor visualization, and thus potential tumor HSP90 targeting and tumor retention from 2 h post injection (FIG. 30B, arrows). The mean (+ standard deviation) uptake values (% ID/g) obtained from ROI analysis were 0.35±0.07, 0.083±0.02, 0.058±0.02, 0.031±0.01 and 0.024±0.008 at 4, 24, 48, 72 and 100 h respectively, consistent with the values obtained in biodistribution studies (FIG. 30D), confirming that non-invasive monitoring of PU-H71 in vivo and reliable quantification of its time-dependent tumor concentration is possible by [$^{124}$I]-PU-H71 PET.

Use of [$^{124}$I]-PU-H71 PET Imaging to Determine the Dose of PU-H71 Needed to Achieve a Pharmacologically Effective PU-H71 Tumor Concentration As noted above, the pharmacokinetics of [$^{124}$I]-PU-H71, and therefore unlabeled PU-H71, in tumor and in blood are notably different: tumor drug concentrations stabilized by ~24 h post-injection after an initial rapid exponential clearance attributable largely to drug clearance from the tumor blood pool. Blood drug levels, in contrast, exhibited rapid and continuous exponential clearance (FIGS. 30B, 30D). The tumor-to-blood activity concentration ratios of [$^{124}$I]-PU-H71 reached values of ~10 and greater by ~12 h postinjection (FIG. 30C). Thus the integrated blood levels of PU-H71 (i.e. the area under the blood time-activity concentration curve, $AUC^{PU\text{-}H71}{}_{blood}$) were not reliable surrogates of the tumor levels of PU-H71. Indeed, the area under the tumor time-activity concentration curve, $AUC^{PU\text{-}H71}{}_{tumor}$ is 15-fold larger than the $AUC^{PU\text{-}H71}{}_{blood}$ (FIG. 30D, 11.4 versus 0.78% ID/g-h for tumor and blood, respectively). Blood pharmacokinetics therefore, are not reliable for designing a dosing regimen for achieving a patient-specific therapeutically effective tumor concentration.

We therefore investigated the ability of [$^{124}$I]-PU-H71 PET to predict the administered PU-H71 dose required to achieve and maintain a therapeutically effective tumor concentration over a selected period of time. For an administered dose of PU-H71 ($PU\text{-}H71_{dose}$ in mg), the drug concentration (mg/mL or g/L) in the tumor water space (using an average water space, W=0.8 mL/g) at a time t post-administration, $[PUH71_{tumor}]_t$, is calculated from the PET-derived [$^{124}$I]-PU-H71 activity concentration in tumor (in % ID/g), $[A_{tumor}]_t$, at equilibrium and achieved at time t post-administration:

$$[PU\text{-}H71_{tumor}]_t = PU\text{-}H71_{dose}\cdot\frac{[A_{tumor}]_t}{100\%}\cdot\frac{1}{W} \tag{1}$$

The drug concentration (in μM) in the tumor water space, $[PU\text{-}H71_{tumor}]$ at the time t postadministration, is therefore:

$$[PU\text{-}H71_{tumor}]_t = PU\text{-}H71_{dose}\cdot\frac{[A_{tumor}]_t}{100\%}\cdot\frac{1}{0.8}\cdot\frac{1\times10^6}{512}\mu M \tag{1a}$$

where the factor 512 is the molecular weight of PU-H71 and the factor $1\times10^6$ converts the concentration to μM.

Conversely, to achieve a selected therapeutically-effective tumor PU-H71 concentration, the required dose of PU-H71 to administer (in mg) for an individual patient can be calculated based upon his or her PET-derived activity concentration in tumor at time t post-administration:

$$PU\text{-}H71_{dose} = [PU\text{-}H71_{tumor}]_t\cdot 0.8\cdot\frac{100\%}{[A_{tumor}]_t}\cdot\frac{512}{1\times10^6} \tag{2}$$

Using the tumor-activity data in FIG. 30D, equation (1a) was employed to calculate the time-dependent PU-H71 concentrations in tumor from 0 to 160 h post-administration (p.a.) for administered doses of 1, 5, 25, 50 and 75 mg/kg PU-H71 (0.02, 0.1, 0.5, 1 and 1.5 mg for a 20 g mouse) (FIG. 31A, lower panel). From preclinical studies with PU-H71 in established cancer cells it is known that a 72 h-exposure of several established breast cancer cells to the HSP90 inhibitor leads to cell growth inhibition with recorded half-inhibitory concentrations ($IC_{50}$) of 0.05 to 0.25 μM, depending on the cell type[100]. Thus, a single dose, at each of the foregoing dose levels, was predicted by [$^{124}$I]-PU-H71 PET to achieve therapeutically effective concentrations in tumor through 72 h p.a. (FIG. 31A, upper panel). For administered doses of PU-H71 of 5, 25, 50 and 75 mg/kg and a $$[A_{tumor}]_{t=24h}$$

value of ~0.14±0.05% ID/g (FIG. 31D), equation (1a) yields the tumor concentrations of PU-H71 of 0.37, 1.83, 3.67 and 5.51 μM, respectively, consistent with concentrations measured in these tumors by LC-MS/MS (FIG. 31B and not shown). A dose of 1 mg/kg yields tumor concentrations of less than 0.05 μM at 48 h and beyond (FIG. 31A) and perhaps thus, represents the lower limit for a therapeutically effective dose in this tumor model.

[$^{124}$I]-PU-H71 PET Accurately Predicts the Delivery of Therapeutically Effective PUH71 Concentrations in Tumor To validate that PET accurately predicted tumor concentrations achieved after injection of 5 to 75 mg/kg PU-H71, and that these concentrations were therapeutically effective in vivo, we investigated the pharmacodynamic effects associated with these doses (FIGS. 31C, 31D). In accord with the above findings suggesting delivery of pharmacologically effective tumor concentration of PU-H71, administration of PU-H71 doses of 5 to 75 mg/kg to mice bearing MDA-MB-468 tumors led to downregulation and/or inhibition of Akt and Raf-1 and induction of apoptosis, as evidenced by PARP cleavage (FIG. 31C, In vivo). These pharmacodynamic changes are similar to those observed in tissue culture, where exposure of MDA-MB-468 cells for 24 h to concentrations of PU-H71 above 0.1 μM resulted in HSP90 inhibition, as demonstrated by a dose-dependent depletion of HSP90-dependent onco-proteins (i.e. Raf-1, Akt) (Reference 100 and FIG. 31D, In vitro). The half inhibitory concentrations determined in vitro to result in onco-client protein degradation $$(EC_{50}^{Raf-1} = 0.13 \pm 0.02\ \mu M \text{ and } EC_{50}^{Akt} = 0.15 \pm 0.02\ \mu M;$$

FIG. 31D) are similar to those determined by [$^{124}$I]-PU-H71 PET to be in tumors and result in the measured pharmacodynamic effects $$(EC_{50}^{Raf-1} = 0.24 \pm 0.03\ \mu M \text{ and } EC_{50}^{Akt} = 0.09 \pm 0.08\ \mu M;$$

FIG. 31C).

Collectively, the consistent PET-predicted tumor concentrations validated by LC-MS/MS measurements and by Western blot pharmacodynamic analyses, demonstrate the ability and the accuracy of the [$^{124}$I]-PU-H71 PET assay to inform the selection of the administered dose of this HSP90 inhibitor required to achieve a therapeutically effective tumor concentration.

Tracer-Dose [$^{124}$I]-PU-H71 Accurately Predicts PU-H71 Tumor Concentrations Over a Range of Doses, Up to Target Saturation in Tumors The pharmacokinetics of tracer, microdose amounts of [$^{124}$I]-PU-H71 might not correlate with those of the macroscopic therapeutic doses. At high PU-H71 doses, factors such as HSP90 target saturation in tumors, distinct plasma protein binding profile or changes in drug metabolism due to potential inhibition of liver metabolizing enzymes, may alter the pharmacokinetics of the agent.

We therefore examined whether at a potentially saturating dose, PET-based predictions of PU-H71 concentration correlate with those experimentally determined by LC-MS/MS (FIG. 31B). Administration of 75 mg/kg PU-H71 to the MDA-MB-468 tumors results in tumor regression and cures[100], and thus at this curative dose, saturation of the tumor HSP90 target or at least occupancy of a therapeutically significant number of target molecules is presumably achieved. Based on tumor concentrations derived from [$^{124}$I]-PU-H71 PET studies or [$^{131}$I]-PU-H71 biodistribution studies, administration to tumor-bearing mice of 75 mg/kg inhibitor yielded tumor concentrations of 5.51±1.78, 3.50±0.27, 2.18±1.78, 1.29±0.29 and 0.69±0.25 μM at 24, 48, 72, 96 and 120 h postadministration, respectively (FIG. 31B). These values are in good agreement with the actual PU-H71 tumor concentrations measured by LC-MS/MS (FIG. 31B, LC-MS/MS), demonstrating the reliability of the PET assay predictions over a range of doses up to those resulting in maximally effective target inhibition (FIG. 31C).

Use of [$^{124}$I]-PU-H71 in Patient Selection for HSP90 Therapy

In addition to providing a clinically practical PET-based approach for monitoring the biodistribution of PU-H71 and informing on the tumor pharmacokinetics of PU-H71, the foregoing analyses suggests an approach to patient screening, distinguishing patients likely to have either a favorable or unfavorable therapeutic response to PU-H71 or other HSP90 therapies.

Specifically, tumors that demonstrate minimal uptake and/or rapid clearance of [$^{124}$I]-PU-H71 may be inaccessible to PU-H71 or other HSP90 inhibitors. Alternatively, such finding may also indicate that the tumor does not depend on HSP90 for survival and thus HSP90 therapy is not apropiate[93,97]. Conversely, tumors with high uptakes and long retention of [$^{124}$I]-PU-H71 (e.g., corresponding to high tumor-to-blood ratios at later time points, FIGS. 30C-30D) would be predicted to be more sensitive to targeting by HSP90 inhibitors. Patient selection can be further guided if the therapeutic doses required to achieve effective tumor concentrations, as predicted by [$^{124}$I]-PU-H71 PET, would result in prohibitive toxicities (e.g., the effective dose is higher than the maximum tolerated dose).

In conclusion the ability of the tumor to retain the HSP90 inhibitor at an effective concentration over a prolonged period of time and to achieve such concentrations at non-toxic inhibitor doses, are two key criteria for HSP90 therapy entry that can be reliably measured by [$^{124}$I]-PU-H71 PET.

Use of Microdose [$^{124}$I]-PU-H71 Co-Injected with Therapeutic-Dose PU-H71 to Assay PU-H71 Tumor Concentrations by PET While [$^{124}$I]-PU-H71 PET estimates well the dose of HSP90 inhibitor needed to result in efficacious tumor concentrations, we investigated whether [$^{124}$]-PU-H71 in tracer amounts (~6.5 ng/g) co-administered with therapeutic amounts of PU-H71 (5 mg/kg to 75 mg/kg or 5,000 ng/g to 75,000 ng/g), could reliably assay the amount of PU-H71 essentially delivered to the tumor (FIG. 31B, PET following co-injection of [$^{124}$I]-PU-H71 and PU-H71). The ability to measure drug exposure in tissues of drug activity could provide critical information for predicting potential response (ex. what concentration has been delivered to the tumor and whether it is sufficient for marked pharmacodynamic response). Sequential measurements over the time of treatment could also be used as an indicator of whether tumor biology, and thus responsiveness, has been altered (ex. a decrease in the concentration delivered to the tumor could indicate potential development of resistance to the HSP90 inhibitor).

Because the radiotracer [$^{124}$I]-PU-H71 and the non-radioactive PU-H71 are injected in a ratio of ~1:10,000, we can reasonably assume that the latter is essentially the only significant form of the drug in the tumor. Thus, for a co-administered dose of PU-H71 (PU-H71$_{dose}$ in mg) and a tracer amount of [$^{124}$I]-PU-H71, the drug concentration in the tumor water space (again using an average water space, W=0.8 mL/g and a MW of 512), is:

$$[PU\text{-}H71_{tumor}] = PU\text{-}H71_{dose} \cdot \frac{[A_{tumor}]_t}{100\%} \cdot 2.44 \times 10^3\ \mu M \quad (3)$$

Solving equation (3) for doses of PU-H71 of 5, 25, 50 and 75 mg/kg (0.1, 0.5, 1 and 1.5 mg for a 20 g mouse) yields the actual tumor concentrations of the HSP90 inhibitor (FIG. 31B, shown only for 75 mg/kg). These values correlate well with the PU-H71 tumor concentrations estimated by [$^{124}$I]-PU-H71 PET and by [$^{131}$I]-PU-H71 tracer biodistributions and validated by LC-MS/MS (FIG. 31B and not shown).

Collectively, these data show that the microdose [$^{124}$I]-PU-H71 PET assay can yield both the dose of PU-H71 needed to result in a specific tumor concentration and the actual concentration of therapeutic PU-H71 delivered to a tumor.

Use of [$^{124}$I]-PU-H71 to Assay the Maximum Tumor Dose, the Dose that Delivers Tumor Target Saturation by an HSP90 Drug

[$^{124}$I]-PU-H71 PET of co-injected [$^{124}$I]-PU-H71 and PU-H71 could potentially evaluate the occupancy of tumor HSP90 targets by an HSP90 inhibitor. For example, demonstration by PET that a given therapeutic dose of HSP90 inhibitor completely or significantly suppresses tumor uptake of [$^{124}$I]-PU-H71, may indicate that the therapeutic dose has saturated the tumor HSP90 targets, and that the administered dose delivers the 'maximum tumor dose' that a single dose of drug can deliver. This target-saturating dose may also be referred to as the maximally effective single dose of drug.

To investigate this possibility, we calculated the number of tumor HSP90 sites occupied by PU-H71 per gram of tumor (HSP90 sites/g tumor), for a tracer dose (~6.5 ng/g) of [$^{124}$I]-PU-H71 co-administered with therapeutic doses (5 to 75 mg/kg or 5,000 to 75,000 ng/g), PU-H71$_{dose}$, of PU-H71. This was obtained using the formula:

$$(Hsp90\text{ sites/g tumor}) = \frac{[A_{tumor}]_t}{100\%} \cdot PU\text{-}H71_{dose} \cdot \frac{1}{W}\text{ nmol/g} \quad (4)$$

Solving equation (4) for co-administered doses of non-radioactive doses of PUH71, PU-H71$_{dose}$, of 5, 25, 50 and 75 mg/kg (5,000, 25,000, 50,000, and 75,000 ng/g, respectively) yields the number of PU-H71 molecules (in nmol) bound per gram of tumor. Because one molecule of ligand occupies the pocket of and binds to one HSP90 molecule[97, 109], equation (4) also yields the number of tumor HSP90 sites (in nmol) occupied by PU-H71/g tumor (FIG. 31E).

Analysis of the binding curve at 24 h post-injection suggests that occupancy of the available HSP90 sites is nearing saturation at a PU-H71$_{dose}$ of 75 mg/kg, with one gram of tumor containing a maximum of 160.7×10$^{-3}$ nmols of HSP90 (FIG. 31E, BMAX), corresponding to 960×10$^{11}$ HSP90 molecules. Using this value, we next calculated the percentage of tumor HSP90 sites occupied by different administered doses of PU-H71 and determined that administration of 5, 25, 50 and 75 mg/kg PU-H71 resulted in 12.1, 57.7, 88.7 and 92.7% of the available HSP90 tumor sites, respectively, being occupied by the inhibitor (FIG. 31F). With near-complete saturation of tumor uptake achieved by a single therapeutic dose of PU-H71 of 75 mg/kg, that dose has occupies most of the available tumor HSP90 sites and therefore increasing the dose further would not be expected to result in increased amounts of drug localizing in tumor but would increase systemic drug exposure and potential patient toxicity.

In summary, analysis of the 'maximum tumor dose', as demonstrated here by [$^{124}$I]-PU-H71 PET, provides information more valuable in trial design than the 'maximum tolerated dose'. Specifically it would indicate a dose that results in maximal tumor (not whole body) exposure, for a single dose administered, leading to the best possible anti-tumor effect while minimizing toxicity associated with a single dose administered. Furthermore, it suggests a new approach to selection of therapeutic dosing frequency, wherein once the maximal tumor dose has been identified, therapeutic dosing frequency could be increased to an end-point of maximum tolerated frequency (rather than the conventional maximum tolerated dose, MTD), thereby maximizing tumor exposure temporally Use of [$^{124}$I]-PU-H71 PET to Design an Efficacious Dose Regimen for HSP90 Therapy The preceding results demonstrated that [$^{124}$I]-PU-H71 PET can be used to predict the dose needed to achieve and maintain a specific tumor concentration over a selected time-period after a single PU-H71 administration. Because tumors demonstrate prolonged retention of PU-H71, repeated administration of PU-H71 at sufficient frequency would potentially result, with each successive dose, in higher cumulative tumor concentrations of PU-H71. A steady-state tumor PU-H71 concentration, specific to the dosage and schedule used, would eventually be achieved. Hence, the data suggests a potential role for [$^{124}$I]-PU-H71 PET imaging of tumor pharmacokinetics in guiding PUH71 dosing design, analogous to the use of plasma pharmacokinetics in guiding dosing towards achieving steady-state plasma concentrations.

To explore this, we estimated the tumor concentrations of PU-H71 that would result upon administration of 5, 25, 50 and 75 mg/kg PU-H71 on a 3 administrations-per-week schedule (3×week; Monday/Wednesday/Friday) with week-ends off (FIG. 32A). Simulations were performed to determine the tumor concentrations of PU-H71 when administered on this schedule and at the indicated doses (FIG. 32A). The tumor AUC, and the average and the minimum tumor concentrations of PU-H71 ([PU-H71]$_{avg}$, and [PUH71]$_{min}$, respectively) which resulted on this schedule and at these doses were also determined (FIG. 32A, inset). Predicted PU-H71 concentrations in tumors ranged from [PU-H71]$_{min}$=0.17 to 2.54 μM and [PU-H71]$_{avg}$=0.49 to 7.45 μM, for administered doses of 5 to 75 mg/kg, respectively (see inset FIG. 32A).

As mentioned, in vitro exposure of MDA-MB-468 breast cancer cells to lower PU-H71 concentrations (0.05 to 1 μM) results in potent cell growth inhibition with a reported IC$_{50}$ of 60 to 100 nM[100]. At higher PU-H71 concentrations (>2 μM), and when these cancer cells are exposed to the drug for 48 h, massive cancer cell killing by apoptosis was noted (i.e.

>70% cells undergoing apoptosis) (FIG. 32B). In light of these in vitro analyses, it is predicted that on the 3×week schedule, administration of doses of 5 to 75 mg/kg PU-H71 will result in therapeutically effective tumor drug concentrations that span values predicting mainly tumor inhibitory effects (at 5 mg/kg) to potent tumor apoptosis (75 mg/kg) (FIG. 32B). Indeed, when mice bearing MDA-MB-468 xenografted tumors were treated with PU-H71 as described above, a dose-dependent response was observed in the PU-H71-treated tumors (FIG. 32C). After a 7-week treatment period, a significant tumor response was noted with 63, 82 and 99% tumor growth inhibition (TGI) observed on the 5, 25 and 50 mg/kg doses, respectively, and a 100% regression at the 75 mg/kg dose (FIG. 32C).

We continued treatment until tumors in the control arm reached the maximum size permitted by our Institutional Animal Care and Use Committee (IUCAC) (FIG. 32D) and sacrificed the mice on a Thursday (24 h after the last Wednesday administered dose). Only animals on the 5 mg/kg arm harbored tumors sufficiently large for analysis by Western blot and LC-MS/MS (tumor volume: 139±66 $mm^3$), although significantly smaller than those treated with vehicle only (tumor volume: 1126±396 $mm^3$) (FIG. 32D).

Solving equation (1a) for administered doses of PU-H71 of 5 mg/kg and using the measured time-activity data for [$^{124}$I]-PU-H71 in tumor (FIG. 30D), yields the PU-H71 tumor concentrations over the treatment period (FIG. 32E). Our simulations suggest that the tumor concentration of PU-H71 at the time of sacrifice should be 0.43 μM (FIG. 32E), which is remarkably similar to the actual concentration of 0.52±0.13 μM determined in these tumors by LC-MS/MS (FIGS. 32F, 32G). Further, the observed pharmacodynamic effect, namely HSP90 inhibition as demonstrated by significant Akt degradation (a 57% decrease; P=0.0017; FIG. 32F and FIG. 32G, left panel) and PARP cleavage (FIG. 32F) in tumors was consistent with a therapeutically effective PU-H71 concentration in tumors at this time (FIG. 32G, right panel). These findings show that the tumor uptake of PU-H71 remained unchanged over the 12 weeks of treatment, consistent with the persisting responsiveness of these tumors to PU-H71 (FIG. 32D and Reference 100), indicating that [$^{124}$I]-PUH71 PET may be used to monitor response persistence or conversely, the potential of acquired resistance to HSP90 therapy.

Use of [$^{124}$I]-PU-H71 PET to Design an Efficacious Schedule Regimen for HSP90 Therapy Considering the prolonged retention of PU-H71 by tumors, we asked whether less frequent administration of the agent would maintain its effectiveness. In the clinical setting, this may be useful as a rationale for continuing therapy at a lower dosage in patients experiencing toxicity or rationally balancing dosage and dose frequency in designing dosing schedules.

Simulations were performed for PU-H71 administered at 75 mg/kg on a schedule of 3—(Mon-Wed-Fri), 2—(Mon and Fri) or 1—(Mon) administration(s) per week (FIG. 33A). These calculations suggest that tumors will be exposed to a $[PU\text{-}H71_{tumor}]_{avg}$ of 7.45, 5.41 and 2.88 μM, on the 3×week, 2×week and 1×week schedules, respectively (FIG. 33A), indicating that the less frequent administration schedule should still deliver therapeutically effective concentrations to the tumor (FIG. 33B). Indeed, significant tumor growth inhibition was obtained on the 1×week schedule, while the 2×week administration led to tumor regressions over the 5 weeks of treatment (FIG. 33C). In the evaluable tumors (i.e. Control and 5 mg/kg treatment arms), changes in pharmacodynamic markers were analyzed when mice were sacrificed at 24 and 96 h following the last administered dose.

Significant and near total depletion of onco-proteins (95% level decrease, P=0.0021 and P=0.0025 at 24 h and 96 h, respectively) was observed at both time points (FIG. 33D), suggesting that target saturating PU-H71 concentrations (>2 μM) should be present in tumors at these time points. In these tumors, the PET-predicted tumor concentration of PU-H71 is 5.51 and 2.18 μM at 24 h and 96 h, respectively (FIG. 33A, 1×week panel), which agrees closely with the actual tumor concentrations of 5.53±0.26 and 3.09±1.40, respectively, measured by LC-MS/MS (FIG. 33*e*).

The methodology described above is readily applicable to human patients. One example is depicted in FIG. 34 and FIG. 35. FIG. 34 shows [$^{124}$I]-PU-H71 PET/CT of a patient with recurrent pancreatic cancer with disease metastatic to lungs and adjacent lymph nodes. PET images at several times post-[$^{124}$I]-PU-H71 injection (4, 24, 48 and 192 h) were quantified and SUV data obtained for [$^{124}$I]-PU-H71 were converted to concentrations for an administered dose of PU-H71 of 20 $mg/m^2$. These tumors show very good uptake of [$^{124}$I]-PU-H71 with retention and visualization even at 192 h (8-days after administration). The [$^{124}$I]-PU-H71 PET/CT predicts that this patient is likely to respond to HSP90 therapy. The retention of PU-H71 in the tumor for times beyond 192 h (8 days) was not predicted by the mouse experiments, where as noted in FIGS. 30A-30D, $^{124}$I-PU-H71 was cleared from the MDA-MB-468 tumors by 150 h post-administration. Calculation of PU-H71 concentrations at various time points from 0 to 192 h also allows for the calculation of a tumor area under the curve (AUC). In FIG. 34, the area under the curve for the various lung nodules and lymph nodes (LN) is calculated from 0 to 192 hours.

The exposure of these tumors to PU-H71 as determined by PU-PET allows for determining and optimal dose and schedule for treating this patient. Specifically, the exposure to PU-H71 of two characteristic tumors, one in the left lung and another in the right hilum LN over the time of the two-week treatment regimen when administered a dose of 20 mg/m2 on a twice-week (Tue and Fri) schedule were calculated and represented as the area-under-the-curve (AUC) and as an average tumor concentration (FIG. 35, top panel). The tumors show good drug exposure with AUCs values of 190 and 499 μM-h, respectively and average tumor concentrations of the Hsp90 inhibitor of 0.71 and 1.57 μM, respectively. In preclinical models of pancreatic cancer such concentrations were effective at inhibiting the growth, reducing their invasive and metastatic potential and inducing apoptosis in pancreatic cancer cells, suggesting that the dose of 20 mg/m2 given on a 2×week schedule (Tue-Fri) is likely to benefit the patient.

As also shown in FIG. 35 (bottom panels, similar simulations were performed at a dose of 40 mg/m2 and 80 mg/m2 on a twice-week (Tue and Fri) schedule. The most optimal as per the PU-PET prediction is a dose of 80 mg/m2 given at a 2×week schedule (Tuesday and Friday), where the tumor exposure and the average tumor concentration over the 0-336 days would reach above 760 and 1998 uM-h and 2.8 and 6.3 uM (FIG. 35, bottom panel), respectively. These values are predicted by the preclinical studies (FIGS. 32A-32G and FIGS. 33A-33E) to result in significant regressions and cures.

FIGS. 36A-36E show shows similar calculations for a HER2+ breast cancer patient with disease metastasized to the lung. The top panels show results from the PET assay with [$^{24}$I]-PU-H71. The middle and bottom panels show tumor concentrations of PU-H71 at various times based on an administered PU-H71 dosage of 10 mg/m2. The pharmacokinetic data is reported in terms of the AUC of the PU-H71 in the tumor between 0 or 336 hours or the average concentration of the drug in the tumor over that time period. The PU-PET data predict that when given twice a week for two weeks, a dose of 10 $mg/m^2$ would deliver a tumor $AUC_{0-336\ h}$ of 103 μM-h and maintain an average tumor concentration of 0.59 μM and thus on this schedule, a dose of 80-100 $mg/m^2$ and beyond would be required for favorable response. When given three times a week for two weeks, a dose of 10 $mg/m^2$ would deliver a tumor $AUC_{0-336\ h}$ of 140.8 μM-h and maintain an average tumor concentration of 0.71 μM and thus on this schedule, a dose of 60 $mg/m^2$ and beyond would be required for favorable response. When given once a week for two weeks, a dose of 10 $mg/m^2$ would deliver a tumor $AUC_{0-336\ h}$ of only 54 μM-h and maintain an average tumor concentration of 0.41 μM and thus on this schedule, a dose of 200 $mg/m^2$ and beyond would be required for favorable response. When given 5 times a week (daily with weekend oft) for two weeks, a dose of 10 $mg/m^2$ would deliver a tumor $AUC_{0-336\ h}$ of 189.8 μM-h and maintain an average tumor concentration of 0.81 μM and thus on this schedule, a dose of 50 $mg/m^2$ and beyond would be required for a favorable response.

Collectively, these data demonstrate the utility of [$^{124}$I]-PU-H71 PET in informing on the design of an efficacious dose and dose-schedule regimen for the personalized clinical use of HSP90 therapies.

Tumor Exposure to PU-H71, as Determined by [$^{124}$I]-PU-H71 PET, Reliably Predicts Anti-Tumor Response to HSP90 Therapy Understanding the number of target sites that require inhibition over the time of treatment to result in cure remains a major challenge in targeted therapy. We therefore simulated, for the several dose and schedule regimens investigated above, the occupancy of HSP90 sites by inhibitor over the period of treatment (FIG. 37A). We then attempted to conduct a correlative analysis of tumor HSP90 occupancy with the observed anti-tumor response (FIG. 37B).

The number of tumor HSP90 sites occupied by PU-H71 per gram of tumor (HSP90 sites/g) when PU-H71 is administered in therapeutic doses (5 to 75 mg/kg or 5,000 to 75,000 ng/g in mice) can be obtained using Equation (4). Because one gram of the MDA-MB-468 tumor contains a maximum of $160.7\times10^{-3}$ nmols of HSP90 (FIG. 31D, BMAX) and given that occupancy of more than 100% of the sites is not possible, we could simulate the occupancy of HSP90 sites over the time of treatment for each dose and schedule regimen (FIG. 37A).

Target occupancy, measured as the average % HSP90 sites occupied and recognized by PU-H71 ((% Occupied HSP90 sites)$_{avg}$) over the time of treatment (FIG. 37B), as the average tumor concentration of PU-H71 recorded over the time of treatment ($[\text{PU-H71}]^{tumor}_{avg}$; FIG. 37C) and as the tumor exposure over the time of treatment as calculated by tumor AUC correlated significantly well with the magnitude of the observed anti-tumor effect ($r^2$=0.7559, 0.8162 and 0.8188, respectively). Our analyses suggest that occupancy of over 80% of the tumor HSP90 sites averaged over the time of treatment (FIG. 37B), or maintenance of an average tumor concentration of 5 μM of the HSP90 inhibitor (FIG. 37C), is needed for MDA-MB-468 tumor regression and cure. Lower occupancy however, as obtained by an average of 15% and above occupied sites or achieved by maintaining an average tumor concentration over the time of treatment of 0.5 μM and above, may still lead to partial response (FIGS. 37B, 37C).

Discussion

Based on the foregoing analysis, we have designed and developed the first non-invasive PET-based assay with potential use in the clinical development of HSP90 inhibitors. We demonstrate its use in determining the intratumoral pharmacokinetics and pharmacodynamics of the parent drug, in determining the dose of HSP90 inhibitor needed to achieve effective tumor concentrations, in assaying the actual concentration of the drug delivered to the tumor and in designing an efficacious dose and schedule regimen based on target modulation efficiency and not maximum tolerated dose (MTD). We also demonstrate its use in selecting patients most likely to have tumor response to HSP90-targeting.

Others have shown in preclinical or clinical studies that carbon 11-, fluorine 18- and nitrogen 13-labeled drugs, such as N-[$^{11}$C]-methyl imatinib[122], 3-N-methyl and 4-carbonyl-[$^{11}$C]-temozolomide[123], N-[2-(dimethylamino)ethyl]acridine-4-carboxamide ([$^{11}$C]DACA)[124], [$^{18}$F]5-FU[124], [$^{18}$F] fluorine derivative of dasatinib[125] and [$^{13}$N]cisplatin[126] were useful to estimate by PET pharmacokinetic parameters for agents whose half-lives are significantly less than the total sampling time during the scan. For HSP90 inhibitors, whose tumor half-lives (i.e. >24 h) are longer than the sampling duration permitted by these isotopes (i.e. 10 min, 20 min and 110 min for $^{11}$C, $^{13}$N and $^{18}$F, respectively), PET pharmacokinetic evaluations using these radioisotopes are inappropriate. Because of the relatively long half-life of $^{124}$I, the [$^{124}$I]-PU-H71 PET assay is thus the first reported assay that is able to non-invasively and quantitatively monitor the tumor pharmacokinetics of HSP90 inhibitors (FIG. 38).

In addition, the [$^{124}$I]-PU-H71 PET assay is a true materialization of the concept of targeted imaging for targeted therapy using radiolabeled biologically-inactive trace amounts of the targeted therapeutic agents for medical imaging[127-131]. While the concept is well recognized and highly advocated for the future of drug development, providing a path towards personalized medicine, there is no precedent for the use of an oncology small-molecule therapeutic agent as an imaging agent to select patients most responsive to its drug action and to advise on the schedule of its administered dose. Because of the presence of iodine in the native structure of PU-H71 and therefore the absence of any perturbation of its structure and biological behavior by incorporation of a radioiodine label, the [$^{124}$I]-PU-H71 PET assay is to our knowledge one of the first such assays. Specifically, the observed biodistribution profile of [$^{124}$I]-PU-H71, namely tumor retention with rapid clearance from non-tumor tissue, mirrors that of the therapeutic agent PU-H71. In addition, while formation of drug metabolites limits the application of labeled drugs for PET[41], our data demonstrate that the [$^{124}$I]-PU-H71 PET assay accurately measures tumor PU-H71 concentrations at both microdose and therapeutic-dose levels, indicating that PU-H71 metabolites do not contribute significantly to the PET-measured tumor activities. Altogether, these findings suggest that [$^{124}$I]-PU-H71 is well-suited for use as a true in vivo 'tracer' of PU-H71.

In the development of targeted cancer therapy it is well understood that clinical trials require knowledge on whether effective tumor concentrations are achieved and whether the target is appropriately modulated. Our data demonstrate that the [$^{124}$I]-PUH71 PET assay quantitatively measures tumor HSP90 inhibitor pharmacokinetics allowing for tumor dose-tumor response correlations that are more informative than conventional tumor response correlations with injected dose or plasma pharmacokinetics. Our data also demonstrate that for PU-H71, tumor pharmacokinetics mirror tumor pharmacodynamics, identifying [$^{124}$I]-PU-H71 PET as a non-invasive measurement of both parameters. Thus, tumor pharmacokinetics, also indicative of target occupancy, have predictive power in understanding both immediate (i.e. target modulation following a one dose inhibitor) and long-term (i.e. target modulation over the designed schedule) response to an HSP90 inhibitor treatment regimen. In addition, by evaluating [$^{124}$I]-PU-H71 tumor pharmacokinetics in individual patients being considered for HSP90 therapy, one may also identify patients most likely to benefit from HSP90 treatment and consequently adjust the therapeutic dose and schedule, based upon tumor uptake and clearance of [$^{124}$I]-PU-H71 (FIG. 38A).

We also show that the assay can guide the development of individualized dosing regimens based on PET-derived tumor HSP90 pharmacokinetics, as an imaging biomarker of the extent of tumor HSP90 targeting and its saturation by an HSP90 inhibitor therapeutic dose, with potential for predicting the anti-tumor effect and outcome over the course of HSP90 therapy (FIG. 38B). Due to these characteristics, the [$^{124}$I]-PU-H71 PET assay is optimal for use in HSP90 inhibitor clinical studies as a pharmacometric tool for understanding (FIG. 38A) and, potentially, predicting tumor response to HSP90 treatment (FIG. 38B).

The [$^{124}$I]-PU-H71 data also provides a more rational and effective dosing strategy in HSP90-targeted therapy based on PET-derived maximally effective tumor concentration rather the conventional maximum tolerated dose (MTD). This approach aims towards a new dosing goal of achieving a maximum tumor dose, an optimal dose level at which tumor targets are nearly saturated by drug, as visualized by PET (FIG. 38*c*). This approach would avoid further dose escalation that may only increase patient toxicity not anti-tumor efficacy. If tumor saturation is observed at a therapeutic dose less than a maximum tolerated dose (MTD) (as determined by a dose-escalation trial, for example), then a dosing strategy might pursue finding the maximum tolerated frequency of dosing at the saturating maximally effective tumor concentration as determined by PET. [$^{124}$I]-PU-H71 PET might explore the duration of tumor saturation after a maximally effective tumor dose to further inform selection of dosing frequency. [$^{124}$I]-PU-H71 PET might be similarly used to guide dose and frequency selection of other HSP90 inhibitors. The ability of a therapeutic dose of an HSP90-targeted agent to competitively inhibit tumor-targeting by [$^{124}$I]-PU-H71 tracer might provide an index of tumor drug saturation. For clinical development of HSP90 inhibitors, [$^{124}$I]-PU-H71 PET might be used to gather tumor pharmacokinetic data from a Phase 1/2 trial population to derive a generally applicable dosing strategy or it might be used on an individual-patient basis for truly 'personalized' dose-schedule selection. PU-H71 PET imaging, we believe, is a clinical tool well suited to testing these hypotheses. With a Phase 0 microdose trial of [$^{124}$I]-PU-H71 currently underway, and the [$^{124}$I]-PU-H71 PET assay being incorporated in an upcoming Phase 1 clinical study of PU-H71 at Memorial Sloan-Kettering Cancer Center, this concept will soon be evaluated in a clinical setting.

In conclusion, [$^{124}$I]-PU-H71 PET, as a targeted assay of tumor HSP90, may dramatically and rationally advance patient selection, dose selection, tumor diagnosis and evaluation of tumor response at the level of the molecular target in HSP90-targeted therapy. As such, the novel [$^{124}$I]-PU-H71 PET assay should facilitate the rational, cost-effective, and optimal clinical development and use of HSP90 inhibitors in cancer. The use of [$^{124}$I]-PU-H71 PET represents a major advance in the design of clinical trials of HSP90 inhibitors and promote the paradigm of targeted imaging pharmacometrics for development of other targeted therapeutics.

5.2.2.2.2. [$^{124}$I]-PU-DZ13 and [$^{124}$I]-PU-HZ151

Other HSP90 inhibitors with endogenous iodine where evaluated for their ability to perform in the HSP90 PET assay. Two such compounds include [$^{124}$I]-PU-DZ13 and [$^{124}$I]-PU-HZ151, were synthesized, as shown in Schemes 16 and 17.

Scheme 16: Synthesis of [$^{124}$I]-PU-DZ13

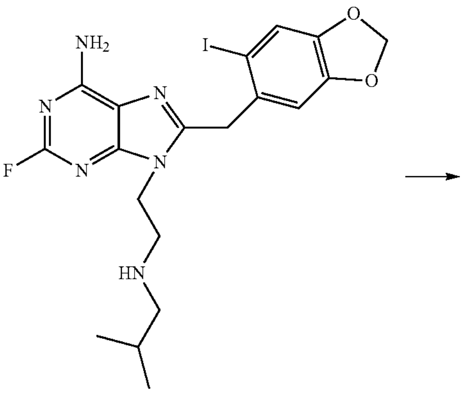

DZ13

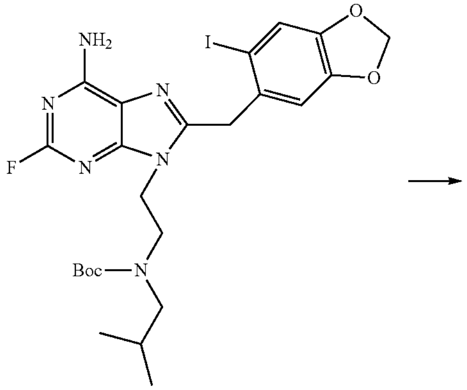

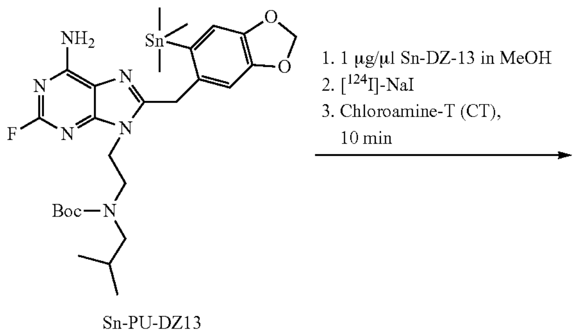

Sn-PU-DZ13

-continued

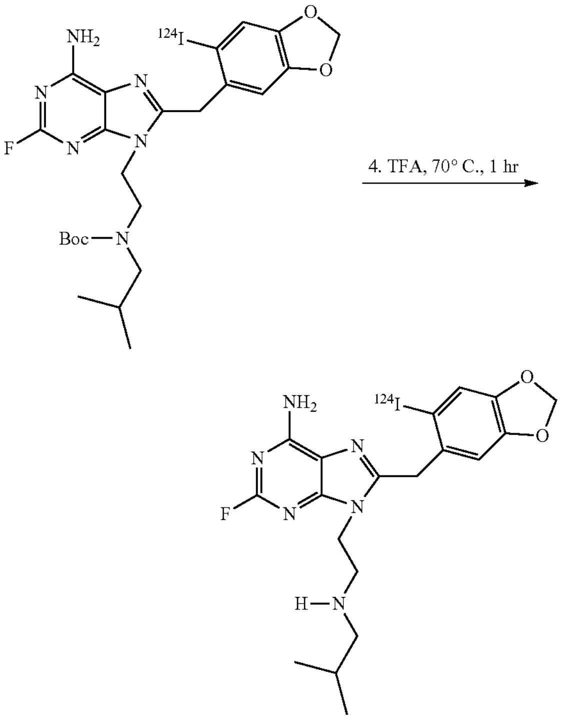

$^{124}$I-PU-DZ13

SCHEME 17: Synthesis of [$^{124}$I]-PU-HZ151.

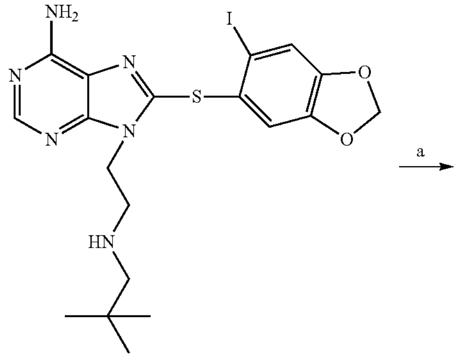

PU-HZ151

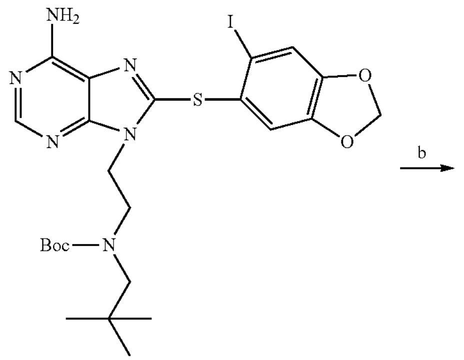

-continued

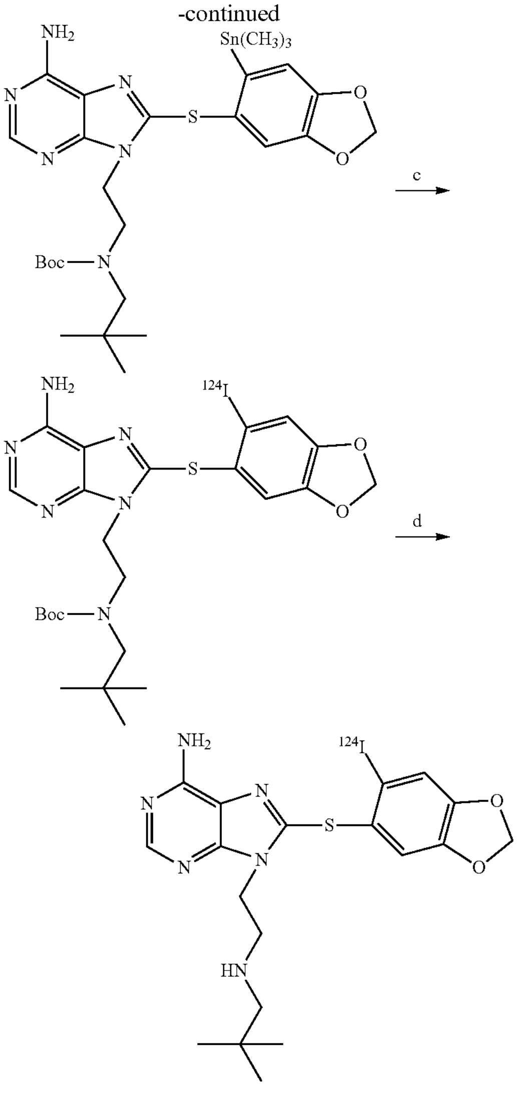

$^{124}$I-PU-HZ151

Reagents and conditions: a. $Et_3N$, $(Boc)_2O$, $CH_2Cl_2$, rt; b. $Pd(PPh_3)_4$, hexamethylditin, dioxane, 90° C.; c. [$^{124}$I]-NaI, chloramine-T, rt, 10 min.; d. TFA, 70° C., 60 min.

The radiochemical yields of these compounds were 36.96±12.97% ([$^{124}$I]-PU-DZ13), 36.45±15.75% ([$^{124}$I]-PU-HZ151) and 45.33±15.76% ([$^{124}$I]-PU-H71); radiochemical purity (>98%) was confirmed by HPLC. The specific activities were 633 mCi/μmol ([$^{124}$I]-DZ13), 576 mCi/μmol ([$^{124}$I]-HZ151) and 1000 mCi/μmol ([$^{124}$I]-PU-H71).

In order to assess the in vitro stability of [$^{124}$I]-PU-H71 and [$^{124}$I]-PU-DZ13, the compounds were incubated in human sera at 37° C. over five days, and analyzed by ITLC to determine if dehalogenation occurred. It was determined that both [$^{124}$I]-PU-H71 and [$^{124}$I]-PU-DZ13 were stable (>98%) over five days (120 h).

The tumor retains [$^{131}$I]-PU-DZ13 when it is administered by both the IV and IP routes, however, tumor retention is higher by IV administration, with statistical significance ($P<0.05$) (24 h post administration, intraperitoneal versus intravenous routes). In the C57BL/6J non-tumor bearing mouse, [$^{131}$I]-PU-DZ13 quickly clears cardiac blood (% ID/g was 3.33±0.13 at 2 min and 0.013±0.00 by 24 h post administration), and has the greatest uptake by the stomach and intestines (3-8% ID/g). Liver and spleen uptakes were not significantly different ($P<0.05$), suggesting reticuloendothelial system (RES) involvement. The kidney uptake of [$^{131}$I]-PU-DZ13, however, implied urinary clearance (% ID/g dropped from 5.53±0.34 at 2 min (data not shown) to 0.06±0.01 by 24 h post administration). In the MDA-MB-468 TNBC mouse model, [$^{131}$I]-PU-DZ13 was retained by the tumor longer when administered by the intravenous route as compared with the intraperitoneal route. By IV administration, the tumor uptake of [$^{131}$I]-PU-DZ13 (1.47±0.22% ID/g at 1 h), slowly decreased (% ID/g=0.56±0.14, 4 h; 0.40±0.03, 12 h; 0.09±0.03, 24 h) over 72 h (0.05±0.00% ID/g). As with non-tumor bearing mice, gastrointestinal and RES uptakes of [$^{131}$I]-PU-DZ13, and renal clearance was seen in MBA-MD-468. The in vivo biodistribution of [$^{131}$I]-PU-DZ13, when co-administered with PU-DZ13 at 25 mg/kg (24 h post administration, intraperitoneal versus intravenous routes), shows that PU-PET predicted tumor concentrations compare favorably with the values determined by LCMS-MS.

In vivo PET imaging detected MDA-MB-468 tumors with [$^{124}$I]-PU-H71 and [$^{124}$I]-PU-DZ13 HSP90 inhibitors. FIG. 39 shows the PET imaging results at 48 h post injection, of mice systemically injected with either inhibitor ([$^{124}$I]-PU-H71 or [$^{124}$I]-PU-DZ13). Both radioiodinated HSP90 inhibitors detected the tumors with PET at each time point. The uptake % ID/g of the two inhibitors were not significantly different in the tumor masses, although [$^{124}$I]-PU-DZ13 qualitatively appeared to have less nonspecific abdominal uptake.

Unlike [$^{124}$I]-PU-DZ13 and [$^{124}$I]-PU-H71, [$^{124}$I]-PU-HZ151 could not detect the tumors in mice possibly because of its rapid metabolism by liver.

5.3. Treating Cancer Patients with PU-H71

The methods described in Section 5.2.1. indicate that radiolabeled HSP90 inhibitors such as [$^{124}$I]-PU-H71 can be used to identify patients that are likely to respond to HSP90 inhibition therapy and to design optimized dosing regimens for individual patients. The dosing regimens are based on such factors as tumor exposure of the inhibitor and occupancy of HSP90 by the inhibitor. These pharmacokinetic parameters are readily assessed using the radiolabeled inhibitors of the present disclosure. Owing to the fact that pharmacokinetic data can be easily obtained from a large pool of individual cancer patients, we have the ability to determine a range of pharmacokinetic parameters that will be suitable for achieving a desired level of efficacy of a particular HSP90 inhibitor without concomitant toxicological problems caused by overdosing with the HSP90 inhibitor.

Accordingly, the disclosure further provides methods of treating patients with solid tumors, hematologic malignancies, and lymphomas with HSP90 inhibitors, particularly PU-H71, to achieve a particular pharmacokinetic profile. The disclosure also provides methods of treating solid tumors, hematologic malignancies, and lymphomas with HSP90 inhibitors, particularly PU-H71, by administering the inhibitor at particular dosage levels and/or particular dosing schedules. In particular embodiments, the tumor to be treated with the HSP90 inhibitor is an "HSP90 dependent tumor". As discussed above, an HSP90 dependent tumor is a tumor whose physiology utilizes HSP90. An HSP90 dependent tumor contains a significant amount of "oncogenic HSP90" relative to the normal housekeeping HSP90. The methodology described in this section can be applied to numerous types of cancers including but not limited to colorectal cancer, pancreatic cancer, thyroid cancer, basal cell carcinoma, melanoma, renal cell carcinoma, bladder cancer, prostate cancer, lung cancer including small cell lung cancer, non-small cell lung cancer and adenocarcinoma, breast cancer of all subtypes, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, multiple myeloma, including other plasma cell disorders, leukemias, myeloproliferative neoplasms and gynecologic cancers including ovarian, cervical, and endometrial cancers.

In one embodiment, the disclosure provides methods of treating a human patient having a solid tumor, lymphoma or hematologic malignancy comprising administering a sufficient amount of PU-H71 to the patient to provide an occupancy of 15% or greater of the oncogenic HSP90 in the patient's tumor, an occupancy of 30% or greater of the oncogenic HSP90 in the patient's tumor, an occupancy of 50% or greater of the oncogenic HSP90 in the patient's tumor, or an occupancy of 60% or greater of the oncogenic HSP90 in the patient's tumor at at least one point in time between about 16 hours to about 24 hours following administration of the drug. For instance, the administration of PU-H71 can provide an occupancy of at least 15%, at least 20%, at least 30%, at least 40%, at least 50%, at least 60%, at least 70%, at least 80%, at least 85%, at least 90%, at least 95% or 100% of the oncogenic HSP90 in the patient at at least one point in time between 16 and 24 hours following administration of the drug. In one particular embodiment, the administration of PU-H71 can provide an occupancy of at least 15%, at least 20%, at least 30%, at least 40%, at least 50%, at least 60%, at least 70%, at least 80%, at least 85%, at least 90%, at least 95% or 100% of the oncogenic HSP90 in the patient at about 24 hours following administration of the drug. In another embodiment, the administration of PU-H71 can provide an occupancy of at least 15%, at least 20%, at least 30%, at least 40%, at least 50%, at least 60%, at least 70%, at least 80%, at least 85%, at least 90%, at least 95% or 100% of the oncogenic HSP90 in the patient in the entire range between 16 hours and 24 hours following administration of the drug. PU-H71 can be administered to provide an occupancy of oncogenic HSP90 bounded by any of the two foregoing values at at least one point in time or in the entire range between about 16 hours to about 24 hours following administration of the drug, e.g., an occupancy of from about 20% to about 80%, an occupancy of from about 30% to about 80%, an occupancy of between 40% and 80%, an occupancy of between 40% and 90%, an occupancy of from about 50% to about 80%, an occupancy of from about 50% to about 90%, an occupancy of from about 60% to about 80%, an occupancy of from about 60% to about 99%, an occupancy of from about 50% to about 99%, an occupancy of from about 50% to about 99.9%, an occupancy of from about 70% to about 99.9%, etc. In another embodiment, PU-H71 is administered at the minimum dosage to achieve 100% occupancy of the oncogenic HSP90. As discussed in Section 5.2.1.1., administering PU-H71 to provide the above oncogenic HSP90 occupancies results in efficacious doses of PU-H71. In one particular embodiment, the patient with the tumor is a human patient with an HSP90 dependent tumor.

In another embodiment, the disclosure provides methods of treating a patient having a solid tumor, lymphoma or hematologic malignancy comprising administering a sufficient amount of PU-H71 to the patient to provide a tumor concentration at 24 hours post administration in the range from about 0.3 μM to about 7.5 μM. For instance, the PU-H71 concentration in the tumor about 24 hours following administration of PU-H71 can be 0.3 μM, 1 μM, 3 μM, 5 μM or 7 μM. PU-H71 can be administered to provide a tumor concentration of the drug after about 24 hours between any of the two foregoing values, e.g., a tumor concentration from about 1 μM to about 3 μM, a tumor concentration from about 1 μM to about 5 μM, a tumor concentration from about 3 μM to about 5 μM, a tumor concentration from about 3 μM to about 7 μM, etc. In one particular embodiment, the patient with the tumor is a human patient with an HSP90 dependent tumor.

In another embodiment, the disclosure provides methods of treating a patient having a solid tumor, lymphoma or hematologic malignancy comprising administering a sufficient amount of PU-H71 to the patient to provide a tumor concentration at about 48 hours post administration in the range of from about 0.05 μM to about 3.5 μM. For instance, the PU-H71 concentration in the tumor at about 48 hours following administration of PU-H71 can be about 0.5 μM, about 1 μM, about 1.5 μM, about 2 μM or about 3 μM. PU-H71 can be administered to provide a tumor concentration of the drug after about 48 hours between any of the two foregoing values, e.g., a tumor concentration from about 1 μM to about 2 μM, a tumor concentration from about 1 μM to about 3 μM, a tumor concentration from about 0.5 μM to about 2 μM, a tumor concentration from about 0.25 μM to about 2 μM, etc. In one particular embodiment, the patient with the tumor is a human patient with an HSP90 dependent tumor.

In another embodiment, the disclosure provides methods of treating a patient having a solid tumor, lymphoma or hematologic malignancy comprising administering a sufficient amount of PU-H71 to the patient to provide a tumor concentration of at about 24 hours post administration in the range of from about 0.3 μM to about 7.5 μM and at about 48 hours post administration in the range from about 0.05 μM to about 3.5 μM. In one particular embodiment, the patient with the tumor is a human patient with an HSP90 dependent tumor.

As discussed in Section 5.2.1.1., the radiolabeled assay provides a convenient means of determining the tumor exposure of PU-H71. The tumor exposure can be measured using various pharmacokinetic parameters such as AUC in the tumor and average tumor concentration of the drug over a particular time period. Based on a wealth of pharmacokinetic data gathered on patients with numerous solid tumors, we have determined that measuring the AUC and average tumor concentration over a particular treatment period (e.g., two weeks) provides important information regarding the efficacy and toxicology of the drug. As discussed above, the term "tumor AUC" refers to the cumulative intracellular concentration of the drug over the time period from administration of the drug to another point in time. For instance, the AUC in the water space of the tumor over a time period of 0 hours to 336 hours is referred to herein as tumor $AUC_{0\text{-}336\ h}$. The "0" time point can refer to the time when the drug is first administered at the onset of a new treatment cycle. Alternatively, the "0" time point can refer to the time point the drug is administered in the middle of a treatment cycle. It will be understood that multiple doses of the drug can be administered at various times between the 0 time point and the 336 hour time point. As discussed below, tumor AUC values and average tumor concentrations that fall within particular ranges provide efficacious doses.

In one embodiment, the disclosure provides methods of treating a patient having a solid tumor, lymphoma or hematologic malignancy comprising administering a sufficient amount of PU-H71 to the patient that provides an $AUC_{0\text{-}336\ h}$ from about 150 to about 4,000 μM-h. For instance the tumor $AUC_{0\text{-}336\ h}$ of PU-H71 can be about 300 μM-h, about 500 μM-h, about 800 μM-h, about 1200 μM-h, about 1500 μM-h, about 2000 μM-h, about 3000 μM-h or about 4000 μM-h. PU-H71 can be administered to provide a tumor $AUC_{0\text{-}336\ h}$ between any of the two foregoing values, e.g., a tumor $AUC_{0\text{-}336\ h}$ ranging from about 300 μM-h to about 800 μM-h, a tumor $AUC_{0\text{-}336\ h}$ ranging from about 500 μM-h to about 800 μM-h, a tumor $AUC_{0\text{-}336\ h}$ ranging from about 500 μM-h to about 1000 μM-h, a tumor $AUC_{0\text{-}336\ h}$ ranging from about 1000 μM-h to about 1500 μM-h, a tumor $AUC_{0\text{-}336\ h}$ ranging from about 1000 μM-h to about 2000 μM-h, a tumor $AUC_{0\text{-}336\ h}$ ranging from about 1500 μM-h to about 2000 μM-h, a tumor $AUC_{0\text{-}336\ h}$ ranging from about 2000 μM-h to about 3000 μM-h, a tumor $AUC_{0\text{-}336\ h}$ ranging from about 2000 μM-h to about 4000 μM-h, a tumor $AUC_{0\text{-}336\ h}$ ranging from about 3000 μM-h to about 4000 μM-h, etc. In one embodiment, the "0" time point is the start of a new treatment cycle. In one particular embodiment, the patient with the tumor is a human patient with an HSP90 dependent tumor.

In another embodiment, the disclosure provides methods of treating a patient having a solid tumor, lymphoma or hematologic malignancy comprising administering a sufficient amount of PU-H71 to the patient that provides an $AUC_{0\text{-}168\ h}$ from about 75 μM-h to about 2,000 μM-h. For instance the tumor $AUC_{0\text{-}168\ h}$ of PU-H71 can be about 75 μM-h, about 250 μM-h, about 400 μM-h, about 600 μM-h, about 750 μM-h, about 1000 μM-h, about 1500 μM-h or about 2000 μM-h. PU-H71 can be administered to provide a tumor $AUC_{0\text{-}168\ h}$ between any of the two foregoing values, e.g., a tumor $AUC_{0\text{-}168\ h}$ ranging from about 150 μM-h to about 400 μM-h, a tumor $AUC_{0\text{-}168\ h}$ ranging from about 250 μM-h to about 400 μM-h, a tumor $AUC_{0\text{-}168\ h}$ ranging from about 200 μM-h to about 500 μM-h, a tumor $AUC_{0\text{-}168\ h}$ ranging from about 500 μM-h to about 750 μM-h, a tumor $AUC_{0\text{-}168\ h}$ arranging from about 500 μM-h to about 1000 μM-h, a tumor $AUC_{0\text{-}168\ h}$ ranging from about 750 μM-h to about 1000 μM-h, a tumor $AUC_{0\text{-}168\ h}$ ranging from about 1000 μM-h to about 1500 μM-h, a tumor $AUC_{0\text{-}168\ h}$ ranging from about 1000 μM-h to about 2000 μM-h, a tumor $AUC_{0\text{-}168\ h}$ ranging from about 1500 μM-h to about 2000 μM-h, etc. In one embodiment, the "0" time point is the start of a new treatment cycle. In one particular embodiment, the patient with the tumor is a human patient with an HSP90 dependent tumor.

In another embodiment, the disclosure provides methods of treating a patient having a solid tumor, lymphoma or hematologic malignancy comprising administering a sufficient amount of PU-H71 to the patient that provides an $AUC_{0\text{-}48\ h}$ from about 10 to about 300 μM-h. For instance the tumor $AUC_{0\text{-}48\ h}$ of PU-H71 can be about 15 μM-h, about 20 μM-h, about 25 μM-h about 30 μM-h, about 40 μM-h, about 50 μM-h, about 80 μM-h, about 100 μM-h, about 150 μM-h or about 200 μM-h. PU-H71 can be administered to provide a tumor $AUC_{0\text{-}48\ h}$ between any of the two foregoing values, e.g., a tumor $AUC_{0\text{-}48\ h}$ ranging from about 10 μM-h to about 100 μM-h, a tumor $AUC_{0\text{-}48\ h}$ ranging from about 10 μM-h to about 80 μM-h, a tumor $AUC_{0\text{-}48\ h}$ ranging from about 15 μM-h to about 80 μM-h, a tumor $AUC_{0\text{-}48\ h}$ ranging from about 15 μM-h to about 50 μM-h, a tumor $AUC_{0\text{-}48\ h}$ ranging from about 20 μM-h to about 50 μM-h, a tumor $AUC_{0\text{-}48\ h}$ ranging from about 20 μM-h to about 40 μM-h, a tumor $AUC_{0\text{-}48\ h}$ ranging from about 20 μM-h to about 30 μM-h, etc. In one embodiment, the "0" time point is the start of a new treatment cycle. In one particular embodiment, the patient with the tumor is a human patient with an HSP90 dependent tumor.

In another embodiment, the disclosure provides methods of treating a patient having a a solid tumor, lymphoma or hematologic malignancy comprising administering a sufficient amount of PU-H71 to the patient that provides an average tumor concentration of PU-H71 (referred to herein as $[PU\text{-}H71]_{avg}$) between 0 and 336 hours from about 0.5 μM to about 7.5 μM. For instance, the $[PU\text{-}H71]_{avg}$ between 0 and 336 hours can be about 1 μM, about 3 μM, about 5 μM, or about 7 μM. PU-H71 can be administered to provide a $[PU\text{-}H71]_{avg}$ between any of two foregoing values, e.g., a $[PU\text{-}H71]_{avg}$ (measured between 0 hours and 336 hours) ranging from about 1 μM to about 5 μM, from about 3 μM to 7 μM, from about 3 μM to about 5 μM, etc. In one embodiment, the "0" time point is the start of a new treatment cycle. In one particular embodiment, the patient with the tumor is a human patient with an HSP90 dependent tumor.

In another embodiment, the disclosure provides methods of treating a patient having a solid tumor, lymphoma or hematologic malignancy comprising administering a sufficient amount of PU-H71 to the patient that provides an average tumor concentration of PU-H71 ($[PU\text{-}H71]_{avg}$) between 0 and 168 hours from about 0.25 μM to about 3.75 μM. For instance, the $[PU\text{-}H71]_{avg}$ between 0 and 168 hours can be about 0.5 μM, about 1.5 μM, about 2.5 μM, or about 3.5 μM. PU-H71 can be administered to provide a $[PU\text{-}H71]_{avg}$ between any of two foregoing values, e.g., a $[PU\text{-}H71]_{avg}$ (measured between 0 hours and 168 hours) ranging from about 0.5 μM to about 2.5 μM, from about 1.5 μM to 3.5 μM, from about 1.5 μM to about 2.5 μM, etc. In one embodiment, the "0" time point is the start of a new treatment cycle. In one particular embodiment, the patient with the tumor is a human patient with an HSP90 dependent tumor.

As will be understood by a person skilled in the art, the total amount of PU-H71 that needs to be administered to achieve the desired "oncogenic HSP90" occupancy, tumor AUC or $[PU\text{-}H71]_{avg}$ is dependent by both the route of administration and the dosing schedule. PU-H71 may be administered by various injectable routes including intravenously, subcutaneously, intramuscularly and intraperitoneally. Alternatively, PU-H71 can be administered orally.

In one embodiment of the present disclosure, PU-H71 is administered intravenously to a human patient having a solid tumor, lymphoma or hematologic malignancy at a dosage ranging from about 5 mg/m2 to about 250 mg/m2 according to a dosing schedule selected from once weekly, twice weekly, three times weekly, four times weekly or five times weekly. In particular embodiments, PU-H71 is administered intravenously to a human patient at a dosage from about 20 mg/m2 to about 60 mg/m2 according to a dosing schedule selected from once weekly, twice weekly, three times weekly, four times weekly or five times weekly. In particular embodiments, PU-H71 is administered intravenously to a human patient at a dosage from about 50 mg/m2 to about 250 mg/m2 according to a dosing schedule selected from once weekly, twice weekly, three times weekly, four times weekly or five times weekly. In other embodiments, PU-H71 is administered intravenously to a human patient at a dosage from about 50 mg/m2 to about 100 mg/m2 according to a dosing schedule selected from once weekly, twice weekly, three times weekly, four times weekly or five times weekly. In other embodiments, PU-H71 is administered intravenously to a human patient at a dosage from about 75 mg/m2 to about 200 mg/m2 according to a dosing schedule selected from once weekly, twice weekly, three times weekly, four times weekly or five times weekly. In still other embodiments, PU-H71 is administered intravenously to a human patient at a dosage from about 75 mg/m2 to about 150 mg/m2 according to a dosing schedule selected from once weekly, twice weekly, three times weekly, four times weekly or five times weekly. In one particular embodiment, the patient with the tumor is a human patient with an HSP90 dependent tumor.

In preferred embodiments, PU-H71 is administered intravenously to a human patient having a solid tumor, lymphoma or hematologic malignancy according to a dosing schedule of once weekly, twice weekly or three times weekly. In a particular embodiment, PU-H71 is administered intravenously in an amount ranging from about 50 mg/m2 to about 150 mg/m2 or from about 70 mg/m2 to about 125 mg/m2 according to a dosing schedule of twice weekly. In another particular embodiment, PU-H71 is administered intravenously in an amount ranging from about 20 mg/m2 to about 100 mg/m2 or from about 40 mg/m2 to about 80 mg/m2 according to a dosing schedule of three times weekly. In another embodiment, PU-H71 is administered intravenously in an amount ranging from about 90 mg/m2 to about 190 mg/m2 or from about 100 mg/m2 to about 250 mg/m2 according to a dosing schedule of once weekly. In one particular embodiment, the patient with the tumor is a human patient with an HSP90 dependent tumor.

In one embodiment, PU-H71 is administered intravenously to a human patient having a solid tumor, lymphoma or hematologic malignancy according to a dosing schedule of once weekly or twice weekly for two weeks followed by one week off. In another particular embodiment, PU-H71 is administered at a dosing schedule of once weekly or twice weekly for one week followed by one week off. Alternatively, PU-H71 can be administered once weekly or twice weekly without any weeks off in between.

5.4. Assessing Pathways and Oncoproteins Dependent on HSP90 for Prognostic and Diagnostic Applications As discussed in Section 5.1., information on the ratio between "oncogenic HSP90" and normal HSP90 in cancer cells can be used to determine the contribution of HSP90 in the survival and proliferation of the cancer cells. Additionally, we have identified particular proteins and pathways that often depend on HSP90 for survival. Identification of the expression levels of these proteins and or these pathways in the cancer cells of a patient can provide important information on the role of HSP90 protein in the patient's cancer, particularly when assessed against patients who have responded to HSP90 therapy. Accordingly, the present disclosure provides methods for determining whether a human cancer present in a patient will likely respond to therapy with an HSP90 inhibitor which comprises (a) obtaining a sample containing cells expressing HSP90 protein from the patient's cancer; (b) assessing for the cells present in the sample the presence of at least one of the following parameters: an activated AKT pathway, a defect in PTEN tumor suppressor function or expression, an activated STAT5 pathway, or a Bcl2 family member, such as Bcl-xL, protein expression; and (c) comparing the assessment obtained in step (b) with a predetermined reference assessment of the same parameter or parameters assessed in step (b) for human cancer cells from one or more cancer patient(s) who responded to therapy with the HSP90 inhibitor so as to thereby determine whether the patient's cancer will likely respond to therapy with the HSP90 inhibitor. In particular embodiments, the cells are breast cancer cells or acute myeloid leukemia (AML) cells.

Despite of the large number of potential new agents entering clinical evaluation every year, only 5% to 8% ever reach registration. Of particular concern is the high rate of failures in Phase 3, where an estimated 50% of oncology agents are stopped in development. Such failures are especially expensive and deprive many patients of potentially more effective treatments. These dire statistics clearly speak for the need to discover and implement predictive biomarkers for patient selection and trial enrichment.

What have we learned from the results obtained in the last years with targeted agents? When a new drug has been administered, either as a single agent or in addition to chemotherapy in a study population not selected by any biomarker, most trials have produced negative results, while in a small minority of cases a statistically significant benefit has been demonstrated. This benefit, however, consisted, at best, of a small or moderate absolute prolongation of overall survival. On the other hand, examples of a greater absolute benefit obtained with the use of targeted agents based on a biomarker-driven patient selection are constantly increasing. Biomarkers provide the possibility to use tumor and patient characteristics to integrate an accurate predictor of efficacy with a specific mechanism based therapy, guiding the selection of treatment for each individual patient. In particular, a validated predictive marker can prospectively identify individuals who are likely to have a positive clinical outcome from a specific treatment.

The present disclosure recognizes these issues and proposes to develop and validate biomarkers for a biomarker-driven patient selection and trial enrichment in the implementation of HSP90 inhibitors into the treatment of cancers.

5.4.1. Markers Predictive of Apoptotic Sensitivity to HSP90 in Breast Cancer

Depending on the genetic making of the tumor, either a cytostatic or a cytotoxic effect may result from HSP90 inhibition in BC. In clinic however, a highly apoptotic not a cytostatic response to treatment is most desired. Thus, to identify the breast cancer tumors more likely to undergo apoptosis when challenged with PU-H71 and other HSP90 inhibitors, we have conducted preliminary studies in cell lines to identify molecular lesions that are associated with highest apoptotic response upon HSP90 inhibition.

These studies propose an HSP90-directed regulation of activated Akt and elevated Bcl-xL and/or Bcl2 and/or Mcl-1 as major elements conferring apoptotic sensitivity of tumors to HSP90 inhibition (i.e. biomarkers predictive of response). A person skilled in the art will appreciate that measurement of an activated Akt pathway may require measuring expression and/or phosphorylation status of one of more proteins associated with this pathway, such as but not limited to Akt, S6, PRAS40, Bcl2, mTOR, IKK, NFkB. Detailed information on the Akt pathway and its activation may be found online in the KEGG PATHWAY database; and the National Cancer Institute's Nature Pathway Interaction Database. See also the websites of Cell Signaling Technology, Beverly, Mass.; BioCarta, San Diego, Calif.; and Invitrogen/Life Technologies Corporation, Clarsbad, Calif. This pathway is composed of, but not restricted to 1-phosphatidyl-D-myo-inositol 4,5-bisphosphate, 14-3-3, 14-3-3-Cdkn1b, Akt, BAD, BCL2, BCL2L1, CCND1, CDC37, CDKN1A, CDKN1B, citrulline, CTNNB1, EIF4E, EIF4EBP1, ERK1/2, FKHR, GAB1/2, GDF15, Glycogen synthase, GRB2, Gsk3, Ikb, IkB-NfkB, IKK (complex), ILK, Integrin, JAK, L-arginine, LIMS1, MAP2K1/2, MAP3K5, MAP3K8, MAPK8IP1, MCL1, MDM2, MTOR, NANOG, NFkB (complex), nitric oxide, NOS3, P110, p70 S6k, PDPK1, phosphatidylinositol-3,4,5-triphosphate, PI3K p85, PP2A, PTEN, PTGS2, RAF1, Ras, RHEB, SFN, SHC1 (includes EG:20416), SHIP, Sos, THEM4, TP53 (includes EG:22059), TSC1, Tsc1-Tsc2, TSC2, YWHAE A person skilled in the art will appreciate that measuring the expression of one or more Bcl-2 family anti-apoptotic molecules, such as Bcl-2, Bcl-xL, Mcl-1 may be necessary to appreciate the contribution of this anti-apoptotic family.

While studies in established BC cells provide valuable information on the BCs more likely to respond to HSP90 therapy, cultured cells cannot entirely recapitulate the real clinical disease. Experimental models of breast cancer encompass a very small number of cell lines, which were developed several decades ago. Although some cell lines retain most of the original features, we found a discrepancy in levels of HSP90 and other features, between patient samples and cell lines, which in part can be a consequence of culture stress. In addition, cultured cell lines do not recapitulate the effect the environment has on tumor cells. All together, we believe that primary explants can resemble the tumor features and response to treatment more faithfully than cell lines.

Thus, to address the question: "What is the spectrum of BC tumors most sensitive to HSP90 therapy?", our studies include evaluation of PU-H71 in clinical breast cancer tumor specimens obtained from de-identified pathology discards.

In these samples we established a correlative relationship between sensitivity of BC tumors to HSP90 inhibitors and expression of select biomarkers. The following phase would be to move forward and propose to use this for patient selection in the next trial. Once the scoring system is defined and validated, patient selection could ultimately be done on FFPE or CTCs to correlate the marker of interest with predicted response. Such diagnostic measures can then be introduced as common practice in selection of BC tumors more likely to respond to HSP90 therapy, in the same fashion HER2-scoring is used to guide patient selection for Trastuzumab therapy.

Test ex vivo the sensitivity of BC samples to PU-H71. Fresh tissue sections of BC patient tumors are exposed ex vivo to PU-H71 to assess the overall sensitivity of cancer cells and effect on normal cells (i.e. vessels, benign ducts if present in section). Concentrations of PU-H71 and exposure times are based on both prior in vitro and in vivo PK analyses with this agent, where it was determined that up to micromolar concentrations of PU-H71 are delivered to and retained into tumors at 24 h and 48 h post administration. Response are determined by one or two measures: 1. quantification in H&E stained samples of cells exhibiting morphologic changes indicative of apoptosis and 2. quantification of TUNEL-positive cells.

Patient tissue procurement: pathology discards from de-identified samples and needle core biopsies during HSP90 inhibitor trials are obtained in accordance with the guidelines and approval of the Institutional Review Board. The freshly procured tissue will be used immediately.

Ex vivo sensitivity examination: Immediately following surgical removal of the mastectomy specimen the tissue is transported to the Tissue Procurement Services (TPS) area of the Pathology suite. Once the lesion is located, tissue is harvested under sterile conditions. The specimen size removed for evaluation is typically 5-10 mm×5-10 mm. Every effort is made to sample the most viable area. Distant from the lesion, a specimen of equivalent size is removed representative of normal breast epithelial tissue. Both specimens are placed in minimal essential media (MEM) with 1% penicillin/streptomycin. A small portion of the lesion and the entire piece of normal breast epithelial tissue undergo a "snap" freeze for future molecular evaluation by WB. The remaining portion of the lesion (mastectomy) is processed for pathological evaluation. For every lesion pathology provides IHC for receptor status, proliferation markers, epithelial markers and one hematoxylin/eosin (H&E) stained slide accompanied by 10 unstained to be further assessed for non-standard biomarkers (e.g. pAKT, BclxL, HSP90 and Hsp70).

From preliminary analyses we have learned that fresh tissue slicing provides a quick and more efficient ex vivo method for HSP90 inhibition evaluation than primary cell isolation. In addition, it preserves the cancer cells in the endogenous environment of the surrounding tissue. This is important since the interaction between stromal cells and tumor cells is known to play a major role in cancer growth and progression. In this method, the tissue (i.e. lesion) is placed in a plastic mold and embedded in 6% agarose. The agarose-embedded tissue is then mounted on the stage of the Vibratome that is submersed in a chilled reservoir (for tissue preservation) containing MEM with 1% penicillin/streptomycin. The tissue is then sliced using metal blades producing serial sections of the lesion that are 200 μm thick. Each section (minus the surrounding agarose-embedding media) is immediately placed in a 24-well tissue culture plate containing MEM with 1% penicillin/streptomycin. From a 5 mm×5 mm piece of tissue approximately 25 sections are produced. This allows for replicate analyses of tissue sections treated with a minimum of 4 doses of the HSP90 inhibitor and one with vehicle only. Replicates can be assayed by both IHC as well as viability assays (automatic plate reader or cytospin preparation) once tissue section undergoes enzymatic dissociation by brief exposure to dispase.

To date, forty-two specimens encompassing all BC subtypes have been acquired. Out of these, nine were of receptor status negative. Both primary tumors (PT) and lymph node metastases (LN) (if present) have been assessed where "fresh tissue sections" 200 um thick were exposed to increasing doses of PU-H71. Treatment of triple negative infiltrating ductal carcinoma (IDC) with PU-H71 attained, in a dose-dependent manner, apoptosis of both the primary tumors and lymph node metastases. Interestingly, LN mets appear more sensitive to PU-H71 than the corresponding PT. Most significantly, normal (e.g. vessels, lymphocytes) and benign (e.g. ducts, lobules) tissue remained unaltered following a 48 hour exposure to PU-H71. Data show a clustering of the TNBC cases in 4 distinct sensitivity groups: very sensitive, with 100% apoptosis noted at 0.5 uM PU-H71 (top curve, FIG. 40A), sensitive with 100% apoptosis at 1 uM PU-H71 (middle curve, FIG. 40A), partly resistant with ~50% apoptosis noted at 1-2.5 uM (bottom curve, FIG. 40A) and resistant (PT #14, no apoptosis noted at any of the tested concentrations, not shown).

As noted in FIG. 40B, several tumors are more sensitive to HSP90 inhibition than predicted from the preliminary data generated on cell lines. Specifically, while MDA-MB-468 is one of the most sensitive breast cancer cell line (Caldas et al PNAS 2009), the studies presented in this invention show that tumor cells of much higher sensitivity to PU-H71 can be found in primary specimens obtained from human breast cancer patients. Specifically, while a 48 h treatment of 0.5 μM PU-H71 is required in the MDA-MB-468 cells to observe about 50% of them undergoing apoptosis, we find that for several HER2+, triple-negative and ER+ breast cancers, concentrations as low as 0.05 μM induce a similar effect. In addition, while a 48 h treatment of about 5 μM PU-H71 is required in the MDA-MB-468 cells to observe about 100% of them undergoing apoptosis (FIG. 32B), we find that for several HER2+, triple-negative and ER+ breast cancers, concentrations as low as 0.5 μM induce a similar effect. Such studies provide information on the required tumor concentrations of PU-H71 that are expected to provide a therapeutic effect.

Investigations in GI and pancreatic cancer resulted in similar findings.

5.4.1.1. Investigate the Expression of Proposed Biomarkers by IHC and WB, and Score Samples by Biomarker Expression.

IHC scores samples based on low to high expression of HSP90, Hsp70, p-Akt/Akt and Bcl-xL. Adequate negative controls are obtained by replacing the primary antibody with antibody dilution buffer. HSP90, p-Akt/Akt, Bcl-xL and Hsp70 staining intensity will be scored (2 times) for each specimen on a scale of 0 to 3, in which 0 represents negative-, 1 weakly positive-, 2 moderately positive-, and 3 strongly positive-staining While IHC alone could be somewhat problematic since scoring is often quite subjective, its use in parallel with a second method like Western blot will "train" and validate the IHC to make correlations with the ex vivo and in patient response. If the amount of protein obtained is not enough for the classic membrane-WB, the ultra-sensitive capillary-WB technology is used. A typical core needle biopsy specimen yields between 20 and 40 mg of tissue, which is sufficient for the proposed IHC, and potentially for capillary WB analyses. This information will be analyzed in the context of clinical response, guiding on the validity of the proposed scoring method. Namely, we will have the ability to correlate clinical response with response predicted by biomarker evaluation. Once the scoring system is defined and validated, patient selection could be ultimately done on FFPE to correlate the marker of interest with predicted response. Such diagnostic measure can then be introduced as common practice in selection of TNBC tumors more likely to respond to HSP90 therapy, in the same fashion as HER2-scoring is used to guide patient selection for Trastuzumab therapy.

For some patients, biopsies may not be possible, either due to an inaccessible tumor (deep internal metastasis) or no granted consent. For these cases, we will aim to probe whether circulating tumor cells (CTCs) harvested from the blood may be of informative value. Depending on the stage of the disease, for advanced-cancer patients, we expect to recover between 1,000 and 10,000 BC cells with this technique. This number of cells is enough for capillary-WB analysis of proteins (or real time qPCR analysis, if needed) and for scoring of HSP90, Hsp70, p-Akt and Bcl-xL expression by immunomagnetic enrichment then flow cytometry.

FIG. 40 shows that breast cancer tumors with activated Akt, as evidenced by high staining with phospho-Akt, Ser473, are also those very sensitive to HSP90 inhibition.

5.4.2. Determinants of Apoptotic Sensitivity to HSP90 Inhibition in Acute Myeloid Leukemia (AML)

Targeted therapies that are designed to induce apoptosis in leukemic cells are the most promising anti-leukemia strategies. We explored biomarkers predictive of apoptotic sensitivity to heat shock protein 90 (HSP90) therapy in AML. We found that addition of HSP90 inhibitors to a panel of genetically distinct AML cell lines potently inhibited cell growth and induced the degradation of several AML cell-specific onco-proteins such as mutant FLT3, TEL-TRKC, AML1-ETO, mutant c-KIT and mutant JAK2. Notably, the proclivity for these cells to undergo apoptosis upon HSP90 inhibition varied considerably. The most sensitive cell lines were MOLM-13, MV-4-11 and MO-91 cells, and for each of these cell lines we observed near 100% killing of the initial cell population after 48-72 h of HSP90 inhibitor treatment. In contrast, only 20% death was seen in HEL and HL-60 cells under these conditions. We next made use of specific inhibitors of known oncogenic signaling pathways known to be dysregulated in AML to demonstrate that apoptotic sensitivity of AML cells to HSP90 inhibition correlated with PI3K-Akt and STAT5 activation, but not with activation of the Raf-MAPK pathway. Importantly, similar results were observed in cells lines, xenograft models and isogenic cell line systems. We also found that dual activation of these two pathways, even in the context of Bcl-xL overexpression, lowers the apoptotic threshold of AML when HSP90 is inhibited. Taken together, our findings suggest that AML patients with activation of Akt and STAT5 signaling are most likely to benefit from HSP90 inhibitor therapy, and clinical trials should aim to enroll patients with specific activation of these important signaling pathways.

Importantly, 50-70% of patients with AML display phosphorylation of both Thr308 and Ser473 Akt. This molecule contributes to proliferation, survival and drug resistance in AML, and is associated with adverse outcome. Taken together, our findings suggest that AML patients with activation of AKT and STAT5 signaling are most likely to benefit from HSP90 inhibitor therapy, and clinical trials should aim to enroll patients with specific activation of these important signaling pathways.

5.4.2.1. HSP90 Inhibition Induces Cell-Type Specific Killing in AML Cell Lines

A number of chemically distinct small molecule HSP90 inhibitors have been reported, and several are in clinical or late-stage preclinical investigation (Chiosis et al., 2008). Among these are the ansamycin natural product derivatives 17-AAG and 17-DMAG, and the synthetic compounds CNF-2024 (BIIB021) and PU-H71, all in clinical evaluation, and PU-DZ13, a close derivative of PU-H71 in pre-clinical development.

To evaluate the sensitivity spectrum of AML cell lines to HSP90 inhibitors, and to investigate a possible relationship between their genetic background and induction of apoptosis by HSP90 therapy, we made use of a varied cell panel. Specifically, we chose Kasumi-1 and SKNO-1, cell lines that contain the AML1-ETO fusion and the mutated c-KIT (N822K) proteins; MOLM-13, a human cell line established from the peripheral blood of a patient at relapse of AML which had evolved from MDS, that contains both the MLL-AF9 fusion protein and the FLT3 ITD mutation; MO-91 that contains the TEL-TRKC fusion protein and also harbors a constitutively activated STAT5; and finally, HEL that contains the JAK2 V617F mutation. The HSP90 inhibitors potently inhibited, in a dose- and cell-dependent manner the growth of each tested AML cell line and also induced cell killing, with notable differences observed among the cell lines. Most sensitive were the MOLM-13 and MO-91 cells where 100% killing of the initial cell population was noted after 72 h, followed by Kasumi-1 and SKNO-1, with 50-80% and HEL with 20%. Normal peripheral blood leukocytes were unaffected at similar concentrations.

The ability of the distinct HSP90 inhibitors to kill the AML cell lines was similar, suggesting cytotoxicity of the compounds occurs through a common mechanism of action, namely HSP90 inhibition.

5.4.2.2 HSP90 Inhibition Induces Apoptosis in AML Cells

PU-H71 was thus chosen to further investigate the mechanisms accountable for AML cell-killing by HSP90 inhibitors. As evidenced by dual acridine orange/ethidium bromide staining, PARP cleavage and activation of caspase 3,7, cytotoxicity of PU-H71 in AML occurred mainly through induction of apoptosis. The number of cells undergoing apoptosis after 72 h of treatment with PU-H71, neared 100% for MOLM-13 and MO-91, 50-60% for SKNO-1 and Kasumi-1, and 30% for HEL, values in good agreement with the observed cell killing. A ten-fold, in MOLM-13 and MO-91, and two-fold, in Kasumi-1 and SKNO-1, increase in caspase-3,7 activation was observed as early as 24 h. Essentially no live cells were detected for the MO-91 cell line after 48 h of HSP90 inhibitor treatment. In the most sensitive cells, MOLM-13 and MO-91, apoptosis was associated with downregulation of the anti-apoptotic molecule Bcl-xL.

5.4.2.3. Inhibition of HSP90 Depletes Key AML Onco-Proteins but this Effect Fails to Correlate with Apoptotic Sensitivity The distinct apoptotic sensitivity of AML cell lines towards HSP90 inhibitors could be due to effective HSP90 inhibition in certain cell lines but ineffective in others. To test this hypothesis we evaluated the effect of PU-H71 on two proteins demonstrated to be HSP90-dependent in a majority of cancers, the RAF-1 and AKT kinases. The HSP90 inhibitor dose-dependently and markedly reduced the steady-state levels of these proteins in all the tested cells. This is in accord with the established mechanism whereby HSP90 is required for the stability and function of these kinases in cancer cells.

In addition to these "pan-cancer" HSP90 client proteins, PU-H71 also led to the degradation of specific leukomogenesis drivers, such as mutant FLT3 in MOLM-13, TEL-TRKC in MO-91, AML1-ETO and mutant cKIT in Kasumi-1 and SKNO-1, and mutant JAK2 in HEL (AML-cell specific HSP90 onco-clients). Mutant FLT3, cKIT and JAK2, and the fusion protein AML1-ETO were previously reported to be sensitive to HSP90 inhibition in AML or other transformed cells. The fusion protein TEL-TRKC however, is a novel client of HSP90, as indicated by our findings showing potent degradation of TEL-TRKC by PU-H71 in the MO-91 cell line.

Collectively, our findings indicate that the HSP90 inhibitors deplete AML cells of key malignancy driving proteins, including the 'two hits' postulated to be necessary events for leukemogenesis, but no correlation is evident between this effect and the ability of HSP90 inhibitors to induce apoptosis in AML cells.

5.4.2.4. Apoptotic Sensitivity to Inhibition of HSP90, PI3K/AKT and JAK/STAT Pathways Overlaps in AML Cells Because a relationship between the genetic make-up and the apoptotic sensitivity to HSP90 inhibition is not evident, a potential answer could lie in the functional differences that lead to an anti-apoptotic phenotype or in a differential expression of certain anti-apoptotic molecules among these cells. Three main pathways have been linked to regulation of apoptosis in AML: the PI3K/AKT/NFkB, the JAK/STAT and the ras/MAPK pathways. More importantly, HSP90 regulates several key molecules along these pathways, and inhibition of HSP90 can lead to combinatorial inhibition of these molecules, such as p-AKT, p-STAT and p-ERK.

To probe the significance of individual pathways to apoptosis in AML cell lines, we used specific small molecules, such as the Akt inhibitor VIII, a quinoxaline compound that potently and selectively inhibits Akt1/Akt2 activity (AKTi), the MAP kinase MEK inhibitor PD98059 (MEKi) and the pan-Jak inhibitor 2-(1,1-Dimethylethyl)-9-fluoro-3,6-dihydro-7H-benz[h]-imidaz[4,5-f]isoquinolin-7-one (JAKi)). We also expanded the AML cell pool by the addition of three additional lines: HL-60, a widely studied promyelocytic cell line positive for myc oncogene expression, THP-1, a cell line that came from the peripheral blood of a one-year old infant male with monocytic AML, and MV4-11, a cell line that contains a 4; 11 translocation and a FLT3 ITD mutation.

The number of apoptotic cells upon treatment with the AKT, JAK and MEK inhibitors (AKTi, JAKi and MEKi) and the HSP90 inhibitor PU-H71, was quantified at 24, 48 and 72 h following the addition of specific inhibitors. Modest or little induction of apoptosis ensued upon the addition of the MEK inhibitor. AKT and JAK inhibitors on the other hand, had variable but potent effects on apoptosis. Analysis of apoptosis indicated that cells sensitive to AKTi were also the ones most likely to apoptose when HSP90 was inhibited (slope=0.9023±0.09572), suggesting that apoptotic sensitivity to HSP90 inhibition potentially correlates with sensitivity to PI3K/AKT pathway inhibition in AML. The correlation between JAK/STAT pathway and HSP90 inhibition was also good (slope=0.8245±0.1490), although two cell lines, MV4-11 and THP-1 were clear outliners. These findings suggest that AML cell addiction for survival on either of or both the PI3K/AKT and JAK/STAT pathway correlates with and potentially dictates apoptotic sensitivity to HSP90 inhibition.

5.4.2.5. Kinetics and Potency of In Vivo Inhibition of AKT and STAT5 SP90 Inhibition Correlate with Tumor Apoptosis We next analyzed the pharmacodynamic effects of HSP90 inhibition in both HEL and MO-91 tumors xenografted in mice. Unlike the cultured cells, the use of the in vivo model allows real-time monitoring of HSP90-dependent pathways inhibition. Because pathways most dependent on HSP90 are also most sensitive to its pharmacologic inhibition, they remain inhibited by PU-H71 for the longest period of time in tumors. Accordingly, in the MO-91 tumors that harbor elevated p-AKT and p-STAT5, and appear addicted to the activation of both pathways, PU-H71 induced marked apoptosis. Apoptosis in MO-91 lasted for 96 h post-administration of one dose of PU-H71, mirroring the potent inhibition of both AKT and STAT. Highest level of cleaved PARP was observed in the interval of 12-72 h post-PU-H71 administration, when both p-AKT and p-STAT5 levels were reduced by 70 to 100% of the initial levels. The effect of PU-H71 on PARP declined by 96 h, when p-AKT, but not p-STAT5, recovered to baseline levels.

HEL xenografted tumors were less sensitive that MO-91 tumors to apoptosis induction by PU-H71. Under culture conditions, HEL cells express elevated p-STAT5, and inhibition of the JAK/STAT pathways by the JAKi or by PU-H71 commits 20-30% of cells to undergo apoptosis. The AKTi on the other hand, has little to no effect in these cells. Accordingly, limited PARP cleavage and caspase-3 activation is noted upon HSP90 inhibition in these cells.

Nonetheless, and in contrast to tissue culture, when xenografted in nude mice, HEL cells demonstrate low to moderate expression level of p-AKT. This is not surprising, as it was reported that AKT activity can be stimulated in AML cells by the environment, such as by cytokines, and in vivo tumors may be more addicted on AKT activity for survival because of stressors unique to tumor tissue, such as hypoxia, acidity and abnormal vascularization. Elevation of AKT activity in xenografted HEL cells appears to be necessary for tumor survival because PU-H71 induces markedly higher apoptosis in HEL tumors than in cultured HEL cells. As with MO-91 tumors, highest level of cleaved PARP was observed when both p-AKT and p-STAT5 levels were reduced by PU-H71 by 70 to 100% of the initial levels (in the interval of 12-48 h post-PU-H71 administration). Cleavage of PARP diminished significantly when p-AKT but not p-STAT5 recovered to baseline levels (72 h).

Collectively, our data suggest that the apoptotic activity of HSP90 inhibitors in AML correlates with and is a measure of downregulation of the activated p-AKT and p-STAT5 species. Besides p-Akt [i.e. Ser 473] the activation state of the Akt-pathway can be determined as a measure of the phosphorylation status of S6, s6k or mTOR, also downregulated by PU-H71 treatment. The observations also imply that additive addiction of AML cells to AKT and STAT-pathway activation also renders them more sensitive to HSP90 inhibition.

5.4.2.6. HSP90 Inhibition Induces Apoptosis in Cells Addicted for Survival on the PI3K/AKT and JAK/STAT Pathways To demonstrate this hypothesis we made use of FL5.12 isogenic cell lines. FL5.12 was derived as an interleukin-3 (IL-3)-dependent cell line with a functional JAK/STAT pathway and it has characteristic features of an early lymphocytic progenitor. Both the parental cells and the transfected cells express moderate-levels of active AKT and STAT5, as evidenced by AKT phosphorylation on Ser473 and STAT5 phosphorylation on Tyr694, respectively. The level of p-STAT5 but not p-AKT is dependent on the presence of IL-3. Introduction of a constitutively activated, myristoylated form of AKT (mAKT) under the control of a doxycycline (DOX)-inducible promoter further allows for the regulation of p-AKT levels in these cells. All together, these cells are a good isogenic model to evaluate the dependence of HSP90 inhibitor apoptotic sensitivity on activated AKT and STAT5-pathways.

When the mAKT-transfected cells were treated with the AKTi, an increase in apoptotic cells from 5-7% to 15-20% was noted. This value reflects the contribution of the endogenous p-AKT to the survival of these cells. When AKT activity was increased by addition of DOX, cells became more addicted to AKT for survival and the AKTi led to 30% apoptotic cells (P=0.015).

When the mAKT-transfected cells were treated with the HSP90 inhibitor, approximately 35-40% apoptotic cells were detected. This value reflects the combined contribution of the endogenous p-AKT and p-STAT5 to the survival of these cells. Further increase in p-AKT levels by Dox, led to an increase in apoptotic cells from 35-40 to 50% upon PU-H71 addition.

Together these findings demonstrate that apoptotic sensitivity of AML cells to HSP90 inhibitors is a reflection of the cell's addiction for survival on the AKT and STAT-pathways.

5.4.2.7. Bcl-xL Overexpression Fails to Inhibit the Apoptotic Effect of HSP90 Inhibition in AML Constitutively high levels of Bcl-xL have been associated with resistance of leukemia cells to various categories of chemotherapeutic agents. We therefore investigated whether introduction of Bcl-xL would overcome dependence of the FL5.12 transfected cells for survival on AKT and STAT and would render them resistant to inhibition of these pathways by PU-H71. To investigate this hypothesis, we made use of FL5.12.mAKT cells stably transfected with an expression vector containing the apoptotic inhibitor Bcl-xL. These cells remain dependent on IL-3 for proliferation in vitro. In these cells, similar to MO-91 cells, a concomitant activation of STAT5 and AKT-pathways and overexpression of Bcl-xL is observed. As the case in MO-91, HSP90 inhibition by PU-H71 led to a reduction in the activity and steady-state levels of these proteins and retained its apoptotic effect.

5.4.2.8. Discussion

Despite of the large number of potential new agents entering clinical evaluation every year, only 5% to 8% ever reach registration. Of particular concern is the high rate of failures in Phase 3, where an estimated 50% of oncology agents are stopped in development. Such failures are especially expensive and deprive many patients of potentially more effective treatments. These dire statistics clearly speak for the need to discover and implement predictive biomarkers for patient selection and trial enrichment. Our study addresses this problem in AML and indicates that apoptotic sensitivity to HSP90 inhibition correlates with accumulative addiction of cells for survival on signaling pathways with anti-apoptotic roles. We identify activated Akt and STAT as major pathways in this regard.

AKT signaling is frequently activated in acute AML patient blasts and strongly contributes to proliferation, survival and drug resistance of these cells. From 50 to 70% of patients with AML display phosphorylation of both Thr308 and Ser473 AKT. Both the disease-free and the overall survival time for patients demonstrating AKT activation was significantly shorter when compared to patients with no AKT activation, collectively suggesting that AKT-inactivation may be a powerful strategy in AML. HSP90 regulates this pathway and several of its key elements, likely in a transformation-dependent manner. Accordingly, a significant correlation was observed between the expression of HSP90 and that of pAKT in primary acute myeloid leukemia (AML) cells, suggesting that HSP90 overexpression is necessary to the AML cell to buffer the increased activity and dependence of the cell on the AKT-pathway.

Constitutive STAT activation also occurs in approximately 70% of AML samples. STAT activation in AML cells has been associated with, but not restricted to, FLT3 ITDs and an autocrine stimulation of IL-6. However, other upstream modulators of STAT pathways may also be playing a role in the activation of STAT. Indeed, KIT mutations have also been found to activate JAK/STAT pathways. AML cases with high STAT5 and FLT3 phosphorylation demonstrated, in general, a lower percentage of spontaneous apoptosis, compared to AML blasts with no spontaneous STAT5 phosphorylation. Translocations involving JAK/STAT genes provide another link between STAT activation and leukemogenesis. The t(9; 12) translocation, which combines the oligomerization domain of the TEL gene with the catalytic domain of JAK2, has been found in both lymphocytic and myeloid leukemia. This translocation constitutively activates downstream effectors such as STAT5 and induces cytokine-independent growth in transfection models. As previously reported and also shown here, several of these STAT-activating proteins require HSP90 to facilitate their aberrant activity.

Taken together, addiction for survival of aggressive AML clones on several activating pathways and molecules, such as AKT and STAT5, renders them also most addicted to HSP90. HSP90 inhibition thus, becomes most effective in killing these cells. Our findings also suggest that concomitant overexpression of the anti-apoptotic Bcl-xL in the context of activated AKT and STAT5 does not significantly alter the sensitivity of these cells towards HSP90. Bcl-xL overexpression is a major contributor to drug resistance in AML. Overexpression of antiapoptotic proteins of the Bcl-2 family (Bcl-2, Bcl-x(L)) causes drug resistance to 122 "standard" chemotherapy agents and is associated with a worse clinical outcome in AML patients.

In conclusion, our findings suggest that AML patients with activation of AKT and STAT5 signaling are most likely to benefit from HSP90 inhibitor therapy (see FIGS. 41A-41C and 42A-42B) and clinical trials should aim to enroll patients with specific activation of these important signaling pathways. Our findings also suggest that introduction of HSP90 inhibitors is warranted in combination with other treatments in Bcl-xL overexpressing AMLs, as a means to lower their apoptotic threshold.

5.5. Use of Radiolabeled HSP90 Inhibitors to Select Neurodegenerative Patients Who Will be Susceptible to HSP90 Inhibition Therapy The use of radiolabeled HSP90 inhibitors to select patients who will be susceptible to HSP90 inhibition therapy was describes in Section 5.2.1. Similar methodology can be used to identify patients suffering from neurodegenerative diseases that are likely to respond to HSP90 therapy. Accordingly, the disclosure provides method for determining whether a patient suffering from a neurodegenerative disease will likely respond to therapy with an HSP90 inhibitor which comprises the following steps:

(a) contacting the brain with a radiolabeled HSP90 inhibitor which binds preferentially to a pathogenic form of HSP90 present in a brain cells of the patient;

(b) measuring the amount of labeled HSP90 inhibitor bound to the brain cells in the sample; and (c) comparing the amount of labeled HSP90 inhibitor bound to the brain cells in the sample measured in step (b) to a reference amount;

wherein a greater amount of labeled HSP90 inhibitor bound to the brain cells measured in step (b) as compared with the reference amount indicates the patient will likely respond to the HSP90 inhibitor.

In one embodiment the reference is from cells of the same patient with the neurodegenerative diseases. For instance, we have determined that normal neurons have little or no "pathogenic HSP90: Accordingly, the reference amount can be determined using normal neurons as the patient in a non-afflicted brain region. In another embodiment, the reference can be from cells of a healthy individual. In another embodiment, the reference amount can be measured from a study population of healthy individuals.

Both malignant transformation and neurodegeneration, as it occurs in Alzheimer's disease, Parkinson's, frontotemporal dementia and other dementias, spinal and bulbar muscular atrophy are complex and lengthy multistep processes characterized by abnormal expression, post-translational modification, and processing of certain proteins. To maintain and allow the accumulation of these dysregulated processes, and to facilitate the step-wise evolution of the disease phenotype, cells must co-opt a compensatory regulatory mechanism. In cancer, this role has been attributed to heat shock protein 90 (HSP90). In this sense, at the phenotypic level, HSP90 appears to serve as a biochemical buffer for the numerous cancer-specific lesions that are characteristic of diverse tumors. A similar role exists for HSP90 in neurodegeneration and thus the PET assay described in Section 5.2.1. can be used to identify the "pathogenic HSP90" in the diseased brain. The "pathogenic HSP90" in neurodegenerative disease plays a role similar to the "oncogenic HSP90" in cancer. The use of HSP90 inhibitors the treatment of neurodegenerative diseases is describe in U.S. Published Application No. 2009/0298857, which is hereby incorporated by reference.

As the HSP90 inhibitor PU-HZ151 shows high binding affinity to neurodegenerative brain HSP90, is capable of strongly inducing HSP70 levels, and is estimated to be brain permeable, we selected it for further in vivo evaluation. PU-HZ151 was described in WO 2008/005937 and it has the following chemical structure:

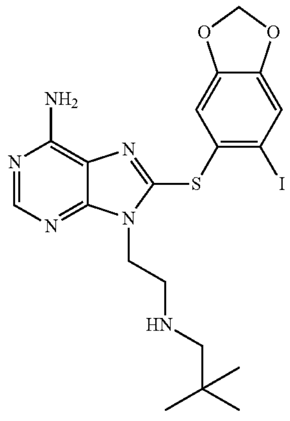

PU-HZ151

Indeed, when administered intraperitoneally to 3×Tg AD mice, PU-HZ151 resulted in significant target modulation as demonstrated by HSP70 induction in the hippocampus (FIG. 43A). The effect was dose dependent (FIG. 43B) with a significant induction of HSP70 detected at as low as the 10 mg/kg administered dose.

We next determined in the brain and plasma of 3×Tg AD mice, the HSP90 inhibitor levels associated with these pharmacodynamic effects (FIG. 43C). When administered intraperitoneally at 50 mg/kg to 3×Tg mice, PU-HZ151 levels in the cortex reached 3.3±0.9 μg/g (~5,000 nM) at 4 h, 0.05±0.08 μg/g (~170 nM) at 12 h, 0.02±0.03 sg/g (~60 nM) at 24 h and 0.02±0.02 μg/g (~53 nM) at 48 h post-administration. In comparison, PU-DZ8, a less effective HSP90 inhibitor, administered at a similar dose (75 mg/kg) reached a brain concentration of only 0.35 μg/g (~700 nM) at 4 h and 0.2 μg/g (~390 nM) at 12 h, and was undetected in the cortex by 24 hours post-administration.

In the plasma, PU-HZ151 reached 2.1±0.1 μg/g (~4,000 nM) at 4 h, but was undetectable beyond 8 h. The exposure of the cortex to PU-HZ151 over the interval of 0 to 48 h, as measured by the area under the curve (AUC), was 2.5-times higher than that of the plasma (17.5 versus 7.1 μM-h). The levels in the cerebellum (disease unaffected brain region in this model) paralleled those of plasma more closely than those recorded in the cortex (diseased brain region in this model). This observation is also supported by the extended retention of inhibitor PU-HZ151 to over 48 h post-administration in this brain region, findings similar to those obtained with inhibitors of this class, such as PU-H71, in tumors.

$^{124}$I-PU-HZ151 and other radiolabeled HSP90 inhibitors can therefore be used to select patients afflicted by an HSP90-dependent neurodegenerative disease and identify those more likely to benefit from such therapy. It can also be used in a fashion similar to PU-H71 in cancer, to determine the pathogenic brain exposure to the HSP90 inhibitor and determine an optimal dose and schedule of administration.

A person skilled in the art can appreciate that the uses described by this invention for PU-H71 in cancer can be achieved in neurodegenerative diseases as well with a radio-labeled, brain permeable HSP90 inhibitor.

6. MATERIALS AND METHODS

6.1. Synthetic Methods

6.1.1. Synthesis of Fluorescently Labeled Probes $^{1}$H NMR spectra were recorded on a Bruker 500 or 600 MHz instrument. Chemical shifts are reported in δ values in ppm downfield from TMS as the internal standard. $^{1}$H data are reported as follows: chemical shift, multiplicity (s=singlet, d=doublet, t=triplet, q=quartet, br=broad, m=multiplet), coupling constant (Hz), integration. High resolution mass spectra were recorded on a Waters LCT Premier system. Low resolution mass spectra were obtained on a Waters Acquity Ultra Performance LC with electrospray ionization and SQ detector. High-performance liquid chromatography analyses were performed on a Waters Autopurification system with PDA, MicroMass ZQ, and ELSD detector, and a reversed phase column (Waters X-Bridge C18, 4.6×150 mm, 5 μm) using a gradient of; method A (a) $H_2O$+0.1% TFA and (b) $CH_3CN$+0.1% TFA, 5 to 95% b over 10 minutes at 1.2 mL/min; method B (a) $H_2O$+0.1% TFA and (b) $CH_3CN$+0.1% TFA, 5 to 95% b over 13 minutes at 1.2 mL/min. Column chromatography was performed using 230-400 mesh silica gel (EMD). All reactions were performed under argon protection. Fluorescein isothiocyanate (FITC), sulforhodamine 101 sulfonyl chloride (Texas Red-Cl) and 4-chloro-7-nitro-1,2,3-benzoxadiazole (NBD-Cl) were purchased from Aldrich.

PU-H71-FITC1 [4] (Scheme 1). Compound 3[21] (15 mg, 0.0263 mmol), FITC (11.3 mg, 0.0289 mmol) and $Et_3N$ (0.1 mL) in DMF (0.2 mL) was stirred for 12 h at rt. The reaction mixture was concentrated under reduced pressure and the residue was purified by HPLC to give 10.1 mg (40%) of 4. $^{1}$H NMR (500 MHz, MeOH-$d_4$) δ 8.17 (s, 1H), 8.05 (s, 1H), 7.93 (s, 1H), 7.65-7.74 (m, 1H), 7.40 (s, 1H), 7.08-7.16 (m, 2H), 6.76-6.89 (m, 2H), 6.66 (s, 2H), 6.50-6.59 (m, 2H), 6.02 (s, 2H), 4.35 (t, J=6.9 Hz, 2H), 3.96 (t, J=6.4 Hz, 2H), 3.78 (br s, 2H), 3.62 (br s, 2H), 2.31 (m, 2H), 1.77 (m, 2H), 1.69 (m, 2H), 1.45 (m, 4H); HRMS (ESI) m/z $[M+H]^+$ calcd. for $C_{42}H_{40}IN_8O_7S_2$, 959.1506; found 959.1530; HPLC (method A) $R_t$=4.52 (96%).

PU-H71-Texas Red [5]. Compound 3[21] (4.6 mg, 0.008 mmol) in DMF (0.25 mL) was cooled to 0° C. by ice/water bath. Then sulforhodamine 101 sulfonyl chloride (3 mg, 0.005 mmol) was added and the solution was stirred for 12 h, allowing the temperature to slowly rise from 0 to 10° C. The reaction mixture was directly purified by HPLC to give 3.4 mg (61%) of 5 as a dark purple solid. $^{1}$H NMR (500 MHz, MeOH-$d_4$) δ 8.56 (d, J=1.4 Hz, 1H), 8.31 (s, 1H), 8.16 (dd, J=1.6, 7.9 Hz, 1H), 7.48 (s, 1H), 7.46 (d, J=7.9 Hz, 1H), 7.28 (s, 1H), 6.58 (s, 2H), 6.08 (s, 2H), 4.47 (t, J=6.8 Hz, 2H), 3.56 (t, J=5.4 Hz, 4H), 3.52 (t, J=5.6 Hz, 4H), 3.15 (t, J=7.6 Hz, 2H), 3.08 (m, 4H), 3.01 (t, J=7.7 Hz, 2H), 2.93 (t, J=6.7 Hz, 2H), 2.68 (m, 4H), 2.35 (m, 2H), 2.11 (m, 4H), 1.90-2.00 (m, 4H), 1.66 (m, 2H), 1.27-1.45 (m, 6H); HRMS (ESI) m/z $[M+H]^+$ calcd. for $C_{52}H_{57}IN_9O_8S_3$, 1158.2537; found 1158.2534; HPLC (method B) $R_t$=9.40 (99%).

PU-H71-NBD1 [8] (Scheme 1). Compound 6[21] (12.2 mg, 0.0229 mmol) and 7[22] (32 mg, 0.1145 mmol) were dissolved in DMF (0.4 mL) and stirred at rt for 20 h. Solvent was removed under reduced pressure and the resulting residue was purified by preparatory TLC ($CH_2Cl_2$:MeOH—$NH_3$ (7N), 10:1) to give 7.9 mg (47%) of 8. $^{1}$H NMR (500 MHz, $CDCl_3$/MeOH-$d_4$) δ 8.32 (d, J=8.8 Hz, 1H), 8.00 (s, 1H), 7.21 (s, 1H), 6.89 (s, 1H), 6.04 (d, J=8.8 Hz, 1H), 5.89 (s, 2H), 4.13 (t, J=6.9 Hz, 2H), 3.32 (m, 2H), 2.51 (t, J=6.9 Hz, 2H), 2.47 (t, J=7.4 Hz, 2H), 1.94 (m, 2H), 1.63 (m, 2H), 1.36-1.45 (m, 2H), 1.21-1.35 (m, 4H); HRMS (ESI) m/z $[M+H]^+$ calcd. for $C_{27}H_{30}IN_{10}O_5S$, 733.1166; found 733.1171; HPLC (method B) $R_t$=8.80 (98%).

PU-H71-FITC2 [9] (Scheme 2). Compound 2[23] (16.7 mg, 0.0326 mmol), FITC (14.0 mg, 0.0359 mmol) and $Et_3N$ (0.1 mL) in DMF (0.2 mL) was stirred for 5 h at rt. The reaction mixture was concentrated under reduced pressure and the residue was purified by HPLC to give 21.2 mg (72%) of 9. $^1H$ NMR (500 MHz, $CDCl_3$) δ 8.15 (s, 1H), 7.86 (s, 1H), 7.77 (d, J=7.9 Hz, 1H), 7.34 (s, 1H), 7.09 (d, J=7.9 Hz, 1H), 7.01 (s, 1H), 6.63-6.71 (m, 4H), 6.51 (d, J=7.3 Hz, 2H), 6.02 (s, 2H), 5.53 (br s, 2H), 4.30 (br s, 2H), 3.64 (br s, 2H), 2.85 (br s, 1H), 2.27 (m, 2H), 1.23 (d, J=6.2 Hz, 6H); HRMS (ESI) m/z $[M+H]^+$ calcd. for $C_{39}H_{33}IN_7O_7S_2$, 902.0928; found 902.0942; HPLC (method B) $R_t$=9.90 (99%).

PU-H71-NBD2 [10]. Compound 2[23] (25.4 mg, 0.050 mmol), NBD-Cl (10.0 mg, 0.05 mmol) and $Et_3N$ (7.6 µL, 0.055 mmol) in DMF (0.35 mL) was stirred for 12 h at rt. The reaction mixture was concentrated under reduced pressure and the residue was purified by preparatory TLC ($CH_2Cl_2$:MeOH—$NH_3$ (7N), 25:1) to give 13.4 mg (40%) of 10. $^1H$ NMR (600 MHz, $CDCl_3$/MeOH-$d_4$) δ 8.25 (d, J=8.9 Hz, 1H), 8.06 (s, 1H), 7.18 (s, 1H), 6.85 (s, 1H), 6.07 (d, J=8.9 Hz, 1H), 5.87 (s, 2H), 4.24 (t, J=6.9 Hz, 2H), 3.74 (m, 2H), 3.18 (m, 1H), 2.12 (m, 2H), 1.22 (d, J=6.5 Hz, 6H); HRMS (ESI) m/z $[M+H]^+$ calcd. for $C_{24}H_{23}IN_9O_5S$, 676.0588; found 676.0593; HPLC (method B) $R_t$=10.37 (99%).

2-(3-(6-amino-8-(6-iodobenzo[d][1,3]dioxol-5-ylthio)-9H-purin-9-yl)propyl)isoindoline-1,3-dione [12] (Scheme 3). 50 mg (0.121 mmol) of Compound 11[23] was dissolved in DMF (2 mL). 43.4 mg (0.1331 mmol) of $C_{52}CO_3$ and 162 mg (0.605 mmol) of N-(3-bromopropyl)-phthalimide were added and the mixture was stirred at rt for 30 minutes. Then additional $C_{52}CO_3$ (8 mg, 0.0242 mmol) was added and the mixture was stirred for 30 minutes. Then additional $C_{52}CO_3$ (8 mg, 0.0242 mmol) was added and the mixture was stirred for 30 minutes. Solvent was removed under reduced pressure and the resulting residue was purified by preparatory TLC ($CH_2Cl_2$:MeOH:AcOH, 15:1:0.5) to give 25 mg (34%) of 12. $^1H$ NMR (500 MHz, $CDCl_3$) δ 8.25 (s, 1H), 7.85 (dd, J=3.0, 5.5 Hz, 2H), 7.74 (dd, J=3.0, 5.4 Hz, 2H), 7.11 (s, 1H), 6.80 (s, 1H), 6.10 (br s, 2H), 6.00 (s, 2H), 4.27 (t, J=7.6 Hz, 2H), 3.77 (t, J=6.7 Hz, 2H), 2.15 (m, 2H); HRMS (ESI) m/z $[M+H]^+$ calcd. for $C_{23}H_{18}IN_6O_4S$, 601.0155; found 601.0169; HPLC (method A) $R_t$=7.74.

9-(3-aminopropyl)-8-(6-iodobenzo[d][1,3]dioxol-5-ylthio)-9H-purin-6-amine [13](Scheme 3). To a suspension of Compound 12 (34 mg, 0.0566 mmol) in MeOH/$CH_2Cl_2$ (0.7:0.1 mL) was added hydrazine hydrate (41 µL, 42.5 mg, 0.849 mmol) and the mixture was stirred at rt for overnight. Solvent was removed under reduced pressure and the resulting residue was purified by preparatory TLC ($CH_2Cl_2$:MeOH—$NH_3$ (7N), 10:1) to give 17 mg (64%) of 13. $^1H$ NMR (500 MHz, $CDCl_3$/MeOH-$d_4$) δ 8.22 (s, 1H), 7.38 (s, 1H), 7.06 (s, 1H), 6.05 (s, 2H), 4.31 (t, J=6.9 Hz, 2H), 2.76 (t, J=6.6 Hz, 2H), 2.05 (m, 2H); HRMS (ESI) m/z $[M+H]^+$ calcd. for $C_{15}H_{16}IN_6O_2S$, 471.0100; found 471.0086; HPLC (method A) $R_t$=5.78.

PU-H71-FITC3 [14] (Scheme 3). Compound 13 (8.4 mg, 0.0179 mmol), FITC (7.7 mg, 0.0196 mmol) and $Et_3N$ (0.1 mL) in DMF (0.2 mL) was stirred for 12 h at rt. The reaction mixture was concentrated under reduced pressure and the residue was purified by HPLC to give 11.4 mg (74%) of 14. $^1H$ NMR (600 MHz, MeOH-$d_4$) δ 8.23 (s, 1H), 8.11 (s, 1H), 7.68 (d, J=8.0 Hz, 1H), 7.35 (s, 1H), 7.20 (s, 1H), 7.09 (d, J=8.0 Hz, 1H), 6.63-6.70 (m, 4H), 6.50 (d, J=8.3 Hz, 2H), 5.97 (s, 2H), 4.34 (t, J=6.5 Hz, 2H), 3.61 (m, 2H), 2.21 (t, J=6.5 Hz, 2H); MS (ESI) m/z 860.1 $[M+H]^+$; HRMS (ESI) m/z $[M+H]^+$ calcd. for $C_{36}H_{27}IN_7O_7S_2$, 860.0458; found 860.0451; HPLC (method B) $R_t$=9.48 (96%).

PU-H71-NBD3 [15] (Scheme 3). Compound 13 (7.2 mg, 0.0153 mmol), NBD-Cl (3.1 mg, 0.0213 mmol) and $Et_3N$ (2.3 µL, 0.0168 mmol) in DMF (0.2 mL) was stirred for 12 h at rt. The reaction mixture was concentrated under reduced pressure and the residue was purified by preparatory TLC ($CH_2Cl_2$:MeOH—$NH_3$ (7N), 20:1) to give 4.1 mg (42%) of 15. $^1H$ NMR (600 MHz, DMF-$d_7$) δ 9.54 (br s, 1H), 8.53 (d, J=8.8 Hz, 1H), 8.22 (s, 1H), 7.51 (br s, 2H), 7.28 (s, 1H), 6.76 (s, 1H), 6.42 (d, J=7.9 Hz, 1H), 6.10 (s, 2H), 4.47 (t, J=7.0 Hz, 2H), 3.67 (m, 2H), 2.35 (m, 2H); HRMS (ESI) m/z $[M+H]^+$ calcd. for $C_{21}H_{17}IN_9O_5S$, 634.0118; found 634.0130; HPLC (method B) $R_t$=9.57 (99%).

Synthesis of tetraethylene glycol-FITC (TEG-FITC). FITC (20 mg, 0.051 mmol), tetraethylene glycol (49.9 mg, 0.257 mmol) and $Et_3N$ (0.1 mL) in DMF (0.4 mL) was stirred for 12 h at rt. The reaction mixture was concentrated under reduced pressure and the residue was purified by HPLC to give 17.3 mg (58%) of TEG-FITC. $^1H$ NMR (600 MHz, MeOH-$d_4$) δ 7.53-8.25 (m, 2H), 7.14 (d, J=8.2 Hz, 1H), 6.72-6.91 (m, 4H), 6.65 (d, J=6.8 Hz, 2H), 4.60 (br s, 2H), 3.77 (m, 2H), 3.31-3.63 (m, 12H); HRMS (ESI) m/z $[M+H]^+$ calcd. for $C_{29}H_{30}NO_{10}S$, 584.1590; found 584.1570; HPLC (method B) $R_t$=8.97 (99%).

2-(4-(6-Amino-8-((6-iodobenzo[d][1,3]dioxol-5-yl)thio)-9H-purin-9-yl)butyl)isoindoline-1,3-dione (16a) (Scheme 4). 200 mg (0.484 mmol) of Compound 11 was dissolved in DMF (8 mL). 466 mg (1.43 mmol) of $Cs_2CO_3$ and 683 mg (2.42 mmol) of N-(4-bromobutyl)phthalimide were added and the mixture was sonicated for 30 min. 31.5 mg (0.097 mmol) of $Cs_2CO_3$ was added and the mixture was again sonicated for 30 min. This was repeated two more times for a total reaction time of 2 h. DMF was removed and the resulting residue was purified by preparatory TLC ($CH_2Cl_2$:MeOH:AcOH, 15:1:0.5) to give 134 mg (45%) of Compound 16a. $^1H$ NMR (500 MHz, $CDCl_3$) δ 8.18 (s, 1H), 7.84 (dd, J=5.5, 3.1 Hz, 2H), 7.72 (dd, J=5.5, 3.1 Hz, 2H), 7.22 (s, 1H), 6.89 (s, 1H), 6.76 (br s, 2H), 5.99 (s, 2H), 4.23 (t, J=7.1 Hz, 2H), 3.69 (t, J=7.0 Hz, 2H), 1.67-1.83 (m, 4H); MS (ESI) m/z 615.2 $[M+H]^+$.

9-(4-Aminobutyl)-8-((6-iodobenzo[d][1,3]dioxol-5-yl)thio)-9H-purin-6-amine (17a) (Scheme 4). To a suspension of Compound 16a (38.9 mg, 0.063 mmol) in 2 mL MeOH/$CH_2Cl_2$ (7:1 mL) was added hydrazine hydrate (46 µL, 0.950 mmol) and the mixture was stirred at rt for 12 h. Solvent was removed under reduced pressure and the resulting residue was purified by preparatory TLC ($CH_2Cl_2$:MeOH—$NH_3$ (7N), 10:1) to give 18 mg (59%) of Compound 17a. $^1H$ NMR (500 MHz, $CDCl_3$/MeOH-$d_4$) δ 8.22 (s, 1H), 7.38 (s, 1H), 7.04 (s, 1H), 6.05 (s, 2H), 4.23 (t, J=7.4 Hz, 2H), 2.78 (t, J=7.1 Hz, 2H), 1.82-1.91 (m, 2H), 1.55-1.63 (m, 2H); MS (ESI) m/z 485.0 $[M+H]^+$.

PU-H71-FITC4 (18a) (Scheme 4): Compound 17a (9.7 mg, 0.020 mmol), FITC (8.57 mg (0.022 mmol) and $Et_3N$ (0.1 mL) in DMF (0.2 mL) was stirred for 3 h at rt. The reaction mixture was directly purified by HPLC to give 5.2 mg (30%) of Compound 18a. $^1H$ NMR (600 MHz, MeOH-$d_4$) δ 8.22 (s, 1H), 8.00 (s, 1H), 7.61 (d, J=7.6 Hz, 1H), 7.37 (s, 1H), 7.19 (s, 1H), 7.06 (d, J=8.2 Hz, 1H), 6.58-6.67 (m, 4H), 6.48 (dd, J=8.7, 2.0 Hz, 2H), 5.97 (s, 2H), 4.30 (t, J=7.0 Hz, 2H), 3.58 (br s, 2H), 1.90-2.00 (m, 2H), 1.61-1.70 (m, 2H); HRMS (ESI) m/z $[M+H]^+$ calcd. for $C_{37}H_{29}IN_7O_7S_2$, 874.0615; found 874.0610; HPLC $R_t$=9.57 (98%).

2-(6-(6-Amino-8-((6-iodobenzo[d][1,3]dioxol-5-yl)thio)-9H-purin-9-yl)hexyl)isoindoline-1,3-dione (16b) (Scheme 4). 200 mg (0.484 mmol) of Compound 11 was dissolved in DMF (8 mL). 466 mg (1.43 mmol) of $Cs_2CO_3$ and 751 mg (2.42 mmol) N-(6-bromohexyl)phthalimide were added and the mixture was sonicated for 2 h. Solvent was removed under reduced pressure and the resulting residue was purified by preparatory TLC ($CH_2Cl_2$:MeOH:AcOH, 15:1:0.5) to give 100 mg (32%) of Compound 16b. $^1H$ NMR (500 MHz, $CDCl_3$) δ 8.26 (s, 1H), 7.83 (dd, J=5.4, 3.1 Hz, 2H), 7.70 (dd, J=5.4, 3.0 Hz, 2H), 7.26 (s, 1H), 6.87 (s, 1H), 6.36 (br s, 2H), 5.96 (s, 2H), 4.18 (t, J=7.5 Hz, 2H), 3.66 (t, J=7.2 Hz, 2H), 1.70-1.79 (m, 2H), 1.60-1.68 (m, 2H), 1.32-1.43 (m, 4H); MS (ESI) m/z 643.2 $[M+H]^+$.

9-(6-Aminohexyl)-8-((6-iodobenzo[d][1,3]dioxol-5-yl)thio)-9H-purin-6-amine (17b) (Scheme 4). To a suspension of Compound 16b (97 mg, 0.1511 mmol) in 4 mL MeOH/$CH_2Cl_2$ (7:1 mL) was added hydrazine hydrate (110 μL, 2.27 mmol) and the mixture was stirred at rt for 12 h. Solvent was removed under reduced pressure and the resulting residue was purified by preparatory TLC ($CH_2Cl_2$:MeOH—$NH_3$ (7N), 10:1) to give 47 mg (61%) of 17b. $^1H$ NMR (500 MHz, $CDCl_3$) δ 8.32 (s, 1H), 7.31 (s, 1H), 6.90 (s, 1H), 5.99 (s, 2H), 5.84 (br s, 2H), 4.20 (t, J=7.5 Hz, 2H), 2.67 (t, J=6.5 Hz, 2H), 1.72-1.84 (m, 2H), 1.31-1.45 (m, 6H); MS (ESI) m/z 513.0 $[M+H]^+$.

PU-H71-FITC5 (Compound 18b) (Scheme 4). Compound 17b (9.7 mg, 0.01894 mmol), FITC (8.11 mg, 0.0208 mmol) and $Et_3N$ (0.1 mL) in DMF (0.2 mL) was stirred for 3 h at rt. The reaction mixture was directly purified by HPLC to give 8.0 mg (47%) of Compound 18b. $^1H$ NMR (600 MHz, MeOH-$d_4$) δ 8.23 (s, 1H), 8.09 (s, 1H), 7.65 (d, J=7.9 Hz, 1H), 7.35 (s, 1H), 7.16 (s, 1H), 7.08 (d, J=8.3 Hz, 1H), 6.71 (d, J=8.8 Hz, 2H), 6.67 (d, J=2.2 Hz, 2H), 6.53 (dd, J=8.8, 2.2 Hz, 2H), 5.96 (s, 2H), 4.24 (t, J=7.1 Hz, 2H), 3.50 (br s, 2H), 1.79-1.88 (m, 2H), 1.52-1.61 (m, 2H), 1.31-1.42 (m, 4H); HRMS (ESI) m/z $[M+H]^+$ calcd. for $C_{39}H_{33}IN_7O_7S_2$, 902.0928; found 902.0939; HPLC 1=10.02 (99%).

2-(8-(6-Amino-8-((6-iodobenzo[d][1,3]dioxol-5-yl)thio)-9H-purin-9-yl)octyl)isoindoline-1,3-dione (16c) (Scheme 4). 200 mg (0.484 mmol) of Compound 11 was dissolved in DMF (8 mL). 466 mg (1.43 mmol) of $Cs_2CO_3$ and 819 mg (2.42 mmol) N-(8-bromooctyl)phthalimide were added and the mixture was sonicated for 1.5 h. Solvent was removed under reduced pressure and the resulting residue was purified by preparatory TLC ($CH_2Cl_2$:MeOH:AcOH, 15:1:0.5) to give 120 mg (34%) of Compound 16c. $^1H$ NMR (500 MHz, $CDCl_3$) δ 8.29 (s, 1H), 7.84 (dd, J=5.5, 3.1 Hz, 2H), 7.70 (dd, J=5.5, 3.1 Hz, 2H), 7.28 (s, 1H), 6.87 (s, 1H), 6.29 (br s, 2H), 5.96 (s, 2H), 4.18 (t, J=7.5 Hz, 2H), 3.67 (t, J=7.3 Hz, 2H), 1.62-1.77 (m, 4H), 1.25-1.36 (m, 8H); MS (ESI) m/z 671.3 $[M+H]^+$.

9-(8-Aminooctyl)-8-((6-iodobenzo[d][1,3]dioxol-5-yl)thio)-9H-purin-6-amine (17c). To a suspension of Compound 16c (90.1 mg, 0.1345 mmol) in 4 mL MeOH/$CH_2Cl_2$ (7:1 mL) was added hydrazine hydrate (98 μL, 2.017 mmol) and the mixture was stirred at rt for 12 h. Solvent was removed under reduced pressure and the resulting residue was purified by preparatory TLC ($CH_2Cl_2$:MeOH—$NH_3$ (7N), 10:1) to give 25 mg (34%) of 17c. $^1H$ NMR (500 MHz, $CDCl_3$) δ 8.33 (s, 1H), 7.31 (s, 1H), 6.90 (s, 1H), 5.99 (s, 2H), 5.72 (br s, 2H), 4.20 (t, J=7.5 Hz, 2H), 2.66 (t, J=7.1 Hz, 2H), 1.70-1.80 (m, 2H), 1.36-1.45 (m, 2H), 1.21-1.35 (m, 8H); MS (ESI) m/z 541.1 $[M+H]^+$.

Synthesis of PU-H71-FITC6 (Compound 18c) (Scheme 4): Compound 17c (15.0 mg, 0.028 mmol), FITC (11.9 mg, 0.031 mmol) and $Et_3N$ (0.1 mL) in DMF (0.2 mL) was stirred for 4 h at rt. The reaction mixture was directly purified by HPLC to give 16.9 mg (66%) of Compound 18c. $^1H$ NMR (600 MHz, MeOH-$d_4$) δ 8.22 (s, 1H), 8.11 (s, 1H), 7.68 (d, J=7.8 Hz, 1H), 7.34 (s, 1H), 7.12 (s, 1H), 7.09 (d, J=8.2 Hz, 1H), 6.72 (d, J=8.7 Hz, 2H), 6.67 (d, J=2.0 Hz, 2H), 6.53 (dd, J=8.7, 2.0 Hz, 2H), 5.96 (s, 2H), 4.20 (t, J=7.1 Hz, 2H), 3.50 (br s, 2H), 1.74-1.81 (m, 2H), 1.52-1.59 (m, 2H), 1.23-1.35 (m, 8H); HRMS (ESI) m/z $[M+H]^+$ calcd. for $C_{41}H_{37}IN_7O_7S_2$, 930.1241; found 930.1231; HPLC $R_t$=10.60 (96%).

Synthesis of PU-FITC7 (Compound 20) (Scheme 7). Compound 19 (15.0 mg, 0.025 mmol), FITC (10.7 mg, 0.0275 mmol) and $Et_3N$ (0.1 mL) in DMF (0.3 mL) was stirred for 8 h at rt. The reaction mixture was directly purified by HPLC to give 23.5 mg (95%) of PU-FITC7. $^1H$ NMR (600 MHz, MeOH-$d_4$, 2 rotamers) δ 8.18-8.22 (m, 1H), 7.75-7.87 (m, 4H), 7.53-7.58 (m, 1H), 7.19-7.23 (m, 1H), 7.05 (d, J=8.2 Hz, 1H), 6.98 (s, 0.15H), 6.95 (s, 0.85H), 6.57-6.75 (m, 4H), 6.46-6.55 (m, 2H), 6.05 (s, 0.3H), 6.00 (s, 1.7H), 3.95-4.05 (m, 2H), 3.55-3.64 (m, 1.7H), 2.86-2.92 (m, 0.3H), 2.03-2.12 (m, 1.7H), 1.93-2.00 (m, 0.3H), 1.18 (d, J=6.5 Hz, 0.9H), 1.13 (d, J=6.5 Hz, 5.1H); HRMS (ESI) m/z $[M+H]^+$ calcd. for $C_{47}H_{36}F_6N_7O_7S_2$, 988.2022; found 988.2005; HPLC $R_t$=11.00 (99%).

Synthesis of PU-FITC8 (Compound 22) (Scheme 8): Compound 21 (19.4 mg, 0.050 mmol), FITC (21.4 mg, 0.055 mmol) and $Et_3N$ (0.1 mL) in DMF (0.4 mL) was stirred for 14 h at rt. The reaction mixture was directly purified by HPLC to give 34.3 mg (88%) of PU-FITC8. $^1H$ NMR (600 MHz, MeOH-$d_4$) δ 8.35 (s, 1H), 7.97 (s, 1H), 7.69 (dd, J=8.2, 1.9 Hz, 1H), 7.20 (dd, J=8.1, 1.9 Hz, 1H), 7.14-7.18 (m, 2H), 6.91 (d, J=8.0 Hz, 1H), 6.76-6.85 (m, 4H), 6.59-6.65 (m, 2H), 6.01 (s, 2H), 4.40 (t, J=6.7 Hz, 2H), 3.82 (t, J=7.4 Hz, 2H), 2.35-2.43 (m, 2H), 1.31 (d, J=6.7 Hz, 6H); HRMS (ESI) m/z $[M+H]^+$ calcd. for $C_{39}H_{34}N_7O_7S_2$, 776.1961; found 776.1978; HPLC $R_t$=10.13 (98%).

Synthesis of PU-FITC9 (Compound 24) (Scheme 9): Compound 23 (10.0 mg, 0.032 mmol), FITC (13.9 mg, 0.036 mmol) and $Et_3N$ (0.1 mL) in DMF (0.3 mL) was stirred at rt for overnight. The reaction mixture was directly purified by HPLC to give 18.3 mg (82%) of PU-FITC9. $^1H$ NMR (600 MHz, MeOH-$d_4$) δ 8.33 (s, 1H), 7.92 (s, 1H), 7.66 (dd, J=8.1, 1.8 Hz, 1H), 7.15 (d, J=8.2 Hz, 1H), 6.73-6.83 (m, 4H), 6.58-6.65 (m, 2H), 4.73-4.76 (m, 2H), 4.23 (t, J=6.5 Hz, 2H), 3.81-3.85 (m, 2H), 3.74-3.81 (m, 2H), 3.41 (s, 3H), 2.28-2.37 (m, 2H), 1.30 (d, J=6.6 Hz, 6H); HRMS (ESI) m/z $[M+H]^+$ calcd. for $C_{35}H_{36}N_7O_7S$, 698.2397; found 698.2399; HPLC $R_t$=9.20 (99%).

Synthesis of DZ13-FITC1 (Scheme 10). PU-DZ13 (20.8 mg, 0.0406 mmol), FITC (17.4 mg, 0.0447 mmol) and $Et_3N$ (0.1 mL) in DMF (0.3 mL) was stirred for 12 h at rt. The reaction mixture was directly purified by HPLC to give 33.7 mg (92%) of DZ13-FITC1. $^1H$ NMR (500 MHz, DMF-$d_7$) δ 9.46 (s, 1H), 8.05 (dd, J=7.0, 1.8 Hz, 1H), 7.76-7.82 (m, 1H), 7.44 (s, 1H), 7.26 (d, J=7.3 Hz, 1H), 6.90 (s, 1H), 6.78 (m, 2H), 6.67-6.72 (m, 4H), 6.11 (s, 2H), 4.59 (t, J=6.0 Hz, 2H), 4.42 (s, 2H), 4.39 (t, J=6.0 Hz, 2H), 3.53 (d, J=6.9 Hz, 2H), 2.17-2.28 (m, 1H), 0.92 (d, J=6.7 Hz, 6H); HRMS (ESI) m/z $[M+H]^+$ calcd. for $C_{40}H_{34}FIN_7O_7S$, 902.1269; found 902.1293; HPLC $R_t$=11.77 (98%).

Synthesis of SNX-FITC (Scheme 11). Compound 25 (9.5 mg, 0.0205 mmol), FITC (8.8 mg, 0.0225 mmol) and $Et_3N$ (0.1 mL) in DMF (0.2 mL) was stirred for 4 h at rt. The reaction mixture was concentrated under reduced pressure and the residue was purified by HPLC to give 13.5 mg (77%) of an orange solid. RMS (ESI) m/z $[M+HH]^+$ calcd. for $C_{44}H_{40}F_3N_6O_7S$, 853.2631; found 853.2630.

6.1.2. Synthesis of Biotinylated Compounds

PU-H71-biotin3. 13 (9.1 mg, 0.0193 mmol), D-biotin (7.1 mg, 0.0290 mmol), DCC (8 mg, 0.0386 mmol) and a catalytic amount of DMAP in $CH_2Cl_2$ (1 mL) was sonicated for 5 h. The reaction mixture was concentrated under reduced pressure and the resulting residue was purified by preparatory TLC ($CH_2Cl_2$:MeOH—$NH_3$ (7N), 10:1) to give 7.5 mg (56%) of PU-H71-biotin3. $^1$H NMR (600 MHz, $CDCl_3$/MeOH-$d_4$) δ 7.97 (s, 1H), 7.17 (s, 1H), 6.86 (s, 1H), 5.84 (s, 2H), 4.23-4.27 (m, 1H), 4.05-4.09 (m, 1H), 4.03 (t, J=7.2 Hz, 2H), 3.02 (t, J=6.4 Hz, 2H), 2.90-2.97 (m, 1H), 2.67 (dd, J=4.9, 12.8 Hz, 1H), 2.49 (d, J=12.8 Hz, 1H), 2.01 (t, J=7.5 Hz, 2H), 1.75-1.83 (m, 2H), 1.34-1.54 (m, 4H), 1.18-1.27 (m, 2H); MS (ESI): m/z 697.1 $[M+H]^+$.

PU-H71-biotin2. 2 (30 mg, 0.059 mmol), D-biotin (19 mg, 0.078 mmol), DCC (24 mg, 0.117 mmol) and a catalytic amount of DMAP in $CH_2Cl_2$ (1 mL) was sonicated for 9 h. The reaction mixture was concentrated under reduced pressure and the resulting residue was purified by preparatory TLC ($CH_2Cl_2$:MeOH—$NH_3$ (7N), 10:1) to give 43.2 mg (99%) of PU-H71-biotin2. $^1$H NMR (600 MHz, $CDCl_3$, 2 rotamers) δ 8.22 (s, 1H), 7.22 (s, 0.6H), 7.21 (s, 0.4H), 6.87 (s, 0.6H), 6.76 (s, 0.4H), 6.25 (br s, 0.6H), 6.16 (br s, 0.4H), 5.88-5.96 (m, 2H), 5.85 (br s, 0.6H), 5.78 (br s, 0.4H), 4.54-4.63 (m, 0.6H), 4.32-4.45 (m, 1.6H), 4.21-4.25 (m, 0.4H), 4.11-4.19 (m, 1.4H), 4.00-4.07 (m, 0.6H), 3.88-3.95 (m, 0.4H), 2.97-3.22 (m, 2.4H), 2.78-2.84 (m, 1H), 2.69-2.77 (m, 0.6H), 2.62-2.68 (m, 1H), 2.22-2.27 (m, 0.6H), 1.94-2.05 (m, 1.4H), 1.74-1.89 (m, 1.4H), 1.43-1.72 (m, 3H), 1.16-1.40 (m, 3.6H), 1.00-1.06 (m, 4H), 0.97 (d, J=6.7 Hz, 2H); MS (ESI): m/z 739.2 $[M+H]^+$.

PU-H71-biotin4. 13 (16.9 mg, 0.0359 mmol), EZ-Link® NHS-LC-Biotin (17.9 mg, 0.0394 mmol) and DIEA (9.3 mg, 12.5 μL, 0.0718 mmol) in DMF (0.5 mL) was stirred at rt for 1 h. The reaction mixture was concentrated under reduced pressure and the resulting residue was purified by preparatory TLC ($CH_2Cl_2$:MeOH—$NH_3$ (7N), 10:1) to give 20.8 mg (72%) of PU-H71-biotin4. $^1$H NMR (500 MHz, $CDCl_3$) δ 8.22 (s, 1H), 7.52 (t, J=5.6 Hz, 1H), 7.36 (s, 1H), 7.03 (s, 1H), 6.66 (t, J=5.5 Hz, 1H), 6.25 (br s, 2H), 6.03 (s, 2H), 4.47-4.52 (m, 1H), 4.28-4.33 (m, 1H), 4.25 (t, J=6.8 Hz, 2H), 3.17-3.25 (m, 4H), 3.11-3.17 (m, 1H), 2.90 (dd, J=5.0, 12.9 Hz, 1H), 2.63-2.79 (m, 1H), 2.24 (t, J=7.4 Hz, 2H), 2.13-2.19 (m, 2H), 1.94-2.02 (m, 2H), 1.58-1.74 (m, 6H), 1.48-1.56 (m, 2H), 1.31-1.46 (m, 4H); MS (ESI): m/z 810.3 $[M+H]^+$.

PU-H71-biotin7. 2 (15 mg, 0.0292 mmol), EZ-Link® NHS-LC-Biotin (14.6 mg, 0.0321 mmol) and DIEA (7.5 mg, 10.2 μL, 0.0584 mmol) in DMF (0.5 mL) was heated at 35° C. for 6 h. The reaction mixture was concentrated under reduced pressure and the resulting residue was purified by preparatory TLC ($CH_2Cl_2$:MeOH—$NH_3$ (7N), 10:1) to give 10.3 mg (41%) of PU-H71-biotin7. In addition, 6.9 mg of unreacted 2 was recovered to give an actual yield of 77%. $^1$H NMR (500 MHz, $CDCl_3$, 2 rotamers) δ 8.26-8.29 (m, 1H), 7.29 (s, 0.4H), 7.28 (s, 0.6H), 6.87 (s, 0.4H), 6.85 (s, 0.6H), 6.76 (br s, 0.4H), 6.74 (br s, 0.6H), 6.51-6.63 (br s, 2H), 5.96-6.00 (m, 2H), 5.68 (br s, 0.4H), 5.58 (br s, 0.6H), 4.56-4.64 (m, 0.4H), 4.45-4.52 (m, 1H), 4.28-4.36 (m, 1H), 4.20-4.27 (m, 2H), 4.01-4.09 (m, 0.6H), 3.08-3.32 (m, 5H), 2.86-2.94 (m, 1H), 2.69-2.76 (m, 1H), 2.31-2.37 (m, 1H), 1.96-2.22 (m, 4H), 1.89-1.96 (m, 1H), 1.30-1.80 (m, 12H), 1.10-1.16 (m, 4H), 1.04-1.09 (m, 2H); MS (ESI): m/z 852.3 $[M+H]^+$.

PU-H71-biotin5. 13 (16.6 mg, 0.0352 mmol), EZ-Link® NHS-LC-LC-Biotin (22.0 mg, 0.0387 mmol) and DIEA (9.1 mg, 12.3 μL, 0.0704 mmol) in DMF (0.5 mL) was stirred at rt for 1 h. The reaction mixture was concentrated under reduced pressure and the resulting residue was purified by preparatory TLC ($CH_2Cl_2$:MeOH—$NH_3$ (7N), 10:1) to give 27.8 mg (86%) of PU-H71-biotin5. $^1$H NMR (500 MHz, $CDCl_3$/MeOH-$d_4$) δ 8.12 (s, 1H), 7.60 (m, 1H), 7.30 (s, 1H), 7.09 (m, 1H), 6.98 (s, 1H), 5.97 (s, 2H), 4.38-4.44 (m, 1H), 4.20-4.24 (m, 1H), 4.17 (t, J=7.1 Hz, 2H), 3.04-3.18 (m, 7H), 2.83 (dd, J=5.0, 12.9 Hz, 1H), 2.64 (d, J=12.8 Hz, 1H), 2.16 (t, J=7.5 Hz, 2H), 2.03-2.12 (m, 4H), 1.88-1.96 (m, 2H), 1.18-1.66 (m, 18H); MS (ESI): m/z 923.4 $[M+H]^+$.

PU-H71-biotin8. 2 (15 mg, 0.0292 mmol), EZ-Link® NHS-LC-LC-Biotin (18.2 mg, 0.0321 mmol) and DIEA (7.5 mg, 10.2 μL, 0.0584 mmol) in DMF (0.5 mL) was heated at 35° C. for 6 h. The reaction mixture was concentrated under reduced pressure and the resulting residue was purified by preparatory TLC ($CH_2Cl_2$:MeOH—$NH_3$ (7N), 10:1) to give 8.2 mg (29%) of PU-H71-biotin8. In addition, 9.6 mg of unreacted 2 was recovered to give an actual yield of 81%. $^1$H NMR (500 MHz, $CDCl_3$/MeOH-$d_4$, 2 rotamers) δ 8.18 (s, 0.4H), 8.16 (s, 0.6H), 7.31 (s, 1H), 6.98 (s, 0.6H), 6.95 (s, 0.4H), 6.80-6.90 (m, 2H), 5.98 (s, 2H), 4.47-4.55 (m, 0.4H), 4.41-4.47 (m, 1H), 4.23-4.27 (m, 1H), 4.16-4.22 (m, 2H), 3.95-4.03 (m, 0.6H), 3.31-3.34 (m, 0.6H), 3.19-3.24 (m, 1.4H), 3.07-3.17 (m, 5H), 2.82-2.89 (m, 1H), 2.64-2.70 (m, 1H), 2.25-2.32 (m, 1H), 1.94-2.16 (m, 7H), 1.18-1.70 (m, 18H), 1.09 (d, J=6.7 Hz, 4H), 1.03 (d, J=6.8 Hz, 2H); MS (ESI): m/z 965.5 $[M+H]^+$.

PU-H71-biotin6. 13 (17.6 mg, 0.0374 mmol), EZ-Link® NHS-$PEG_4$-Biotin (24.2 mg, 0.0411 mmol) and DIEA (9.7 mg, 13 μL, 0.0704 mmol) in DMF (0.5 mL) was stirred at rt for 1 h. The reaction mixture was concentrated under reduced pressure and the resulting residue was purified by preparatory TLC ($CH_2Cl_2$:MeOH—$NH_3$ (7N), 10:1) to give 31.0 mg (88%) of PU-H71-biotin6. $^1$H NMR (500 MHz, $CDCl_3$) δ 8.29 (s, 1H), 7.51 (t, J=5.8 Hz, 1H), 7.32 (s, 1H), 7.03 (t, J=5.3 Hz, 1H), 6.90 (s, 1H), 6.79 (s, 1H), 6.57 (br s, 2H), 6.01 (s, 2H), 5.97 (s, 1H), 4.48-4.53 (m, 1H), 4.25-4.35 (m, 3H), 3.79 (t, J=6.1 Hz, 2H), 3.59-3.68 (m, 12H), 3.57 (t, J=5.1 Hz, 2H), 3.40-3.46 (m, 2H), 3.18-3.24 (m, 2H), 3.12-3.18 (m, 1H), 2.90 (dd, J=5.0, 12.8 Hz, 1H), 2.75 (d, J=12.7 Hz, 1H), 2.54 (t, J=6.0 Hz, 2H), 2.20 (t, J=7.4 Hz, 2H), 1.40-2.01 (m, 2H), 1.59-1.79 (m, 4H), 1.38-1.48 (m, 2H); MS (ESI): m/z 944.4 $[M+H]^+$.

PU-H71-biotin9. 2 (15 mg, 0.0292 mmol), EZ-Link® NHS-$PEG_4$-Biotin (18.9 mg, 0.0321 mmol) and DIEA (7.5 mg, 10.2 μL, 0.0584 mmol) in DMF (0.5 mL) was heated at 35° C. for 6 h. The reaction mixture was concentrated under reduced pressure and the resulting residue was purified by preparatory TLC ($CH_2Cl_2$:MeOH—$NH_3$ (7N), 10:1) to give 9.3 mg (32%) of PU-H71-biotin9. In addition, 9.0 mg of unreacted 2 was recovered to give an actual yield of 81%. $^1$H NMR (500 MHz, $CDCl_3$/MeOH-$d_4$, 2 rotamers) δ 8.18 (s, 0.4H), 8.16 (s, 0.6H), 7.30-7.32 (m, 1H), 6.98 (s, 0.6H), 6.96 (s, 0.4H), 5.98 (s, 2H), 4.49-4.56 (m, 0.4H), 4.39-4.46 (m, 1H), 4.22-4.27 (m, 1H), 4.15-4.21 (m, 2H), 3.99-4.07 (m, 0.6H), 3.66-3.71 (m, 2H), 3.51-3.61 (m, 12H), 3.45-3.50 (m, 2H), 3.29-3.38 (m, 2H), 3.16-3.25 (m, 2H), 3.07-3.12 (m, 1H), 2.81-2.88 (m, 1H), 2.63-2.68 (m, 1H), 2.57-2.63 (m, 1.2H), 2.41-2.47 (m, 0.8H), 1.98-2.18 (m, 4H), 1.52-1.70 (m, 4H), 1.32-1.41 (m, 2H), 1.08 (d, J=6.7 Hz, 4H), 1.02 (d, J=6.8 Hz, 2H); MS (ESI): m/z 986.5 $[M+H]^+$.

PU-H71-biotin. 6 (4.2 mg, 0.0086 mmol) and EZ-Link® Amine-$PEO_3$-Biotin (5.4 mg, 0.0129 mmol) in DMF (0.2 mL) was stirred at rt for 24 h. The reaction mixture was concentrated and the residue chromatographed ($CHCl_3$: MeOH—$NH_3$ (7N), 5:1) to give 1.1 mg (16%) of PU-H71-biotin. $^1$H NMR ($CDCl_3$) δ 8.30 (s, 1H), 8.10 (s, 1H), 7.31

(s, 1H), 6.87 (s, 1H), 6.73 (br s, 1H), 6.36 (br s, 1H), 6.16 (br s, 2H), 6.00 (s, 2H), 4.52 (m, 1H), 4.28-4.37 (m, 3H), 3.58-3.77 (m, 10H), 3.55 (m, 2H), 3.43 (m, 2H), 3.16 (m, 1H), 2.92 (m, 1H), 2.80 (m, 2H), 2.72 (m, 1H), 2.66 (m, 2H), 2.17 (t, J=7.0 Hz, 2H), 2.04 (m, 2H), 1.35-1.80 (m, 6H); MS (ESI): m/z 872.2 $[M+H]^+$ 6.1.3. Synthesis of ANCA-Labeled Compounds Synthesis of N-(3-(6-Amino-8-((6-iodobenzo[d][1,3]dioxol-5-yl)thio)-9H-purin-9-yl)propyl)-2-cyanoacetamide (Compound 26) (Scheme 17). Compound 13' (120.3 mg, 0.256 mmol) in $CH_2Cl_2$ (4 mL) was added cyanoacetic acid (26 mg, 0.307 mmol) and DCC (63 mg, 0.307 mmol) and stirred at rt for 5 h. The reaction mixture was concentrated and purified by chromatography ($CH_2Cl_2$:MeOH—$NH_3$ (7N), 100:1 to 50:1) to give 131 mg (95%) of Compound 26. $^1H$ NMR (600 MHz, $CDCl_3$/MeOH-$d_4$): δ 8.25 (s, 1H), 7.40 (s, 1H), 7.08 (s, 1H), 6.07 (s, 2H), 4.27 (t, J=5.9 Hz, 2H), 3.57 (s, 2H), 3.27 (t, J=5.1 Hz, 2H), 1.98-2.06 (m, 2H); MS (m/z): $[M+H]^+$ 538.0.

Synthesis of PU-ANCA (Compound 28 (Scheme 17). Compound 326 (44 mg, 0.0825 mmol) in DMF (1 mL) was added 27 (19 mg, 0.075 mmol) and piperidine (10 μL) and heated at 70° C. for 24 h. The reaction mixture was concentrated and purified by preparatory TLC ($CH_2Cl_2$: MeOH—$NH_3$ (7N), 12.5:1) to give 24.3 mg (42%) of Compound 28 as an orange solid. $^1H$ NMR (600 MHz, DMF-$d_7$): δ 8.73 (t, J=5.8 Hz, 1H), 8.38 (d, J=1.1 Hz, 1H), 8.36 (s, 1H), 8.29 (s, 1H), 8.18 (dd, J=8.8, 1.7 Hz, 1H), 7.95 (d, J=9.2 Hz, 1H), 7.92 (d, J=8.8 Hz, 1H), 7.56 (dd, J=9.2, 2.5 Hz, 1H), 7.52 (br s, 2H), 7.49 (s, 1H), 7.34 (d, J=2.2 Hz, 1H), 6.95 (s, 1H), 6.16 (s, 2H), 4.40 (t, J=6.9 Hz, 2H), 3.44-3.47 (m, 4H), 3.38-3.43 (m, 2H), 2.53-2.58 (m, 4H), 2.30 (s, 3H), 2.09-2.15 (m, 2H); $^{13}C$ NMR (150 MHz, DMF-$d_7$): δ 161.5, 156.0, 153.5, 151.7, 151.5, 151.2, 149.5, 148.8, 144.4, 137.2, 133.6, 130.3, 129.2, 127.4, 127.0, 126.5, 125.2, 120.1, 119.3, 118.9, 117.4, 111.0, 108.5, 103.0, 102.9, 89.4, 54.9, 47.9, 45.6, 41.3, 40.5, 37.2; HRMS (ESI) m/z $[M+H]^+$ calcd. for $C_{34}H_{33}IN_9O_3S$, 774.1472; found 774.1473.

6.1.4. Synthesis of Radiolabeled Compounds

The parent compounds of PU-H71, PU-HZ151 and PU-DZ13 were synthesized as suitable for radioiodination (i.e. Sn-precursors). For radioiodination, the synthesis follows the reaction shown in Scheme 19. Briefly, the PU-compounds were solvated in methanol (25 μg PU-H71 and PU-HZ151; 15 μg PU-DZ13), and added to NaI (5-10 μL) ([$^{124}I$] isotope for imaging, [$^{131}I$] for biodistribution), followed by oxidation with Chloramine T (CT, 10 μL, 10 min) in acidic media (2 mg/mL in acetic acid). The hot (radiolabeled) compounds were synthesized with the amine protecting group BOC (tert-Butyloxycarbonyl), which was removed under acidic conditions (e.g. trifluroacetic acid (TFA), hydrochloric acid HCl)) for each compound and purified using high pressure liquid chromatography (HPLC). The PU-DZ13 and PU-HZ151 precursors were radiolabeled using 15 μL methanol (MeOH) to solvate, 10 min incubation at room temperature (RT) in CT after the addition of the radiolabel, which was followed by the addition of 50 μL of TFA, and one h incubation at 70° C. The PU-H71 precursor was radiolabeled with 20 μL MeOH and 15 μL CT directly following the addition of the radiolabel, after which time the solution was heated at 50° C. for 5 min, and then allowed to cool for 2 min. Afterwards, 10 μL of methionine methyl ester (formulated from 0.5 g/mL in $H_2O$) and 10 μL concentrated HCl were added prior to incubation at 50° C. (1 h). The radiolabeled products were collected and the solvents were removed under reduced pressure, using a rotary evaporator. The specific activity of [$^{124}I$]-PU-H71 was ~1000 mCi/μmol, which was in line with our previous experiences with this class of [$^{124}I$] compound. For in vivo administration, the [$^{124}I$]-PU-compounds were formulated in sterile 0.9% saline solution.

6.2. Evaluating the Role of HSP90 in Cancer Cells

The methods described in this section relate to the disclosure in Section 5.1.

Cell Lines and Primary Cells: The CML cell lines K562, Kasumi-4, MEG-01 and KU182, triple-negative breast cancer cell line MDA-MB-468, HER2+ breast cancer cell line SKBr3, melanoma cell line SK-Mel-28, prostate cancer cell lines LNCaP and DU145, pancreatic cancer cell line Mia-PaCa-2, colon fibroblast, CCCD18Co cell lines were obtained from the American Type Culture Collection. The CML cell line KCL-22 was obtained from the Japanese Collection of Research Bioresources. The NIH-3T3 fibroblast cells were transfected as previously described[65]. Cells were cultured in DMEM/F12 (MDA-MB-468, SKBr3 and Mia-PaCa-2), RPMI (K562, SK-Mel-28, LNCaP, DU145 and NIH-3T3) or MEM (CCD18Co) supplemented with 10% FBS, 1% L-glutamine, 1% penicillin and streptomycin. Kasumi-4 cells were maintained in IMDM supplemented with 20% FBS, 10 ng/ml Granulocyte macrophage colony-stimulating factor (GM-CSF) and 1×Pen/Strep. PBL (human peripheral blood leukocytes) (n=3) and cord blood (n=5) were obtained from patient blood purchased from the New York Blood Center. Thirty five ml of the cell suspension was layered over 15 ml of Ficoll-Paque plus (GE Healthcare). Samples were centrifuged at 2,000 rpm for 40 min at 4° C., and the leukocyte interface was collected. Cells were plated in RPMI medium with 10% FBS and used as indicated. Primary human chronic and blast crisis CML and AML cells were obtained with informed consent. The manipulation and analysis of specimens was approved by the University of Rochester, Weill Cornell Medical College and University of Pennsylvania Institutional Review Boards. Mononuclear cells were isolated using Ficoll-Plaque (Pharmacia Biotech, Piscataway, NY) density gradient separation. Cells were cryopreserved in freezing medium consisting of Iscove's modified Dulbecco medium (IMDM), 40% fetal bovine serum (FBS), and 10% dimethylsulfoxide (DMSO) or in CryoStor™ CS-10 (Biolife). When cultured, cells were kept in a humidified atmosphere of 5% $CO_2$ at 37° C.

Cell lysis for chemical and immuno-precipitation: Cells were lysed by collecting them in Felts Buffer (HEPES 20 mM, KCl 50 mM, $MgCl_2$ 5 mM, NP40 0.01%, freshly prepared $Na_2MoO_4$ 20 mM, pH 7.2-7.3) with added 1 μg/μL of protease inhibitors (leupeptin and aprotinin), followed by three successive freeze (in dry ice) and thaw steps. Total protein concentration was determined using the BCA kit (Pierce) according to the manufacturer's instructions.

Immunoprecipitation: The Hsp90 antibody (H9010) or normal IgG (Santa Cruz Biotechnology) was added at a volume of 10 μL to the indicated amount of cell lysate together with 40 μL of protein G agarose beads (Upstate), and the mixture incubated at 4° C. overnight. The beads were washed five times with Felts lysis buffer and separated by SDS-PAGE, followed by a standard western blotting procedure.

Chemical precipitation: HSP90 inhibitors beads or Control beads, containing an HSP90 inactive chemical (ethanolamine) conjugated to agarose beads, were washed three times in lysis buffer. Unless otherwise indicated, the bead conjugates (80 μL) were then incubated at 4° C. with the indicated amounts of cell lysates (120-500 μg), and the volume was adjusted to 200 μL with lysis buffer. Following incubation, bead conjugates were washed 5 times with the lysis buffer and proteins in the pull-down analyzed by Western blot. For depletion studies, 2-4 successive chemical precipitations were performed, followed by immunoprecipitation steps, where indicated.

Reagents: The HSP90 inhibitors, the solid-support immobilized and the fluorescein-labeled derivatives were synthesized as previously reported[75-77]. We purchased Gleevec from LC Laboratories, AS703026 from Selleck, KN-93 from Tocris, and PP242, BMS-345541 and sodium vanadate from Sigma. All compounds were used as DMSO stocks.

Western Blotting: Cells were either treated with PU-H71 or DMSO (vehicle) for 24 h and lysed in 50 mM Tris, pH 7.4, 150 mM NaCl and 1% NP40 lysis buffer supplemented with leupeptin (Sigma Aldrich) and aprotinin (Sigma Aldrich). Protein concentrations were determined using BCA kit (Pierce) according to the manufacturer's instructions. Protein lysates (15-200 μg) were electrophoretically resolved by SDS/PAGE, transferred to nitrocellulose membrane and probed with the following primary antibodies against: HSP90 (1:2000, SMC-107A/B; StressMarq), Bcr-Abl (1:75, 554148; BD Pharmingen), PI3K (1:1000, 06-195; Upstate), mTOR (1:200, Sc-1549; Santa Cruz), p-mTOR (1:1000, 2971; Cell Signaling), STAT3 (1:1000, 9132; Cell Signaling), p-STAT3 (1:2000, 9145; Cell Signaling), STAT5 (1:500, Sc-835; Santa Cruz), p-STAT5 (1:1000, 9351; Cell Signaling), RICTOR (1:2000, NB100-611; Novus Biologicals), RAPTOR (1:1000, 2280; Cell Signaling), P90RSK (1:1000, 9347; Cell Signaling), Raf-1 (1:300, Sc-133; Santa Cruz), CARM1 (1:1000, 09-818; Millipore), CRKL (1:200, Sc-319; Santa Cruz), GRB2 (1:1000, 3972; Cell Signaling), FAK (1:1000, Sc-1688; Santa Cruz), BTK (1:1000, 3533; Cell Signaling), A-Raf (1:1000, 4432; Cell Signaling), PRKD2 (1:200, sc-100415, Santa Cruz), HCK (1:500, 06-833; Milipore), p-HCK (1:500, ab52203; Abcam) and β-actin (1:2000, A1978; Sigma). The membranes were then incubated with a 1:3000 dilution of a corresponding horseradish peroxidase conjugated secondary antibody. Detection was performed using the ECL-Enhanced Chemiluminescence Detection System (Amersham Biosciences) according to manufacturer's instructions.

Densitometry: Gels were scanned in Adobe Photoshop 7.0.1 and quantitative densitometric analysis was performed using Un-Scan-It 5.1 software (Silk Scientific).

Radioisotope binding studies and HSP90 quantification studies: Saturation studies were performed with $^{131}$I-PU-H71 and cells (K562, MDA-MB-468, SKBr3, LNCaP, DU-145, MRC-5 and PBL). Briefly, triplicate samples of cells were mixed with increasing amount of $^{131}$I-PU-H71 either with or without 1 μM unlabeled PU-H71. The solutions were shaken in an orbital shaker and after 1 hr the cells were isolated and washed with ice cold Tris-buffered saline using a Brandel cell harvester. All the isolated cell samples were counted and the specific uptake of $^{131}$I-PU-H71 determined. These data were plotted against the concentration of $^{131}$I-PU-H71 to give a saturation binding curve. For the quantification of PU-bound HSP90, $9.2\times10^7$ K562 cells, $6.55\times10^7$ KCL-22 cells, $2.55\times10^7$ KU182 cells and $7.8\times10^7$ MEG-01 cells were lysed to result in 6382, 3225, 1349 and 3414 μg of total protein, respectively. To calculate the percentage of HSP90, cellular HSP90 expression was quantified by using standard curves created of recombinant HSP90 purified from HeLa cells (Stressgen #ADI-SPP-770).

Pulse-Chase. K562 cells were treated with $Na_3VO_4$ (1 mM) with or without PU-H71 (5 μM), as indicated. Cells were collected at indicated times and lysed in 50 mM Tris pH 7.4, 150 mM NaCl and 1% NP-40 lysis buffer, and were then subjected to western blotting procedure.

Tryptic digestion: K562 cells were treated for 30 min with vehicle or PU-H71 (50 μM). Cells were collected and lysed in 50 mM Tris pH 7.4, 150 mM NaCl, 1% NP-40 lysis buffer. STAT5 protein was immunoprecipitated from 500 μg of total protein lysate with an anti-STAT5 antibody (Santa Cruz, sc-835). Protein precipitates bound to protein G agarose beads were washed with trypsin buffer (50 mM Tris pH 8.0, 20 mM $CaCl_2$) and 33 ng of trypsin has been added to each sample. The samples were incubated at 37° C. and aliquots were collected at the indicated time points. Protein aliquots were subjected to SDS-PAGE and blotted for STAT5.

Activated STAT5 DNA binding assay: The DNA-binding capacity of STAT5a and STAT5b was assayed by an ELISA-based assay (TransAM, Active Motif, Carlsbad, CA) following the manufacturer instructions. Briefly, $5\times10^6$ K562 cells were treated with PU-H71 1 and 10 μM or control for 24 h. Ten micrograms of cell lysates were added to wells containing pre-adsorbed STAT consensus oligonucleotides (5'-TTCCCGGAA-3'). For control treated cells the assay was performed in the absence or presence of 20 pmol of competitor oligonucleotides that contains either a wild-type or mutated STAT consensus binding site. Interferon-treated HeLa cells (5 μg per well) were used as positive controls for the assay. After incubation and washing, rabbit polyclonal anti-STAT5a or anti-STAT5b antibodies (1:1000, Active Motif) was added to each well, followed by HPR-anti-rabbit secondary antibody (1:1000, Active Motif). After HRP substrate addition, absorbance was read at 450 nm with a reference wavelength of 655 nm (Synergy4, Biotek, Winooski, VT). In this assay the absorbance is directly proportional to the quantity of DNA-bound transcription factor present in the sample. Experiments were carried out in four replicates. Results were expressed as arbitrary units (AU) from the mean absorbance values with SEM.

Quantitative Chromatin Immunoprecipitation (Q-ChIP): Q-ChIP was made as previously described with modifications[83]. Briefly, $10^8$ K562 cells were fixed with 1% formaldehyde, lysed and sonicated (Branson sonicator, Branson). STAT5 N20 (Santa Cruz) and HSP90 (Zymed) antibodies were added to the pre-cleared sample and incubated overnight at 4° C. Then, protein-A or G beads were added, and the sample was eluted from the beads followed by decrosslinking. The DNA was purified using PCR purification columns (Qiagen). Quantification of the ChIP products was performed by quantitative PCR (Applied Biosystems 7900HT) using Fast SYBR Green (Applied Biosystems). Target genes containing STAT binding site were detected with the following primers: CCND2 (5-GTTGTTCTGGTCCCTTTAATCG and 5-ACCTCGCATACCCAGAGA), MYC (5-ATGCGTTGCTGGGTTATTT and 5-CAGAGCGTGGGATGTTAGTG) and for the intergenic control region (5-CCACCTGAGTCTGCAATGAG and 5-CAGTCTCCAGCCTT1GTTCC).

Real time QPCR: RNA was extracted from PU-H71-treated and control K562 cells using RNeasy Plus kit (Qiagen) following the manufacturer instructions. cDNA was synthesized using High Capacity RNA-to-cDNA kit (Applied Biosystems). We amplified specific genes with the following primers: MYC (5-AGAAGAGCATCTTCCGCATC and 5-CCTTTAAACAGTGCCCAAGC), CCND2 (5-TGAGCTGCTGGCTAAGATCA and 5-ACGGTACTGCTGCAGGCTAT), BCL-XL (5-CTTTTGTGGAACTCTATGGGAACA and 5-CAGCGGTTGAAGCGTTCCT), MCL1 (5-AGACCT- TACGACGGGTTGG and 5-ACATTCCTGATGCCACCTTC), CCND1 (5-CCTGTCCTACTACCGCCTCA and 5-GGCTTC-GATCTGCTCCTG), HPRT (5-CGTCTTGCTCGAGATGTGATG and 5-GCACACAGAGGGCTACAATGTG), GAPDH (5-CGACCACTITGTCAAGCTCA and 5-CCCTGTTGCTGTAGCCAAAT), RPL13A (5-TGAGT-GAAAGGGAGCCAGAAG and 5-CAGATGCCCCACT-CACAAGA). Transcript abundance was detected using the Fast SYBR Green conditions (initial step of 20 sec at 95° C. followed by 40 cycles of 1 sec at 95° C. and 20 sec at 60° C.). The $C_T$ value of the housekeeping gene (RPL13A) was subtracted from the correspondent genes of interest ($\Delta C_T$). The standard deviation of the difference was calculated from the standard deviation of the $C_T$ values (replicates). Then, the $\Delta C_T$ values of the PU-H71-treated cells were expressed relative to their respective control-treated cells using the $\Delta\Delta C_T$ method. The fold expression for each gene in cells treated with the drug relative to control treated cells is determined by the expression: $2^{-\Delta\Delta CT}$. Results were represented as fold expression with the standard error of the mean for replicates.

HSP70 knock-down. Transfections were carried out by electroporation (Amaxa) and the Nucleofector Solution V (Amaxa), according to manufacturer's instructions. HSP70 knockdown studies were performed using siRNAs designed as previously reported[84] against the open reading frame of HSP70 (HSPA1A; accession number NM_005345). Negative control cells were transfected with inverted control siRNA sequence (HSP70C; Dharmacon RNA technologies). The active sequences against HSP70 used for the study are HSP70A (5'-GGACGAGUUUGAGCACAAG-3') and HSP70B (5'-CCAAGCAGACGCAGAUCUU-3'). Sequence for the control is HSP70C (5'-GGACGAGUU-GUAGCACAAG-3'). Three million cells in 2 mL media (RPMI supplemented with 1% L-glutamine, 1% penicillin and streptomycin) were transfected with 0.5 μM siRNA according to the manufacturer's instructions. Transfected cells were maintained in 6-well plates and at 84 h, lysed followed by standard Western blot procedures.

Kinase screen[85] (FIG. 44). For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 min). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μm non-biotinylated affinity ligand) and incubated at room temperature with shaking for 30 minutes. The kinase concentration in the eluates was measured by qPCR. KINOMEscan's selectivity score (S) is a quantitative measure of compound selectivity. It is calculated by dividing the number of kinases that bind to the compound by the total number of distinct kinases tested, excluding mutant variants. TREEspot™ is a proprietary data visualization software tool developed by KINOMEscan[85]. Kinases found to bind are marked with circles in FIG. 44, where larger circles indicate higher-affinity binding. The kinase dendrogram was adapted and is reproduced with permission from Science and Cell Signaling Technology, Inc.

Lentiviral vectors, lentiviral production and K562 cells transduction. Lentiviral constructs of shRNA knock-down of CARM1 were purchased from the TRC lentiviral shRNA libraries of Openbiosystem: pLKO.1-shCARM1-KD1 (catalog No: RHS3979-9576107) and pLKO.1-shCARM1-KD2 (catalog No: RHS3979-9576108). The control shRNA (shRNA scramble) was Addgene plasmid 1864. GFP was cloned in to replace puromycin as the selection marker. Lentiviruses were produced by transient transfection of 293T as in the previously described protocol[86]. Viral supernatant was collected, filtered through a 0.45-μm filter and concentrated. K562 cells were infected with high-titer lentiviral concentrated suspensions, in the presence of 8 μg/ml polybrene (Aldrich). Transduced K562 cells were sorted for green fluorescence (GFP) after 72 hours transfection.

RNA extraction and quantitative Real-Time PCR (qRT-PCR). For qRT-PCR, total RNA was isolated from $10^6$ cells using the RNeasy mini kit (QIAGEN, Germany), and then subjected to reverse-transcription with random hexamers (SuperScript III kit, Invitrogen). Real-time PCR reactions were performed using an ABI 7500 sequence detection system. The PCR products were detected using either Sybr green I chemistry or TaqMan methodology (PE Applied Biosystems, Norwalk, CT). Details for real-time PCR assays were described elsewhere[87]. The primer sequences for CARM1 qPCR are TGATGGCCAAGTCTGTCAAG(forward) and TGAAAGCAACGTCAAACCAG(reverse).

Cell viability, Apoptosis, and Proliferation assay. Viability assessment in K562 cells untransfected or transfected with CARM1 shRNA or scramble was performed using Trypan Blue. This chromophore is negatively charged and does not interact with the cell unless the membrane is damaged. Therefore, all the cells that exclude the dye are viable. Apoptosis analysis was assessed using fluorescence microscopy by mixing 2 μL of acridine orange (100 μg/mL), 2 μL of ethidium bromide (100 μg/mL), and 20 μL of the cell suspension. A minimum of 200 cells was counted in at least five random fields. Live apoptotic cells were differentiated from dead apoptotic, necrotic, and normal cells by examining the changes in cellular morphology on the basis of distinctive nuclear and cytoplasmic fluorescence. Viable cells display intact plasma membrane (green color), whereas dead cells display damaged plasma membrane (orange color). An appearance of ultrastructural changes, including shrinkage, heterochromatin condensation, and nuclear degranulation, are more consistent with apoptosis and disrupted cytoplasmic membrane with necrosis. The percentage of apoptotic cells (apoptotic index) was calculated as: % Apoptotic cells=(total number of cells with apoptotic nuclei/total number of cells counted)×100. For the proliferation assay, $5\times10^3$ K562 cells were plated on a 96-well solid black plate (Corning). The assay was performed according to the manufacturer's indications (CellTiter-Glo Luminescent Cell Viability Assay, Promega). All experiments were repeated three times. Where indicated, growth inhibition studies were performed using the Alamar blue assay. This reagent offers a rapid objective measure of cell viability in cell culture, and it uses the indicator dye resazurin to measure the metabolic capacity of cells, an indicator of cell viability. Briefly, exponentially growing cells were plated in microtiter plates (Corning #3603) and incubated for the indicated times at 37° C. Drugs were added in triplicates at the indicated concentrations, and the plate was incubated for 72 h. Resazurin (55 μM) was added, and the plate read 6 h later using the Analyst GT (Fluorescence intensity mode, excitation 530 nm, emission 580 nm, with 560 nm dichroic mirror). Results were analyzed using the Softmax Pro and the GraphPad Prism softwares. The percentage cell growth inhibition was calculated by comparing fluorescence readings obtained from treated versus control cells. The $IC_{50}$ was calculated as the drug concentration that inhibits cell growth by 50%.

Quantitative analysis of synergy between mTOR and HSP90 inhibitors: To determine the drug interaction between pp242 (mTOR inhibitor) and PU-H71 (HSP90 inhibitor), the combination index (CI) isobologram method of Chou-Talalay was used as previously described[88,89]. This method, based on the median-effect principle of the law of mass action, quantifies synergism or antagonism for two or more drug combinations, regardless of the mechanisms of each drug, by computerized simulation. Based on algorithms, the computer software displays median-effect plots, combination index plots and normalized isobolograms (where non constant ratio combinations of 2 drugs are used). PU-H71 (0.5, 0.25, 0.125, 0.0625, 0.03125, 0.0125 μM) and pp242 (0.5, 0.125, 0.03125, 0.0008, 0.002, 0.001 μM) were used as single agents in the concentrations mentioned or combined in a non constant ratio (PU-H71:pp242; 1:1, 1:2, 1:4, 1:7.8, 1:15.6, 1:12.5). The Fa (fraction killed cells) was calculated using the formulae Fa=1−Fu; Fu is the fraction of unaffected cells and was used for a dose effect analysis using the computer software (CompuSyn, Paramus, New Jersey, USA).

6.3. Fluorescently Labeled Probes in Cellular Assays 6.3.1. Flow Cytometry Analysis of Fluorescent-PU-H71 Binding The human acute myelogenous leukemia (AML) cell lines MOLM-13 and MV4-11 cells were a gift from Dr. Stephen D. Nimer, MSKCC, and were maintained in RPMI1640 medium supplemented with 10% fetal bovine serum (FBS) and 1×Pen/Strep in a humidified atmosphere of 5% $CO_2$ at 37° C. Cells were plated in 6-well plates at the density of $5\times10^5$ cells/mL, and treated with the indicated derivatives (1 μM) at 37° C. for 4 h. For detection of HSP90 binding in live cells, cells were washed twice with FACS buffer (PBS, 0.05% FBS), and prior to analysis, stained with 1 μg/ml of DAPI (Invitrogen) in FACS buffer at room temperature. The fluorescence intensities from live cells (DAPI negative) representing PU-H71-fluorescent derivative binding were captured by flow cytometry (LSR-II, BD Biosciences), and analyzed by FlowJo software (Tree Star, Ashland, OR). For evaluation of HSP90 binding in fixed cells, cells were washed, fixed for 30 min with BD Cytofix buffer (BD, Biosciences, San Jose, CA), and then permeabilized for 30 min on ice using BD Perm buffer III (BD Biosciences, San Jose, CA). Complete cell permeabilization was determined with DAPI. Cells were analyzed by flow cytometry as mentioned above. For competition tests, primary AML samples at the density of $2\times10^6$ cells/ml were treated with 1 μM unconjugated PU-H71 for 4 h followed by treatment of 1 μM PU-H71-FITC2 for 1 h. Cells were collected, washed twice, stained for CD45 to distinguish blasts from normal lymphocytes incubated for 30 min at 4° C., washed and stained with 7-AAD in FACS buffer to be analyzed by flow cytometry.

6.3.2. Flow Cytometry. CD34 Isolation

CD34+ cell isolation was performed using CD34 MicroBead Kit and the automated magnetic cell sorter autoMACS according to the manufacturer's instructions (Miltenyi Biotech, Auburn, CA). Viability assay—CML cells lines were plated in 48-well plates at the density of $5\times10^5$ cells/ml, and treated with indicated doses of PU-H71. Cells were collected every 24 h, stained with Annexin V-V450 (BD Biosciences) and 7-AAD (Invitrogen) in Annexin V buffer (10 mM HEPES/NaOH, 0.14 M NaCl, 2.5 mM $CaCl_2$). Cell viability was analyzed by flow cytometry (BD Biosciences). For patient samples, primary blast crisis CML cells were plated in 48-well plates at $2\times10^6$ cells/ml, and treated with indicated doses of PU-H71 for up to 96 h. Cells were stained with CD34-APC, CD38-PE-CY7 and CD45-APC-H7 antibodies (BD Biosciences) in FACS buffer (PBS, 0.05% FBS) at 4° C. for 30 min prior to Annexin V/7-AAD staining. PU-H71 binding assay—CML cells lines were plated in 48-well plates at the density of $5\times10^5$ cells/ml, and treated with 1 μM PU-H71-FITC. At 4 h post treatment, cells were washed twice with FACS buffer. To measure PU-H71-FITC binding in live cells, cells were stained with 7-AAD in FACS buffer at room temperature for 10 min, and analyzed by flow cytometry (BD Biosciences). At 48 h, and 96 h post PU-H71-FITC treatment, cells were stained with Annexin V-V450 (BD Biosciences) and 7-AAD in Annexin V buffer, and subjected to flow cytometry to measure viability determined by AnnexinV/7AAD double negative gates. To evaluate the binding of PU-H71-FITC to leukemia patient samples, primary bp or cpCML cells were plated in 48-well plates at $2\times10^6$ cells/ml, and treated with 1 μM PU-H71-FITC. At 24 h post treatment, cells were washed twice, and stained with CD34-APC (or CD34-PECy7), CD38-PE-CY7 (or CD38-PE) and CD45-APC-H7 antibodies in FACS buffer at 4° C. for 30 min prior to 7-AAD staining. At 48 h, and 96 h post treatment, cells were stained with CD34-APC (or CD34-PECy7), CD38-PE-CY7 (or CD38-PE) and CD45-APC-H7 antibodies followed by Annexin V-V450 and 7-AAD staining to measure cell viability in blast, lymphocytes and CD34+ cell populations. For competition test, CML cell lines at the density of $5\times10^5$ cells/ml or primary CML samples at the density of $2\times10^6$ cells/ml were treated with 1 μM unconjugated PU-H71 for 4 h followed by treatment of 1 μM PU-H71-FITC for 1 h. Cells were collected, washed twice, stained for 7-AAD in FACS buffer, and analyzed by flow cytometry. HSP90 staining—Cells were fixed with fixation buffer (BD Biosciences) at 4° C. for 30 min, and permeabilized in Perm Buffer III (BD Biosciences) on ice for 30 min. Cells were stained with anti-HSP90 phycoerythrin conjugate (PE) (F-8 clone, Santa Cruz Biotechnologies; CA) for 60 minutes. Cells were washed and then analyzed by flow cytometry. Normal mouse IgG2a-PE was used as isotype control.

6.3.3. Fluorescent Microscopy Analysis of PU-H71-FITC2 (9) Binding

MV4-11 cells were plated in 48-well plates at the density of $5\times10^5$ cells/ml, and treated with 1 μM PU-H71-FITC2 or PU-H71-NBD1. At 24 h post treatment, cells were blocked with 3% BSA/FACS buffer at room temperature for 30 min and incubated with $Na^+/K^+$-ATPase α 1 antibody (Novus Biologicals) in 3% BSA/FACS buffer at room temperature for 30 min. Cells were washed three times with FACS buffer and incubated with goat anti-rabbit Alexa Fluor 568 (Invitrogen) in 3% BSA/FACS buffer at room temperature for 20 min. Cells were then washed three times with FACS buffer, incubated with 1 μg/ml DAPI in FACS buffer for 10 min, mounted on slides, and observed under confocal microscope (Zeiss).

Western Blotting: Cells were either treated with the fluorescent PU-H71 derivatives, TEG-FITC or DMSO (vehicle) for 24 h and lysed in 50 mM Tris, pH 7.4, 150 mM NaCl and 1% NP40 lysis buffer supplemented with leupeptin (Sigma Aldrich) and aprotinin (Sigma Aldrich). Protein concentrations were determined using BCA kit (Pierce) according to the manufacturer's instructions. Protein lysates (50 μg) were electrophoretically resolved by SDS/PAGE, transferred to nitrocellulose membrane and probed with the following primary antibodies against: Raf-1 (1:300, Sc-133; Santa Cruz), FLT3 (1:1000, sc-480; Santa Cruz) and β-actin (1:2000, A1978; Sigma). The membranes were then incubated with a 1:3000 dilution of a corresponding horseradish peroxidase conjugated secondary antibody. Detection was performed using the ECL-Enhanced Chemiluminescence Detection System (Amersham Biosciences) according to manufacturer's instructions.

6.3.4. Tumor Stem Cell Assays

PU-H71 binding assay—Primary samples were plated in 48-well plates at $2\times10^6$ cells/ml, and treated with 1 μM PU-H71-FITC2 or TEG-FITC. At 4 h post treatment, cells were washed once with FACS buffer (PBS, 0.05% FBS), and stained with CD34-APC, CD38-PE-CY7 and CD45-APC-H7 antibodies (BD Biosciences) in FACS buffer (PBS+0.5% FBS) at 4° C. for 30 min prior to 7-AAD (Invitrogen) staining. The MFI of bound PU-H71-FITC2 was evaluated in the BD-LSR II flow cytometer) and normalized to TEG-FITC. Values were represented as ratio of binding of PUH71-FITC in LSCs (CD45dim, CD34+, CD38− gate) relative to lymphocytes (CD45hi vs SSC gate).

Stem cell viability assay—Primary cells were plated in 48-well plates at $2\times10^6$ cells/ml, and treated with 1 uM PU-H71 for 48 h. Cells were stained with CD34-APC, CD38-PE-CY7 and CD45-APC-H7 antibodies (BD Biosciences) in FACS buffer (PBS, 0.05% FBS) at 4° C. for 30 min prior to Annexin V-V450 (BD Biosciences) and 7-AAD staining in Annexin V buffer (10 mM HEPES/NaOH, 0.14 M NaCl, 2.5 mM $CaCl_2$). Cell viability was determined as the percentage of annexin V-/7AAD-cells normalized to untreated cells.

Statistical Analysis. Unless otherwise indicated, data were analyzed by unpaired 2-tailed t tests as implemented in GraphPad Prism (version 4; GraphPad Software). A P value of less than 0.05 was considered significant. Unless otherwise noted, data are presented as the mean±SD or mean±SEM of duplicate or triplicate replicates. Error bars represent the SD or SEM of the mean. If a single panel is presented, data are representative of 2 or 3 individual experiments.

6.3.5. Evaluation of PU-FITC Binding in Primary Leukemia Samples and in Leukemia and Solid Tumor Cell Lines Procedure: Peripheral blood (PB) or bone marrow (BM) mononuclear cells from leukemia patients are either isolated from fresh samples using Ficoll density gradients or from viably frozen aliquotes. Cells are treated with 1 μM PU-FITC and at 4 h post-treatment cells will be washed and stained with antibodies to distinguish different subpopulations (CD45-APC-H7 to identify blasts (CD45 dim vs SSC gate) and lymphocytes (CD45hi vs. SSC gate)) and 7-AAD staining to discriminate dead cells. PU-FITC binding will be evaluated using a BD LSR-II instrument. The instrument is set up using CST beads prior the experiment. A calibration curve using commercially available beads labeled with different fluorescent intensities (Quantum Alexa Fluor 488 kit) is used for the quantitation of AF488/FITC fluorescence intensities for PU-FITC binding. Binding to lymphocytes is used to determine background binding of PU-FITC for each patient sample. PU-FITC binding is evaluated as the fold difference in mean fluorescence intensity (MFI) of blasts relative to lymphocytes. A non-specific control (TEG-FITC) is used to determine non-specific binding. We propose to evaluate at least 100 primary leukemia samples. For each assay we use a minimum of 900,000 total mononuclear cells. We collect at least 50,000 events for the analysis. Analysis is performed using FlowJo software. Binding of PU-FITC on a larger panel of commercially available cell lines (lymphomas, multiple myeloma, breast cancer, prostate, pancreatic and lung cancer cell lines) can be evaluated. Because cell lines do not have their own internal control, we use the calculated delta MFI for TEG-FITC subtracted from PU-FITC (quantified using the calibration curves performed with the fluorescent beads) or the binding to HL-60 cells as described above.

Evaluation of sensitivity to Hsp90 inhibitors: To determine the sensitivity of all samples evaluated for PU-FITC binding, cells are plated in 96-well plates and treated with increasing doses of PU-H71. In cell lines and a select subset of primary samples, where sufficient material is available, their sensitivity is also tested to other chemically distinct Hsp90i (17-AAG, NVP-AUY922 and STA9090 or other Hsp90i currently in clinical evaluation) (5). Cells are collected 48 h later and stained with CD45-APC-H7 to distinguish blast and normal lymphocytes (for primary cells). Cells are then washed and stained with Annexin V-V450 and 7-AAD in Annexin V buffer (10 mM HEPES/NaOH, 0.14 M NaCl, 2.5 mM $CaCl_2$)). Cell viability will be analyzed by flow cytometry.

Statistical considerations: The primary goal is to evaluate our assay for fold PU binding so that it best distinguishes Hsp90i responders versus nonresponders. These experiments are done in vitro, using 150 samples, including primary samples and cell lines. Response is defined if greater than 50% of cells are alive. The area under the receiver operating characteristic (ROC) curve is calculated to assess the ability of fold PU binding in distinguishing response versus no response. For our purposes, we define an AUC of 0.87 or higher (compared to a null AUC of 0.75) to indicate that fold PU binding can distinguish Hsp90i responders from the nonresponders. For a sample of 150, and assuming a 30% response rate, we will have 80% power to detect a difference in AUC from 0.75 to 0.87 with a type I error of 5%. As the response rate decreases, the power also decreases. As an example, if we assume a 20% response rate, we will have 80% power to detect a difference in AUC from 0.75 to 0.89 with a type I error of 5%.

6.3.6. Measuring PU-FITC Binding in Live Tumor Cell Lines in the Presence or Absence of pgp Inhibitors Adherent cancer cell lines are plated and allowed to adhere overnight at 37° C., 5% $CO_2$. Cells are either pre-treated (5 uM) with the pgp inhibitors (PSC 833, Tocris Biosciences or Reversan, Tocris Biosciences) or DMSO vehicle for 2 hrs prior to the addition of media containing 1 uM of DMSO, PU-FITC9 (a negative PU-FITC control) and PU-FITC2 (PU-H71 drug labeled with FITC). Cells are incubated with the FITC drug or control conjugates for an additional 4 hrs, 37° C., 5% CO2. Cells are then trypsinized, washed twice with 1×FACS buffer (1×PBS+0.5% FBS) and pellet resuspended in 500 ul 1×FACS buffer containing a cell viability dye (1 μg/ml DAPI). Samples are run on the BD LSRII flow cytometer and 10-20,000 events collected. Prior to each experimental run, lasers are normalized on the LSRII with CST beads (BD Biosciences). The binding of PU-FITC in tumor cells is determined in DAPI-ve live cells by measuring the FITC median fluorescence intensity (MFI). The non-specific FITC signal from the FITC9 and DMSO controls is subtracted from the PU-FITC signal.

6.3.7 Dissociated Tumor Cells and Circulating Tumor Cells

Dissociation of Tumor Cells and measurement of PU-FITC binding—EGFR+ tumors obtained from mice were dissociated according to manufacturer's protocol (tissue dissociation kit, Millipore). Briefly, 1 g of fresh tissue is cut into small pieces (e.g., ~10-20 pieces per g tissue) using a scalpel. The minced tissue is washed twice in PBS and transferred in dissociation solution for 50 mins at 37° C. with gentle agitation. Following dissociation, the cells are washed, strained using a sieve and un-dissociated tissue fragments discarded. The dissociated tissue is transferred to a fresh tube containing 1× Dissociation Buffer with Protease Inhibitors. Cells are washed twice in the dissociation buffer containing protease inhibitors. Cells are re-suspended to $1\times10^6$ cells/ml in media. Samples are equally divided into 3 tubes cells and treated with 1p M (per $1\times10^6$ cells/ml) of DMSO, PU-FITC9 (negative FITC control) and PU-FITC2 (PU-H71 drug labelled to FITC) for 4 hrs at 37° C., 5% $CO_2$. Control EGFR+ cell lines [AspcI (Low binding); BxPc3 (high binding)] spiked with thawed PBMC's obtained from the blood bank are stained concurrently with the dissociated tumor cells as mentioned above. Cells are washed twice with 1×FACS buffer (1×PBS+0.5% FBS) and stained for 30 mins on ice with anti-human EGFR-PE (BD Biosciences), anti-human CD14-APC-Cy7 (ebiosciences) or CD14− PE-Texas Red (invitrogen) and anti-human CD45-APC (ebiosciences). Cells are then washed twice with 1×FACS buffer (1×PBS+0.5% FBS) and pellet re-suspended in 500 ul 1×FACS buffer containing a cell viability dye (1 ug/ml DAPI). Samples are run on the BD LSRII flow cytometer and 100-200,000 events collected. Lasers are normalized on the LSRII with CST beads (BD Biosciences) prior to each experimental run. The drug accumulation of PU-FITC in tumor cells is determined by measuring the FITC Median Fluorescence Intensity (MFI) in EGFR+ cells (EGFR+ CD45−) and EGFR− cells (EGFR-CD45+CD14−). The non-specific FITC signal from the PU-FITC9 and DMSO controls is subtracted. Values are calculated as a ratio of the MFI of Tumor (EGFR+CD45−CD14−): MFI of EGFR-CD45+ CD14− cells. To normalize MFI values across patient Quantum FITC standardizations beads (Bangs laboratories) will be run with each sample and a standard curve generated. This allows quantitation of the FITC fluorescence intensity in molecules of equivalent soluble fluorochrome (MESF units). PU-FITC2 accumulation in each sample can be quantitated across samples by extrapolating values generated from the standard curve Measure PU-FITC binding to EpCAM+ circulating tumor cells in PBMC's: All experimental blood sampling procedures were performed under the Institutional Review Board-approved protocols at Memorial Sloan Kettering Cancer Center. 8 mls of peripheral blood is withdrawn into anticoagulant EDTA tubes from cancer patients enrolled on PU-H71 clinical trials. PBMC's are isolated on ficoll gradients, cells are counted and viability determined by trypan blue dye exclusion assay. PBMC's are spun down and re-suspended to $2\times10^6$ cells/ml. Samples are equally divided into 3 tubes and treated with 1 μM (per $2\times10^6$ cells/ml) of DMSO, PU-FITC9 (negative FITC control) and PU-FITC2 (PU-H71 drug labelled to FITC) for 4 hrs at 37° C., 5% $CO_2$. Controls EpCAM+ cell lines [AspcI (Low binding); BxPc3 (high binding)] are spiked with freshly thawed PBMC's obtained from the blood bank and stained concurrently with the patient PBMC's as mentioned above. Cells are washed twice with 1×FACS buffer (1×PBS+0.5% FBS) and stained for 30 mins on ice with anti-human EpCAM-PE (miltenyi biotech), anti-human CD14-APC-Cy7 (ebiosciences) or CD14−PE-Texas Red (invitrogen) and anti-human CD45-APC (ebiosciences). Cells are then washed twice with 1×FACS buffer (1×PBS+0.5% FBS) and pellet resuspended in 500 ul 1×FACS buffer containing a cell viability dye (1 ug/ml DAPI). Samples are run on the BD LSRII flow cytometer and 100-200,000 events collected. Lasers are normalized on the LSRII with CST beads (BD Biosciences) prior to each experimental run. The binding of PU-FITC in tumor cells is determined by measuring the FITC Median Fluorescence Intensity (MFI) in EpCAM+ cells (EpCAM+ CD45−) and EpCAM-cells (EpCAM-CD45+CD14−). The non-specific FITC signal from the FITC9 and DMSO controls is subtracted. Values are calculated as a ratio of the MFI of Tumor (EpCAM+CD45−CD14−): MFI of EpCAM-CD45+CD14− cells. To normalize MFI values across patient Quantum FITC standardizations beads (Bangs laboratories) will be run with each patient sample and a standard curve generated. This allows quantitation of the FITC fluorescence intensity in molecules of equivalent soluble fluorochrome (MESF units). PU-FITC2 binding in each sample can be quantitated across samples by extrapolating values generated from the standard curve.

Modifications to protocol: PBMC's obtained from patients will be split into 2 tubes. Both will be stained with PU-FITC as mentioned above, and stained with EpCAM-PE or the isotypic control and CD14-PE-Texas red and CD45-APC. Samples will be processed as mentioned above. Threshold ratio values will be determined using PU-FITC low and high accumulating cell lines spiked with PBMC's 6.3.8. Analysis of PU-H71 Binding in Tissues Examination of the sensitivity of gastric patient tumor specimens to HSP90 inhibitors using ex vivo tumor tissue resources and correlate with PU-H71-FITC staining: Immediately following surgical removal of the gastrectomy specimen the tissue is transported to the Tissue Procurement Services (TPS) area of the Pathology suite. Once the lesion is located, tissue is harvested under sterile conditions. The specimen size removed for evaluation is typically 5-10 mm×5-10 mm. Every effort is made to sample the most viable area. Distant from the lesion, a specimen of equivalent size is removed representative of normal gastric epithelial tissue. Both specimens are placed in minimal essential media (MEM) with 1% penicillin/streptomycin. A small portion of the lesion and the entire piece of normal gastric epithelial tissue undergo a "snap" freeze for future molecular evaluation by WB. The remaining portion of the lesion (gastrectomy) is processed for pathological evaluation. For every lesion pathology provides IHC for proliferation markers, epithelial markers and one hematoxylin/eosin (H&E) stained slide accompanied by 10 unstained to be further assessed for staining with fluorescein labeled PU-H71 (PU-FITC). Formalin-fixed paraffin-embedded sections or frozen sections are analyzed for PUH71-FITC2 staining. In parallel, a portion of the tissue is prepared for ex vivo analysis of the sensitivity of the tumor to PU-H71. From preliminary analyses we have learned that fresh tissue slicing preserves the cancer cells in the endogenous environment of the surrounding tissue. In this method, the tissue (i.e. lesion) is placed in a plastic mold and embedded in 6% agarose. The agarose-embedded tissue is then mounted on the stage of the Vibratome that is submersed in a chilled reservoir (for tissue preservation) containing MEM with 1% penicillin/streptomycin. The tissue is then sliced using metal blades producing serial sections of the lesion that are 200 μm thick. Each section (minus the surrounding agarose-embedding media) is immediately placed in a 24-well tissue culture plate containing MEM with 1% penicillin/streptomycin. From a 5 mm×5 mm piece of tissue approximately 25 sections are produced. This allows for replicate analyses of tissue sections treated with a minimum of 4 doses of the Hsp90 inhibitor and one with vehicle only. Replicates can be assayed by both IHC as well as viability assays (automatic plate reader or cytospin preparation) once tissue section undergoes enzymatic dissociation by brief exposure to dispase. The degree of apoptosis induced by PU-H71 in these gastric tumor slices will then be correlated with PU-H71-FITC staining. PU-H71 uptake (as measured by IHC scoring of PU-H71-FITC staining) correlates with the sensitivity of these tumors to Hsp90 inhibition. Similar protocols have been developed for breast and pancreatic cancer.

6.4. ANCA-Labeled Probes in Cellular Assays

Fluorescent probe treatment: Adherent cells were treated when 70% confluent with 5 μM PUH71-ANCA for 1 hour under standard tissue culture conditions. Following treatment the media was aspirated, the slides washed 3 times with PBS and then replenished with complete media.

Fluorescence Emission Spectrum: Fluorescence emission was determined using an inverted fluorescent confocal microscope (Leica $SP_5$) and scanning cancer and non-cancerous cells on chamber slides at 5 nm increments from 400 nm to 600 nm.

Confocal Microscopy: Following treatment fluorescence of cells was observed using an inverted fluorescent confocal microscope (Leica $SP_5$). Confocal images were acquired at the appropriate fluorescence emission peak of the bound high affinity species (~530 nm). Images were uploaded into NIH ImageJ software. The fluorescence intensity of individuals cells from several random fields were measured and corrected for background.

Response Modeling: A standard curve of $IC_{50}$ vs. fluorescence density integrity was established for 12 breast cancer cell lines and 2 normal breast cell lines. Cell lines grown on multi-well plates where five wells were analyzed for response (vehicle only, 0.25 μM, 0.50 μM, 1.0 μM and 2.5 μM PUH71-treated) and one well was analyzed for fluorescence intensity of bound (PUH71-ANCA-treated). The $IC_{50}$ of all cell lines was plotted on the y-axis and the density integrity (fluorescence intensity) was plotted on the x-axis. This standard curve is used to model and predict response of breast cancer specimens, such as those obtained from biopsy, surgery or fine needle aspirates, to HSP90 therapy.

Response Measurement in Cancer Biopsies: Patient biopsies, once procured are placed in sterile saline and delivered immediately to the tissue procurement area of the Pathology Department. A portion of the lesion is taken for fresh tissue sectioning performed on a Vibratome (Leica VT1000). Sections 200 μm thick are cut and immediately placed in multi-well plates in minimal essential media with growth factors and antibiotics and placed in 37° C. in an air-5% $CO_2$ atmosphere at constant humidity. The sections are then treated with the PUH71-ANCA for 45 minutes to 1 hour. Following treatment the section is washed 2× with PBS and then OCT-embedded (fresh frozen). The OCT-embedded specimen is then cut into several 4 μm thick sections and transferred to charged slides. The nuclear counterstain, DAPI is then applied to the slide. The slides are then observed on a confocal microscope (Leica $SP_5$) and analyzed at 530 nm fluorescent emission peak to determine the percentage of probe-bound to the oncogenic HSP90 species.

6.5. Studies with Radiolabeled HSP90 Inhibitors

Reagents. [$^{124}$I]-PU-H71 and [$^{124}$I]-PU-H71 were synthesized and purified as previously reported[132].

Cell Lines. The MDA-MB-468 human breast cancer cell line was obtained from the American Type Culture Collection. Cells were cultured routinely in DME-HG supplemented with 10% FBS, 1% L-glutamine, 1% penicillin, and streptomycin.

In Vivo Studies. All animal studies were conducted in compliance with MSKCC's Institutional Animal Care and Use Committee (IACUC) guidelines. Female athymic nu/nu mice (NCRNU-M, 20-25 g, 6 weeks old) were obtained from Harlan Laboratories and were allowed to acclimatize at the MSKCC vivarium for 1 week prior to implanting tumors. Mice were provided with food and water ad libitum. MDA-MB-468 tumor xenografts were established on the forelimbs of mice by sub-cutaneous (s.c.) injection of $1\times10^7$ cells in a 200 μL cell suspension of a 1:1 v/v mixture of PBS with reconstituted basement membrane (BD Matrigel™, Collaborative Biomedical Products Inc., Bedford, MA). Before administration, a solution of PU-H71 was formulated in PBS (pH 7.4).

In vivo Biodistribution Studies. For acute in vivo biodistribution studies, mice (n=5) with MDA-MB-468 breast tumor xenografts on forelimbs were injected intravenously in the tail vein with 0.93-1.1 MBq (25-50 μCi) of [$^{124}$I]-PU-H71 or [$^{131}$I]-PU-H71 in 200 μL of saline. For dose estimation experiments groups of mice (n=5) were injected with [$^{124}$I]-PU-H71 or [$^{131}$I]-PU-H71 diluted in a sterile solution containing PU-H71 corresponding to 5, 25, 50 or 75 mg/kg of body weight of mice. Activity in the syringe before and after administration was assayed in a dose calibrator (CRC-15R; Capintec) to determine the activity administered to each animal. Animals (n=4 per group) were euthanized by $CO_2$ asphyxiation at different time points post-administration of the tracer and organs including tumor(s) were harvested and weighed. Part of tumor tissue was frozen immediately post-harvesting for further biochemical and histological analyses. $^{124}$I was measured in a scintillation γ-counter (Perkin Elmer 1480 Wizard 3 Auto Gamma counter, Waltham, MA) using 400-600 keV energy window. Count data were background and decay-corrected to the time of injection, and the percent injected dose per gram (% ID/g) for each tissue sample was calculated by using a measured calibration factor to convert count rate to activity and the activity was normalized to the activity injected to yield the activity concentration in % ID/g.

Small-Animal PET Imaging. For small-animal imaging studies mice with MDA-MB-468 breast cancer xenografts on forelimbs were used. Imaging was performed with a dedicated small-animal PET scanner (Focus 120 microPET; Concorde Microsystems, Knoxville, TN). Mice were maintained under 2% isoflurane (Baxter Healthcare, Deerfield, IL) anesthesia in oxygen at 2 L/min during the entire scanning period. In suitable cases, to reduce the thyroid uptake of free iodide arising from metabolism of tracer mice received 0.01% potassium iodide solution in their drinking water starting 48 h prior to tracer administration. For PET imaging each mouse was administered 9.25 MBq (250 μCi) of [$^{124}$I]-PU-H71 via the tail vein. Sequential list-mode acquisitions (10-30 min) were obtained for each animal at various time points post tracer administration. An energy window of 420-580 keV and a coincidence timing window of 6 ns were used. The resulting list-mode data were sorted into 2-dimensional histograms by Fourier rebinning; transverse images were reconstructed by filtered back projection (FBP). The image data were corrected for non-uniformity of scanner response, dead-time count losses, and physical decay to the time of injection. There was no correction applied for attenuation, scatter or partial-volume averaging. The measured reconstructed spatial resolution of the Focus 120 is 1.6-mm FWHM at the center of the field of view. ROI analysis of the reconstructed images was performed using ASIPro software (Concorde Microsystems, Knoxville, TN), and the maximum pixel value was recorded for each tissue/organ ROI. A system calibration factor (i.e., μCi/mL/cps/voxel) that was derived from reconstructed images of a mouse-size water-filled cylinder containing $^{18}F$ and was used to convert the $^{124}I$ voxel count rates to activity concentrations (after adjustment for the $^{124}I$ positron branching ratio). The resulting image data were then normalized to the administered activity to parameterize the microPET images in terms of % ID/g (corrected for decay to the time of injection).

LC-MS/MS analyses. Frozen tissue was dried and weighed prior to homogenization in acetonitrile/H2O (3:7). PU-H71 was extracted in methylene chloride, and the organic layer was separated and dried under vacuum. Samples were reconstituted in mobile phase. Concentrations of PU-H71 in tissue or plasma were determined by high-performance LC-MS/MS. PU-H71-$d_6$ was added as the internal standard[133]. Compound analysis was performed on the 6410 LC-MS/MS system (Agilent Technologies) in multiple reaction monitoring (MRM) mode using positive-ion electrospray ionization. For tissue samples, a Zorbax Eclipse XDB-C18 column (2.1×50 mm, 3.5 μm) was used for the LC separation, and the analyte was eluted under an isocratic condition (80% $H_2O$+0.1% HCOOH: 20% $CH_3CN$) for 3 minutes at a flow rate of 0.4 mL/min. For plasma samples, a Zorbax Eclipse XDB-C18 column (4.6×50 mm, 5 μm) was used for the LC separation, and the analyte was eluted under a gradient condition ($H_2O$+0.1% HCOOH:$CH_3CN$, 95:5 to 70:30) at a flow rate of 0.35 ml/min.

Pharmacodynamic analyses. For protein analysis, tumors were homogenized in SDS lysis buffer (50 mM Tris, pH 7.4, 2% SDS) and subjected to Western blot analysis. Protein concentrations were determined using the BCA kit (Pierce) according to the manufacturer's instructions. Protein lysates (20-100 μg) were electrophoretically resolved by SDS/PAGE, transferred to nitrocellulose membrane, and probed with the indicated primary antibodies: Anti-Hsp90 from mouse (1:500, SPA-830; Stressgen), anti-Akt from rabbit (1:500, 9272; Cell Signaling), anti-phospho-Akt (Ser 473) from rabbit (1:500, 9271S; Cell Signaling), anti-PARP (p85 fragment) from rabbit (1:250, G7341; Promega). Membranes were then incubated with a 1:5,000 dilution of a peroxidase-conjugated corresponding secondary antibody. Equal loading of the protein samples was confirmed by parallel Western blots for β-actin (1:5,000, ab8227-50; Abcam). Detection was performed using the ECL Enhanced Chemiluminescence Detection System (Amersham Biosciences) according to the manufacturer's instructions.

Densitometry. Gels were scanned in Adobe Photoshop and quantitative densitometric analysis was performed using Un-Scan-It 5.1.

Efficacy Studies. Mice (n=5) bearing MDA-MB-468 tumors reaching a volume of 100-150 $mm^3$ were treated i.p. (i.p.) using different doses and schedules, as indicated. Tumor volume was determined by measurement with Vernier calipers, and tumor volume was calculated as the product of its length×width$^2$×0.4. Tumor volume was expressed on indicated days as the median tumor volume±SD indicated for groups of mice. Percent (%) tumor growth inhibition values were measured on the final day of study for drug-treated compared with vehicle treated mice and are calculated as $100\times\{1-[(\text{Treated}_{Final\ day}-\text{Treated}_{Day\ 1})/(\text{Control}_{Final\ day}-\text{Control}_{Day\ 1})]\}$. Tumor regression values were determined by calculating the ratio of median tumor volumes at the time when treatment was initiated to median tumor volume on the final day of study for a given treatment group. Percent (%) tumor regression is $100\times[1-(\text{Treated}_{Final\ day}/\text{Treated}_{Day\ 1})]$.

Acridine Orange/Ethidium Bromide Cell Viability Assay. The Easycount ViaSure kit (Immunocon) was used in conjunction with the Easycount system to count dead and live cells automatically. The ViaSure Staining Reagent uses a mixture of ready-to-use nucleic acid dyes, acridine orange and ethidium bromide, to identify live and dead cells, respectively, in a single test. Acridine orange is taken up by both viable and non-viable cells and emits green fluorescence if intercalated into double-stranded nucleic acid (DNA) or red fluorescence if bound to single-stranded nucleic acid (RNA). Ethidium bromide is taken up only by non-viable cells and emits red fluorescence by intercalation into DNA. Viable cells have uniform green nuclei with organized structure. Early apoptotic cells (which still have intact membranes but have started to undergo DNA cleavage) have green nuclei, but perinuclear chromatin condensation is visible as bright green patches or fragments. Late apoptotic cells have orange to red nuclei with condensed or fragmented chromatin. Necrotic cells have a uniformly orange to red nuclei with organized structure. A total of at least 200 cells per condition were counted.

Simulations. A double exponential function $x(t)=\alpha_1 \exp(-\beta_1 t)+\alpha_2 \exp(-\beta_2 t)$ was fitted to the measurements. In general, sum of exponentials have been used to analyze pharmacokinetics data[123]. The Generalized Nonlinear Model package (http://cran.rproject.org/web/packages/gnm/index.html) in R statistical language (www.r-project.org) has been used to fit the model to the data. Several fits were initially sought, and the best one was employed for further simulations of different drug administration scenarios. A script in R has been developed.

Statistical Analysis. Unless otherwise indicated, data were analyzed by unpaired 2-tailed t tests as implemented in GraphPad Prism (version 4; GraphPad Software). A P value of less than 0.05 was considered significant. Unless otherwise noted, data are presented as the mean±standard deviation (SD) or mean±standard error of the mean (SEM) of duplicate or triplicate replicates. Error bars represent the SD or SEM of the mean. If a single panel is presented, data are representative of 2 or 3 individual experiments.

Human Studies. A once-daily dose of a potassium iodide solution (SSKI) is administered for 14 days beginning day before injection. A single tracer-injection (4-11.0 mCi; <100 μg) is administered by slow peripheral IV bolus. Patients undergo non-invasive PET-based assays at 0 h (dynamic scan), 3-4 h, 24 h and 40-80 h and/or 160-200 h (static scans). In our PU-PET pilot trial, a more demanding schedule has been well-tolerated by patients without difficulties in patient recruitment or 'drop-out'. Time-points are selected based upon our human $^{124}I$-PUH71 PK data:

(1) $^{124}I$-PUH71 clears rapidly from the blood circulation, in a bi-exponential manner—a rapid clearance (blood $t_{1/2}\approx20$ min.), followed by slow clearance at negligibly-low blood-levels;

(2) tumor PUH71-tracer concentrations by PET imaging, have been variable, being either quantitatively greater than or equivalent to background tissue tracer-levels, with differential uptake and/or retention of tracer being evident from 4-to-24 or 48 and beyond 72 h after tracer-injection;

(3) PUH71-avid tumor concentrations have been either sustained or have shown a monoexponential-type clearance, over a period of days.

We have optimized our $^{124}$I-PUH71 PET image acquisition protocol to ensure robust count-statistics. A dedicated research PET/CT scanner (GE Discovery DSTE) obtains quantitative biodistribution images with attenuation-, decay- and scatter-corrections and adjustment for system sensitivity. CT scans for attenuation correction and anatomic co-registration are performed prior to tracer-injection, scaled to body weight (up to 85 mA for ≥81 kg). The CT protocol is designed to suffice for anatomic localization of tracer-signal and for attenuation correction, while minimizing radiation exposure. No intravenous or oral radiographic contrast is administered. PET data are reconstructed using a standard ordered subset expected maximization iterative algorithm. Emission data is corrected for scatter, attenuation and decay.

PU-tumor avidity is a binary outcome defined on visual inspection of PET imagery, as tumor tracer-signal judged to be distinctly-higher than reference blood pool or organ background, at any time-point. Tumor PU-H71 concentrations are assessed quantitatively from PET data by (1) highest tumor Standardized Uptake Value (SUV) at any time-point; and (2) the integral of tumor SUV as a function of time post PU-H71-injection between the first and last PET time-points (i.e. PU-PET SUVmax readings or molar concentrations calculated from such SUV readings are graphed as a function of time post-PU administration and AUC values and average tumor concentrations of Hsp90 inhibitor calculated as shown in FIG. 27).

These parameters (or other as defined) are then correlated with response on the therapeutic trials with HSP90 inhibitors. On these studies, tumor response is evaluated per-tumor and per-patient. The timing of tumor response assessments are made as per therapy trial protocol. Tumor response assessment is from clinical imaging performed closest to the end of 1 cycle (one cycle typically being 3-5 weeks). Tumor response is defined by RECIST 1.1, for CT or MRI, and/or PERCIST 1.0 for FDG PET-CT (36,37). If discordant, the more favorable response will be used. Clinical response will be judged according to cancer-specific therapy trial response criteria.

Tumor PUH71-avidity data on PET imagery is dichotomized in two ways:

(1) by using a binary outcome of qualitative/visual judgment of tumors as being 'avid' or 'non-avid' (discussed above);

(2) by using ROC curves calculated for clustered data, a cutpoint for tumor-avidity that has the best operating characteristics in discriminating between tumor-response versus no response will be calculated (40).

For both dichotomizations, the sensitivity, specificity and other measures of classification are calculated using patient response as the truth. If each patient has a single tumor, a sample size of 40 patients will produce a two-sided confidence interval with a maximum width of 0.324. As the number of tumors per patient increases, the confidence interval width will generally decrease overall. An exploratory analysis designed to find a patient-level summary statistic for tumor-avidity that best correlates with overall RECIST patient-level response is performed. Patient-level summary statistics for avidity that are investigated include 1) the highest tumor SUV and/or AUC and 2) the average of all tumor SUV and/or AUCs. This patient-level data is used to construct an ROC curve and a cutoff for patient summarized tumor-avidity that is based on the Youden index and the point closest to (0,1) will be calculated.

In preclinical studies, uptake and retention at a certain time point or over a period of time is best correlated with the observed response. Preliminary data suggest that both prolonged tumor retention (for over 24-48 h) as well as tumor-exposure as measured by AUC are pertinent parameters to predict tumor response to Hsp90 inhibition therapy. Specifically, in preliminary investigations in MDA-MB-468 tumors, several parameters were calculated such as the tumor area-under-the-curve (AUC), the average and minimum tumor concentrations of PU-H71, target occupancy measured as the average % Hsp90 sites occupied and recognized by PU-H71 ((% Occupied Hsp90 sites)$_{avg}$) over the time of treatment. We found that the average tumor concentration of PU-H71 recorded over the time of treatment, the tumor AUC and the % "oncogenic Hsp90" occupancy correlated significantly well with the magnitude of the observed anti-tumor effect ($r^2$=0.8162, 0.8188 and 0.7559, respectively) (FIG. 37). These suggest that most appropriate parameters to predict response to Hsp90i are those that measure time-dependent exposure, i.e. uptake and retention.

6.6. Studies to Identify Markers Predictive of Apoptotic Sensitivity to HSP90 in Breast Cancer and AML Cells: Kasumi-1, SKNO-1, MOLM-13, MO-91, HEL, HL-60, THP-1, MV4-11 were grown in RPMI media supplemented with 10 mM HEPES, 4.5 g/L glucose, 1.5 g/L sodium bicarbonate, 1 mM sodium pyruvate, 10% FBS, and 1% penicillin/streptomycin. The stable transfectants of FL5.12 were previously described (18-Karnauskas 2003). In brief, for the generation of FL5.mAKT the myristylated AKT was cloned in the doxycycline inducible vector pRevTRE (Clontech) (this clone is designated mAKT). As a control, cell were transfected with vector alone (this clone is designated Vector). For generation of FL5.mAkt.Bcl-xL, the human Bcl-xL cDNA was cloned into the EcoRI site of the pBabePuro vector, and transfected into FL5.mAkt3 as described (18) (this clone is designated mAKT.Bcl-xL). These lines were cultured as described previously using DME-HG media supplemented with 10 mM HEPES, 10% FBS media containing 1 mg/ml Geneticin (G418) (Sigma #G9516) and 1 or 2 ng/mL of IL-3 (RD Systems #403 ML).

PBL (human peripheral blood leukocytes) were isolated from patient blood purchased from the New York Blood Center. Thirty five ml of the cell suspension was layered over 15 ml of Ficoll-Paque plus (GE Healthcare). Samples were centrifuged at 2,000 rpm for 40 min at 4° C., and the leukocyte interface was collected. Cells were plated in RPMI medium with 10% FBS and treated next day with appropriate concentrations of PU-H71 for the indicated times.

Reagents: The Hsp90 inhibitors were synthesized as previously reported. We purchased from Calbiochem the Akt Inhibitor VIII, Isozyme-Selective, Akti-1/2 (#124018), the PD98059 MEK inhibitor (#513000) and the pan-JAK Inhibitor I (#420099). These compounds were used at concentrations as indicated by the vendor to result in inhibition of their target pathways. All compounds, except for in vivo studies, were used as DMSO stocks.

Growth Inhibition: Growth inhibition studies were performed using the Alamar blue assay. This reagent offers a rapid objective measure of cell viability in cell culture, and it uses the indicator dye resazurin to measure the metabolic capacity of cells, an indicator of cell viability. Briefly, exponentially growing AML cell lines were plated at $2\times10^4$ cells/well in microtiter plates (Corning #3650) and incubated for the indicated times at 37° C. Drugs were added in triplicates at the indicated concentrations, and the plate was incubated for 72 h. Resazurin (55 μM) was added, and the plate read 6 h later using the Analyst GT (Fluorescence intensity mode, excitation 530 nm, emission 580 nm, with 560 nm dichroic mirror). Results were analyzed using the Softmax Pro software. The percentage cell growth inhibition was calculated by comparing fluorescence readings obtained from treated versus control cells, accounting for initial cell population (time zero). The $IC_{50}$ was calculated as the drug concentration that inhibits cell growth by 50%.

Apoptosis Assay: Cells were treated for 24, 48 or 72 h with vehicle (DMSO) or inhibitors as indicated. Following staining with Acridine Orange and Ethidium Bromide (1:1 mix of 100 □g/ml), cells were visualized with a fluorescent microscope (Zeiss Axiovert 40 CFL) and counted. Percentage of apoptotic cells was determined from 200-300 cells counted in each group. The percentage of apoptotic cells was calculated as: % Apoptotic cells=(total number of cells with apoptotic nuclei/total number of cells counted)x100. Acridine orange is taken up by both viable and nonviable cells and emits green fluorescence if intercalated into double stranded nucleic acid (DNA) or red fluorescence if bound to single stranded nucleic acid (RNA). Ethidium bromide is taken up only by nonviable cells and emits red fluorescence by intercalation into DNA. Viable cells have uniform green nuclei with organized structure. Early apoptotic cells (which still have intact membranes but have started to undergo DNA cleavage) have green nuclei, but perinuclear chromatin condensation is visible as bright green patches or fragments. Late apoptotic cells have orange to red nuclei with condensed or fragmented chromatin. Necrotic cells have a uniformly orange to red nuclei with organized structure.

Caspase 3,7 Activation Assay: Cells were plated and treated as described in the growth inhibition assay section. Following a 24 h or 48 h exposure of cells to Hsp90 inhibitors, 100 μL buffer containing 10 mM Hepes, pH 7.5, 2 mM EDTA, 0.1% CHAPS, 0.1 mg/mL PMSF, Complete Protease Inhibitor mix (#1697498; Roche), and the caspase substrate Z-DEVD-R110 (#R22120; Molecular Probes) at 25 μM was added to each well. Plates were placed on an orbital shaker to promote cell lysis and reaction. The fluorescence signal of each well was measured in an Analyst GT (Molecular Dev ices) microplate reader (excitation 485 nm; emission at 530 nm). The percentage increase in caspase-3,7 activity was calculated by comparison of the fluorescence reading obtained from treated versus control cells. All experimental data were analyzed using SOFTmax Pro 4.3.1 and plotted using Prism 4.0 (Graphpad Software Inc., San Diego, CA).

Western blot: Cells were grown to 60-70% confluence and treated with inhibitor or vehicle for the indicated times. Protein lysates were prepared in 50 mM Tris pH 7.4, 150 mM NaCl and 1% NP-40 lysis buffer. Protein concentrations were measured using the BCA kit (Pierce) according to the manufacturer's instructions. Protein lysates (10-100 μg) were resolved by SDS-PAGE, transferred onto nitrocellulose membrane and incubated with the indicated primary antibodies. To activate AKT, FL5.12-derived cell lines were pre-treated with 1 μg/ml Dox for 18 h prior to treatment with inhibitors.

Antibodies: Anti-AKT from rabbit (1:500, 9272; Cell Signaling), anti-phospho-AKT (Ser 473) from rabbit (1:500, 9271 S; Cell Signaling), anti-RAF-1 from rabbit (1:300, sc-133; Santa Cruz Biotechnology), anti-PARP (p85 fragment) from rabbit (1:250, G7341; Promega), anti-Bcl-xL from rabbit (1:1,000, 2762; Cell Signaling), anti-JAK2 from rabbit (1:500, 3773; Cell Signaling), anti-c-KIT from mouse (1:1,000, 3308; Cell Signaling), anti-AML1 from rabbit (1:500, 4334; Cell Signaling), anti-FLT3 from rabbit (1:1,000, 3462; Cell Signaling), anti-TRKC from rabbit (1:1,000, ab43078; Abcam), STAT5, p-STAT5, p-ERK and anti-β-Actin from mouse (1:3,000, ab8227-50; Abcam). The membranes were then incubated with 1:3,000 dilution of a perioxidase-conjugated corresponding secondary antibody and proteins were detected via ECL-Enhanced Chemiluminescence Detection System (Amersham Biosciences).

Pharmacodynamic Study: Four- to 6-week-old nu/nu athymic female mice were obtained from Taconic Farms. Experiments were carried out under an Institutional Animal Care and Use Committee-approved protocol, and institutional guidelines for the proper and humane use of animals in research were followed. HEL and MO-91 cells were subcutaneously implanted in the right flank of mice using a 20-gauge needle and allowed to grow. Before administration, a solution of PU-H71-HCl was formulated in sterile PBS. For this assay, tumors were allowed to reach 6-8 mm in diameter before treatment. Mice bearing MO-91 and HEL tumors were administered intraperitoneally (i.p.) 75 mg/kg PU-H71. Animals were sacrificed by $CO_2$ euthanasia at 12, 24, 48, 72, and 96 h post administration of PU-H71. Tumors were homogenized and proteins analyzed by western blot as described above.

Densitometry. Gels were scanned in Adobe Photoshop 7.0.1 and quantitative densitometric analysis was performed using Un-Scan-It 5.1.

Statistics. We performed statistical analysis and graph plotting with Prism 4.0 (GraphPad Software). We presented all data as mean±s.d. A P value of less than 0.05 was considered significant.

Stat5 phosphoflow—Primary cells were stained with CD34-APC, CD38-PE-CY7 and CD45-APC-H7 antibodies (BD Biosciences) in FACS buffer at 4° C. for 30 min. Cells were washed once, fixed with 4% paraformaldehyde at room temperature for 30 min, and permeabilized with PBS/0.1% Triton X-100 on ice for 10 min. Cells were stained with p-Stat5-PE or isotype control (BD Biosciences) at 4° C. overnight. Cells were then washed once with PBS, and subjected to flow cytometry analysis using BD-LSR II flow cytometer (BD Biosciences). The MFI of p-Stat5 staining was normalized to isotype control.

Stem cell viability assay—Primary cells were plated in 48-well plates at $2\times10^6$ cells/ml, and treated with 1 μM PU-H71 for 48 h. Cells were stained with CD34-APC, CD38-PE-CY7 and CD45-APC-H7 antibodies (BD Biosciences) in FACS buffer (PBS, 0.05% FBS) at 4° C. for 30 min prior to Annexin V-V450 (BD Biosciences) and 7-AAD staining in Annexin V buffer (10 mM HEPES/NaOH, 0.14 M NaCl, 2.5 mM $CaCl_2$). Cell viability was normalized to untreated cells.

6.7. Studies to Identify Neurodegenerative Patients Susceptible to HSP90 Inhibition Therapy The transgenic model of AD (3×Tg-AD), which expresses the human APPswe, PS1M146V and tauP301L, progressively develops both Abeta and tau pathology in an age-dependent manner in disease-relevant brain regions (Billings et al., 2005; Oddo et al., 2005; Oddo et al., 2003). This mouse model is established by co-injection of APP and tau cDNA constructs into PS1M146 knockin mouse embryos. These mice develop intracellular Aβ preceding amyloid plaque deposition, consistent with the observations in patients with mild cognitive impairment (MCI) and patients with Down's syndrome. They also develop extracellular Abeta deposit prior to tangle formation, allowing us to study the events involved in these two AD development stages. The tau pathology is first apparent in pyramidal cells of hippocampus CA1 region and progresses into cortex, mimicking distribution pattern in human AD brain (Mesulam, 2000). Therefore, the AD 3×-tg mouse model shows many similarities to human AD and provides the opportunity to study the effect and retention of Hsp90 inhibitors in the pathogenically affected and in the normal brain regions.

Determination of brain and plasma drug concentrations. The aqueous solution of compound PU-HZ151 as HCl salt was administered i.p. to 3×Tg AD mice (35 g average body weight) at the indicated doses. Mice were killed by $CO_2$ euthanasia at different time points after the treatment according to protocols approved by MSKCC Institutional Animal Care and Use Committee. Hemibrains were separated into corticolimbic and subcortical regions, quickly frozen in liquid nitrogen and stored at −80° C. Plasma was obtained from blood that was collected into a 1.5 mL Eppendorf tube cooled in ice and subject to centrifuge. Frozen brain tissue was dried and weighed prior to homogenization in acetonitrile/$H_2O$ (3:7). The mixture was extracted with methylene chloride, the organic layer separated and dried under vacuum. Plasma (50 uL) was mixed with acetonitrile (0.25 mL) and centrifuged. The resulting supernatants were dried under vacuum. Samples were reconstituted in mobile phase. Concentrations of compound in brain and plasma were determined by high-performance LC-MS/MS. Haloperidol was added as the internal standard. Compound analysis was performed on the 6410 LC-MS/MS system (Agilent Technologies) in multiple reaction monitoring (MRM) mode using positive-ion electrospray ionization. A Zorbax Eclipse XDB-C18 column (2.1×50 mm, 3.5 μm) was used for the LC separation, and the analyte was eluted under an isocratic condition (65% $H_2O$+0.1% HCOOH: 35% $CH_3CN$) for 5 minutes at a flow rate of 0.35 ml/min.

Pharmacodynamic analyses. For protein analysis, selected brain region (hippocampus) was homogenized in SDS lysis buffer (50 mM Tris pH 7.4, 2% SDS) and subjected to Western blot analysis. Levels of proteins were be analyzed by immunoblotting with anti-Hsp70 and Hsp90 antibodies.

7. EMBODIMENTS

The invention can be illustrated by the following embodiments enumerated in the numbered paragraphs below:

1. A method for determining whether a tumor will likely respond to therapy with an HSP90 inhibitor which comprises the following steps:
   (a) contacting the tumor or a sample containing cells from the tumor with a detectably labeled HSP90 inhibitor which binds preferentially to a tumor-specific form of HSP90 present in a tumor or tumor cells;
   (b) measuring the amount of labeled HSP90 inhibitor bound to the tumor or the tumor cells in the sample; and
   (c) comparing the amount of labeled HSP90 inhibitor bound to the tumor or the tumor cells in the sample measured in step (b) to a reference amount of the labeled HSP90 inhibitor bound to normal cells;
   wherein a greater amount of labeled HSP90 inhibitor bound to the tumor or the tumor cells measured in step (b) as compared with the reference amount indicates the tumor will likely respond to the HSP90 inhibitor.
2. A method of embodiment 1, wherein the greater the ratio of the amount of labeled HSP90 inhibitor bound to the tumor or the tumor cells measured in step (b) as compared with the reference amount, the greater the magnitude of the likely response to the HSP90 inhibitor therapy.
3. A method of embodiment 1, wherein the greater the amount of labeled HSP90 inhibitor bound to the tumor or the tumor cells measured in step (a), the greater the magnitude of the likely response to the HSP90 inhibitor therapy.
4. A method of embodiment 1, wherein the reference amount of the labeled HSP90 inhibitor bound to normal cells is the amount of the labeled HSP90 inhibitor bound to normal cells in the sample containing cells from the tumor.
5. A method of embodiment 1, wherein the reference amount of the labeled HSP90 inhibitor bound to normal cells is a predetermined amount of the labeled HSP90 inhibitor bound to normal cells in a reference sample.
6. A method of embodiment 1, wherein the detectably labeled HSP90 inhibitor is fluorescently labeled.
7. A method of embodiment 1, wherein the detectably labeled HSP90 inhibitor is biotin-labeled.
8. A method of embodiment 1, wherein the detectably labeled HSP90 inhibitor is radioactively labeled.
9. A method of embodiment 1, wherein the tumor is associated with a cancer selected from the group consisting of colorectal cancer, pancreatic cancer, thyroid cancer, a leukemia including acute myeloid leukemia, acute lymphoblastic leukemia and chronic myeloid leukemia, multiple myeloma, basal cell carcinoma, melanoma, renal cell carcinoma, bladder cancer, prostate cancer, a lung cancer including small cell lung cancer and non-small cell lung cancer, breast cancer, neuroblastoma, myeloproliferative disorders, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers.
10. A method of embodiment 9, wherein the cancer is breast cancer.
11. A method of embodiment 9, wherein the cancer is a leukemia.
12. A method of embodiment 11, wherein the leukemia is chronic myeloid leukemia.
13. A method of embodiment 9, wherein the cancer is gastric cancer.
14. A method of embodiment 9, wherein the cancer is pancreatic cancer.
15. A method of embodiment 1, wherein the tumor cell is a tumor stem cell.
16. A method of embodiment 1, wherein in step (a) the tumor is contacted, and is present, in a subject.
17. A method of embodiment 1, wherein in step (a) the sample containing tumor cells is contacted and is a tissue sample.
18. A method of embodiment 1, where the tissue sample is a sample obtained during a biopsy, a fine needle aspiration or a surgical procedure.

19. A method of embodiment 1, wherein in step (a) the sample is contacted and comprises a biological fluid.
20. A method of embodiment 19, wherein the biological fluid is blood or bone marrow.
21. A method of embodiment 1, wherein in step (a) the sample is contacted and comprises disrupted tumor cells.
22. A method of embodiment 1, wherein in step (a) the sample is contacted and comprises live cells.
23. A method of embodiment 1, wherein in step (a) the sample is contacted and comprises frozen cells.
24. A method of embodiment 1, wherein in step (a) the sample is contacted and comprises fixed and permeabilized cells.
25. A method of embodiment 1, wherein in step (a) the sample is contacted and comprises formalin-fixed, paraffin-embedded cells.
26. A method of embodiment 1, wherein the detectably labeled HSP90 inhibitor is a labeled form of the HSP90 inhibitor to be administered as therapy.
27. A method of embodiment 1, wherein the HSP90 inhibitor to be administered as therapy is PU-H71 or an analog, homolog or derivative of PU-H71.
28. A method of embodiment 27, wherein the HSP90 inhibitor is PU-H71.
29. A method of embodiment 1, wherein the detectably labeled HSP90 inhibitor is a form of PU-H71 or of an analog, homolog, or derivative of PU-H71.
30. A method of embodiment 1, wherein the detectably labeled HSP90 inhibitor is a form of PU-H71.
31. A method of embodiment 30, wherein the detectably labeled HSP90 inhibitor is $[^{124}I]$-PU-H71.
32. A method of embodiment 30, wherein the detectably labeled HSP90 inhibitor is PU-H71-FITC2 or PU-H71-NBD1.
33. A method of embodiment 30, wherein the detectably labeled HSP90 inhibitor is a biotinylated analog of PU-H71.
34. A method of embodiment 33, wherein the biotinylated analog of PU-H71 is PU-H71-biotin-5, PU-H71-biotin-6, PU-H71-biotin-8 or PU-H71-biotin-9.
35. A method for determining whether a cancer patient with an imageable tumor will likely respond to therapy with an inhibitor of HSP90 which comprises the following steps:
    (a) administering to the patient a radiolabeled HSP90 inhibitor which binds preferentially to a tumor-specific form of HSP90 present in the tumor or in tumor cells of the tumor;
    (b) measuring uptake of the radiolabeled HSP90 inhibitor by the patient's tumor at a plurality of time points after the administration in step (a);
    (c) measuring uptake of the radiolabeled HSP90 inhibitor by a predetermined healthy tissue of the patient at the same plurality of time points after the administration in step (a);
    (d) computing a ratio of the uptake measured at multiple time points in step (b) with the uptake measured at the same time points in step (c); and
    (e) determining the likelihood the cancer patient will respond to therapy with the inhibitor of HSP90, wherein a ratio greater than 2 computed in step (d) at multiple time points indicates that the patient will likely respond.
36. A method of embodiment 35, wherein the tumor is associated with a cancer selected from the group consisting of colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers.
37. A method of embodiment 36, wherein the cancer is breast cancer, lymphoma, neuroblastoma, gastric cancer, or pancreatic cancer.
38. A method of embodiment 35, wherein the radiolabeled HSP90 inhibitor is a radiolabeled form of the HSP90 inhibitor to be administered as therapy.
39. A method of embodiment 36, wherein the HSP90 inhibitor to be administered as therapy is PU-H71 or an analog, homolog, or derivative of PU-H71.
40. A method of embodiment 35, wherein the radiolabeled HSP90 inhibitor is a radiolabeled form of PU-H71.
41. A method of embodiment 40, wherein the radiolabeled form of PU-H71 is $[^{124}I]$-PU-H71.
42. A method for determining whether a cancer patient with an imageable tumor will likely respond to therapy with a predetermined dose of an inhibitor of HSP90 which comprises the following steps:
    (a) administering to the patient a radiolabeled form of the HSP90 inhibitor which binds preferentially to a tumor-specific form of HSP90 present in the tumor or in tumor cells of the tumor;
    (b) measuring uptake of the radiolabeled form of the HSP90 inhibitor by the patient's tumor at a plurality of time points after the administration in step (a);
    (c) calculating for the predetermined dose of the HSP90 inhibitor, the concentrations of the HSP90 inhibitor which would be present in the patient's tumor at each of such plurality of time points, based on the uptake measured at such plurality of time points in step (b); and
    (d) comparing the concentrations of the HSP90 inhibitor calculated in step (c) with reference concentrations of the HSP90 inhibitor which would need to be present in the tumor at such plurality of time points for the HSP90 inhibitor to be effective in treating the tumor
    wherein the patient will likely respond to therapy with the predetermined dose of the HSP90 inhibitor if the concentrations of the HSP90 inhibitor calculated in step (c) would equal or exceed the concentrations of the HSP90 inhibitor needed to effectively treat the tumor and would not be toxic to the patient.
43. A method of embodiment 40, wherein the tumor is associated with a cancer selected from the group consisting of colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers.

44. A method of embodiment 43, wherein the cancer is breast cancer, lymphoma, neuroblastoma, gastric cancer, or pancreatic cancer.
45. A method of embodiment 42, wherein the HSP90 inhibitor to be administered as therapy is PU-H71 or an analog, homolog, or derivative of PU-H71.
46. A method of embodiment 42, wherein the radiolabeled HSP90 inhibitor is a radiolabeled form of PU-H71.
47. A method of embodiment 46, wherein the radiolabeled form of PU-H71 is $[^{124}I]$-PU-H71.
48. A method for determining, for a specific cancer patient with an imageable tumor, an effective dose and frequency of administration for therapy with an inhibitor of HSP90 which comprises the following steps:
(a) administering to the patient a radiolabeled form of the HSP90 inhibitor which binds preferentially to a tumor-specific form of HSP90 present in a tumor or tumor cells;
(b) measuring uptake of the radiolabeled form of the HSP90 inhibitor by the patient's tumor at a plurality of time points after the administration in step (a); and
(c) calculating the dose and frequency of administration needed to maintain in the tumor at each of such plurality of time points a concentration of the HSP inhibitor effective to treat the tumor, based on the uptake measured at such time points in step (b), thereby determining, for the cancer patient, the effective dose and frequency of administration for therapy with the inhibitor of HSP90.
49. A method of embodiment 48, wherein the tumor is associated with a cancer selected from the group consisting of colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers.
50. A method of embodiment 49, wherein the cancer is breast cancer, lymphoma, neuroblastoma, gastric cancer, or pancreatic cancer.
51. A method of embodiment 48, wherein the radiolabeled HSP90 inhibitor is a radiolabeled form of the HSP90 inhibitor to be administered as therapy.
52. A method of embodiment 48, wherein the HSP90 inhibitor to be administered as therapy is PU-H71 or an analog, homolog, or derivative of PU-H71.
53. A method of embodiment 48, wherein the radiolabeled HSP90 inhibitor is a radiolabeled form of PU-H71.
54. A method of embodiment 53, wherein the radiolabeled form of PU-H71 is $[^{124}I]$-PU-H71.
55. A method for determining the concentration of a HSP90 inhibitor present in an imageable tumor in a cancer patient which comprises the following steps:
(a) co-administering to the patient a predetermined amount of the HSP90 inhibitor and a predetermined amount of a radiolabeled form of the HSP90 inhibitor which binds preferentially to a tumor-specific form of HSP90 present in a tumor or tumor cells;
(b) periodically measuring the uptake of the radiolabeled HSP90 inhibitor by the patient's tumor at one or more predefined time point(s) after the co-administration in step (a); and
(c) determining the concentration of the HSP90 inhibitor present in the tumor at any such time point based on the measurements of the uptake of the radiolabeled HSP90 inhibitor in step (b).
56. A method of embodiment 54, wherein the tumor is associated with a cancer selected from the group consisting of colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers.
57. A method of embodiment 56, wherein the cancer is breast cancer, lymphoma, neuroblastoma, gastric cancer, or pancreatic cancer.
58. A method of embodiment 55, wherein the radiolabeled HSP90 inhibitor is a radiolabeled form of the HSP90 inhibitor to be administered as therapy.
59. A method of embodiment 55, wherein the HSP90 inhibitor to be administered as therapy is PU-H71 or an analog, homolog, or derivative of PU-H71.
60. A method of embodiment 55, wherein the radiolabeled HSP90 inhibitor is a radiolabeled form of PU-H71.
61. A method of embodiment 60, wherein the radiolabeled form of PU-H71 is $[^{124}I]$-PU-H71.
62. A method for determining the responsiveness to therapy with an inhibitor of HSP90 of an imageable tumor in a cancer patient which comprises the following steps:
(a) administering a radiolabeled form of the HSP90 inhibitor which binds preferentially to a tumor-specific form of HSP90 present in a tumor or tumor cells, to the patient at multiple time points within the period during which the patient is receiving the inhibitor of HSP90 as therapy; and
(b) measuring the concentration of the radiolabeled HSP90 inhibitor in the patient's tumor at such multiple time points after the administration in step (a); and
(c) comparing the concentrations of the radiolabeled HSP90 inhibitor measured in step (b) with the minimum concentrations of the HSP90 inhibitor needed to effectively treat the tumor, wherein measured concentrations greater than the minimum needed to treat the tumor indicate that the patient is likely to respond to therapy with the HSP90 inhibitor.
63. A method of embodiment 62, wherein the tumor is associated with a cancer selected from the group consisting of colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, and gynecologic cancers including ovarian, cervical, and endometrial cancers.

64. A method of embodiment 63, wherein the cancer is breast cancer, lymphoma, neuroblastoma, gastric cancer, or pancreatic cancer.
65. A method of embodiment 62, wherein the radiolabeled HSP90 inhibitor is a radiolabeled form of the HSP90 inhibitor to be administered as therapy.
66. A method of embodiment 62, wherein the HSP90 inhibitor to be administered as therapy is PU-H71 or an analog, homolog, or derivative of PU-H71.
67. A method of embodiment 62, wherein the radiolabeled HSP90 inhibitor is a radiolabeled form of PU-H71.
68. A method of embodiment 67, wherein the radiolabeled form of PU-H71 is [$^{124}$I]-PU-H71.
69. A method for determining whether a human cancer present in a patient will likely respond to therapy with an HSP90 inhibitor which comprises:
    (a) obtaining a sample containing cells from the patient's cancer, which cells express HSP90 protein alone or in addition to HSP70 protein;
    (b) assessing for the cells present in the sample obtained in step (a) the presence of at least one of the following parameters: an activated AKT pathway, a defect in PTEN tumor suppressor function or expression, an activated STAT5 pathway, or Bcl-xL protein expression; and
    (c) comparing the assessment obtained in step (b) with a predetermined reference assessment of the same parameter or parameters assessed in step (b) for human cancer cells from one or more cancer patient (s) who responded to therapy with the HSP90 inhibitor so as to thereby determine whether the patient's cancer will likely respond to therapy with the HSP90 inhibitor.
70. A method of embodiment 69, wherein the human cancer is breast cancer.
71. A method of embodiment 69, wherein the cancer cells are associated with acute myeloid leukemia.

8. REFERENCES

1. Whitesell, L.; Lindquist, S. L., HSP90 and the chaperoning of cancer. *Nat. Rev. Cancer* 2005, 5, 761-772.
2. Workman, P.; Burrows, F.; Neckers, L.; Rosen, N., Drugging the cancer chaperone HSP90: combinatorial therapeutic exploitation of oncogene addiction and tumor stress. *Ann. N.Y. Acad. Sci.* 2007, 1113, 202-216.
3. Luo, W.; Sun, W.; Taldone, T.; Rodina, A.; Chiosis, G., Heat shock protein 90 in neurodegenerative diseases. *Mol. Neurodegener.* 2010, 5:24.
4. Taldone, T.; Gozman, A.; Maharaj, R.; Chiosis, G., Targeting HSP90: small-molecule inhibitors and their clinical development. *Curr. Opin. Pharmacol.* 2006, 8, 370-374.
5. Janin, Y. L., ATPase inhibitors of heat-shock protein 90, second season. *Drug Discovery Today* 2010, 15, 342-353.
6. Kamal, A.; Thao, L.; Sensintaffar, J.; Zhang, L.; Boehm, M. F.; Fritz, L. C.; Burrows, F. J., A high-affinity conformation of HSP90 confers tumour selectivity on HSP90 inhibitors. *Nature* 2003,425, 407-410.
7. Dickey, C. A.; Kamal, A.; Lundgren, K.; Klosak, N.; Bailey, R. M.; Dunmore, J.; Ash, P.; Shoraka, S.; Zlatkovic, J.; Eckman, C. B.; Patterson, C.; Dickson, D. W.; Nahman, N. S.; Hutton, M.; Burrows, F.; Petrucelli, L., The high-affinity HSP90-CHIP complex recognizes and selectively degrades phosphorylated tau client proteins. *J. Clin. Invest.* 2007, 117, 648-658.
8. Chiosis, G.; Neckers, L., Tumor selectivity of HSP90 inhibitors: the explanation remains elusive. *ACS Chem. Biol.* 2006, 1, 279-284.
9. Peters, J. M.; Ansari, M. Q., Multiparameter flow cytometry in the diagnosis and management of acute leukemia. *Arch. Pathol. Lab. Med.* 2011, 135, 44-54.
10. Covey, T. M.; Cesano, A., Modulated multiparametric phosphoflow cytometry in hematological malignancies: technology and clinical applications. *Best Pract. Res. Clin. Haematol.* 2010, 23, 319-331.
11. Jennings, C. D.; Foon, K. A., Recent advances in flow cytometry: application to the diagnosis of hematologic malignancy. *Blood* 1997, 90, 2863-2892.
12. Leopoldo, M.; Lacivita, E.; Berardi, F.; Perrone, R., Developments in fluorescent probes for receptor research. *Drug Discov. Today* 2009, 14, 706-712.
13. Llauger-Bufi, L.; Felts, S. J.; Huezo, H.; Rosen, N.; Chiosis, G., Synthesis of novel fluorescent probes for the molecular chaperone HSP90. *Bioorg Med Chem Lett.* 2003, 13, 3975-3978.
14. Moulick, K.; Clement, C. C.; Aguirre, J.; Kim, J.; Kang, Y.; Felts, S.; Chiosis, G., Synthesis of a red-shifted fluorescence polarization probe for HSP90. *Bioorg Med Chem Lett.* 2006, 16, 4515-4518.
15. Howes, R.; Barril, X.; Dymock, B. W.; Grant, K.; Northfield, C. J.; Robertson, A. G.; Surgenor, A.; Wayne, J.; Wright, L.; James, K.; Matthews, T.; Cheung, K. M.; McDonald, E.; Workman, P.; Drysdale, M. J., A fluorescence polarization assay for inhibitors of HSP90. *Anal Biochem.* 2006, 350, 202-213.
16. Tsutsumi, S.; Scroggins, B.; Koga, F.; Lee, M. J.; Trepel, J.; Felts, S.; Carreras, C.; Neckers, L., A small molecule cell-impermeant HSP90 antagonist inhibits tumor cell motility and invasion. *Oncogene* 2008, 27, 2478-2487.
17. Taldone, T.; Chiosis, G., Purine-scaffold HSP90 inhibitors. *Curr Top Med Chem* 2009, 9, 1436-1446.
18. Patel, H. J.; Modi, S.; Chiosis, G.; Taldone, T., Advances in the discovery and development of heat-shock protein 90 inhibitors for cancer treatment. *Expert Opin. Drug Discov.* 15 Mar. 2011 (doi: 10.1517/17460441.2011.563296).
19. Papac, D. I.; Patton, J. S.; Reeves, L.; Bulka, K.; DeMie, L.; Roman, O.; Bradford, C.; Kim, S.-H.; Tangallapally, R.; Trovato, R.; Markovitz, B.; Bajji, A.; Wettstein, D.; Baichwal, V.; Mather, G., Comparative in vitro and in vivo metabolism of MPC-3100, an oral HSP90 inhibitor, in rat, dog, monkey and human. 102nd AACR annual meeting, abstract number 3233. Orlando, Fl, Apr. 2-6, 2011.
20. Immormino, R. M.; Kang, Y.; Chiosis, G.; Gewirth, D. T., Structural and quantum chemical studies of 8-arylsulfanyl adenine class HSP90 inhibitors. *J. Med. Chem.* 2006, 49, 4953-4960.
21. Taldone, T.; Zatorska, D.; Patel, P. D.; Zong, H.; Rodina, A.; Ahn, J. H.; Moulick, K.; Guzman, M. L.; Chiosis, G., Design, Synthesis and Evaluation of Small Molecule HSP90 Probes. *Bioorg. Med. Chem.* 2011, 19, 2603-2614.
22. Taliani, S.; Simorini, F.; Sergianni, V.; La Motta, C.; Da Settimo, F.; Cosimelli, B.; Abignente, E.; Greco, G.; Novellino, E.; Rossi, L.; Gremigni, V.; Spinetti, F.; Chelli, B.; Martini, C., New fluorescent 2-phenylindolglyoxylamide derivatives as probes targeting the peripheral-type benzodiazepine receptor: design, synthesis, and biological evaluation. *J Med Chem.* 2007, 50, 404-407.

23. He, H.; Zatorska, D.; Kim, J.; Aguirre, J.; Llauger, L.; She, Y.; Wu, N.; Immormino, R. M.; Gewirth, D. T.; Chiosis, G., Identification of potent water soluble purine-scaffold inhibitors of the heat shock protein 90. *J. Med Chem.* 2006, 49, 381-390.

24. Vial, J. P.; Lacombe, F., Immunophenotyping of acute leukemia: utility of CD45 for blast cell identification. *Methods Cell Biol.* 2001, 64, 343-358.

25. Ley, T. J. et al. DNA sequencing of a cytogenetically normal acute myeloid leukaemia genome *Nature* 456, 66-72 (2008).

26. Parsons, D. W. et al. An integrated genomic analysis of human glioblastoma multiforme. Science 321, 1807-1812 (2008).

27. Hanash, S. & Taguchi, A. The grand challenge to decipher the cancer proteome. *Nat. Rev. Cancer* 10, 652-660 (2010).

28. Kolch, W. & Pitt, A. Functional proteomics to dissect tyrosine kinase signalling pathways in cancer. *Nat. Rev. Cancer* 10, 618-629 (2010).

29. Nomura, D. K., Dix, M. M. & Cravatt, B. F. Activity-based protein profiling for biochemical pathway discovery in cancer. *Nat. Rev. Cancer* 10, 630-638 (2010).

30. Brehme, M. et al. Charting the molecular network of the drug target Bcr-Abl. *Proc. Natl. Acad Sci. USA* 106, 7414-7419 (2009).

31. Ashman, K. & Villar, E. L. Phosphoproteomics and cancer research. *Clin. Transl. Oncol.* 11, 356-362 (2009).

32. Zuehlke, A. & Johnson, J. L. HSP90 and co-chaperones twist the functions of diverse client proteins. *Biopolymers* 93, 211-217 (2010).

33. Workman, P., Burrows, F., Neckers, L. & Rosen, N. Drugging the cancer chaperone HSP90: combinatorial therapeutic exploitation of oncogene addiction and tumor stress. *Ann. N. Y. Acad Sci.* 1113, 202-216 (2007).

34. Kamal, A. et al. A high-affinity conformation of HSP90 confers tumour selectivity on HSP90 inhibitors, *Nature* 425, 407-410 (2003).

35. Janin, Y. L. ATPase inhibitors of heat-shock protein 90, second season. *Drug Discov. Today* 15, 342-353 (2010).

36. Tsaytler, P. A., Krijgsveld, J., Goerdayal, S. S., Rudiger, S. & Egmond, M. R. Novel HSP90 partners discovered using complementary proteomic approaches. *Cell Stress Chaperones* 14, 629-638 (2009).

37. da Rocha Dias, S. et al. Activated B-RAF is an HSP90 client protein that is targeted by the anticancer drug 17-allylamino-17-demethoxygeldanamycin. *Cancer Res.* 65, 10686-10691 (2005).

38. Grbovic, O. M. et al. V600E B-Raf requires the HSP90 chaperone for stability and is degraded in response to HSP90 inhibitors. *Proc. Natl. Acad Sci. USA* 103, 57-62 (2006).

39. Taldone, T. & Chiosis, G. Purine-scaffold HSP90 inhibitors. *Curr. Top. Med. Chem.* 9, 1436-1446 (2009).

40. Dezwaan, D. C. & Freeman, B. C. HSP90: the Rosetta stone for cellular protein dynamics?*Cell Cycle* 7, 1006-1012 (2008).

41. Ren, R. Mechanisms of BCR-ABL in the pathogenesis of chronic myelogenous leukaemia. *Nat. Rev. Cancer* 5, 172-183 (2005).

42. Burke, B, A. & Carroll, M. BCR-ABL: a multi-faceted promoter of DNA mutation in chronic myelogeneous leukemia. Leukemia 24, 1105-1112 (2010).

43. McClellan, A. J. et al. Diverse cellular functions of the HSP90 molecular chaperone uncovered using systems approaches. Cell 131, 121-135 (2007).

44. Carayol, N. et al. Critical roles for mTORC2- and rapamycin-insensitive mTORC1-complexes in growth and survival of BCR-ABL-expressing leukemic cells. *Proc. Natl. Acad. Sci. USA.* 107, 12469-12474 (2010).

45. Nobukuni, T., Kozma, S. C. & Thomas, G. hvps34, an ancient player, enters a growing game: mTOR Complex1/S6K1 signaling. *Curr. Opin. Cell Biol.* 19, 135-141 (2007).

46. McCubrey, J. A. et al. Targeting survival cascades induced by activation of Ras/Raf/MEK/ERK, PI3K/PTEN/Akt/mTOR and Jak/STAT pathways for effective leukemia therapy. *Leukemia* 22, 708-722 (2008).

47. Hticker, H. & Karin, M. Regulation and function of IKK and IKK-related kinases. *Sci. STKE.* 2006(357):re13.

48. Mihailovic, T. et al. Protein kinase D2 mediates activation of nuclear factor kappaB by Bcr-Abl in Bcr-Abl+ human myeloid leukemia cells. *Cancer Res.* 64, 8939-8944 (2004).

49. Hendriks, R. W. & Kersseboom, R. Involvement of SLP-65 and Btk in tumor suppression and malignant transformation of pre-B cells. *Semin. Immunol.* 18, 67-76 (2006).

50. Mahajan, S. et al. Transcription factor STAT5A is a substrate of Bruton's tyrosine kinase in B cells. *J. Biol. Chem.* 276, 31216-31228 (2001).

51. Oda, A., Wakao, H. & Fujita, H. Calpain is a signal transducer and activator of transcription (STAT) 3 and STAT5 protease. Blood 99, 1850-1852 (2002).

52. Si, J. & Collins, S. J. Activated Ca2+/calmodulin-dependent protein kinase IIgamma is a critical regulator of myeloid leukemia cell proliferation. *Cancer Res.* 68, 3733-3742 (2008).

53. Salgia, R. et al. Increased tyrosine phosphorylation of focal adhesion proteins in myeloid cell lines expressing p210BCR/ABL. *Oncogene* 11, 1149-1155 (1995).

54. Le, Y. et al. FAK silencing inhibits leukemogenesis in BCR/ABL-transformed hematopoietic cells. *Am. J. Hematol.* 84, 273-278 (2009).

55. Sawyers, C. L. The role of myc in transformation by Bcr-Abl. *Leuk. Lymphoma.* 11, 45-46 (1993).

56. Naka, K. et al. TGF-beta-FOXO signaling maintains leukemia-initiating cells in chronic myeloid leukemia. *Nature* 463, 676-678 (2010).

57. Bedford, M. T. & Clarke, S. G. Protein arginine methylation in mammals: who, what, and why. *Mol. Cell* 33, 1-13 (2009).

58. Maloney, A. et al. Gene and protein expression profiling of human ovarian cancer cells treated with the heat shock protein 90 inhibitor 17-allylamino-17-demethoxygeldanamycin. *Cancer Res.* 67, 3239-3253 (2007).

59. Jaganathan, S., Yue, P. & Turkson, J. Enhanced sensitivity of pancreatic cancer cells to concurrent inhibition of aberrant signal transducer and activator of transcription 3 and epidermal growth factor receptor or Src. *J. Pharmacol. Exp. Ther.* 333, 373-381 (2010).

60. Apsel, B., et al. Targeted polypharmacology: discovery of dual inhibitors of tyrosine and phosphoinositide kinases. *Nature Chem. Biol.* 4, 691-699 (2008).

61. Deininger, M. W. & Druker, B. J. Specific targeted therapy of chronic myelogenous leukemia with imatinib. *Pharmacol. Rev.* 55, 401-423 (2003).

62. Katzav, S. Flesh and blood: the story of Vavi, a gene that signals in hematopoietic cells but can be transforming in human malignancies. *Cancer Lett.* 255, 241-254 (2007).

63. Pratt, W. B., Morishima, Y. & Osawa, Y. The HSP90 chaperone machinery regulates signaling by modulating ligand binding clefts. *J. Biol. Chem.* 283, 22885-22889 (2008).
64. de Groot, R. P., Raaijmakers, J. A., Lammers, J. W., Jove, R. & Koenderman, L. STAT5 activation by BCR-Abl contributes to transformation of K562 leukemia cells. *Blood* 94, 1108-1112 (1999).
65. An, W. G., Schulte, T. W. & Neckers, L. M. The heat shock protein 90 antagonist geldanamycin alters chaperone association with p210bcr-abl and v-src proteins before their degradation by the proteasome. *Cell Growth Differ.* 11, 355-360 (2000).
66. Klejman, A. et al. The Src family kinase Hck couples BCR/ABL to STAT5 activation in myeloid leukemia cells. *EMBO J.* 21, 5766-5774 (2002).
67. Xu, D. & Qu, C. K. Protein tyrosine phosphatases in the JAK/STAT pathway. *Front. Biosci.* 13, 4925-4932 (2008).
68. Lim, C. P. & Cao, X. Structure, function and regulation of STAT proteins. *Mol. BioSyst,* 2, 536-550 (2006).
69. Paukku, K. & Silvennoinen, O. STATs as critical mediators of signal transduction and transcription: lessons learned from STAT5. *Cytokine Growth Factor Rev.* 15, 435-455 (2004).
70. Cerchietti, L. C. et al. A purine scaffold HSP90 inhibitor destabilizes BCL-6 and has specific antitumor activity in BCL-6-dependent B cell lymphomas. *Nat. Med.* 15, 1369-1376 (2009).
71. Hom, T., Sandmann, T. & Boutros, M. Design and evaluation of genome-wide libraries for RNA interference screens. *Genome Biol.* 2010; 11(6):R61.
72. Rix, U. & Superti-Furga, G. Target profiling of small molecules by chemical proteomics. *Nat. Chem. Biol.* 5, 616-624 (2009).
73. Trinkle-Mulcahy, L. et al. Identifying specific protein interaction partners using quantitative mass spectrometry and bead proteomes. *J. Cell. Biol.* 183, 223-239 (2008).
74. Dierov, J., Dierova. R. & Carroll, M. BCR/ABL translocates to the nucleus and disrupts an ATR-dependent intra-S phase checkpoint. *Cancer Cell* 5, 275-85 (2004).
75. Taldone, T. et al. Design, Synthesis and Evaluation of Small Molecule HSP90 Probes. Publ.ID: BMC9085 (2011).
76. Taldone, T. et al. Synthesis and Evaluation of Fluorescent HSP90 Probes for Use in Flow Cytometry. BMCL (2011).
77. He, H. et al. Identification of potent water soluble purine-scaffold inhibitors of the heat shock protein 90. *J. Med. Chem.* 49, 381-390 (2006).
78. Winkler, G S. et al. Isolation and mass spectrometry of transcription factor complexes. *Methods* 26, 260-269 (2002).
79. Erdjument-Bromage, H. et al. Micro-tip reversed-phase liquid chromatographic extraction of peptide pools for mass spectrometric analysis. *J. Chromatogr. A* 826, 167-181 (1998).
80. Trinkle-Mulcahy, L., et al. Identifying specific protein interaction partners using quantitative mass spectrometry and bead proteomes. *J. Cell. Biol.* 183, 223-239 (2008).
81. Munday, D. et al. Quantitative proteomic analysis of A549 cells infected with human respiratory syncytial virus. *Mol. Cell Proteomics* 9, 2438-2459 (2010).
82. Andersen, J. N. et al. Pathway-Based Identification of Biomarkers for Targeted Therapeutics: Personalized Oncology with PI3K Pathway Inhibitors. *Sci. Transl. Med.* 2, 43ra55 (2010).
83. Cerchietti, L. C. et al. A purine scaffold HSP90 inhibitor destabilizes BCL-6 and has specific antitumor activity in BCL-6-dependent B cell lymphomas. *Nat. Med.* 15, 1369-1376 (2009)
84. Powers, M. V., Clarke, P. A., Workman, P. Dual targeting of Hsc70 and Hsp72 inhibits HSP90 function and induces tumor-specific apoptosis. *Cancer Cell* 14, 250-262 (2008).
85. Fabian, M. A. et al. A small molecule-kinase interaction map for clinical kinase inhibitors. *Nat. Biotechnol.* 23, 329-336 (2005).
86. Moffat, J. et al. A Lentiviral RNAi Library for Human and Mouse Genes Applied to an Arrayed Viral High-Content Screen. *Cell* 124, 1283-1298 (2006).
87. Zhao, X. et al. Methylation of RUNX1 by PRMT1 abrogates SIN3A binding and potentiates its transcriptional activity. *Genes Dev.* 22, 640-653 (2009).
88. Chou, T. C. Theoretical basis, experimental design, and computerized simulation of synergism and antagonism in drug combination studies. *Pharmacol. Rev.* 58, 621-681 (2006).
89. Chou, T. C. & Talalay, P. Quantitative analysis of dose-effect relationships: the combined effects of multiple drugs or enzyme inhibitors. *Adv. Enzyme Regul.* 22, 27-55 (1984).
90. Dierov, J., Dierova. R. & Carroll, M. BCR/ABL translocates to the nucleus and disrupts an ATR-dependent intra-S phase checkpoint. *Cancer Cell* 5, 275-85 (2004).
91. Beliakoff, J. & Whitesell, L. HSP90: an emerging target for breast cancer therapy. *Anticancer Drugs.* 15, 651-662 (2004).
92. Calderwood, S. K. Heat shock proteins in breast cancer progression—a suitable case for treatment?*Int. J. Hyperthermia* 26, 681-685 (2010).
93. Pick, E. et al. High HSP90 expression is associated with decreased survival in breast cancer. *Cancer Res.* 67, 2932-2937 (2007).
94. Stravopodis, D. J., Margaritis, L. H. & Voutsinas, G. E. Drug-mediated targeted disruption of multiple protein activities through functional inhibition of the HSP90 chaperone complex. *Curr. Med. Chem.* 14, 3122-3138 (2007).
95. Pashtan, I., Tsutsumi, S., Wang, S., Xu, W. & Neckers, L. Targeting HSP90 prevents escape of breast cancer cells from tyrosine kinase inhibition. *Cell Cycle* 7, 2936-2941 (2008).
96. Citri, A., Kochupurakkal, B. S. & Yarden, Y. The achilles heel of ErbB-2/HER2: regulation by the HSP90 chaperone machine and potential for pharmacological intervention. *Cell Cycle* 3, 51-60 (2004).
97. Workman, P., Burrows, F., Neckers, L. & Rosen, N. Drugging the cancer chaperone HSP90: combinatorial therapeutic exploitation of oncogene addiction and tumor stress. *Ann. N Y. Acad. Sci.* 1113, 202-216(2007).
98. Modi, S., et al. Combination of trastuzumab and tanespimycin (17-AAG, KOS-953) is safe and active in trastuzumab-refractory HER-2 overexpressing breast cancer: a phase I dose-escalation study. *J. Clin. Oncol.* 25, 5410-5417 (2007).
99. Murphy, C. G. & Fomier, M. HER2-positive breast cancer: beyond trastuzumab. *Oncology* (*Williston Park*) 24, 410-415 (2010).
100. Caldas-Lopes, M. E., et al. Heat shock protein 90 inhibitor PU-H71, a multimodal inhibitor of malignancy, induces complete responses in triple-negative breast cancer models. *Proc. Natl. Acad. Sci. USA* 106, 8368-8373 (2009).

101. Tan, D. S., et al. Biomarker-driven early clinical trials in oncology: a paradigm shift in drug development. *Cancer J.* 15, 406-420 (2009).
102. Trepel, J., Mollapour, M., Giaccone, G. & Neckers, L. Targeting the dynamic HSP90 complex in cancer. *Nat. Rev. Cancer* 10, 537-549 (2010).
103. Holland, J. P., et al. Measuring the Pharmacodynamic Effects of a Novel HSP90 Inhibitor on HER2/neu Expression in Mice Using 89Zr-DFO-Trastuzumab. *PLoS ONE* 5(1): e8859 (2010).
104. Nagengast, W. B., et al. 89Zr-bevacizumab PET of early antiangiogenic tumor response to treatment with HSP90 inhibitor NVP-AUY922. *J. Nucl. Med.* 51, 761-767 (2010).
105. Zhang, H., et al. Identification of new biomarkers for clinical trials of HSP90 inhibitors. *Mol. Cancer. Ther.* 5, 1256-1264 (2006).
106. Vilenchik, M., et al. Targeting wide-range oncogenic transformation via PU24FCl, a specific inhibitor of tumor HSP90. *Chem. Biol.* 11, 787-797 (2004).
107. Chandarlapaty, S., et al. SNX2112, a synthetic heat shock protein 90 inhibitor, has potent antitumor activity against HER kinase-dependent cancers. *Clin. Cancer Res.* 14, 240-248 (2008).
108. Eccles, S. A., et al. NVP-AUY922: a novel heat shock protein 90 inhibitor active against xenograft tumor growth, angiogenesis, and metastasis. *Cancer Res.* 68, 2850-2860 (2008).
109. Patel, H., Modi, S., Chiosis, G. & Taldone, T. Advances in the discovery and development of HSP90 inhibitors for cancer treatment. *Expert Opin. Drug Discovery* 6, 559-587 (2011).
110. Gambhir, S. S. Molecular imaging of cancer with positron emission tomography. *Nat. Rev. Cancer* 2, 683-693 (2002).
111. Mankoff, D. A. Molecular imaging to select cancer therapy and evaluate treatment response. *J. Nucl. Med.* Mol. Imaging 53, 181-192 (2009).
112. Visioni, A. & Kim, J. Positron emission tomography for benign and malignant disease. *Surg. Clin. North Am.* 91, 249-266 (2011).
113. Pentlow, K. S., et al. Quantitative imaging of iodine-124 with PET. *J. Nucl. Med.* 37, 1557-1562 (1996).
114. Taldone, T. & Chiosis, G. Purine-scaffold HSP90 inhibitors. *Curr. Top. Med. Chem.* 9, 1436-1446 (2009).
115. Cerchietti, L. C., et al. A purine scaffold HSP90 inhibitor destabilizes BCL6 and has specific anti-tumor activity in BCL6 dependent DLBCLs in vitro and in vivo. *Nat. Med.* 15, 1369-1376 (2009).
116. Marubayashi, S., et al. HSP90 as a therapeutic target in JAK2-dependent myeloproliferative neoplasms. *J. Clin. Invest.* 120, 3578-3593 (2010).
117. Breinig, M., et al. Targeting the heat shock protein HSP90 with non-quinone inhibitors: A novel chemotherapeutic approach in human hepatocellular carcinoma. *Hepatology* 50, 102-112 (2009).
118. Rodina, A., et al. Selective compounds define HSP90 as a major inhibitor of apoptosis in small-cell lung cancer. *Nat. Chem. Biol.* 3, 498-507 (2007).
119. Li, Z. S., Schmauss, C., Cuenca, A., Ratcliffe, E. & Gershon, M. D. Physiological modulation of intestinal motility by enteric dopaminergic neurons and the D2 receptor: analysis of dopamine receptor expression, location, development, and function in wild-type and knockout mice. *J. Neurosci.* 26, 2798-2807 (2006).
120. Zuckier, L. S., et al. Kinetics of perrhenate uptake and comparative biodistribution of perrhenate, pertechnetate, and iodide by NaI symporter-expressing tissues in vivo. *J. Nucl. Med.* 45, 500-507 (2004).
121. Lundh, C., Lindencrona, U., Schmitt, A., Nilsson, M. & Forssell-Aronsson, E. Biodistribution of free 211At and 125I—in nude mice bearing tumors derived from anaplastic thyroid carcinoma cell lines. *Cancer Biother. Radiopharm.* 21, 591-600 (2006).
122. Chopra A. [N-11C-methyl]-[4-[(4-Methyl-1-piperazinyl)methyl]-N-[4-methyl-3-[[4-(3-pyridyl)-2-pyrimidinyl]amino]phenyl]benzamide. Molecular Imaging and Contrast Agent Database (MICAD) [Internet]. Bethesda (MD): National Center for Biotechnology Information (US); 2004-2010.
123. Rosso, L., et al. A new model for prediction of drug distribution in tumor and normal tissues: pharmacokinetics of temozolomide in glioma patients. *Cancer Res.* 69, 120-127 (2009).
124. Saleem, A., Aboagye, E. O., Matthews, J. C. & Price, P. M. Plasma pharmacokinetic evaluation of cytotoxic agents radiolabelled with positron emitting radioisotopes. *Cancer Chemother. Pharmacol.* 61, 865-873 (2008).
125. Leung K. 18F]—N-(2-Chloro-6-methylphenyl)-2-(6-(4-(2-fluoroethyl)piperazin-1-yl)-2-methylpyrimidin-4-ylamino)thiazole-5-carboxamide. Molecular Imaging and Contrast Agent Database (MICAD) [Internet]. Bethesda (MD): National Center for Biotechnology Information (US); 2004-2010.
126. Ginos, J. Z., et al. [13N]cisplatin PET to assess pharmacokinetics of intra-arterial versus intravenous chemotherapy for malignant brain tumors. *J. Nucl. Med.* 28, 1844-1852 (1987).
127. Higgins, L. J. & Pomper, M. G. The evolution of imaging in cancer: current state and future challenges. *Semin. Oncol.* 38, 3-15 (2011).
128. Marik, J. & Junutula, J. R. Emerging role of immunoPET in receptor targeted cancer therapy. *Curr. Drug Deliv.* 8, 70-78 (2011).
129. Bhojani, M. S., Van Dort, M., Rehemtulla, A. & Ross, B. D. Targeted imaging and therapy of brain cancer using theranostic nanoparticles. *Mol. Pharm.* 7, 1921-1929 (2010).
130. Yang, D. J., Kim, E. E. & Inoue T. Targeted molecular imaging in oncology. *Ann. Nucl. Med.* 20, 1-11 (2006).
131. Workman, P., et al. Minimally invasive pharmacokinetic and pharmacodynamic technologies in hypothesis-testing clinical trials of innovative therapies. *J. Natl. Cancer Inst.* 98, 580-598 (2006).
132. Pillarsetty, N., et al. Radiosynthesis of the iodine-124 labeled HSP90 inhibitor PUH71. *J. Labelled Comp. Radiopharm. xx*, (2011).
133. Taldone, T., Zatorska, D., Kang, Y. & Chiosis, G. A facile and efficient synthesis of d6-labeled PU-H71, a purine-scaffold HSP90 inhibitor. *J. Labelled Comp. Radiopharm.* 53, 47-49 (2010).

The invention claimed is:

1. A method for determining whether a tumor in a subject will respond to therapy with an HSP90 inhibitor which comprises the following steps:

(a) administering to the subject a radiolabeled HSP90 inhibitor;

(b) measuring the amount of radiolabeled HSP90 inhibitor bound to the tumor or the tumor cells in the sample; and (c) comparing the amount of radiolabeled HSP90 inhibitor bound to the tumor or the tumor cells in the sample measured in step (b) to the amount of radiolabeled HSP90 inhibitor bound to a reference;

wherein a greater amount of radiolabeled HSP90 inhibitor bound to the tumor or the tumor cells measured in step (b) as compared with the reference amount indicates the tumor will likely respond to the HSP90 inhibitor;

wherein the radiolabeled HSP90 inhibitor is a compound or a pharmaceutically acceptable salt thereof of

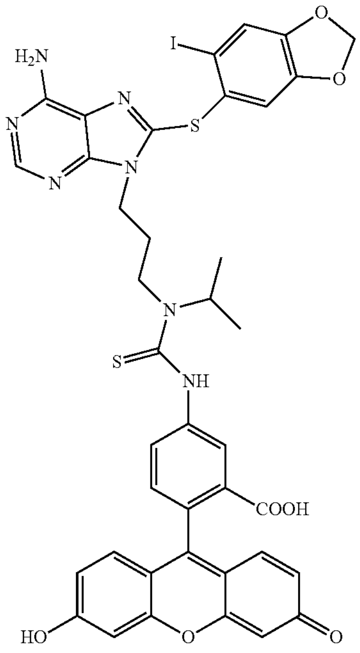

,

-continued

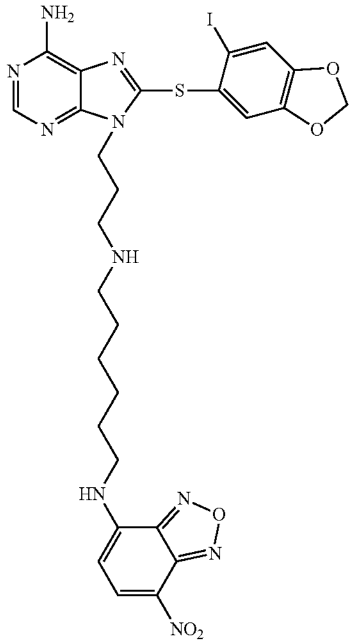

,

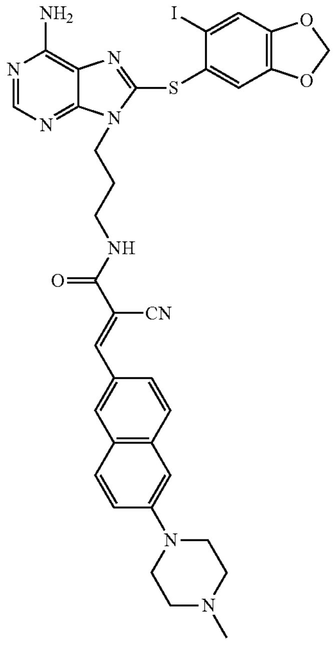

,

-continued
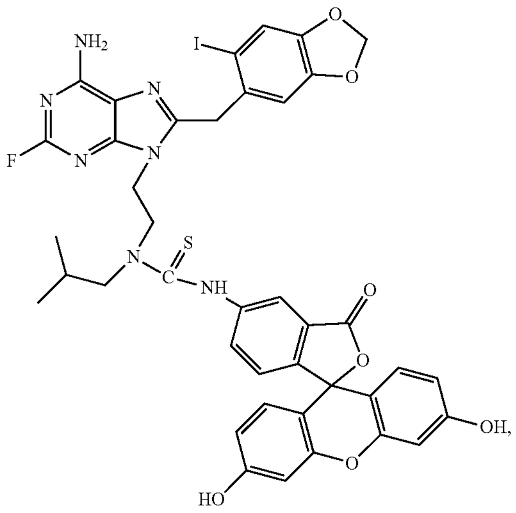
or
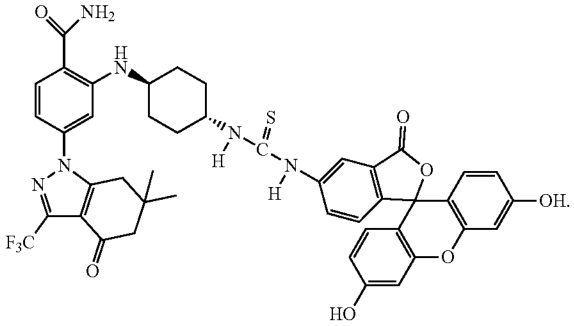
2. A compound or a pharmaceutically acceptable salt thereof selected from:
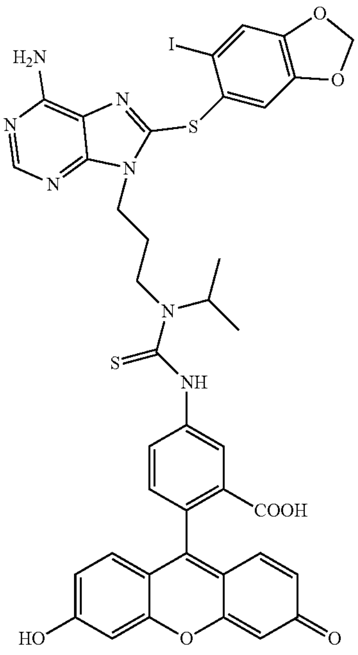
,
-continued
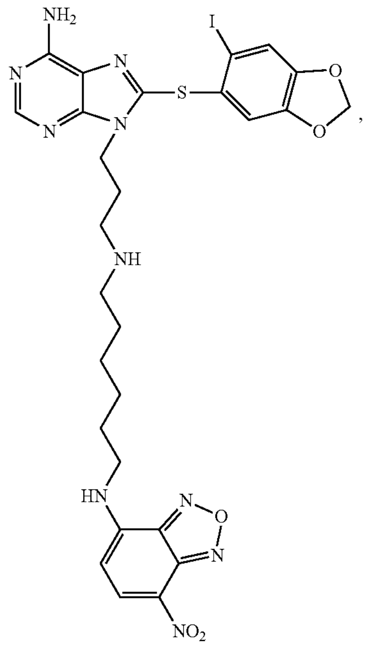
,
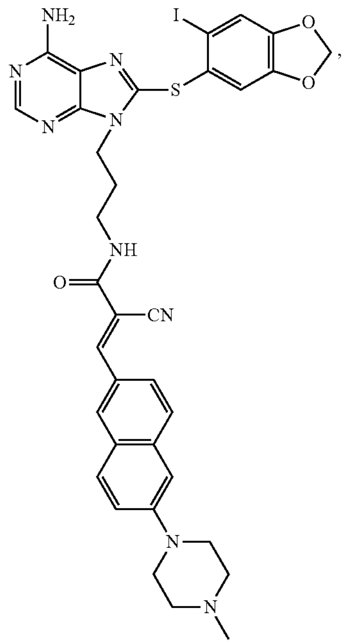
, -continued
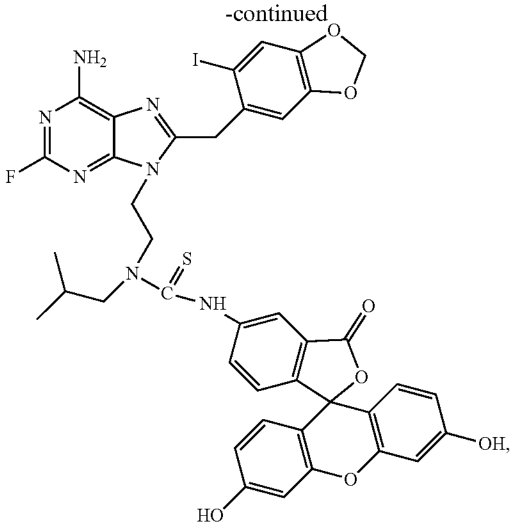
or
-continued
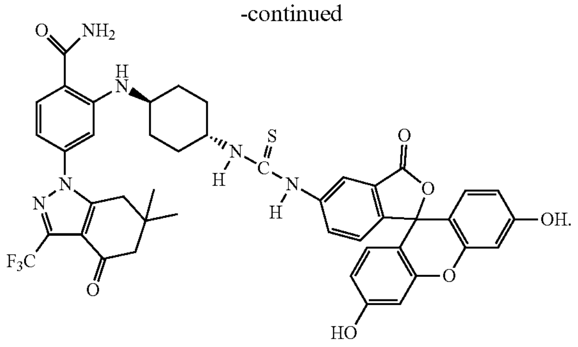
3. A pharmaceutical composition comprising
a compound or pharmaceutically acceptable salt thereof of claim 2; and
a pharmaceutically acceptable carrier.
* * * * *

SEQUENCE LISTING

```
Sequence total quantity: 27
SEQ ID NO: 1          moltype = DNA  length = 22
```

-continued

```
FEATURE               Location/Qualifiers
misc_feature          1..22
                      note = CCND2 primer
source                1..22
                      mol_type = other DNA
                      organism = synthetic construct
SEQUENCE: 1
gttgttctgg tccctttaat cg                                              22

SEQ ID NO: 2          moltype = DNA  length = 18
FEATURE               Location/Qualifiers
misc_feature          1..18
                      note = CCND2 primer
source                1..18
                      mol_type = other DNA
                      organism = synthetic construct
SEQUENCE: 2
acctcgcata cccagaga                                                   18

SEQ ID NO: 3          moltype = DNA  length = 20
FEATURE               Location/Qualifiers
misc_feature          1..20
                      note = MYC primer
source                1..20
                      mol_type = other DNA
                      organism = synthetic construct
SEQUENCE: 3
atgcgttgct gggttatttt                                                 20

SEQ ID NO: 4          moltype = DNA  length = 20
FEATURE               Location/Qualifiers
misc_feature          1..20
                      note = MYC primer
source                1..20
                      mol_type = other DNA
                      organism = synthetic construct
SEQUENCE: 4
cagagcgtgg gatgttagtg                                                 20

SEQ ID NO: 5          moltype = DNA  length = 20
FEATURE               Location/Qualifiers
misc_feature          1..20
                      note = Intergenic control region primer
source                1..20
                      mol_type = other DNA
                      organism = synthetic construct
SEQUENCE: 5
ccacctgagt ctgcaatgag                                                 20

SEQ ID NO: 6          moltype = DNA  length = 20
FEATURE               Location/Qualifiers
misc_feature          1..20
                      note = Intergenic control region primer
source                1..20
                      mol_type = other DNA
                      organism = synthetic construct
SEQUENCE: 6
cagtctccag cctttgttcc                                                 20

SEQ ID NO: 7          moltype = DNA  length = 20
FEATURE               Location/Qualifiers
misc_feature          1..20
                      note = MYC primer
source                1..20
                      mol_type = other DNA
                      organism = synthetic construct
SEQUENCE: 7
agaagagcat cttccgcatc                                                 20

SEQ ID NO: 8          moltype = DNA  length = 20
FEATURE               Location/Qualifiers
misc_feature          1..20
                      note = MYC primer
source                1..20
                      mol_type = other DNA
                      organism = synthetic construct
SEQUENCE: 8
cctttaaaca gtgcccaagc                                                 20
```

```
SEQ ID NO: 9            moltype = DNA  length = 20
FEATURE                 Location/Qualifiers
misc_feature            1..20
                        note = CCND2 primer
source                  1..20
                        mol_type = other DNA
                        organism = synthetic construct
SEQUENCE: 9
tgagctgctg gctaagatca                                       20

SEQ ID NO: 10           moltype = DNA  length = 20
FEATURE                 Location/Qualifiers
misc_feature            1..20
                        note = CCND2 primer
source                  1..20
                        mol_type = other DNA
                        organism = synthetic construct
SEQUENCE: 10
acggtactgc tgcaggctat                                       20

SEQ ID NO: 11           moltype = DNA  length = 24
FEATURE                 Location/Qualifiers
misc_feature            1..24
                        note = BCL-XL primer
source                  1..24
                        mol_type = other DNA
                        organism = synthetic construct
SEQUENCE: 11
cttttgtgga actctatggg aaca                                  24

SEQ ID NO: 12           moltype = DNA  length = 19
FEATURE                 Location/Qualifiers
misc_feature            1..19
                        note = BCL-XL primer
source                  1..19
                        mol_type = other DNA
                        organism = synthetic construct
SEQUENCE: 12
cagcggttga agcgttcct                                        19

SEQ ID NO: 13           moltype = DNA  length = 19
FEATURE                 Location/Qualifiers
misc_feature            1..19
                        note = MCL1 primer
source                  1..19
                        mol_type = other DNA
                        organism = synthetic construct
SEQUENCE: 13
agaccttacg acgggttgg                                        19

SEQ ID NO: 14           moltype = DNA  length = 20
FEATURE                 Location/Qualifiers
misc_feature            1..20
                        note = MCL1 primer
```

```
source                  1..20
                        mol_type = other DNA
                        organism = synthetic construct
SEQUENCE: 14
acattcctga tgccaccttc                                            20

SEQ ID NO: 15           moltype = DNA  length = 20
FEATURE                 Location/Qualifiers
misc_feature            1..20
                        note = CCND1 primer
source                  1..20
                        mol_type = other DNA
                        organism = synthetic construct
SEQUENCE: 15
cctgtcctac taccgcctca                                            20

SEQ ID NO: 16           moltype = DNA  length = 18
FEATURE                 Location/Qualifiers
misc_feature            1..18
                        note = CCND1 primer
source                  1..18
                        mol_type = other DNA
                        organism = synthetic construct
SEQUENCE: 16
ggcttcgatc tgctcctg                                              18

SEQ ID NO: 17           moltype = DNA  length = 21
FEATURE                 Location/Qualifiers
misc_feature            1..21
                        note = HPRT primer
source                  1..21
                        mol_type = other DNA
                        organism = synthetic construct
SEQUENCE: 17
cgtcttgctc gagatgtgat g                                          21

SEQ ID NO: 18           moltype = DNA  length = 22
FEATURE                 Location/Qualifiers
misc_feature            1..22
                        note = HPRT primer
source                  1..22
                        mol_type = other DNA
                        organism = synthetic construct
SEQUENCE: 18
gcacacagag ggctacaatg tg                                         22

SEQ ID NO: 19           moltype = DNA  length = 20
FEATURE                 Location/Qualifiers
misc_feature            1..20
                        note = GAPDH primer
source                  1..20
                        mol_type = other DNA
                        organism = synthetic construct
SEQUENCE: 19
cgaccacttt gtcaagctca                                            20

SEQ ID NO: 20           moltype = DNA  length = 20
FEATURE                 Location/Qualifiers
misc_feature            1..20
                        note = GAPDH primer
source                  1..20
                        mol_type = other DNA
                        organism = synthetic construct
SEQUENCE: 20
ccctgttgct gtagccaaat                                            20

SEQ ID NO: 21           moltype = DNA  length = 21
FEATURE                 Location/Qualifiers
misc_feature            1..21
                        note = RPL13A primer
source                  1..21
                        mol_type = other DNA
                        organism = synthetic construct
SEQUENCE: 21
tgagtgaaag ggagccagaa g                                          21

SEQ ID NO: 22           moltype = DNA  length = 20
FEATURE                 Location/Qualifiers
misc_feature            1..20
```

-continued

```
                        note = RPL13A primer
source                  1..20
                        mol_type = other DNA
                        organism = synthetic construct
SEQUENCE: 22
cagatgcccc actcacaaga                                              20

SEQ ID NO: 23           moltype = RNA  length = 19
FEATURE                 Location/Qualifiers
misc_feature            1..19
                        note = HSP70A, an active sequence against HSP70
source                  1..19
                        mol_type = other RNA
                        organism = synthetic construct
SEQUENCE: 23
ggacgagttt gagcacaag                                               19

SEQ ID NO: 24           moltype = RNA  length = 19
FEATURE                 Location/Qualifiers
misc_feature            1..19
                        note = HSP70B, an active sequence against HSP70
source                  1..19
                        mol_type = other RNA
                        organism = synthetic construct
SEQUENCE: 24
ccaagcagac gcagatctt                                               19

SEQ ID NO: 25           moltype = RNA  length = 19
FEATURE                 Location/Qualifiers
misc_feature            1..19
                        note = HSP70C, an active sequence against HSP70
source                  1..19
                        mol_type = other RNA
                        organism = synthetic construct
SEQUENCE: 25
ggacgagttg tagcacaag                                               19

SEQ ID NO: 26           moltype = DNA  length = 20
FEATURE                 Location/Qualifiers
misc_feature            1..20
                        note = CARM1 forward primer
source                  1..20
                        mol_type = other DNA
                        organism = synthetic construct
SEQUENCE: 26
tgatggccaa gtctgtcaag                                              20

SEQ ID NO: 27           moltype = DNA  length = 20
FEATURE                 Location/Qualifiers
misc_feature            1..20
                        note = CARM1 reverse primer
source                  1..20
                        mol_type = other DNA
                        organism = synthetic construct
SEQUENCE: 27
tgaaagcaac gtcaaaccag                                              20
```